(12) United States Patent
Hennequin et al.

(10) Patent No.: US 7,504,408 B2
(45) Date of Patent: Mar. 17, 2009

(54) QUINZOLINE DERIVATIVES FOR USE IN THE TREATMENT OF CANCER

(75) Inventors: Laurent Francois Andre Hennequin, Macclesfield (GB); Keith Hopkinson Gibson, Macclesfield (GB); Kevin Michael Foote, Macclesfield (GB)

(73) Assignee: AstraZeneca AB, Sodertalje (SE)

(*) Notice: Subject to any disclaimer, the term of this patent is extended or adjusted under 35 U.S.C. 154(b) by 634 days.

(21) Appl. No.: 10/520,266

(22) PCT Filed: Jul. 4, 2003

(86) PCT No.: PCT/GB03/02874
§ 371 (c)(1), (2), (4) Date: Jan. 6, 2005

(87) PCT Pub. No.: WO2004/004732
PCT Pub. Date: Jan. 15, 2004

(65) Prior Publication Data
US 2005/0250797 A1    Nov. 10, 2005

(30) Foreign Application Priority Data
Jul. 9, 2002 (GB) .................. 0215825.1
Jun. 5, 2003 (GB) .................. 0312897.2

(51) Int. Cl.
A61K 31/517 (2006.01)
C07D 239/88 (2006.01)
C07D 239/94 (2006.01)
C07D 239/93 (2006.01)

(52) U.S. Cl. .......... 514/266.24; 544/283; 544/287; 544/293

(58) Field of Classification Search .......... 514/266.24; 544/283, 287, 293
See application file for complete search history.

(56) References Cited

U.S. PATENT DOCUMENTS

| | | | |
|---|---|---|---|
| 5,409,930 A | 4/1995 | Spada et al. | 514/248 |
| 5,656,643 A | 8/1997 | Spada et al. | 514/312 |
| RE36,256 E | 7/1999 | Spada et al. | 514/249 |
| 7,115,615 B2 * | 10/2006 | Hennequin et al. | 514/266.24 |
| 7,141,577 B2 * | 11/2006 | Ple | 514/266.24 |
| 7,157,467 B2 * | 1/2007 | Moore et al. | 514/266.24 |
| 7,223,756 B2 * | 5/2007 | Moore et al. | 514/234.5 |

FOREIGN PATENT DOCUMENTS

| | | |
|---|---|---|
| EP | 0326330 | 8/1989 |
| EP | 0607439 | 7/1994 |
| EP | 0 837 063 A | 4/1998 |
| WO | WO 96/09294 | 3/1996 |
| WO | WO 97/03069 | 1/1997 |
| WO | WO 97/17329 | 5/1997 |
| WO | WO 98/02434 | 1/1998 |
| WO | WO 99/35146 | 7/1999 |
| WO | WO 00/18761 | 4/2000 |
| WO | 01/21594 A | 3/2001 |
| WO | WO 01/21594 | 3/2001 |
| WO | WO 01/94341 | 12/2001 |
| WO | 02/16352 A | 2/2002 |
| WO | WO 02/16352 | 2/2002 |
| WO | WO 02/085895 | 10/2002 |
| WO | WO 03/008409 | 1/2003 |
| WO | WO 03/047582 | 6/2003 |
| WO | WO 2004/005284 | 1/2004 |

* cited by examiner

*Primary Examiner*—James O. Wilson
*Assistant Examiner*—Tamthom N Truong
(74) *Attorney, Agent, or Firm*—Morgan, Lewis & Bockius LLP

(57) ABSTRACT

The invention concerns quinazoline derivatives of Formula (I)

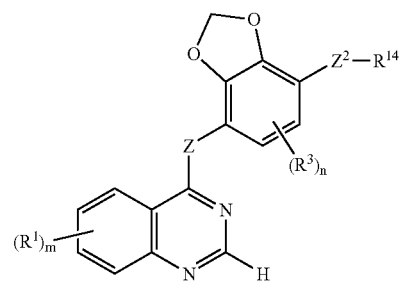

wherein each of Z, m, $R^1$, n, $R^3$, $Z^2$ and $R^{14}$ have any of the meanings defined hereinbefore in the description; processes for their preparation, pharmaceutical compositions containing them and their use in the manufacture of a medicament for use as an anti-invasive or anti-proliferative agent in the containment and/or treatment of solid tumour disease.

12 Claims, No Drawings

QUINZOLINE DERIVATIVES FOR USE IN THE TREATMENT OF CANCER

RELATED APPLICATION INFORMATION

The present application is a U.S. National Phase Application of International Application No. PCT/GB2003/002874 (filed Jul. 4, 2003) which claims the benefit of Great Britain Patent Application No. 0215825.1 (filed Jul. 9, 2002) and Great Britain Patent Application No. 0312897.2 (filed Jun. 5, 2003).

The invention concerns certain novel quinazoline derivatives, or pharmaceutically-acceptable salts thereof, which possess anti-tumour activity and are accordingly useful in methods of treatment of the human or animal body. The invention also concerns processes for the manufacture of said quinazoline derivatives, pharmaceutical compositions containing them and their use in therapeutic methods, for example in the manufacture of medicaments for use in the prevention or treatment of solid tumour disease in a warm-blooded animal such as man.

Many of the current treatment regimes for cell proliferation diseases such as psoriasis and cancer utilise compounds which inhibit DNA synthesis. Such compounds are toxic to cells generally but their toxic effect on rapidly dividing cells such as tumour cells can be beneficial. Alternative approaches to anti-tumour agents which act by mechanisms other than the inhibition of DNA synthesis have the potential to display enhanced selectivity of action.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis,* 1986, 1, 91). Oncogenes give rise to the production of peptides which are receptors for growth factors. Activation of the growth factor receptor complex subsequently leads to an increase in cell proliferation. Oncogenes often encode abnormal versions of signal pathway components, such as receptor tyrosine kinases, serine-threonine kinases, or downstream signaling molecules such as the ras genes. The ras genes code for closely related small guanine nucleotide binding proteins which hydrolyse bound guanosine triphosphate (GTP) to guanosine diphosphate (GDP). Ras proteins are active in promoting cell growth and transformation when they are bound to GTP and inactive when they are bound to GDP. Transforming mutants of p21ras are defective in their GTPase activity and hence remain in the active GTP bound state. The ras oncogene is known to play an integral role in certain cancers and has been found to contribute to the formation of over 20% of all cases of human cancer.

When activated by ligand such as a growth factor, cell surface receptors which are coupled to the mitogenic response can initiate a chain of reactions which leads to the activation of guanine nucleotide exchange activity on ras proteins. When ras protein is in its active GTP-bound state, a number of other proteins interact directly with ras at the plasma membrane resulting in signal transmission through several distinct pathways. The best characterised effector protein is the product of the raf proto-oncogene. The interaction of raf and ras is a key regulatory step in the control of cell proliferation. Ras-mediated activation of the raf serine-threonine kinase in turn activates the dual-specificity MEK (MEK1 and MEK2), which is the immediate upstream activator of mitogen activated protein kinase (MAPKs known as extracellular signal regulated protein kinases or ERK1 and ERK2). To date, no substrates of MEK other than MAPK have been identified, though recent reports indicate that MEK may also be activated by other upstream signal proteins such as MEKK1 and Cot/Tp1-2. Activated MAPK translocates and accumulates in the nucleus, where it can phosphorylate and activate transcription factors such as Elk-1 and Sap1a, leading to the enhanced expression of genes such as c-fos.

The ras-dependent raf-MEK-MAPK cascade is one of the key signalling pathways responsible for transmitting and amplifying mitogenic signals from cell surface to the nucleus resulting in changes in gene expression and cell fate. This ubiquitous pathway appears, essential for normal cell proliferation and constitutive activation of this pathway is sufficient to induce cellular transformation. Transforming mutants of p21ras are constitutively active, resulting in raf, MEK and MAPK activity and cell transformation. Inhibition of MEK activity using either antisense raf, a dominant negative MEK mutant or the selective inhibitor PD098059 has been shown to block the growth and morphological transformation of ras-transformed fibroblasts.

The mechanism of activation of raf, MEK and MAPK is through phosphorylation on specific serine, threonine or tyrosine residues. Activated raf and other kinases phosphorylate MEK1 on S218 and S222 and MEK2 on S222 and S226. This results in MEK activation and subsequent phosphorylation and activation of ERK1 on T190 and Y192 and ERK2 on T183 and Y185 by the dual specificity MEKs. Whilst MEK can be activated by a number of protein kinases, and active MAPKs phosphorylate and activate a number of substrate proteins including transcription factors and other protein kinases, MEKs appear specific and sole activators of MAPKs and could act as a focal point for cross-cascade regulation. MEK1 and MEK2 isoforms show unusual specificity and also contain a proline-rich insert between catalytic subdomains IX and X which is not present in any of the other known MEK family members. These differences between MEK and other protein kinases, together with the known role of MEK (MEK1, MEK 2) and, more recently MEK 5, in proliferative signalling suggest it may be possible to discover and employ selective MEK inhibitors as therapeutic agents for use in proliferative disease.

Accordingly, it has been recognised that an inhibitor of the MAPK kinase pathway should be of value as an anti-proliferative agent for use in the containment and/or treatment of solid tumour disease.

It is also known that several oncogenes encode tyrosine kinase enzymes and that certain growth factor receptors are also tyrosine kinase enzymes (Yarden et al., *Ann. Rev. Biochem.,* 1988, 57, 443; Larsen et al., *Ann. Reports in Med. Chem.,* 1989, Chpt. 13). The first group of tyrosine kinases to be identified arose from such viral oncogenes, for example pp60$^{v\text{-}Src}$ tyrosine kinase (otherwise known as v-Src), and the corresponding tyrosine kinases in normal cells, for example pp60$^{c\text{-}Src}$ tyrosine kinase (otherwise known as c-Src).

Receptor tyrosine kinases are important in the transmission of biochemical signals which initiate cell replication. Some of them are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research,* 1993, 60, 43-73) based on families of growth factors which bind to different receptor tyrosine kinases. The classification includes Class I receptor tyrosine kinases comprising the EGF family of receptor tyrosine kinases such as the EGF, TGFα, Neu and erbB receptors, Class II receptor tyrosine kinases comprising the insulin family of receptor tyrosine kinases such as the insulin and IGFI receptors and insulin-related receptor (IRR) and Class II receptor tyrosine kinases comprising the platelet-derived growth factor (PDGF) family of receptor tyrosine kinases such as the PDGFα, PDGFβ, and colony-stimulating factor 1 (CSF1) receptors.

It is also known that certain tyrosine kinases belong to the class of non-receptor tyrosine kinases which are located intracellularly and are involved in the transmission of biochemical signals such as those that influence tumour cell motility, dissemination and invasiveness and subsequently metastatic tumour growth (Ullrich et al., *Cell* 1990, 61 203-212, Bolen et al., *FASEB J.*, 1992, 6, 3403-3409, Brickell et al., *Critical Reviews in Oncogenesis*, 1992, 3, 401-406, Bohlen et al., *Oncogene*, 1993, 8, 2025-2031, Courtneidge et al., *Semin. Cancer Biol.*, 1994, 5, 239-246, Lauffenburger et al., *Cell*, 1996, 84, 359-369, Hanks et al., *BioEssays*, 1996, 19, 137-145, Parsons et al., *Current Opinion in Cell Biology*, 1997, 9, 187-192, Brown et al., *Biochimica et Biophysica Acta*, 1996, 1287, 121-149 and Schlaepfer et al., *Progress in Biophysics and Molecular Biology*, 1999, 71, 435-478). Various classes of non-receptor tyrosine kinases are known including the Src family such as the Src, Lyn and Yes tyrosine kinases, the Abl family such as Abl and Arg and the Jak family such as Jak 1 and Tyk 2.

It is known that the Src family of non-receptor tyrosine kinases are highly regulated in normal cells and in the absence of extracellular stimuli are maintained in an inactive conformation. However, some Src family members, for example c-Src tyrosine kinase, are frequently significantly activated (when compared to normal cell levels) in common human cancers such as gastrointestinal cancer, for example colon, rectal and stomach cancer (Cartwright et al., *Proc. Natl. Acad. Sci. USA*, 1990, 87,558-562 and Mao et al., *Oncogene*, 1997, 15, 3083-3090), and breast cancer (Muthuswamy et al., *Oncogene*, 1995, 11, 1801-1810). The Src family of non-receptor tyrosine kinases has also been located in other common human cancers such as non-small cell lung cancers (NSCLCs) including adenocarcinomas and squamous cell cancer of the lung (Mazurenko et al., *European Journal of Cancer*, 1992, 28, 372-7), bladder cancer (Fanning et al., *Cancer Research*, 1992, 52, 1457-62), oesophageal cancer (Jankowski et al., *Gut*, 1992, 33, 1033-8), cancer of the prostate, ovarian cancer (Wiener et al., *Clin. Cancer Research*, 1999, 5, 2164-70) and pancreatic cancer (Lutz et al., *Biochem. and Biophys. Res. Comm.*, 1998, 243, 503-8). As further human tumour tissues are tested for the Src family of non-receptor tyrosine kinases it is expected that its widespread prevalence will be established.

It is further known that the predominant role of c-Src non-receptor tyrosine kinase is to regulate the assembly of focal adhesion complexes through interaction with a number of cytoplasmic proteins including, for example, focal adhesion kinase and paxillin. In addition c-Src is coupled to signalling pathways that regulate the actin cytoskeleton which facilitates cell motility. Likewise, important roles are played by the c-Src, c-Yes and c-Fyn non-receptor tyrosine kinases in integrin mediated signalling and in disrupting cadherin-dependent cell-cell junctions (Owens et al., *Molecular Biology of the Cell*, 2000, 11, 51-64 and Klinghoffer et al., *EMBO Journal*, 1999, 18, 2459-2471). Cellular motility is necessarily required for a localised tumour to progress through the stages of dissemination into the blood stream, invasion of other tissues and initiation of metastatic tumour growth. For example, colon tumour progression from localised to disseminated, invasive metastatic disease has been correlated with c-Src non-receptor tyrosine kinase activity (Brunton et al., *Oncogene*, 1997, 14, 283-293, Fincham et al., *EMBO J.* 1998, 17, 81-92 and Verbeek et al., *Exp. Cell Research*, 1999, 248, 531-537).

Accordingly it has been recognised that an inhibitor of such non-receptor tyrosine kinases should be of value as a selective inhibitor of the motility of tumour cells and as a selective inhibitor of the dissemination and invasiveness of mammalian cancer cells leading to inhibition of metastatic tumour growth. In particular an inhibitor of such non-receptor tyrosine kinases should be of value as an anti-invasive agent for use in the containment and/or treatment of solid tumour disease.

We have now found that surprisingly certain quinazoline derivatives possess potent anti-tumour activity. It is believed that the compounds disclosed in the present invention provide an anti-tumour effect by way of inhibition of MEK enzymes that are involved in the MAPK kinase pathway and/or by way of inhibition of one or more of the non-receptor tyrosine-specific protein kinases that are involved in the signal transduction steps which lead to the invasiveness and migratory ability of metastasising tumour cells. In particular, it is believed that the compounds of the present invention provide an anti-tumour effect by inhibition of one or more of the MEK enzymes and/or by way of inhibition of the Src family of non-receptor tyrosine kinases, for example by inhibition of one or more of c-Src, c-Yes and c-Fyn. It is also known that c-Src non-receptor tyrosine kinase enzyme is involved in the control of osteoclast-driven bone resorption (Soriano et al., *Cell*, 1991, 64, 693-702; Boyce et al., *J. Clin. Invest.*, 1992, 90, 1622-1627; Yoneda et al., *J. Clin. Invest.*, 1993, 91, 2791-2795 and Missbach et al., *Bone*, 1999, 24, 437-49). An inhibitor of c-Src non-receptor tyrosine kinase is therefore of value in the prevention and treatment of bone diseases such as osteoporosis, Paget's disease, metastatic disease in bone and tumour-induced hypercalcaemia.

The compounds of the present invention are also useful in inhibiting the uncontrolled cellular proliferation which arises from various non-malignant diseases such as inflammatory diseases (for example rheumatoid arthritis and inflammatory bowel disease), fibrotic diseases (for example hepatic cirrhosis and lung fibrosis), glomerulonephritis, multiple sclerosis, psoriasis, hypersensitivity reactions of the skin, blood vessel diseases (for example atherosclerosis and restenosis), allergic asthma, insulin-dependent diabetes, diabetic retinopathy and diabetic nephropathy.

The compounds of the invention may possess inhibitory acitivity against the MEK enzymes that are involved in the MAPK kinase pathway. They may also possess an inhibitory activity against the Src family of non-receptor tyrosine kinases. Generally the compounds of the present invention may also possess potent inhibitory activity against the Src family of non-receptor tyrosine kinases, for example by inhibition of c-Src and/or c-Yes, whilst possessing less potent inhibitory activity against other tyrosine kinase enzymes such as the receptor tyrosine kinases, for example EGF receptor tyrosine kinase and/or VEGF receptor tyrosine kinase.

It is stated in EP 837 063 that a range of 4-aminoquinazoline derivatives are useful in treating hyperproliferative diseases such as cancers. There is no disclosure therein of any 7-alkynyl-1,3-benzodioxol-4-yl-containing quinazolines or 7-alkenyl-1,3-benzodioxol-4-yl-containing quinazolines.

According to one aspect of the invention there is provided a quinazoline derivative of the Formula I

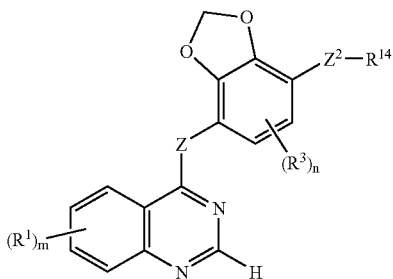

I wherein Z is an O, S, SO, SO$_2$, N(R$^2$) or C(R$^2$)$_2$ group, wherein each R$^2$ group, which may be the same or different, is hydrogen or (1-6C)alkyl;

m is 0, 1, 2,3 or4;

each R$^1$ group, which may be the same or different, is selected from halogeno, trifluoromethyl, cyano, isocyano, nitro, hydroxy, mercapto, amino, formyl, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino or from a group of the formula:

Q$^1$-X$^1$— wherein X$^1$ is a direct bond or is selected from O, S, SO, SO$_2$, N(R$^4$), CO, CH(OR$^4$), CON(R$^4$), N(R$^4$)CO, SO$_2$N(R$^4$), N(R$^4$)SO$_2$, OC(R$^4$)$_2$, SC(R$^4$)$_2$ and N(R$^4$)C(R$^4$)$_2$, wherein R$^4$ is hydrogen or (1-6C)alkyl, and Q$^1$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, or (R$^1$)$_m$ is (1-3C)alkylenedioxy, and wherein adjacent carbon atoms in any (2-6C)alkylene chain within a R$^1$ substituent are optionally separated by the insertion into the chain of a group selected from O, S, SO, SO$_2$, N(R$^5$), CO, CH(OR$^5$), CON(R$^5$), N(R$^5$)CO, SO$_2$N(R$^5$), N(R$^5$)SO$_2$, CH=CH and C≡C wherein R$^5$ is hydrogen or (1-6C)alkyl or, when the inserted group is N(R$^5$), R$^5$ may also be (2-6C)alkanoyl, and wherein any CH$_2$=CH— or HC≡C— group within a R$^1$ substituent optionally bears at the terminal CH$_2$= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl, di-[(1-6C)alkyl]amino-(1-6C)alkyl or from a group of the formula:

Q$^2$-X$^2$— wherein X$^2$ is a direct bond or is selected from CO and N(R$^6$)CO, wherein R$^6$ is hydrogen or (1-6C)alkyl, and Q$^2$ is aryl, aryl-(1-6C)alkyl, heteroaryl, heteroaryl-(1-6C)alkyl, heterocyclyl or heterocyclyl-(1-6C)alkyl, and wherein any CH$_2$ or CH$_3$ group within a R$^1$ substituent optionally bears on each said CH$_2$ or CH$_3$ group one or more halogeno or (1-6C)alkyl substituents or a substituent selected from hydroxy, cyano, amino, carboxy, carbamoyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxyalkylamino di-[(1-6C)alkoxyalkyl]amino or hydroxy (1-6C)alkylamino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino or from a group of the formula:

—X$^3$-Q$^3$ wherein X$^3$ is a direct bond or is selected from O, S, SO, SO$_2$, N(R$^7$), CO, CH(OR$^7$), CON(R$^7$), N(R$^7$)CO, SO$_2$N(R$^7$), N(R$^7$)SO$_2$, C(R$^7$)$_2$O, C(R$^7$)$_2$S and N(R$^7$)C(R$^7$)$_2$, wherein R$^7$ is hydrogen or (1-6C)alkyl, and Q$^3$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a substituent on R$^1$ optionally bears 1, 2 or 3 substituents, which may be the same or different, selected from halogeno, trifluoromethyl, cyano, nitro, hydroxy, amino, carboxy, carbamoyl, formyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino or from a group of the formula:

—X$^4$—R$^8$ wherein X$^4$ is a direct bond or is selected from O and N(R$^9$), wherein R$^9$ is hydrogen or (1-6C)alkyl, and R$^8$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, or a group of the formula:

—X$^5$-Q$^4$ wherein X$^5$ is a direct bond or is selected from O, N(R$^{10}$) and CO, wherein R$^{10}$ is hydrogen or (1-6C)alkyl, and Q$^4$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, (1-6C)alkyl, (2-8C)alkenyl, (2-8C)alkynyl and (1-6C)alkoxy, and wherein any heterocyclyl group within a substituent on R$^1$ optionally bears 1 or 2 oxo or thioxo substituents;

n is 0, 1 or 2; and

R$^3$ is selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)

alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino or from a group of the formula:

—$X^6$—$R^{11}$ wherein $X^6$ is a direct bond or is selected from O and $N(R^{12})$, wherein $R^{12}$ is hydrogen or (1-6C)alkyl, and $R^{11}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl;

$Z^2$ is a C≡C or $C(R^{13})$=$C(R^{13})$ group, wherein each $R^{13}$ group, which may be the same or different, is hydrogen or (1-6C)alkyl; and $R^{14}$ is selected from halogeno, cyano, isocyano, formyl, carboxy, (2-8C)alkenyl, (2-8C)alkynyl, (1-6C)alkoxycarbonyl, N-(1-6C)alkylcarbamoyl, N,N-di-[(1-6C)alkyl]carbamoyl, (2-6C)alkanoyl, N-(1-6C)alkylsulphamoyl, N,N-di-[(1-6C)alkyl]sulphamoyl, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, from a group of formula:

$(CH_2)_x$—$N(R^c)$—$C(O)$—$NR^aR^b$ wherein x is 0, 1, 2 or 3, $R^c$ is hydrogen or (1-6C)alkyl and $R^a$ and $R^b$ are each independently selected from hydrogen and (1-6C)alkyl or $R^a$ and $R^b$ together with the nitrogen to which they are attached form a 4 to 7 membered heterocyclyl optionally containing up to two further heteroatoms selected from oxygen, nitrogen or sulphur, or from a group of the formula:

—$X^7$-$Q^5$ wherein $X^7$ is a direct bond or is selected from CO, $CH(OR^{15})$, $CON(R^{15})$ or $SO_2N(R^{15})$, wherein $R^{15}$ is hydrogen or (1-6C)alkyl, and $Q^5$ is aryl, aryl-(1-6C)alkyl, (3-7C)cycloalkyl, (3-7C)cycloalkyl-(1-6C)alkyl, heteroaryl, heteroaryl-(1-6C)alkyl, heterocyclyl heterocyclyl-(1-6C)alkyl or heterocyclyloxy-(1-6C)alkyl, and wherein any CH, $CH_2$ or $CH_3$ group within a $R^{14}$ substituent optionally bears on each said CH, $CH_2$ or $CH_3$ group one or more halogeno, (1-6C)alkyl or (3-6C)cycloalkyl substituents or a substituent selected from hydroxy, cyano, amino, carboxy, carbamoyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino or from a group of the formula:

—$X^8$-$Q^6$ wherein $X^8$ is a direct bond or is selected from O, S, SO, $SO_2$, $N(R^{16})$, CO, $CH(OR^{16})$, $CON(R^{16})$, $N(R^{16})CO$, $SO_2N(R^{16})$, $N(R^{16})SO_2$, $C(R^{16})_2O$, $C(R^{16})_2S$ and $N(R^{16})C(R^{16})_2$, wherein $R^{16}$ is hydrogen or (1-6C)alkyl, and $Q^6$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a substituent on $R^{14}$ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino or from a group of the formula:

—$X^9$—$R^{17}$ wherein $X^9$ is a direct bond or is selected from O and $N(R^{18})$, wherein $R^{18}$ is hydrogen or (1-6C)alkyl, and $R^{17}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, or from a group of the formula:

—$X^{10}$-$Q^7$ wherein $X^{10}$ is a direct bond or is selected from O, $N(R^{19})$ and CO, wherein $R^{19}$ is hydrogen or (1-6C)alkyl, and $Q^7$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, (1-6C)alkyl, (2-8C)alkenyl, (2-8C)alkynyl and (1-6C)alkoxy, and wherein any heterocyclyl group within a substituent on $R^{14}$ optionally bears 1 or 2 oxo or thioxo substituents;

or a pharmaceutically-acceptable salt thereof.

According to a further aspect of the invention there is provided a quinazoline derivative of the Formula I

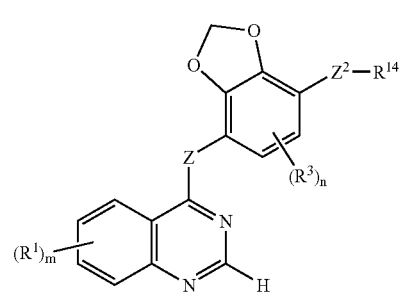

I wherein Z is an O, S, SO, $SO_2$, $N(R^2)$ or $C(R^2)_2$ group, wherein each $R^2$ group, which may be the same or different, is hydrogen or (1-6C)alkyl;

m is 0, 1, 2, 3 or 4;

each $R^1$ group, which may be the same or different, is selected from halogeno, trifluoromethyl, cyano, isocyano, nitro, hydroxy, mercapto, amino, formyl, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, $\underline{N}$-(1-6C)alkylcarbamoyl, $\underline{N},\underline{N}$-di-[(1-6C)alkyl]carbamoyl, (2-6C)alkanoyl, (2-6C)alkanoyloxy, (2-6C)alkanoylamino, $\underline{N}$-(1-6C)alkyl-(2-6C)alkanoylamino, (3-6C)alkenoylamino, $\underline{N}$-(1-6C)alkyl-(3-6C)alkenoylamino, (3-6C)alkynoylamino, $\underline{N}$-(1-6C)alkyl-(3-6C)alkynoylamino, $\underline{N}$-(1-6C)alkylsulphamoyl, $\underline{N},\underline{N}$-di-[(1-6C)alkyl]sulphamoyl, (1-6C)alkanesulphonylamino, $\underline{N}$-(1-6C)alkyl-(1-6C)alkanesulphonylamino or from a group of the formula:

$$Q^1-X^1-$$

wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1-6C)alkyl, and $Q^1$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, or $(R^1)_m$ is (1-3C)alkylenedioxy, and wherein adjacent carbon atoms in any (2-6C)alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, $CH=CH$ and $C\equiv C$ wherein $R^5$ is hydrogen or (1-6C)alkyl or, when the inserted group is $N(R^5)$, $R^5$ may also be (2-6C)alkanoyl, and wherein any $CH_2=CH-$ or $HC\equiv C-$ group within a $R^1$ substituent optionally bears at the terminal $CH_2=$ or $HC\equiv$ position a substituent selected from halogeno, carboxy, carbamoyl, (1-6C)alkoxycarbonyl, $\underline{N}$-(1-6C)alkylcarbamoyl, $\underline{N},\underline{N}$-di-[(1-6C)alkyl]carbamoyl, amino-(1-6C)alkyl, (1-6C)alkylamino-(1-6C)alkyl, di-[(1-6C)alkyl]amino-(1-6C)alkyl or from a group of the formula:

$$Q^2-X^2-$$

wherein $X^2$ is a direct bond or is selected from CO and $N(R^6)CO$, wherein $R^6$ is hydrogen or (1-6C)alkyl, and $Q^2$ is aryl, aryl-(1-6C)alkyl, heteroaryl, heteroaryl-(1-6C)alkyl, heterocyclyl or heterocyclyl-(1-6C)alkyl, and wherein any $CH_2$ or $CH_3$ group within a $R^1$ substituent optionally bears on each said $CH_2$ or $CH_3$ group one or more halogeno or (1-6C)alkyl substituents or a substituent selected from hydroxy, cyano, amino, carboxy, carbamoyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, $\underline{N}$-(1-6C)alkylcarbamoyl, $\underline{N},\underline{N}$-di-[(1-6C)alkyl]carbamoyl, (2-6C)alkanoyl, (2-6C)alkanoyloxy, (2-6C)alkanoylamino, $\underline{N}$-(1-6C)alkyl-(2-6C)alkanoylamino, $\underline{N}$-(1-6C)alkylsulphamoyl, $\underline{N},\underline{N}$-di-[(1-6C)alkyl]sulphamoyl, (1-6C)alkanesulphonylamino, $\underline{N}$-(1-6C)alkyl-(1-6C)alkanesulphonylamino or from a group of the formula:

$$-X^3-Q^3$$

wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R^7)_2$, wherein $R^7$ is hydrogen or (1-6C)alkyl, and $Q^3$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, $\underline{N}$-(1-6C)alkylcarbamoyl, $\underline{N},\underline{N}$-di-[(1-6C)alkyl]carbamoyl, (2-6C)alkanoyl, (2-6C)alkanoyloxy, (2-6C)alkanoylamino, $\underline{N}$-(1-6C)alkyl-(2-6C)alkanoylamino, $\underline{N}$-(1-6C)alkylsulphamoyl, $\underline{N},\underline{N}$-di-[(1-6C)alkyl]sulphamoyl, (1-6C)alkanesulphonylamino, $\underline{N}$-(1-6C)alkyl-(1-6C)alkanesulphonylamino or from a group of the formula:

$$-X^4-R^8$$

wherein $X^4$ is a direct bond or is selected from O and $N(R^9)$, wherein $R^9$ is hydrogen or (1-6C)alkyl, and $R^8$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, or a group of the formula:

$$-X^5-Q^4$$

wherein $X^5$ is a direct bond or is selected from O, $N(R^{10})$ and CO, wherein $R^{10}$ is hydrogen or (1-6C)alkyl, and $Q^4$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, (1-6C)alkyl, (2-8C)alkenyl, (2-8C)alkynyl and (1-6C)alkoxy, and wherein any heterocyclyl group within a substituent on $R^1$ optionally bears 1 or 2 oxo or thioxo substituents;

n is 0, 1 or 2; and $R^3$ is selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, $\underline{N}$-(1-6C)alkylcarbamoyl, $\underline{N},\underline{N}$-di-[(1-6C)alkyl]carbamoyl, (2-6C)alkanoyl, (2-6C)alkanoyloxy, (2-6C)alkanoylamino, $\underline{N}$-(1-6C)alkyl-(2-6C)alkanoylamino, (3-6C)alkenoylamino, $\underline{N}$-(1-6C)alkyl-(3-6C)alkenoylamino, (3-6C)alkynoylamino, $\underline{N}$-(1-6C)alkyl-(3-6C)alkynoylamino, $\underline{N}$-(1-6C)alkylsulphamoyl, $\underline{N},\underline{N}$-di-[(1-6C)alkyl]sulphamoyl, (1-6C)alkanesulphonylamino, $\underline{N}$-(1-6C)alkyl-(1-6C)alkanesulphonylamino or from a group of the formula:

$$-X^6-R^{11}$$

wherein $X^6$ is a direct bond or is selected from O and $N(R^{12})$, wherein $R^{12}$ is hydrogen or (1-6C)alkyl, and $R^{11}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl;

$Z^2$ is a $C\equiv C$ or $C(R^{13})=C(R^{13})$ group, wherein each $R^{13}$ group, which may be the same or different, is hydrogen or (1-6C)alkyl; and $R^{14}$ is selected from halogeno, cyano, isocyano, formyl, carboxy, (2-8C)alkenyl, (2-8C)alkynyl, (1-6C)alkoxycarbonyl, N-(1-6C)alkylcarbamoyl, N,N-di-[(1-6C)alkyl]carbamoyl, (2-6C)alkanoyl, N-(1-6C)alkylsulphamoyl, N,N-di-[(1-6C)alkyl]sulphamoyl, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl or from a group of the formula:

—$X^7$-$Q^5$ wherein $X^7$ is a direct bond or is selected from CO, CH($OR^{15}$), CON($R^{15}$) or $SO_2$N($R^{15}$), wherein $R^{15}$ is hydrogen or (1-6C)alkyl, and $Q^5$ is aryl, aryl-(1-6C)alkyl, (3-7C)cycloalkyl, (3-7C)cycloalkyl-(1-6C)alkyl, heteroaryl, heteroaryl-(1-6C)alkyl, heterocyclyl or heterocyclyl-(1-6C)alkyl, and wherein any CH, $CH_2$ or $CH_3$ group within a $R^{14}$ substituent optionally bears on each said CH, $CH_2$ or $CH_3$ group one or more halogeno or (1-6C)alkyl substituents or a substituent selected from hydroxy, cyano, amino, carboxy, carbamoyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino or from a group of the formula:

—$X^8$-$Q^6$ wherein $X^8$ is a direct bond or is selected from O, S, SO, $SO_2$, N($R^{16}$), CO, CH($OR^{16}$), CON($R^{16}$), N($R^{16}$)CO, $SO_2$N($R^{16}$), N($R^{16}$)$SO_2$, C($R^{16}$)$_2$O, C($R^{16}$)$_2$S and N($R^{16}$)C($R^{16}$)$_2$, wherein $R^{16}$ is hydrogen or (1-6C)alkyl, and $Q^6$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a substituent on $R^{14}$ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino or from a group of the formula:

—$X^9$—$R^{17}$ wherein $X^9$ is a direct bond or is selected from O and N($R^{18}$), wherein $R^{18}$ is hydrogen or (1-6C)alkyl, and $R^{17}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, or from a group of the formula:

—X-$Q^7$ wherein $X^{10}$ is a direct bond or is selected from O, N($R^{19}$) and CO, wherein $R^{19}$ is hydrogen or (1-6C)alkyl, and $Q^7$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, (1-6C)alkyl, (2-8C)alkenyl, (2-8C)alkynyl and (1-6C)alkoxy, and wherein any heterocyclyl group within a substituent on $R^{14}$ optionally bears 1 or 2 oxo or thioxo substituents;

or a pharmaceutically-acceptable salt thereof.

In this specification the generic term "alkyl" includes both straight-chain and branched-chain alkyl groups such as propyl, isopropyl and tert-butyl, and also (3-7C)cycloalkyl groups such as cyclopropyl, cyclobutyl, cyclopentyl, cyclohexyl and cycloheptyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes methoxy, ethoxy, cyclopropyloxy and cyclopentyloxy, (1-6C)alkylamino includes methylamino, ethylamino, cyclobutylamino and cyclohexylamino, and di-[(1-6Calkyl]amino includes dimethylamino, diethylamino, N-cyclobutyl-N-methylamino and N-cyclohexyl-N-ethylamino.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below.

A suitable value for any one of the 'Q' groups ($Q^1$ to $Q^7$) when it is aryl or for the aryl group within a 'Q' group is, for example, phenyl or naphthyl, preferably phenyl.

A suitable value for any one of the 'Q' groups ($Q^1$, $Q^3$, $Q^5$ or $Q^6$) when it is (3-7C)cycloalkyl or for the (3-7C)cycloalkyl group within a 'Q' group is, for example, cyclopropyl, cyclobutyl, cyclopentyl, cyclohexyl, cycloheptyl or bicyclo[2.2.1]heptyl and a suitable value for any one of the 'Q' groups ($Q^1$, $Q^3$ or $Q^6$) when it is (3-7C)cycloalkenyl or for the (3-7C)cycloalkenyl group within a 'Q' group is, for example, cyclobutenyl, cyclopentenyl, cyclohexenyl or cycloheptenyl.

A suitable value for any one of the 'Q' groups ($Q^1$ to $Q^7$) when it is heteroaryl or for the heteroaryl group within a 'Q' group is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl.

A suitable value for any one of the 'Q' groups ($Q^1$ to $Q^7$) when it is heterocyclyl or for the heterocyclyl group within a 'Q' group is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, tetrahydropyranyl, oxepanyl, tetrahydrothienyl, 1,1-dioxotetrahydrothienyl, tetrahydrothiopyranyl, 1,1-dioxotetrahydrothiopyranyl, azetidinyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl, preferably tetrahydrofuranyl, tetrahydropyranyl, pyrrolidinyl, morpholinyl, 1,1-dioxotetrahydro-4H-1,4-thiazinyl, piperidinyl or piperazinyl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for a 'Q' group when it is heterocyclyl-(1-6C)alkyl is, for example 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, piperidin-4-ylmethyl, 2-piperidin-3-ylethyl, 3-piperidin-1-ylpropyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, preferably 3-morpholinopropyl, 3-piperazin-1-ylpropyl, 3-piperidin-1-ylpropyl, 3-piperidin-4y;propyl, 3-(1,1-dioxotetrahydro-4H-1,4,-thiazin-4-yl-propyl) and 3-pyrrolidin-1-ypropyl.

A suitable value for a 'Q' group when it is heteroaryl-(1-6C)alkyl is, for example, heteroarylmethyl, 2-heteroarylethyl and 3-heteroarylpropyl. The invention comprises corresponding suitable values for 'Q' groups when, for example, rather than a heteroaryl-(1-6C)alkyl group, an aryl-(1-6C)alkyl, (3-7C)cycloalkyl-(1-6C)alkyl, (3-7C)cycloalkenyl-(1-6C)alkyl or heterocyclyl-(1-6C)alkyl group is present.

In structural Formula I there is a hydrogen atom at the 2-position on the quinazoline ring. It is to be understood thereby that the $R^1$ substituents may only be located at the 5-, 6-, 7- or 8-positions on the quinazoline ring i.e. that the 2-position remains unsubstituted. It is further to be understood that the $R^3$ group that may be present on the 1,3-benzodioxol-4-yl group within structural Formula I may be located on the phenyl ring or on the methylene group within the dioxol group. Preferably, any $R^3$ group that is present on the 1,3-benzodioxol-4-yl group within structural Formula I is located on the phenyl ring thereof.

For the avoidance of doubt, the positions on structural Formula I are numbered as follows:

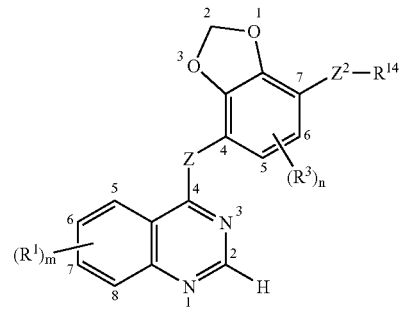

Suitable values for any of the 'R' groups ($R^1$ to $R^{19}$ and $R^a$, $R^b$ and $R^c$) or for various groups within an $R^1$, $R^3$ or $R^{14}$ group include:

| | |
|---|---|
| for halogeno | fluoro, chloro, bromo and iodo; |
| for (1-6C)alkyl: | methyl, ethyl, propyl, isopropyl and tert-butyl; |
| for (2-8C)alkenyl: | vinyl, isopropenyl, allyl and but-2-enyl; |
| for (2-8C)alkynyl: | ethynyl, 2-propynyl and but-2-ynyl; |
| for (1-6C)alkoxy: | methoxy, ethoxy, propoxy, isopropoxy and butoxy; |
| for (2-6C)alkenyloxy: | vinyloxy and allyloxy; |
| for (2-6C)alkynyloxy: | ethynyloxy and 2-propynyloxy; |
| for (1-6C)alkylthio: | methylthio, ethylthio and propylthio; |
| for (1-6C)alkylsulphinyl: | methylsulphinyl and ethylsulphinyl; |
| for (1-6C)alkylsulphonyl: | methylsulphonyl and ethylsulphonyl; |
| for (1-6C)alkylamino: | methylamino, ethylamino, propylamino, isopropylamino and butylamino; |
| for di-[(1-6C)alkyl]amino: | dimethylamino, diethylamino, N-ethyl-N-methylamino and diisopropylamino; |
| for (1-6C)alkoxycarbonyl: | methoxycarbonyl, ethoxycarbonyl, propoxycarbonyl and tert-butoxycarbonyl; |
| for N-(1-6C)alkylcarbamoyl: | N-methylcarbamoyl, N-ethylcarbamoyl and N-propylcarbamoyl; |
| for N,N-di-[(1-6C)alkyl]carbamoyl: | N,N-dimethylcarbamoyl, N-ethyl-N-methylcarbamoyl and N,N-diethylcarbamoyl; |
| for (2-6C)alkanoyl: | acetyl and propionyl; |
| for (2-6C)alkanoyloxy: | acetoxy and propionyloxy; |
| for (2-6C)alkanoylamino: | acetamido and propionamido; |
| for N-(1-6C)alkyl-(2-6C)alkanoylamino: | N-methylacetamido and N-methylpropionamido; |
| for N-(1-6C)alkylsulphamoyl: | N-methylsulphamoyl and N-ethylsulphamoyl; |
| for N,N-di-[(1-6C)alkyl]sulphamoyl: | N,N-dimethylsulphamoyl; |
| for (1-6C)alkanesulphonylamino: | methanesulphonylamino and ethanesulphonylamino; |
| for N-(1-6C)alkyl-(1-6C)alkanesulphonylamino: | N-methylmethanesulphonylamino and N-methylethanesulphonylamino; |
| for (3-6C)alkenoylamino: | acrylamido, methacrylamido and crotonamido; |
| for N-(1-6C)alkyl-(3-6C)alkenoylamino: | N-methylacrylamido and N-methylcrotonamido; |
| for (3-6C)alkynoylamino: | propiolamido; |
| for N-(1-6C)alkyl-(3-6C)alkynoylamino: | N-methylpropiolamido; |
| for amino-(1-6C)alkyl: | aminomethyl, 2-aminoethyl, 1-aminoethyl and 3-aminopropyl; |
| for (1-6C)alkyl- | methylaminomethyl, ethylaminomethyl, |

-continued

| | |
|---|---|
| amino-(1-6C)alkyl: | 1-methylaminoethyl, 2-methylaminoethyl, 2-ethylaminoethyl and 3-methylaminopropyl; |
| for di-[(1-6C)alkyl]amino-(1-6C)alkyl: | dimethylaminomethyl, diethylaminomethyl, 1-dimethylaminoethyl, 2-dimethylaminoethyl and 3-dimethylaminopropyl; |
| for halogeno-(1-6C)alkyl: | chloromethyl, 2-chloroethyl, 1-chloroethyl and 3-chloropropyl; |
| for hydroxy-(1-6C)alkyl: | hydroxymethyl, 2-hydroxyethyl, 1-hydroxyethyl and 3-hydroxypropyl; |
| for (1-6C)alkoxy-(1-6C)alkyl: | methoxymethyl, ethoxymethyl, 1-methoxyethyl, 2-methoxyethyl, 2-ethoxyethyl and 3-methoxypropyl; |
| for cyano-(1-6C)alkyl: | cyanomethyl, 2-cyanoethyl, 1-cyanoethyl and 3-cyanopropyl; |
| for (2-6C)alkanoylamino-(1-6C)alkyl: | acetamidomethyl, propionamidomethyl and 2-acetamidoethyl; and |
| for (1-6C)alkoxycarbonylamino-(1-6C)alkyl: | methoxycarbonylaminomethyl, ethoxycarbonylaminomethyl, tert-butoxycarbonylaminomethyl and 2-methoxycarbonylaminoethyl. |

A suitable value for $(R^1)_m$ when it is a (1-3C)alkylenedioxy group is, for example, methylenedioxy or ethylenedioxy and the oxygen atoms thereof occupy adjacent ring positions.

When, as defined hereinbefore, an $R^1$ group forms a group of the formula $Q^1-X^1-$ and, for example, $X^1$ is a $OC(R^4)_2$ linking group, it is the carbon atom, not the oxygen atom, of the $OC(R^4)_2$ linking group which is attached to the quinazoline ring and the oxygen atom is attached to the $Q^1$ group. Similarly, when, for example a $CH_3$ group within a $R^1$ substituent bears a group of the formula $-X^3-Q^3$ and, for example, $X^3$ is a $C(R^7)_2O$ linking group, it is the carbon atom, not the oxygen atom, of the $C(R^7)_2O$ linking group which is attached to the $CH_3$ group and the oxygen atom is linked to the $Q^3$ group. A similar convention applies to the attachment of the groups of the formulae $Q^3-X^3-$ and $-X^8-Q^6$.

As defined hereinbefore, adjacent carbon atoms in any (2-6C)alkylene chain within a $R^1$ substituent may be optionally separated by the insertion into the chain of a group such as O, $CON(R^5)$ or C≡C. For example, insertion of a C≡C group into the ethylene chain within a 2-morpholinoethoxy group gives rise to a 4-morpholinobut-2-ynyloxy group and, for example, insertion of a CONH group into the ethylene chain within a 3-methoxypropoxy group gives rise to, for example, a 2-(2-methoxyacetamido)ethoxy group.

When, as defined hereinbefore, any CH, $CH_2$ or $CH_3$ group within a $R^1$ or $R^{14}$ substituent optionally bears on each said CH, $CH_2$ or $CH_3$ group one or more halogeno or (1-6C)alkyl substituents, there is suitably 1 halogeno or (1-6C)alkyl substituent present on each said CH group, there are suitably 1 or 2 such substituents present on each said $CH_2$ group and there are suitably 1, 2 or 3 such substituents present on each said $CH_3$ group.

When, as defined hereinbefore, any CH, $CH_2$ or $CH_3$ group within a $R^1$ or $R^{14}$ substituent optionally bears on each said CH, $CH_2$ or $CH_3$ group a substituent as defined hereinbefore, suitable $R^1$ or $R^{14}$ substituents so formed include, for example, hydroxy-substituted heterocyclyl-(1-6C)alkoxy groups such as 2-hydroxy-3-piperidinopropoxy and 2-hydroxy-3-morpholinopropoxy.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular novel compounds of the invention include, for example, quinazoline derivatives of the Formula I, or pharmaceutically-acceptable salts thereof, wherein, unless otherwise stated, each of Z, m, $R^1$, n, $R^3$, $Z^2$ and $R^{14}$ has any of the meanings defined hereinbefore or in paragraphs (a) to (ii) hereinafter:

(a) Z is O, S, SO, $SO_2$, $CH_2$ or NH;

(b) Z is O;

(c) Z is NH;

(d) $R^1$ substituents may only be located at the 5-, 6- and/or 7-positions on the quinazoline ring i.e. the 2- and 8-positions remain unsubstituted;

(e) $R^1$ substituents may only be located at the 6- and/or 7-positions on the quinazoline ring i.e. the 2-, 5- and 8-positions remain unsubstituted;

(f) $R^1$ substituents may only be located at the 5- and/or 7-positions on the quinazoline ring i.e. the 2-, 6- and 8-positions remain unsubstituted;

(g) m is 1 or 2, and each $R^1$ group, which may be the same or different, is selected from halogeno, trifluoromethyl, hydroxy, amino, carbamoyl, (1-6C)alkyl, (2-8C)alkenyl, (2-8C)alkynyl, (1-6C)alkoxy, (2-6C)alkenyloxy, (2-6C)alkynyloxy, or from a group of the formula:

$Q^1-X^1-$ wherein $X^1$ is a direct bond or is O and $Q^1$ is heterocyclyl or heterocyclyl-(1-6C)alkyl, and wherein adjacent carbon atoms in any (2-6C)alkylene chain within a $R^1$ substituent are optionally separated by the insertion into the chain of an O, and wherein any $CH_2$ or $CH_3$ group within a $R^1$ substituent optionally bears on each said $CH_2$ or $CH_3$ group one or more halogeno groups, and wherein any heterocyclyl group within a substituent on $R^1$ optionally bears 1, 2 or 3 substituents, which may be the same or different, selected from halogeno, (1-6C)alkyl, (2-6C)alkanoyl, hydroxy and hydroxy(1-6C)alkyl, and wherein any heterocyclyl group within a substituent on $R^1$ optionally bears 1 or 2 oxo substituents;

(h) m is 1 or 2, and each $R^1$ group, which may be the same or different, is selected from halogeno, trifluoromethyl, hydroxy, amino, carbamoyl, (1-6C)alkyl, (2-8C)alkenyl, (2-8C)alkynyl, (1-6C)alkoxy, (2-6C)alkenyloxy, (2-6C)alkenyloxy, (2-6C)alkynyloxy, or from a group of the formula:

$Q^1-X^1-$ wherein $X^1$ is a direct bond or is O and $Q^1$ is heterocyclyl or heterocyclyl-(1-6C)alkyl, and wherein adjacent carbon atoms in any (2-6C)alkylene chain within a $R^1$ substituent are optionally separated by the insertion into the chain of an O, and wherein any $CH_2$ or $CH_3$ group within a $R^1$ substituent optionally bears on each said $CH_2$ or $CH_3$ group one or more halogeno groups or a group selected from amino, (1-6C)alkylamino, di-[(1-6C)alkyl]amino, (1-6C)alkoxyalkylamino di-[(1-6C)alkoxyalkyl]amino or hydroxy(1-6C)alkylamino, and wherein any heterocyclyl group within a substituent on $R^1$ optionally bears 1, 2 or 3 substituents, which may be the same or different, selected from halogeno, halogeno(1-6C)

alkyl, (1-6C)alkyl, (1-6C)alkoxy, formyl, (2-6C)alkanoyl, hydroxy and hydroxy(1-6C)alkyl, and wherein any heterocyclyl group within a substituent on $R^1$ optionally bears 1 or 2 oxo substituents;

(i) m is 1 or 2, and each $R^1$ group, which may be the same or different, is selected from methoxy, ethoxy, propoxy, isopropoxy, or from a group of the formula:

$Q^1-X^1-$ wherein $X^1$ is O and $Q^1$ is piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4$\underline{H}$-1,4-thiazin-4-yl)ethyl, 3-(1,1-dioxotetrahydro-4$\underline{H}$-1,4-thiazin-4-yl)propyl, 2-piperidinoethyl, 3-piperidinopropyl, 4-piperidinobutyl, piperidin-4-ylmethyl, 2-piperidin-3-ylethyl, 3-piperidin-1-ylpropyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein adjacent carbon atoms in any (2-6C)alkylene chain within a $R^1$ substituent are optionally separated by the insertion into the chain of a O, and wherein any $CH_2$ or $CH_3$ group within a $R^1$ substituent optionally bears on each said $CH_2$ or $CH_3$ group one or more fluoro or chloro groups, and wherein any heterocyclyl group within a substituent on $R^1$ optionally bears 1, 2 or 3 substituents, which may be the same or different, selected from methyl, ethyl, acetyl, hydroxy and hydroxymethyl, and wherein any heterocyclyl group within a substituent on $R^1$ optionally bears 1 or 2 oxo substituents;

(j) m is 1 or 2, and each $R^1$ group, which may be the same or different, is selected from methoxy, ethoxy, propoxy, isopropoxy, 2-methylpropoxy, or from a group of the formula:

$Q^1-X^1-$ wherein $X^1$ is O and $Q^1$ is piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, tetrahydro-2$\underline{H}$-pyran-4-yl, 2-(1,1-dioxotetrahydro-4$\underline{H}$-1,4-thiazin-4-yl)ethyl, 3-(1,1-dioxotetrahydro-4$\underline{H}$-1,4-thiazin-4-yl)propyl, 2-piperidinoethyl, 3-piperidinopropyl, 4-piperidinobutyl, piperidin-4-ylmethyl, 2-piperidin-3-ylethyl, 3-piperidin-1-ylpropyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein adjacent carbon atoms in any (2-6C)alkylene chain within a $R^1$ substituent are optionally separated by the insertion into the chain of a O, and wherein any $CH_2$ or $CH_3$ group within a $R^1$ substituent optionally bears on each said $CH_2$ or $CH_3$ group one or more fluoro, chloro or bromo groups or a substituent selected from amino, methylamino, dimethylamino, methoxyethylamino, di-(methoxyethyl)amino, or hydroxypropylamino, and wherein any heterocyclyl group within a substituent on $R^1$ optionally bears 1, 2 or 3 substituents, which may be the same or different, selected from methyl, ethyl, methoxy, ethoxy, formyl, acetyl, hydroxyl, hydroxymethyl, fluoroethyl or hydroxypropylamino, and wherein any heterocyclyl group within a substituent on $R^1$ optionally bears 1 or 2 oxo substituents;

(k) m is 2 and each $R^1$ group, which may be the same or different, is selected from methoxy, ethoxy, propoxy, isopropoxy, or from a group of the formula:

$Q^1-X^1-$ wherein $X^1$ is O and $Q^1$ is piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4$\underline{H}$-1,4-thiazin-4-yl)ethyl, 3-(1,1-dioxotetrahydro-4$\underline{H}$-1,4-thiazin-4-yl)propyl, 2-piperidinoethyl, 3-piperidinopropyl, 4-piperidinobutyl, 2-piperidin-3-ylethyl, 3-piperidin-3-ylpropyl, piperidin-4-ylmethyl, 3-piperidin-1-ylpropyl, 2-piperidin-4ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein adjacent carbon atoms in any (2-6C)alkylene chain within a $R^1$ substituent are optionally separated by the insertion into the chain of a O, and wherein any $CH_2$ or $CH_3$ group within a $R^1$ substituent optionally bears on each said $CH_2$ or $CH_3$ group one or more fluoro or chloro groups, and wherein any heterocyclyl group within a substituent on $R^1$ optionally bears 1, 2 or 3 substituents, which may be the same or different, selected from methyl, ethyl, acetyl, hydroxy and hydroxymethyl, and wherein any heterocyclyl group within a substituent on $R^1$ optionally bears 1 or 2 oxo substituents;

(l) m is 2, and each $R^1$ group, which may be the same or different, is selected from methoxy, ethoxy, propoxy, isopropoxy, 2-methylpropoxy, or from a group of the formula:

$Q^1-X^1-$ wherein $X^1$ is O and $Q^1$ is piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, tetrahydro-2$\underline{H}$-pyran-4-yl, 2-(1,1-dioxotetrahydro-4$\underline{H}$-1,4-thiazin-4-yl)ethyl, 3-(1,1-dioxotetrahydro-4$\underline{H}$-1,4-thiazin-4-yl)propyl, 2-piperidinoethyl, 3-piperidinopropyl, 4-piperidinobutyl, piperidin-4-ylmethyl, 2-piperidin-3-ylethyl, 3-piperidin-1-ylpropyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein any CH$_2$ or CH$_3$ group within a R$^1$ substituent optionally bears on each said CH$_2$ or CH$_3$ group one or more fluoro, chloro groups or a substituent selected from amino, methylamino, methoxy, dimethylamino, methoxyethylamino, di-(methoxyethyl)amino, or hydroxypropylamino, and wherein any heterocyclyl group within a substituent on R$^1$ optionally bears 1 or 2 substituents, which may be the same or different, selected from methyl, ethyl, methoxy, ethoxy, formyl, acetyl, hydroxyl, hydroxymethyl, fluoroethyl or hydroxypropylamino, and wherein any heterocyclyl group within a substituent on R$^1$ optionally bears 1 or 2 oxo substituents;

(m) m is 2 and each R$^1$ group, which may be the same or different, is located at the 6- and 7-positions and R$^1$ is selected from methoxy, ethoxy, propoxy, isopropoxy, or from a group of the formula:

Q$^1$-X$^1$— wherein X$^1$ is O and Q$^1$ is 1-, 2-, or 3-pyrrolidinyl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, piperidin-4-ylmethyl, 3-piperidin-1-ylpropyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein adjacent carbon atoms in any (2-6C)alkylene chain within a R$^1$ substituent are optionally separated by the insertion into the chain of a O, and wherein any CH$_2$ or CH$_3$ group within a R$^1$ substituent optionally bears on each said CH$_2$ or CH$_3$ group one or more fluoro or chloro groups, and wherein any heterocyclyl group within a substituent on R$^1$ optionally bears 1, 2 or 3 substituents, which may be the same or different, selected from methyl, ethyl, acetyl, hydroxy and hydroxymethyl, and wherein any heterocyclyl group within a substituent on R$^1$ optionally bears 1 or 2 oxo substituents;

(n) m is 2 and each R$^1$ group, which may be the same or different, is located at the 6- and 7-positions and R$^1$ is selected from methoxy, ethoxy, propoxy, isopropoxy, 2-methylpropoxy, or from a group of the formula:

Q$^1$-X$^1$— wherein X$^1$ is O and Q$^1$ is 1-, 2-, or 3-pyrrolidinyl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, tetrahydro-2H-pyran-4-yl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, piperidin-4-ylmethyl, 3-piperidin-1-ylpropyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein any CH$_2$ or CH$_3$ group within a R$^1$ substituent optionally bears on each said CH$_2$ or CH$_3$ group one or more fluoro or chloro groups or a substituent selected from amino, methylamino, methoxy, dimethylamino, methoxyethylamino di-(methoxyethyl)amino or hydroxypropylamino, and wherein any heterocyclyl group within a substituent on R$^1$ optionally bears 1 or 2 substituents, which may be the same or different, selected from methyl, ethyl, methoxy, ethoxy, formyl, acetyl, hydroxyl, hydroxymethyl, fluoroethyl or hydroxypropylamino, and wherein any heterocyclyl group within a substituent on R$^1$ optionally bears 1 or 2 oxo substituents;

(o) m is 2 and each R$^1$ group, which may be the same or different, is located at the 5- and 7-positions and R$^1$ is selected from methoxy, ethoxy, propoxy, isopropoxy, 2-methylpropoxy, or from a group of the formula:

Q$^1$-X$^1$— wherein X$^1$ is O and Q$^1$ is 1-, 2-, or 3-pyrrolidinyl, piperidino, piperidin-3-yl, piperidin-4yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, tetrahydro-2H-pyran-4-yl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, piperidin-4-ylmethyl, 3-piperidin-1-ylpropyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein any CH$_2$ or CH$_3$ group within a R$^1$ substituent optionally bears on each said CH$_2$ or CH$_3$ group one or more fluoro or chloro groups or a substituent selected from amino, methylamino, methoxy, dimethylamino, methoxyethylamino, di-(methoxyethyl)amino or hydroxypropylamino, and wherein any heterocyclyl group within a substituent on R$^1$ optionally bears 1, 2 or 3 substituents, which may be the same or different, selected from methyl, ethyl, methoxy, ethoxy, formyl, acetyl, hydroxyl, hydroxymethyl, fluoroethyl or hydroxypropylamino, and wherein any heterocyclyl group within a substituent on R$^1$ optionally bears 1 or 2 oxo substituents;

(p) m is 2 and each R$^1$ group, which may be the same or different, is located at the 6- and 7-positions and is selected from methoxy or from a group of the formula:

Q$^1$-X$^1$— wherein X$^1$ is O and Q$^1$ is selected from 3-pyrrolidinyl, 3-pyrrolidin-1-ylpropyl, piperidin-4-yl, piperidin-4-ylmethyl, 3-piperidin-1-ylpropyl, 3-morpholin-4-ylpropyl, 2-morpholin-4-ylethyl, 4-morpholin-4-ylbutyl, 3-(1,1-dioxotetrahydro-4H-1,4-thiazin-4-yl)propyl or 3-piperazin-1-ylpropyl, and wherein any heterocyclyl group within a substituent on R$^1$ optionally bears 1 substituent selected from methyl, acetyl, hydroxy, hydroxymethyl and 2-fluoroethyl, and wherein any heterocyclyl group within a substituent on R¹ optionally bears 1 or 2 oxo substituents;

(q) m is 2 and each R¹ group, which may be the same or different, is located at the 6- and 7-positions and is selected from methoxy, ethoxy, propoxy, 2-methylpropoxy, isopropoxy or from a group of the formula:

$$Q^1-X^1—$$

wherein X¹ is O and Q¹ is selected from 3-pyrrolidin-1-ylpropyl, 3-piperidin-1-ylpropyl, 3-piperidin-4-ylpropyl, 3-morpholin-4-ylpropyl, 2-morpholin-4-ylethyl, 4-morpholin-4-ylbutyl, 3-(1,1-dioxotetrahydro-4H-1,4-thiazin-4-yl)propyl 2-piperazin-1-ylethyl, 3-piperazin-1-ylpropyl or 4-piperazin-1-ylbutyl, and wherein any CH₂ or CH₃ group within a R¹ substituent optionally bears on each said CH₂ or CH₃ group a substituent selected from chloro, dimethylamino, di-(methoxyethyl)amino or hydroxypropylamino, and wherein any heterocyclyl group within a substituent on R¹ optionally bears 1 or 2 substituents selected from methyl, formyl, acetyl, hydroxy, hydroxymethyl, methoxy and 2-fluoroethyl, and wherein any heterocyclyl group within a substituent on R¹ optionally bears 1 or 2 oxo substituents;

(r) m is 2 and each R¹ group, which may be the same or different, is located at the 5- and 7-positions and is selected from methoxy, isopropoxy or from a group of the formula:

$$Q^1-X^1—$$

wherein X¹ is O and Q¹ is selected from tetrahydro-2H-pyran-4-yl, 3-morpholin-4-ylpropyl, 2-morpholin-4-ylethyl, 4-morpholin-4-ylbutyl, 2-piperazin-1-ylethyl, 3-piperazin-1-ylpropyl or 4piperazin-1-ylbutyl, and wherein any heterocyclyl group within a substituent on R¹ optionally bears 1 or 2 substituents selected from methyl, formyl or acetyl, and wherein any heterocyclyl group within a substituent on R¹ optionally bears 1 or 2 oxo substituents;

(s) m is 2 and one R¹ group which is located at the 6-position is methoxy and the second R¹ group is selected from a group of the formula:

$$Q^1X^1—$$

wherein X¹ is O and Q¹ is selected from 3-morpholin-4-ylpropyl, 2-morpholin-4-ylethyl, 4-morpholin-4-ylbutyl, 3-(1,1-dioxotetrahydro-4H-1,4-thiazin-4-yl)propyl, 3-piperazin-1-ylpropyl, piperidin-4-ylmethyl, 3-piperidin-1-ylpropyl or 3-pyrrolidin-1-ylpropyl, and wherein any heterocyclyl group within a substituent on R¹ optionally bears 1 substituent selected from methyl, acetyl, hydroxy, hydroxymethyl and 2-fluoroethyl, and wherein any heterocyclyl group within a substituent on R¹ optionally bears 1 or 2 oxo substituents;

(t) m is 2 and one R¹ group which is located at the 6-position is methoxy and the second R¹ group which is located at the 7-position is selected from methoxy, ethoxy, propoxy, 2-methylpropoxy, isopropoxy or from a group of the formula:

$$Q^1-X^1—$$

wherein X¹ is O and Q¹ is selected from 3-pyrrolidin-1-ylpropyl, 3-piperidin-1-ylpropyl, 3-piperidin-4-ylpropyl, 3-morpholin-4-ylpropyl, 2-morpholin-4-ylethyl, 4-morpholin-4-ylbutyl, 3-(1,1-dioxotetrahydro-4H-1,4-thiazin-4-yl)propyl 2-piperazin-1-ylethyl, 3-piperazin-1-ylpropyl or 4-piperazin-1-ylbutyl, and wherein any CH₂ or CH₃ group within a R¹ substituent optionally bears on each said CH₂ or CH₃ group a substituent selected from chloro, dimethylamino, di-(methoxyethyl)amino or hydroxypropylamino, and wherein any heterocyclyl group within a substituent on R¹ optionally bears 1 or 2 substituents selected from methyl, formyl, acetyl, hydroxy, hydroxymethyl, methoxy and 2-fluoroethyl, and wherein any heterocyclyl group within a substituent on R¹ optionally bears 1 or 2 oxo substituents;

(u) m is 2 and one R¹ group which is located at the 5-position is selected from isopropoxy or from tetrahydro-2H-pyran-4-yloxy and the second R¹ group is at the 7-position and is selected from is selected from methoxy, 3-morpholin-4-ylpropoxy, 3-(4-acetylpiperazin-1-yl)propoxy, 3-(4-formylacetylpiperazin-1-yl)propoxy and 3-(3-oxo-4-methyl-piperazin-1-yl)propyoxy;

(v) m is 2 and one R¹ which is located at the 6-position is methoxy and the second R¹ is at the 7-position and is selected from methoxy, ethoxy, isopropoxy, 2-methoxyethoxy, 2-methylpropoxy, 2-[3-(hydroxy)propylamino]ethoxy, 3-(dimethylamino)propoxy, 3-morpholin-4-ylpropoxy, 3-(2,6-dimethylmorpholin-4-yl)propoxy, 3-(1,1-dioxotetrahydro-4H-1,4-thiazin-4-yl)propoxy, 3-(4-acetylpiperazin-1-yl)propoxy, 2-(4-methylpiperazin-1-yl)ethoxy, 3-(4-hydroxymethylpiperidin-1-yl)propoxy, 3-(4-methylpiperazin-1-yl)propoxy, 4-(4-methylpiperazin-1-yl)butoxy, 3-(3-oxo-4-methylpiperazin-1-yl)propoxy, 3-(2-oxo-4-methylpiperazin-1-yl)propoxy, 3-(dimethylamino)propoxy, 3-[bis(2-methoxyethyl)amino]propoxy, 3-(4-formylpiperazin-1-yl)propoxy, 3-[-(2-fluoroethyl)piperazin-1-yl]propoxy, 3-[4-(2-fluoroethyl)piperazin-1-yl]propoxy, 3-(4-methoxypiperidin-1-yl)propoxy, 3-(4hydroxypiperidin-1-yl)propoxy, 3-(4-methylpiperidin-4-yl)propoxy, 2-morpholin-4-ylethoxy, 3-chloropropoxy, 4-morpholin-4-ylbutoxy or 3-[(2-hydroxymethyl)pyrrolidin-1-yl]propoxy.

(w) n is 0;

(x) n is 1 and the R³ group is located at the 5- or 6-position of the 1,3-benzodioxol-4-yl group, especially the 6-position, and is selected from chloro, bromo, trifluoromethyl, cyano, hydroxy, methyl, ethyl, methoxy and ethoxy;

(y) n is 1 and the R³ group is located at the 5- or 6-position of the 1,3-benzodioxol-4-yl group, especially the 5-position, and is selected from fluoro, chloro, bromo, trifluoromethyl, cyano, hydroxy, methyl, ethyl, methoxy and ethoxy;

(z) n is 1 and the R³ is located at the 5-position of the 1,3-benzodioxol-4-yl group, and is selected from chloro and bromo, and is especially chloro;

(aa) Z² is a C≡C group;

(bb) Z² is a CH=CH group;

(cc) R¹⁴ is selected from cyano, carboxy, (1-6C)alkoxycarbonyl, N-(1-6C)alkylcarbamoyl, N,N-di-[(1-6C)alkyl]carbamoyl, (2-6C)alkanoyl, halogeno-(1-6C)alkyl, (1-6C)alkoxy-(1-6C)alkyl or from a group of the formula:

$$—X^7-Q^5$$

wherein X⁷ is a direct bond or CO and Q⁵ is heterocyclyl or heterocyclyl-(1-6C)alkyl, and wherein any CH₂ or CH₃ group within a R¹⁴ substituent optionally bears on each said CH₂ or CH₃ group a (1-6C)alkoxy group and wherein any heterocyclyl group within a substituent on R¹⁴ optionally bears 1 or 2 oxo substituents;

(dd) $R^{14}$ is selected from hydroxy-(1-6C)alkyl, (1-6C)alkoxy-(1-6C)alkyl, (1-6C)alkylamino-(1-6C)alkyl, di-[(1-6C)alkyl]amino-(1-6C)alkyl, from a group of formula:

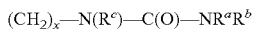

wherein x is 0, 1, 2 or 3, $R^c$ is hydrogen or (1-6C)alkyl and $R^a$ and $R^b$ are each independently selected from hydrogen and (1-6C)alkyl or $R^a$ and $R^b$ together with the nitrogen to which they are attached form morpholino or from a group of the formula:

wherein $X^7$ is a direct bond and $Q^5$ is aryl, heteroaryl, heterocyclyl, heterocyclyl-(1-6C)alkyl or heterocyclyloxy-(1-6C)alkyl, and wherein any CH, $CH_2$ or $CH_3$ group within a $R^{14}$ substituent optionally bears on each said CH, $CH_2$ or $CH_3$ group one or more halogeno, (1-6C)alkyl, (1-6C)alkoxy, carbamoyl, (1-6C)alkoxy, N-(1-6C)alkylcarbamoyl, N,N-di-[(1-6C)alkyl]carbamoyl or from a group of the formula:

wherein $X^8$ is a direct bond or O and $Q^6$ is aryl, (3-7C)cycloalkyl, (3-7C)cycloalkyl-(1-6C)alkyl, heterocyclyl or heterocyclyl-(1-6C)alkyl, and wherein any aryl, cycloalkyl or heterocyclyl group within a substituent on $R^{14}$ optionally bears 1, 2 or 3 substituents, which may be the same or different, selected from halogeno, hydroxyl, amino, (1-6C)alkyl or (1-6C)alkanoyl, and wherein any heterocyclyl group within a substituent on $R^{14}$ optionally bears 1 or 2 oxo or thioxo substituents;

(ee) $R^{14}$ is selected from (1-6C)alkoxy-(1-6C)alkyl, di-[(1-6C)alkyl]amino-(1-6C)alkyl, hydroxyl-(1-6C)alkyl or from a group of formula:

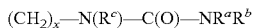

wherein x is 0, 1, 2 or 3, $R^c$ is hydrogen or (1-6C)alkyl and $R^a$ and $R^b$ are each independently selected from hydrogen and (1-6C)alkyl or $R^a$ and $R^b$ together with the nitrogen to which they are attached form morpholino, or from a group of the formula:

wherein $X^7$ is a direct bond and $Q^5$ is aryl, heteroaryl, heterocyclyl, heterocyclyl-(1-6C)alkyl, or heterocyclyloxy-(1-6C)alkyl, and wherein any CH, $CH_2$ or $CH_3$ group within a $R^{14}$ substituent optionally bears on each said CH, $CH_2$ or $CH_3$ group a substituent selected from (1-6C)alkoxy, carbamoyl, N-(1-6C)alkylcarbamoyl or a group of the formula:

wherein $X^8$ is a direct bond or O and $Q^6$ is (3-7C)cycloalkyl or heterocyclyl, and wherein any heterocyclyl group within a substituent on $R^{14}$ optionally bears 1 oxo substituent;

(ff) $R^{14}$ is selected from methoxymethyl, 1-methoxyethyl, 2-methoxyethyl, methoxyisopropyl, 2-methoxypropyl, ethoxymethyl, methoxyethoxymethyl, hydroxymethyl, carbamoylmethoxymethyl, methylcarbamoylmethoxymethyl, isopropoxymethyl, (dimethyamino)methyl, hydroxyisopropyl, (cyclopropylmethoxy)methyl, (cyclopentylmethoxy)methyl from a group of formula:

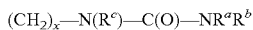

wherein x is 1, $R^c$ is hydrogen and $R^a$ and $R^b$ are each independently selected from hydrogen, and methyl or $R^a$ and $R^b$ together with the nitrogen to which they are attached form morpholino, or x is 1 and $R^a$, $R^b$ and $R^c$ are all methyl, or is selected from 2-oxo-pyrrolidin-1-ylmethyl, pyridin-2-yl, (tetrahydrofuran-3-ylmethoxy)methyl, (tetrahydrofuran-3-yloxy)methyl, [(1,3 dioxolan-2-yl)methoxy]methyl, phenyl, pyridin-3-yl, pyrazin-2-yl, pyrimidin-2-yl, 1H-pyrazol-4-yl or 1H-pyrazol-5-yl;

(gg) $R^{14}$ is methoxymethyl;
(hh) $R^{14}$ is a group of formula:

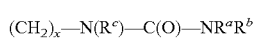

wherein x is 1, $R^c$ is hydrogen or (1-3C) alkyl, especially methyl, and $R^a$ $R^b$ are each independently selected from hydrogen and (1-3C)alkyl, especially methyl; and
(ii) $R^{14}$ is a heterocyclyl or a heterocyclyl-(1-6C)alkyl where the heterocyclyl is selected from pyridin-2-yl, pyridin-3-yl, pyrazin-3-yl, pyrimidin-2-yl, 2-pyrrolidin-1-yl, 1H-pyrazol-4-yl or 1H-pyrazol-5-yl and the heterocycyl is optionally substituted by 1, 2, or 3 substituents selected from halogeno, hydroxyl, amino, (1-6C)alkyl or (1-6C)alkanoyl or 2 oxo or thioxo substituents.

A particular compound of the invention is a quinazoline derivative of the Formula I wherein Z is O or NH m is 1 and the $R^1$ group is located at the 5-, 6-, or 7-position or m is 2 and each $R^1$ group, which may be the same or different, is located at the 5- and 7-positions or at the 6- and 7-positions and $R^1$ is selected from methoxy, ethoxy, propoxy, isopropoxy, 2-methylpropoxy or from a group of the formula:

wherein $X^1$ is O and $Q^1$ is piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, tetrahydro-2H-pyran-4-yl, 2-(1,1-dioxotetrahydro-4H-1,4-thiazin-4yl)ethyl, 3-(1,1-dioxotetrahydro-4H-1,4-thiazin-4-yl)propyl, 2-piperidinoethyl, 3-piperidinopropyl, 4-piperidinobutyl, piperidin-4-ylmethyl, 2-piperidin-3-ylethyl, 3-piperidin-1-ylpropyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein adjacent carbon atoms in any (2-6C)alkylene chain within a $R^1$ substituent are optionally separated by the insertion into the chain of a O, and wherein any $CH_2$ or $CH_3$ group within a $R^1$ substituent optionally bears on each said $CH_2$ or $CH_3$ group one or more fluoro, chloro or bromo groups or a substituent selected from amino, methoxy, methylamino, dimethylamino, methoxyethylamino, di-(methoxyethyl)amino, or hydroxypropylamino, and wherein any heterocyclyl group within a substituent on $R^1$ optionally bears 1, 2 or 3 substituents, which may be the same or different, selected from methyl, ethyl, methoxy, ethoxy, formyl, acetyl, hydroxyl, hydroxymethyl, fluoroethyl or hydroxypropylamino, and wherein any heterocyclyl group within a substituent on $R^1$ optionally bears 1 or 2 oxo substituents;

n is 0 or 1 and $R^3$ group, if present, is located at the 5- or 6-position of the 1,3-benzodioxol-4-yl group and is selected from fluoro, chloro, bromo, trifluoromethyl, cyano, hydroxy, methyl, ethyl, methoxy and ethoxy;

$Z^2$ is a C≡C or CH═CH group; and $R^{14}$ is selected from hydroxy-(1-6C)alkyl, (1-6C)alkoxy-(1-6C)alkyl, (1-6C)alkylamino-(1-6C)alkyl, di-[(1-6C)alkyl]amino-(1-6C)alkyl, from a group of formula:

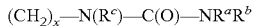
$(CH_2)_x$—N($R^c$)—C(O)—N$R^a R^b$ wherein x is 0, 1, 2 or 3, $R^c$ is hydrogen or (1-6C)alkyl and $R^a$ and $R^b$ are each independently selected from hydrogen and (1-6C)alkyl or $R^a$ and $R^b$ together with the nitrogen to which they are attached form morpholino or from a group of the formula:

—$X^7$-$Q^5$ wherein $X^7$ is a direct bond and $Q^5$ is aryl, heteroaryl, heterocyclyl, heterocyclyl-(1-6C)alkyl or heterocyclyloxy-(1-6C)alkyl, and wherein any CH, CH$_2$ or CH$_3$ group within a $R^{14}$ substituent optionally bears on each said CH, CH$_2$ or CH$_3$ group one or more halogeno, (1-6C)alkyl, (1-6C)alkoxy, carbamoyl, (1-6C)alkoxy, N-(1-6C)alkylcarbamoyl, N,N-di-[(1-6C)alkyl]carbamoyl or from a group of the formula:

—$X^8$-$Q^6$ wherein $X^8$ is a direct bond or O and $Q^6$ is aryl, (3-7C)cycloalkyl, (3-7C)cycloalkyl-(1-6C)alkyl, heterocyclyl or heterocyclyl-(1-6C)alkyl, and wherein any aryl, cycloalkyl or heterocyclyl group within a substituent on $R^{14}$ optionally bears 1, 2 or 3 substituents, which may be the same or different, selected from halogeno, hydroxyl, amino, (1-6C)alkyl or (1-6C)alkanoyl, and wherein any heterocyclyl group within a substituent on $R^{14}$ optionally bears 1 or 2 oxo or thioxo substituents;

or a pharmaceutically acceptable acid addition salt thereof.

A particular compound of the invention is a quinazoline derivative of the Formula I wherein Z is NH m is 2, and the first $R^1$ group is a 6-methoxy group and the second $R^1$ group is located at the 7-position and is selected from methoxy, ethoxy, 3-(4-methylpiperazin-1-yl)propoxy, 3-morpholinopropoxy, 2-morpholin-4-ylethoxy, 4-morpholin-4-ylbutoxy, 3-(1,1-dioxotetrahydro-4H-1,4-thiazin-4-yl)propoxy, 2-fluoroethoxy, 3-[4-(2-fluoroethyl)piperazin-1-yl]propoxy, 3-(4-acetylpiperazin-1-yl)propoxy, 3-piperazin-1-ylpropoxy, -(4-methylpiperazin-1-yl)propoxy, 3-(3-oxopiperazin-1-yl)propoxy, 3-[4-(2-fluoroethylpiperazin-1-yl)propoxy, 3-(3-oxopiperazin-1-yl)propoxy, 2-(2-pyrrolidin-1-ylethoxy)ethoxy, 3-[2-(hydroxymethyl)pyrrolidin-1-yl]propoxy, 2-(2-methoxyethoxy)ethoxy, 3-chloropropoxy, 2-(2-chloroethoxy)ethoxy, 1-methylpiperidin-4-ylmethoxy or 3-(4-hydroxypiperidin-1-yl)propoxy, n is 0 or 1 and $R^3$ group, if present, is located at the 5 position of the 1,3-benzodioxol group and is selected from fluoro or chloro;

$Z^2$ is a C≡C or CH═CH group; and $R^{14}$ is selected from cyano, (1-6C)alkoxycarbonyl, N-(1-6C)alkylcarbamoyl, N,N-di-[(1-6C)alkyl]carbamoyl, (2-6C)alkanoyl, halogeno-(1-6C)alkyl, (1-6C)alkoxy-(1-6C)alkyl or from a group of the formula:

—$X^7$-$Q^5$ wherein $X^7$ is a direct bond or CO and $Q^5$ is heterocyclyl or heterocyclyl-(1-6C)alkyl, and wherein any CH$_2$ or CH$_3$ group within a $R^{14}$ substituent optionally bears on each said CH$_2$ or CH$_3$ group a (1-6C)alkoxy group;

or a pharmaceutically acceptable acid addition salt thereof.

A particular compound of the invention is a quinazoline derivative of the Formula I wherein Z is NH m is 2, and the first $R^1$ group is a 6-methoxy group and the second $R^1$ group is located at the 7-position and is selected from methoxy, 2-methoxyethoxy, 2-fluoroethoxy, 3-chloroethoxy, isopropoxy, isopropylmethoxy, 3-dimethylaminopropoxy, 2-dimethylaminoethoxy, dimethylaminoisopropoxy, 2-[3-(hydroxy)propylamino]ethoxy, 3-[bis(2-methoxyethyl)amino]propoxy, 2-(2-methoxyethoxy)ethoxy, 3-chloropropoxy, 2-(2-chloroethoxy)ethoxy, 3-piperazin-1-ylpropoxy, 2-piperazin-1-ylethoxy, 4-piperazin-1-ylbutoxy, 2-(4-methylpiperazin-1-yl)ethoxy, 3-(4-methylpiperazin-1-yl)propoxy, 4-(4-methylpiperazin-1-yl)butoxy, 3-[4-(2-fluoroethyl)piperazin-1-yl]propoxy, 2-[4-(2-fluoroethyl)piperazin-1-yl]ethoxy, 4-[4-(2-fluoroethyl)piperazin-1-yl]butoxy, 3-(4-acetylpiperazin-1-yl)propoxy, 2-(4-acetylpiperazin-1-yl)ethoxy, 4-(4-acetylpiperazin-1-yl)butoxy, 3-(4-formylpiperazin-1-yl)propoxy, 2-(4-formylpiperazin-1-yl)ethoxy, 4-(4-formylpiperazin-1-yl)butoxy, 3-morpholinopropoxy, 2-morpholin-4-ylethoxy, 4-morpholin-4-ylbutoxy, 3-(2,6-dimethylmorpholin-4-yl)propoxy, 2-(2,6-dimethylmorpholin-4-yl)ethoxy, 4-(2,6-dimethylmorpholin-4-yl)butoxy, 3-(1,1-dioxotetrahydro-4H-1,4-thiazin-4-yl)propoxy, 3-[2-(hydroxymethyl)pyrrolidin-1-yl]propoxy, 4-[2-(hydroxymethyl)pyrrolidin-1-yl]butoxy, 2-[2-(hydroxymethyl)pyrrolidin-1-yl]ethoxy, 3-(4-hydroxypiperidin-1-yl)propoxy, 2-(4-hydroxypiperdin-1-yl)ethoxy, 4-(4-hydroxypiperidin-1-yl)butoxy, 1-methylpiperidin-4-ylmethoxy, 3-(1-methylpiperidin-4-yl)propoxy, 3-(4-methoxypiperidin-1-yl)propoxy, 3-(4-methoxypiperidin-1-yl)ethoxy or 4-(4-methoxypiperidin-1-yl)butoxy and wherein any heterocyclyl group within a substituent on $R^1$ optionally bears 1 or 2 oxo substituents;

n is 0 or 1 and $R^3$ group, if present, is located at the 5-position of the 1,3-benzodioxol-yl group and is selected from fluoro, chloro, bromo, trifluoromethyl, cyano, hydroxy, methyl, ethyl, methoxy and ethoxy;

$Z^2$ is a C≡C or CH═CH group; and $R^{14}$ is selected from (1-6C)alkoxy-(1-6C)alkyl, di-[(1-6C)alkyl]amino-(1-6C)alkyl, hydroxyl-(1-6C)alkyl or from a group of formula:

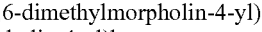
$(CH_2)_x$—N($R^c$)—C(O)—N$R^a R^b$ wherein x is 0, 1, 2 or 3, $R^c$ is hydrogen or (1-6C)alkyl and $R^a$ and $R^b$ are each independently selected from hydrogen and (1-6C)alkyl or $R^a$ and $R^b$ together with the nitrogen to which they are attached form morpholino, or from a group of the formula:

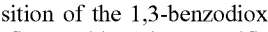
—$X^7$-$Q^5$ wherein $X^7$ is a direct bond and $Q^5$ is aryl, heteroaryl, heterocyclyl, heterocyclyl-(1-6C)alkyl, or heterocyclyloxy-(1-6C)alkyl, and wherein any CH, CH$_2$ or CH$_3$ group within a $R^{14}$ substituent optionally bears on each said CH, CH$_2$ or CH$_3$ group a substituent selected from (1-6C)alkoxy, carbamoyl, N-(1-6C)alkylcarbamoyl or a group of the formula:

—$X^8$-$Q^6$ wherein $X^8$ is a direct bond or O and $Q^6$ is (3-7C)cycloalkyl or heterocyclyl and wherein any heterocyclyl group within a substituent on $R^{14}$ optionally bears 1 oxo substituent;

or a pharmaceutically acceptable acid addition salt thereof.

A particular compound of the invention is a quinazoline derivative of the Formula I wherein Z is NH m is 2, and the first $R^1$ group is a 6-methoxy group and the second $R^1$ group is located at the 7-position and is selected from methoxy, 2-methoxyethoxy, isopropoxy, isopropylmethoxy, 3-dimethylaminopropoxy, dimethylaminoisopropoxy, 2-[3-(hydroxy)propylamino]ethoxy, 3-[bis(2-methoxyethyl) amino]propoxy, 2-(4-methylpiperazin-1-yl)ethoxy, 3-(3-oxo-4-methylpiperazin-1-yl)propoxy, 3-(2-oxo-4-methylpiperazin-1-yl)propoxy, 3-morpholinopropoxy, 2-morpholin-4-ylethoxy, 4-morpholin-4-ylbutoxy, 3-(2,6-dimethylmorpholin-4-yl)propoxy, 3-(1,1-dioxotetrahydro-4H-1,4-thiazin-4-yl)propoxy, 2-fluoroethoxy, 3-[4-(2-fluoroethyl)piperazin-1-yl]propoxy, 3-(4-acetylpiperazin-1-yl) propoxy, 3-(4-formylpiperazin-1-yl)propoxy, 3-piperazin-1-ylpropoxy, 3-(4-hydroxypiperidin-1-yl)propoxy, 3-[2-(hydroxymethyl)pyrrolidin-1-yl]propoxy, 2-(2-methoxyethoxy)ethoxy, 3-chloropropoxy, 2-(2-chloroethoxy)ethoxy, 1-methylpiperidin-4-ylmethoxy, 3-(4-methoxypiperidin-1-yl)propoxy or 3-(4-hydroxypiperidin-1-yl)propoxy, n is 1 and $R^3$ group, if present, is located at the 6 position of the 1,3-benzodioxol group and is selected from fluoro, chloro or bromo;

$Z^2$ is a C≡C or CH=CH group; and $R^{14}$ is selected from methoxymethyl, 1-methoxyethyl, 2-methoxyethyl, methoxyisopropyl, 2-methoxypropyl, ethoxymethyl, methoxyethoxymethyl, hydroxymethyl, carbamoylmethoxymethyl, methylcarbamoylmethoxymethyl, isopropoxymethyl, di-(methylamino)methyl, hydroxyisopropyl, (cyclopropylmethoxy)methyl, (cyclopentylmethoxy) methyl from a group of formula:

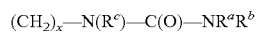

wherein x is 1, $R^c$ is hydrogen and $R^a$ and $R^b$ are each independently selected from hydrogen, and methyl or $R^a$ and $R^b$ together with the nitrogen to which they are attached form morpholino, or x is 1 and $R^a$, $R^b$ and $R^c$ are all methyl, or is selected from 2-oxo-pyrrolidin-1-ylmethyl, pyridin-2-yl, (tetrahydrofuran-3-ylmethoxy)methyl, (tetrahydrofuran-3-yloxy)methyl, [(1,3-dioxolan-2-yl)methoxy]methyl, phenyl, pyridin-3-yl, pyrazin-3-yl, pyrimidin-2-yl, 1H-pyrazol-4-yl or 1H-pyrazol-5-yl;

or a pharmaceutically acceptable acid addition salt thereof.

A further particular compound of the invention is a quinazoline derivative of formula I wherein Z is NH m is 2;

and the first $R^1$ group is a 6-methoxy group and the second $R^1$ group is located at the 7-position and is selected from 3-morpholino-4-ylpropoxy, 2-morpholin-4-ylethoxy, 4-morpholin-4-ylbutoxy, 3-(1,1-dioxotetrahydro-4H-1,4-thiazin-4-yl)propoxy, 3-(4-acetylpiperazin-1-yl)propoxy, 3-(4-methylpiperazin-1-yl)propoxy, 3-piperazin-1-ylpropoxy, 3-[4(2-fluoroethylpiperazin-1-yl)propoxy, 3-(3-oxopiperazin-1-yl)propoxy, 1-methylpiperidin-4-yl)methoxy, 3-(4-hydroxypiperidin-1-yl)propoxy or 3-[2-(hydroxymethyl)pyrrolidin-1-yl]propoxy;

n is 0 or 1 and $R^3$ group, if present, is located at the 5 position of the 1,3-benzodioxol group and is selected from fluoro or chloro;

$Z^2$ is a C≡C or CH=CH group; and $R^{14}$ is methoxymethyl;

or a pharmaceutically acceptable acid addition salt thereof.

A particular compound of the invention is a quinazoline derivative of the Formula I wherein Z is NH m is 2 and each $R^1$ group, which may be the same or different, is located at the 5- and 7-positions and $R^1$ is selected from methoxy, ethoxy, propoxy, isopropoxy, 2-methylpropoxy, or from a group of the formula:

wherein $X^1$ is O and $Q^1$ is 1-, 2-, or 3-pyrrolidinyl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, tetrahydro-2H-pyran-4-yl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, piperidin-4-ylmethyl, 3-piperidin-1-ylpropyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein any $CH_2$ or $CH_3$ group within a $R^1$ substituent optionally bears on each said $CH_2$ or $CH_3$ group one or more fluoro or chloro groups or a substituent selected from amino, methylamino, methoxy, dimethylamino, methoxyethylamino, di-(methoxyethyl)amino or hydroxypropylamino, and wherein any heterocyclyl group within a substituent on $R^1$ optionally bears 1, 2 or 3 substituents, which may be the same or different, selected from methyl, ethyl, methoxy, ethoxy, formyl, acetyl, hydroxyl, hydroxymethyl, fluoroethyl or hydroxypropylamino, and wherein any heterocyclyl group within a substituent on $R^1$ optionally bears 1 or 2 oxo substituents;

n is 0 or 1 and $R^3$ group, if present, is located at the 5 position of the 1,3-benzodioxol group and is selected from fluoro or chloro;

$Z^2$ is a C≡C or CH=CH group; and $R^{14}$ is selected from (1-6C)alkoxy-(1-6C)alkyl, di-[(1-6C)alkyl]amino-(1-6C)alkyl, hydroxyl-(1-6C)alkyl or from a group of formula:

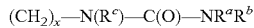

wherein x is 0, 1, 2 or 3, $R^c$ is hydrogen or (1-6C)alkyl and $R^a$ and $R^b$ are each independently selected from hydrogen and (1-6C)alkyl or $R^a$ and $R^b$ together with the nitrogen to which they are attached form morpholino, or from a group of the formula:

wherein $X^7$ is a direct bond and $Q^5$ is aryl, heteroaryl, heterocyclyl, heterocyclyl-(1-6C)alkyl, or heterocyclyloxy-(1-6C) alkyl, and wherein any CH, $CH_2$ or $CH_3$ group within a $R^{14}$ substituent optionally bears on each said CH, $CH_2$ or $CH_3$ group a substituent selected from (1-6C)alkoxy, carbamoyl, N-(1-6C)alkylcarbamoyl or a group of the formula:

—X$^8$-Q$^6$ wherein X$^8$ is a direct bond or O and Q$^6$ is (3-7C)cycloalkyl or heterocyclyl and wherein any heterocyclyl group within a substituent on R$^{14}$ optionally bears 1 oxo substituent;

or a pharmaceutically acceptable acid addition salt thereof.

A particular compound of the invention is a quinazoline derivative of the Formula I wherein Z is NH m is 2 and the first R$^1$ group is at the 5-position and is selected from isopropoxy, tetrahydro-2H-pyran-4-yloxy and the second R$^1$ group is at the 7-position and is selected from methoxy, 3-morpholin-4-ylpropoxy, 3-(4-acetylpiperazin-1-yl)propoxy, 3-(4-formylacetylpiperazin-1-yl)propoxy and 3-(3-oxo-4methyl-piperazin-1-yl)propyoxy n is 1 and R$^3$ group is located at the 5-position of the 1,3-benzodioxol-4-yl group and is chloro;

Z$^2$ is a C≡C or CH=CH group; and

R$^{14}$ is selected from methoxymethyl, 2-methoxyethyl, methoxyisopropyl and pyridin-2-yl, or a pharmaceutically acceptable acid addition salt thereof.

Particular compounds of the invention include, for example, the quinazoline derivatives of the Formula I described above hereinafter as examples 1, 2 and 3, namely 6-methoxy-N-[7-(3-methoxyprop-1-ynyl)-1,3-benzodioxol-4-yl]-7-(3-morpholin-4-ylpropoxy)quinazolin-4-amine, N-[5-chloro-7-(3-methoxyprop-1-ynyl)-1,3-benzodioxol-4-yl]-6-methoxy-7-(3-morpholin-4-ylpropoxy)quinazolin-4-amine and 6-methoxy-N-[5-chloro-7-(3-methoxyprop-1-ynyl)-1,3-benzodioxol-4yl]-7-[3-(4-methylpiperazin-1-yl)propoxy]quinazolin-4-amine and also include 6-methoxy-N-[5-fluoro-7-(3-methoxyprop-1-ynyl)-1,3-benzodioxol-4-yl]-7-[3-morpholin-4-ylpropoxy]quinazolin-4-amine, 6-methoxy-N-[5-fluoro-7-(3-methoxyprop-1-ynyl)-1,3-benzodioxol-4-yl]-7-[3-(1,1-dioxothiomorpholin-4-yl)propoxy]quinazolin-4-amine, 6-methoxy-N-[5-fluoro-7-(3-methoxyprop-1-ynyl)-1,3-benzodioxol-4-yl]-7-[3-(4-acetylpiperazin-1-yl)propoxy]quinazolin-4-amine.

Further particular compounds include N-[5-chloro-7-(4-methoxybut-1-yn-1-yl)-1,3-benzodioxol-4-yl]-6-methoxy-7-(3-morpholin-4-ylpropoxy)quinazolin-4-amine, N-[5-fluoro-7-(4-methoxybut-1-yn-1-yl)-1,3-benzodioxol-4-yl]-6-methoxy-7-(3-morpholin-4-ylpropoxy)quinazolin-4-amine, N-[5chloro-7-(3-ethoxyprop-1-yn-1-yl)-1,3-benzodioxol-4-yl]-6-methoxy-7-(3-morpholin-4-ylpropoxy)quinazolin-4-amine, N-{5-chloro-7-[3-(2-methoxyethoxy)prop-1-yn-1-yl]-1,3-benzodioxol-4-yl}-6-methoxy-7-(3-morpholin-4-ylpropoxy)quinazolin-4-amine, N-[5-Chloro-7-(3-isopropoxyprop-1-yn-1-yl)-1,3-benzodioxol-4-yl]-6-methoxy-7-(3-morpholin-4-ylpropoxy)quinazolin-4-amine, N-{5-chloro-7-[3-(cyclopropylmethoxy)prop-1-yn-1-yl]-1,3-benzodioxol-4-yl}-6-methoxy-7-(3-morpholin-4-ylpropoxy)quinazolin-4-amine, 7-[3-(4-acetylpiperazin-1-yl)propoxy]-N-[5-chloro-7-(4-methoxybut-1-yn-1-yl)-1,3-benzodioxol-4-yl]-6-methoxyquinazolin-4-amine, (1-{3-[(4-{[5-chloro-7-(4-methoxybut-1-yn-1-yl)-1,3-benzodioxol-4yl]amino}-6-methoxyquinazolin-7-yl)oxy]propyl}piperidin-4-yl)methanol, N-[3-(6-chloro-7-{[6-methoxy-7-(3-morpholin-4-ylpropoxy)quinazolin-4-yl]amino}-1,3-benzodioxol-4-yl)prop-2-yn-1-yl]morpholine-4-carboxamide, N'-[3-(6-chloro-7-{[6-methoxy-7-(3-morpholin-4-ylpropoxy)quinazolin-4-yl]amino}-1,3-benzodioxol-4-yl)prop-2-yn-1-yl]-N,N-dimethylurea, N-[3-(6-chloro-7-{[6-methoxy-7-(3-morpholin-4-ylpropoxy)quinazolin-4-yl]amino}-1,3-benzodioxol-4-yl)prop-2-yn-1-yl]-N'-methylurea, N-[5-chloro-7-(4-methoxybut-1-yn-1-yl)-1,3-benzodioxol-4-yl]-6-methoxy-7-[3-(4-methylpiperazin-1-yl)propoxy]quinazolin-4-amine, N-[5-chloro-7-(4-methoxybut-1-yn-1-yl)-1,3-benzodioxol-4-yl]-7-[3-(dimethylamino)propoxy]-6-methoxyquinazolin-4-amine, 7-{3-[bis(2-methoxyethyl)amino]propoxy}-N-[5-chloro-7-(4-methoxybut-1-yn-1-yl)-1,3-benzodioxol-4-yl]-6-methoxyquinazolin-4-amine, 4-{3-[(4-{[5-chloro-7-(4-methoxybut-1-yn-1-yl)-1,3-benzodioxol-4-yl]amino}-6-methoxyquinazolin-7-yl)oxy]propyl}piperazine-1-carbaldehyde, N-[5-chloro-7-(4-methoxybut-1-yn-1-yl)-1,3-benzodioxol-4-yl]-7-{3-[4-(2-fluoroethyl)piperazin-1-yl]propoxy}-6-methoxyquinazolin-4-amine, N-[5-chloro-7-(4-methoxybut-1-yn-1-yl)-1,3-benzodioxol-4-yl]-6-methoxy-7-[3-(4-methoxypiperidin-1-yl)propoxy]quinazolin-4-amine, N'-(3-{6-chloro-7-[(6,7-dimethoxyquinazolin-4-yl)amino]-1,3-benzodioxol-4-yl}prop-2-yn-1-yl)-N,N-dimethylurea, 4-{3-[(4-{[5-chloro-7-(4-methoxybut-1-yn-1-yl)-1,3-benzodioxol-4-yl]amino}-6-methoxyquinazolin-7-yl)oxy]propyl}-1-methylpiperazin-2-one, 1-[3-(6-chloro-7-{[6-methoxy-7-(3-morpholin-4-ylpropoxy)quinazolin-4-yl]amino}-1,3-benzodioxol-4-yl)prop-2-yn-1-yl]pyrrolidin-2-one, N-[3-(6-chloro-7-{[6-methoxy-7-(3-morpholin-4-ylpropoxy)quinazolin-4-yl]amino}-1,3-benzodioxol-4-yl)prop-2-yn-1-yl]-N,N',N'-trimethylurea, 4-{3-[(4-{[5-Chloro-7-(3-methoxyprop-1-yn-1-yl)-1,3-benzodioxol-4-yl]amino}-6-methoxyquinazolin-7-yl)oxy]propyl}-1-methylpiperazin-2-one, N-[5-Chloro-7-(3-methoxyprop-1-yn-1-yl)-1,3-benzodioxol-4-yl]-7-(3-chloropropoxy)-6-methoxyquinazolin-4-amine, N'-{3-[6-Chloro-7-({6-methoxy-7-[3-(4-methyl-3-oxopiperazin-1-yl)propoxy]quinazolin-4-yl}amino)-1,3-benzodioxol-4-yl]prop-2-yn-1-yl}-N,N-dimethylurea, 1-{3-[(4-{[5-Chloro-7-(3-methoxyprop-1-yn-1-yl)-1,3-benzodioxol-4-yl]amino}-6-methoxyquinazolin-7-yl)oxy]propyl}-4-methylpiperazin-2-one, 1-{3-[(4-{[5-Chloro-7-(4-methoxybut-1-yn-1-yl)-1,3-benzodioxol-4-yl]amino}-6-methoxyquinazolin-7-yl)oxy]propyl}-4-methylpiperazin-2-one, N'-{3-[6-Chloro-7-({6-methoxy-7-[3-(4-methyl-2-oxopiperazin-1-yl)propoxy]quinazolin-4-yl}amino)-1,3-benzodioxol-4-yl]prop-2-yn-1-yl}-N,N-dimethylurea, N-[5-Chloro-7-(4-methoxypent-1-yn-1-yl)-1,3-benzodioxol-4-yl]-6-methoxy-7-(3-morpholin-4-ylpropoxy)quinazolin-4-amine, 4-{3-[(4-{[5-Chloro-7-(4-methoxypent-1-yn-1-yl)-1,3-benzodioxol-4-yl)amino}-6-methoxyquinazolin-7-yl)oxy]propyl}-1-methylpiperazin-2-one, 1-{3-[(4-{[5-Chloro-7-(pyridin-2-ylethynyl)-1,3-benzodioxol-4-yl]amino}-6-methoxyquinazolin-7-yl)oxy]propyl}-4-methylpiperazin-2-one, N'-{3-[6-Chloro-7-({7-[3-(cis-2,6-dimethylmorpholin-4-yl)propoxy]-6-methoxyquinazolin-4-yl}amino)-1,3-benzodioxol-4-yl]prop-2-yn-1-yl}-N,N-dimethylurea, N-[5-chloro-7-(3-methoxyprop-1-yn-1-yl)-1,3-benzodioxol-4-yl]-6-methoxy-7-[(1-methylpiperdin-4-yl)methoxy]quinazolin-4-amine, N-[5-chloro-7-(3-methoxyprop-1-yn-1-yl)-1,3-benzodioxol-4-yl]-6-methoxy-7-(2-morpholin-4-ylethoxy)quinazolin-4-amine, N-[5-chloro-7-(3-methoxyprop-1-yn-1-yl)-1,3-benzodioxol-4-yl]-7-ethoxy-6-methoxyquinazolin-4-amine, N-[5-chloro-7-(3-methoxyprop-1-yn-1-yl)-1,3-benzodioxol-4-yl]-7-isopropoxy-6-methoxyquinazolin-4-amine, N-[5-chloro-7-(3-methoxyprop-1-yn-1-yl)-1,3-benzodioxol-4-yl]-7-(2-methoxyethoxy)-6-methoxyquinazolin-4-amine, N-[5-chloro-7-(3-methoxyprop-1-yn-1-yl)-1,3-benzodioxol-4-yl]-7-(2-methylpropoxy)-6-methoxyquinazolin-4-amine, N-[5-chloro-7-(3-methoxyprop-1-yn-1-yl)-1,3-benzodioxol-4-yl]-6-methoxy-7-(4-morpholin-4-ylbutoxy)quinazolin-4-amine, 7-[4-(4-acetylpiperazin-1-yl)butoxy]-N-[5-chloro-7-(3-methoxyprop-1-yn-1-yl)-1,3-benzodioxol-4-yl]-6-methoxyquinazolin-4-amine N-[5-chloro-7-(3-methoxyprop-1-yn-1-yl)-1,3-benzodioxol-4-yl]-7-{3-(cis-2,6-dimethylmorpholin-4-yl)propoxy}-6-methoxyquinazolin-4-amine, 3-({2-[(4-{[5-chloro-7-(3-methoxyprop-1-yn-1-yl)-1,3-benzodioxol-4-yl]amino}-6-methoxyquinazolin-7-yl)oxy]ethyl}amino)propan-1-ol, N-[5-chloro-7-(3-methoxyprop-1-yn-1-yl)-1,3-benzodioxol-4-yl]-6-methoxy- 7-[2-(4-methylpiperazin-1-yl)ethoxy]quinazolin-4-amine, N-[5-chloro-7-(3-methoxyprop-1-yn-1-yl)-1,3-benzodioxol-4-yl]-6,7-dimethoxyquinazolin-4-amine, 3-(6-chloro-7-{[6-methoxy-7-(3-morpholin-4-ylpropoxy)quinazolin-4-yl]amino}-1,3-benzodioxol-4-yl)prop-2-yn-1-ol, N-[5-chloro-7-(phenylethynyl)-1,3-benzodioxol-4-yl]-6-methoxy-7-(3-morpholin-4-ylpropoxy)quinazolin-4-amine, N-[5-chloro-7-(pyridin-2-ylethynyl)-1,3-benzodioxol-4-yl]-6-methoxy-7-(3-morpholin-4-ylpropoxy)quinazolin-4-amine, N-{5-chloro-7-[3-(cyclopentylmethoxy)prop-1-yn-1-yl]-1,3-benzodioxol-4-yl}-6-methoxy-7-(3-morpholin-4-ylpropoxy)quinazolin-4-amine, N-[5-chloro-7-[(tetrahydrofuran-3-yloxy)methyl]-1,3-benzodioxol-4-yl]-6-methoxy-7-(3-morpholin-4-ylpropoxy)quinazolin-4-amine, N-[5-chloro-7-[(tetrahydrofuran-3-ylmethoxy)methyl]-1,3-benzodioxol-4-yl]-6-methoxy-7-(3-morpholin-4-ylpropoxy)quinazolin-4-amine, N-[5-chloro-7-{[(1,3-dioxolan-2-yl)methoxy]methyl}-1,3-benzodioxol-4-yl]-6-methoxy-7-(3-morpholin-4-ylpropoxy)quinazolin-4-amine, N-{5-chloro-7-[3-dimethylaminoprop-1-yn-1-yl]-1,3-benzodioxol-4-yl}-6-methoxy-7-(3-morpholin-4-ylpropoxy)quinazolin-4-amine, N-[5chloro-7-(pyridin-3-ylethynyl)-1,3-benzodioxol-4-yl]-6-methoxy-7-(3-morpholin-4-ylpropoxy)quinazolin-4-amine, N-[5-chloro-7-(pyrazin-2-ylethynyl)-1,3-benzodioxol-4-yl]-6-methoxy-7-(3-morpholin-4-ylpropoxy)quinazolin-4-amine, N-[5-chloro-7-(pyrimidin-2-ylethynyl)-1,3-benzodioxol-4-yl]-6-methoxy-7-(3-morpholin-4-ylpropoxy)quinazolin-4-amine, N-[5-chloro-7-(1H-pyrazol-4-ylethynyl)-1,3-benzodioxol-4-yl]-6-methoxy-7-(3-morpholin-4-ylpropoxy)quinazolin-4-amine, N-[5-chloro-7-(pyridin-2-ylethynyl)-1,3-benzodioxol-4-yl]-7-[3-(cis-2,6dimethylmorpholin-4-yl]propoxy)]-6-methoxyquinazolin-4-amine, N-(5-chloro-7-(pyridin-2-ylethynyl)-1,3-benzodioxol-4-yl)-6,7-dimethoxyquinazolin-4-amine, 4-{3-[(4-{[5-Chloro-7-(3-isopropoxyprop-1-yn-1-yl)-1,3-benzodioxol-4-yl]amino}-6-methoxyquinazolin-7-yl)oxy]propyl}-1-methylpiperazin-2-one, N-[5-chloro-7-(1H-pyrazol-5-ylethynyl)-1,3-benzodioxol-4-yl]-6-methoxy-7-(3-morpholin-4-ylpropoxy)quinazolin-4-amine, 4-{3-[(4-{[5-chloro-7-(pyridin-2-ylethynyl)-1,3-benzodioxol-4-yl]amino}-6-methoxyquinazolin-7-yl)oxy]propyl}-1-methylpiperazin-2-one, 4-{6-chloro-7-[(6,7-dimethoxyquinazolin-4-yl)amino]-1,3-benzodioxol-4-yl}-2-methylbut-3-yn-2-ol, 2-[(3-{6-chloro-7-[(6,7-dimethoxyquinazolin-4-yl)amino]-1,3-benzodioxol-4-yl}prop-2-yn-1-yl)oxy]-N-methylacetamide, 2-[(3-{6-chloro-7-[(6,7-dimethoxyquinazolin-4-yl)amino]-1,3-benzodioxol-4-yl}prop-2-yn-1-yl)oxy]-N,N-dimethylacetamide, N-[5-chloro-7-(3-methoxybut-1-yn-1-yl)-1,3-benzodioxol-4-yl]-6,7-dimethoxyquinazolin-4-amine, N-[5-chloro-7-(3-methoxybut-1-yn-1-yl)-1,3-benzodioxol-4-yl]-6-methoxy-7-(3-morpholin-4-ylpropoxy)quinazolin-4-amine, N-[5-bromo-7-(3-methoxyprop-1-yn-1-yl)-1,3-benzodioxol-4-yl]-6-methoxy-7-(3-morpholin-4-ylpropoxy)quinazolin-4-amine. N-[5-chloro-7-(3-methoxyprop-1-yn-1-yl)-1,3-benzodioxol-4-yl]-7-[3-(dimethylamino)propoxy]-6-methoxyquinazolin-4-amine, 4-{3-[(4-{[5-chloro-7-(3-methoxybut-1-yn-1-yl)-1,3-benzodioxol-4-yl]amino}-6-methoxyquinazolin-7-yl)oxy]propyl}-1-methylpiperazin-2-one, N-[5-bromo-7-(3-methoxybut-1-yn-1-yl)-1,3-benzodioxol-4-yl]-6-methoxy-7-(3-morpholin-4-ylpropoxy)quinazolin-4-amine and 4{3-[(4-{[5-bromo-7-(3-methoxyprop-1-yn-1-yl)-1,3-benzodioxol-4-yl) amino}-6-methoxyquinazolin-7-yl)oxy]propyl}-1-methylpiperazin-2-one.

A quinazoline derivative of the Formula I, or a pharmaceutically-acceptable salt thereof, may be prepared by any process known to be applicable to the preparation of chemically-related compounds. Such processes, when used to prepare a quinazoline derivative of the Formula I are provided as a further feature of the invention and are illustrated by the following representative process variants in which, unless otherwise stated, m, $R^1$, Z, n, $R^3$, $Z^2$ and $R^{14}$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) For the production of those compounds of the Formula I wherein Z is an O, S or $N(R^2)$ group, the reaction of a quinazoline of the Formula II

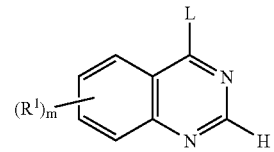

wherein L is a displaceable group and m and $R^1$ have any of the meanings defined hereinbefore except that any functional group is protected if necessary, with a compound of the Formula III

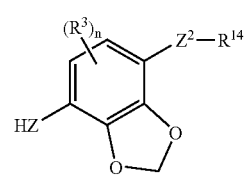

wherein Z is O, S, or $N(R^2)$ and n, $R^3$, $R^2$, $Z^2$ and $R^{14}$ have any of the meanings defined hereinbefore except that any functional group is protected if necessary, whereafter any protecting group that is present is removed by conventional means.

The reaction may conveniently be carried out in the presence of a suitable acid or in the presence of a suitable base. A suitable acid is, for example, an inorganic acid such as, for example, hydrogen chloride or hydrogen bromide. A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal amide, for example sodium hexamethyldisilazane or sodium bis(trimethylsilyl)amide or, for example, an alkali metal hydride, for example sodium hydride.

A suitable displaceable group L is, for example, a halogeno, alkoxy, aryloxy or sulphonyloxy group, for example a chloro, bromo, methoxy, phenoxy, pentafluorophenoxy, methanesulphonyloxy or toluene-4-sulphonyloxy group. The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 0 to 250° C., preferably in the range 0 to 120° C.

Typically, the quinazoline of the Formula II may be reacted with a compound of the Formula III in the presence of an aprotic solvent such as N,N-dimethylacetamide conveniently in the presence of a base, for example potassium carbonate, sodium hexamethyldisilazane, sodium bis(trimethylsilyl)amide and at a temperature in the range, for example, 0 to 150° C., preferably in the range, for example, 0 to 70° C.

The quinazoline derivative of the Formula I may be obtained from this process in the form of the free base or alternatively it may be obtained in the form of a salt with the acid of the formula H-L wherein L has the meaning defined hereinbefore. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, 2$^{nd}$ Edition, by T. Green et al., also published by John Wiley & Son, for general guidance on protecting groups.

Quinazoline starting materials of the Formula II may be obtained by conventional procedures such as those disclosed in International Patent Applications WO 98/13354. For example, a 3,4-dihydroquinazolin-4-one of Formula IV,

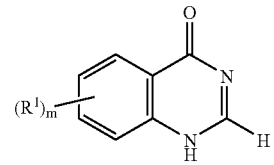

IV wherein m and $R^1$ have any of the meanings defined hereinbefore except that any functional group is protected if necessary, may be reacted with a halogenating agent such as thionyl chloride, phosphoryl chloride or a mixture of carbon tetrachloride and triphenylphosphine whereafter any protecting group that is present is removed by conventional means.

The 4-chloroquinazoline so obtained may be converted, if required, into a 4-(4-chloro-2-fluorophenoxy)quinazoline by reaction with 4-chloro-2-fluorophenol in the presence of a suitable base such as potassium carbonate and in the presence of a suitable solvent such as N,N-dimethylformamide.

1,3-Benzodiaxol-4-amine starting materials (Formula III, for example when Z is NH) may be obtained by conventional procedures as illustrated in the Examples. Corresponding (Formula III, when Z is O or S) may be obtained by conventional procedures.

(b) For the production of those compounds of the Formula I wherein at least one $R^1$ group is a group of the formula $Q^1-X^1-$ wherein $Q^1$ is an aryl-(1-6C)alkyl, (3-7C)cycloalkyl-(1-6C)alkyl, (3-7C)cycloalkenyl-(1-6C)alkyl, heteroaryl-(1-6C)alkyl or heterocyclyl-(1-6C)alkyl group or an optionally substituted alkyl group and $X^1$ is an oxygen atom, the coupling, conveniently in the presence of a suitable dehydrating agent, of a quinazoline of the Formula V

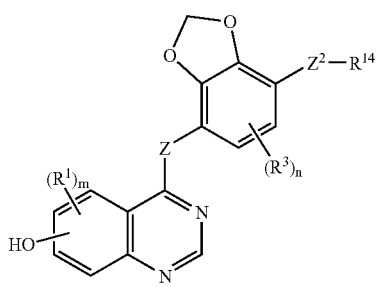

wherein m, $R^1$, Z, n, $R^3$, $Z^2$ and $R^{14}$ have any of the meanings defined hereinbefore except that any functional group is protected if necessary, with an appropriate alcohol of the formula $Q^1$-OH wherein any functional group is protected if necessary, whereafter any protecting group that is present is removed by conventional means.

A suitable dehydrating agent is, for example, a carbodiimide reagent such as dicyclohexylcarbodiimide or 1-(3-dimethylaminopropyl)-3-ethylcarbodiimide or a mixture of an azo compound such as diethyl or di-tert-butyl azodicarboxylate and a phosphine such as triphenylphosphine. The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

(c) For the production of those compounds of the Formula I wherein $R^1$ is an amino-substituted (1-6C)alkoxy group (such as 2-homopiperidin-1-ylethoxy or 3-dimethylaminopropoxy), the reaction of a compound of the Formula I wherein $R^1$ is a halogeno-substituted (1-6C)alkoxy group with a heterocyclyl compound or an appropriate amine.

The reaction is conveniently carried out in the presence of a suitable inert diluent or carrier as defined hereinbefore, for example 2-methoxyethanol, and at a temperature in the range 10 to 150° C., preferably at or near ambient temperature.

(d) For the production of those compounds of the Formula I wherein an $R^1$ group contains a (1-6C)alkoxy or substituted (1-6C)alkoxy group or a (1-6C)alkylamino or substituted (1-6C)alkylamino group, the alkylation, conveniently in the presence of a suitable base as defined hereinbefore, of a quinazoline derivative of the Formula I wherein the $R^1$ group contains a hydroxy group or a primary or secondary amino group as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1-6C)alkyl chloride, bromide or iodide or a substituted (1-6C)alkyl chloride, bromide or iodide, conveniently in the presence of a suitable base as defined hereinbefore, in a suitable inert solvent or diluent as defined hereinbefore and at a temperature in the range, for example, 10 to 140° C., conveniently at or near ambient temperature.

Conveniently for the production of those compounds of the Formula I wherein $R^1$ contains a (1-6C)alkylamino or substituted (1-6C)alkylamino group, a reductive amination reaction may be employed. For example, for the production of those compounds of the Formula I wherein $R^1$ contains a N-methyl group, the corresponding compound containing a N—H group may be reacted with formaldehyde in the presence of a suitable reducing agent. A suitable reducing agent is, for example, a hydride reducing agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. The reaction is performed at a temperature in the range, for example, 10 to 80° C., conveniently at or near ambient temperature.

(e) For the production of those compounds of the Formula I wherein Z is a SO or $SO_2$ group, wherein an $R^1$ or $R^3$ substituent is a (1-6C)alkylsulphinyl or (1-6C)alkylsulphonyl group or wherein an $R^1$, $R^3$ or $R^{14}$ substituent contains a SO or $SO_2$ group, the oxidation of a compound of Formula I wherein Z is a S group or wherein an $R^1$ or $R^3$ substituent is a (1-6C)alkylthio group or wherein an $R^1 R^3$ or $R^{14}$ substituent contains a S group as appropriate.

Conventional oxidation reagents and reaction conditions for such partial or complete oxidation of a sulphur atom are well known to the organic chemist.

(f) The reaction, conveniently in the presence of a suitable base as defined hereinbefore and in the presence of a suitable catalyst, of a compound of the Formula VI

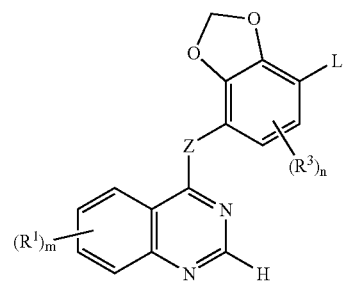

wherein L is a displaceable group as defined hereinbefore and m, $R^1$, Z, n and $R^3$ have any of the meanings defined hereinbefore except that any functional group is protected if necessary, with a compound of the Formula VII $$HZ^2\text{-}R^{14} \qquad \text{VII}$$

wherein $Z^2$ is a C≡C or $C(R^{13})$=$C(R^{13})$ group and $R^{13}$ and $R^{14}$ have any of the meanings defined hereinbefore except that any functional group is protected if necessary, whereafter any protecting group that is present is removed by conventional means.

Conveniently the displaceable group is a halogeno group such as iodo, bromo or chloro. A suitable catalyst is, for example, an organometallic reagent, for example an organopalladium compound such as tetrakis(triphenylphosphine)palladium(0) or bis(triphenylphosphine)palladium(II) dichloride. The conversion reaction is conveniently carried out in the presence of a suitable inert diluent or carrier as defined hereinbefore and at a temperature in the range –30 to +120° C., depending on the substrate.

(g) For the production of a compound of the Formula I wherein $R^{14}$ is a carboxy group, the cleavage of a compound of the Formula I wherein $R^{14}$ is a (1-6C)alkoxycarbonyl group.

The cleavage reaction is conveniently carried out by the hydrolysis of the (1-6C)alkoxycarbonyl group in the presence of a suitable base, for example an alkali or alkaline earth metal carbonate or hydroxide such as sodium carbonate, potassium carbonate, calcium carbonate, sodium hydroxide or potassium hydroxide and in the presence of a suitable inert diluent or carrier as defined hereinbefore such as methanol and at a temperature in the range 10 to 150° C., preferably at or near 40° C.

(h) The reaction, conveniently in the presence of a suitable dehydrating agent as defined hereinbefore, of a compound of the Formula I wherein $R^{14}$ is a carboxy group with an appropriate amine to form a further compound of the Formula I wherein $R^{14}$ is a carbamoyl, N-(1-6C)alkylcarbamoyl, N,N-di-[(1-6C)alkyl]carbamoyl or heterocyclylcarbonylamino group.

The reaction is conveniently carried out in the presence of a suitable inert diluent or carrier as defined hereinbefore and at a temperature in the range, for example, 10 to 150° C., preferably at or near ambient temperature. (i) A coupling reaction, conveniently in the presence of a suitable base such as diisopropylamine, of a compound of the Formula VIII

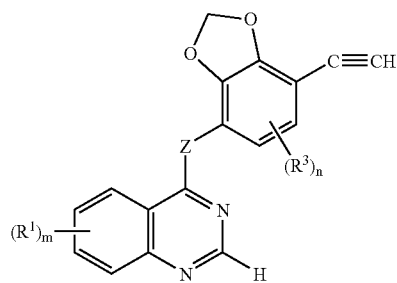

VIII wherein m, $R^1$, Z, n and $R^3$ have any of the meanings defined hereinbefore except that any functional group is protected if necessary, with a compound of the Formula IX

L-$R^{14}$    IX wherein L is a displaceable group, particularly a halogeno group for example iodo, and $R^{14}$ has any of the meanings defined hereinbefore except that any functional group is protected if necessary, whereafter any protecting group that is present is removed by conventional means.

The reaction is conveniently carried out under a nitrogen atmosphere in the presence of a suitable solvent, such as ethyl acetate, and a catalyst such as bis(triphenylphosphine) palladium(I)chloride and copper(I)iodide at a temperature in the range of, for example, 0 to –30° C.

When a pharmaceutically-acceptable salt of a quinazoline derivative of the Formula I is required, for example an acid-addition salt, it may be obtained by, for example, reaction of said quinazoline derivative with a suitable acid using a conventional procedure.

Biological Assays

The following assays can be used to measure the effects of the compounds as inhibitors of the MAPK pathway.

(a) Assay to Detect MEK Inhibition

To evaluate inhibitors of the MAPK pathway, a coupled assay was carried out which measures phosphorylation of serine/threonine residues present in the substrate in the presence or absence of inhibitor. Recombinant glutathione S-transferase fusion protein containing human p45MEK1 (GST-MEK) was activated by c-raf (Sf9 insect cell lysate from triple baculoviral infection with c-raf/ras/lck) and used for the assay. Active GST-MEK was first used to activate a recombinant glutathione S-transferase fusion protein containing p44MAP kinase (GST-MAPK) in the presence of ATP and $Mg^{2+}$ for 60 minutes at room temperature in the presence or absence of potential inhibitors. The activated GST-MAPK was then incubated with myelin basic protein (MBP) as substrate for 10 minutes at room temperature in the presence of ATP, $Mg^{2+}$ and $^{33}$P-ATP. The reaction was stopped by addition of 20% v/v phosphoric acid. Incorporation of $^{33}$P into the myelin basic protein was determined by capture of the substrate on a filter mat, washing and counting using scintillation methods. The extent of inhibition was determined by comparison with untreated controls.

The final assay solution contained 10 mM Tris, pH 7.5, 0.05 mM EGTA, 8.33 µm [$\gamma^{33}$P]ATP, 8.33 mM $Mg(OAc)_2$, 0.5 mM sodium orthovanadate, 0.05% w/v BSA, 6.5 ng GST-MEK, 1 µg GST-MAPK and 16.5 µg MBP in a reaction volume of 60 µl.

(b) In Vitro MAP Kinase Assay

To determine whether compounds were inhibiting GST-MEK or GST-MAPK, a direct assay of MAPK activity was employed. GST-MAPK was activated by a constitutively active GST-MEK fusion protein containing two point mutations (S217E, S221E) and used for the assay in the presence and absence of potential inhibitors. The activated GST-MAPK was incubated with substrate (MBP) for 60 min at room temperature in the presence of ATP, $Mg^{2+}$ and $^{33}$P-ATP. The reaction was stopped by addition of 20% v/v phosphoric acid. Incorporation of $^{33}$P into the myelin basic protein was determined by capture of the substrate on a filter mat, washing and counting using scintillation methods.

The final assay solution contained 12 mM Tris, pH 7.5, 0.06 mM EGTA, 30 µM [$\gamma^{33}$P]ATP, 10 mM $Mg(OAc)_2$, 0.6 mM sodium orthovanadate, 0.06% w/v BSA, 28 ng GST-MAPK and 16.5 µg MBP in a reaction volume of 60 µl.

(c) Cell Proliferation Assays

Cells were seeded into multi-well plates at 20,000-40,000 cells/ml in growth medium containing 5% FCS and incubated overnight at 37° C. The compounds were prepared in fresh medium at an appropriate concentration and added to the wells containing the cells. These were then incubated for a further 72 hours. Cells were then either removed from the wells by incubating with trypsin/EDTA and counted using a Coulter counter, or treated with XTT/PMS in PBSA and optical densities read at 450 nm.

The following assays can be used to measure the effects of the compounds of the present invention as c-Src tyrosine kinase inhibitors, as inhibitors in vitro of the proliferation of c-Src transfected fibroblast cells, as inhibitors in vitro of the migration of A549 human lung tumour cells and as inhibitors in vivo of the growth in nude mice of xenografts of A549 tissue.

(d) In Vitro Src Enzyme Assay

The ability of test compounds to inhibit the phosphorylation of a tyrosine containing polypeptide substrate by the enzyme c-Src kinase was assessed using a conventional Elisa assay.

A substrate solution [100 µl of a 20 µg/ml solution of the polyamino acid Poly(Glu, Tyr) 4:1 (Sigma Catalogue No. P0275) in phosphate buffered saline (PBS) containing 0.2 mg/ml of sodium azide] was added to each well of a number of Nunc 96-well immunoplates (Catalogue No. 439454) and the plates were sealed and stored at 4° C. for 16 hours. The excess of substrate solution was discarded, and aliquots of Bovine Serum Albumin (BSA; 150 µl of a 5% solution in PBS) were transferred into each substrate-coated assay well and incubated for 1 hour at ambient temperature to block non specific binding. The assay plate wells were washed in turn with PBS containing 0.05% v/v Tween 20 (PBST) and with Hepes pH7.4 buffer (50 mM, 300 µl/well) before being blotted dry.

Each test compound was dissolved in dimethyl sulphoxide and diluted with distilled water to give a series of dilutions (from 100 µM to 0.001 µM). Portions (25 µl) of each dilution of test compound were transferred to wells in the washed assay plates. "Total" control wells contained diluted DMSO instead of compound. Aliquots (25 µl) of an aqueous magnesium chloride solution (80 mM) containing adenosine-5'-triphosphate (ATP; 40 µM) was added to all test wells except the "blank" control wells which contained magnesium chloride without ATP.

Active human c-Src kinase (recombinant enzyme expressed in Sf9 insect cells; obtained from Upstate Biotechnology Inc. product 14-117) was diluted immediately prior to use by a factor of 1:10,000 with an enzyme diluent which comprised 100 mM Hepes pH7.4 buffer, 0.2 mM sodium orthovanadate, 2 mM dithiothreitol and 0.02% BSA. To start the reactions, aliquots (50 µl) of freshly diluted enzyme were added to each well and the plates were incubated at ambient temperature for 20 minutes. The supernatant liquid in each well was discarded and the wells were washed twice with PBST. Mouse IgG anti-phosphotyrosine antibody (Upstate Biotechnology Inc. product 05-321; 100 µl) was diluted by a factor of 1:6000 with PBST containing 0.5% w/v BSA and added to each well. The plates were incubated for 1 hour at ambient temperature. The supernatant liquid was discarded and each well was washed with PBST (×4). Horse radish peroxidase (HRP)-linked sheep anti-mouse Ig antibody (Amersham Catalogue No. NXA 931; 100 µl) was diluted by a factor of 1:500 with PBST containing 0.5% w/v BSA and added to each well. The plates were incubated for 1 hour at ambient temperature. The supernatant liquid was discarded and the wells were washed with PBST (×4).

A PCSB capsule (Sigma Catalogue No. P4922) was dissolved in distilled water (100 ml) to provide phosphate-citrate pH5 buffer (50 mM) containing 0.03% sodium perborate. An aliquot (50 ml) of this buffer was mixed with a 50 mg tablet of 2,2'-azinobis(3-ethylbenzothiazoline-6-sulphonic acid) (ABTS; Boehringer Catalogue No. 1204 521). Aliquots (100 µl) of the resultant solution were added to each well. The plates were incubated for 20 to 60 minutes at ambient temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibition of enzyme activity.

(e) In Vitro c-Src Transfected NIH 3T3 (c-src 3T3) Fibroblast Proliferation Assay This assay determined the ability of a test compound to inhibit the proliferation of National Institute of Health (NIH) mouse 3T3 fibroblast cells that had been stably-transfected with an activating mutant (Y530F) of human c-Src.

Using a similar procedure to that described by Shalloway et al., *Cell*, 1987, 49, 65-73, NIH 3T3 cells were transfected with an activating mutant (Y530F) of human c-Src. The resultant c-Src 3T3 cells were typically seeded at $1.5 \times 10^4$ cells per well into 96-well tissue-culture-treated clear assay plates (Costar) each containing an assay medium comprising Dulbecco's modified Eagle's medium (DMEM; Sigma) plus 0.5% foetal calf serum (FCS), 2 mM glutamine, 100 units/ml penicillin and 0.1 mg/ml streptomycin in 0.9% aqueous sodium chloride solution. The plates were incubated overnight at 37° C. in a humidified (7.5% $CO_2$: 95% air) incubator.

Test compounds were solubilised in DMSO to form a 10 mM stock solution. Aliquots of the stock solution were diluted with the DMEM medium described above and added to appropriate wells. Serial dilutions were made to give a range of test concentrations. Control wells to which test compound was not added were included on each plate. The plates were incubated overnight at 37° C. in a humidified (7.5%. $CO_2$: 95% air) incubator.

BrdU labelling reagent (Boehringer Mannheim Catalogue No. 647 229) was diluted by a factor of 1:100 in DMEM medium containing 0.5% FCS and aliquots (20 µl) were added to each well to give a final concentration of 10 µM.) The plates were incubated at 37° C. for 2 hours. The medium was decanted. A denaturating solution (FixDenat solution, Boehringer Mannheim Catalogue No. 647 229; 50 µl) was added to each well and the plates were placed on a plate shaker at ambient temperature for 45 minutes. The supernatant was decanted and the wells were washed with PBS (200 µl per well). Anti-BrdU-Peroxidase solution (Boehringer Mannheim Catalogue No. 647 229) was diluted by a factor of 1:100 in PBS containing 1% BSA and 0.025% dried skimmed milk (Marvel (registered trade mark), Premier Beverages, Stafford, GB) and an aliquot (100 µl) of the resultant solution was added to each well. The plates were placed on a plate shaker at ambient temperature for 90 minutes. The wells were washed with PBS (×5) to ensure removal of non-bound antibody conjugate. The plates were blotted dry and tetramethylbenzidine substrate solution (Boehringer Mannheim Catalogue No. 647 229; 100 µl) was added to each well. The plates were gently agitated on a plate shaker while the colour developed during a 10 to 20 minute period. The absorbance of the wells was measured at 690 nm. The extent of inhibition of cellular proliferation at a range of concentrations of each test compound was determined and an anti-proliferative $IC_{50}$ value was derived.

(f) In Vitro Microdroplet Migration Assay

This assay determines the ability of a test compound to inhibit the migration of adherent mammalian cell lines, for example the human tumour cell line A549.

RPMI medium(Sigma) containing 10% FCS, 1% L-glutamine and 0.3% agarose (Difco Catalogue No. 0142-01) was warmed to 37° C. in a water bath. A stock 2% aqueous agar solution was autoclaved and stored at 42° C. An aliquot (1.5 ml) of the agar solution was added to RPMI medium (10 ml) immediately prior to its use. A549 cells (Accession No. ATCC CCL185) were suspended at a concentration of $2 \times 10^7$ cells/ml in the medium and maintained at a temperature of 37° C.

A droplet (2 µl) of the cell/agarose mixture was transferred by pipette into the centre of each well of a number of 96-well, flat bottomed non-tissue-culture-treated microtitre plate (Bibby Sterilin Catalogue No. 642000). The plates were placed briefly on ice to speed the gelling of the agarose-containing droplets. Aliquots (90 µl) of medium which had been cooled to 4° C. were transferred into each well, taking care not to disturb the microdroplets. Test compounds were diluted from a 10 mM stock solution in DMSO using RPMI medium as described above. Aliquots (10 µl) of the diluted test compounds were transferred to the wells, again taking care not to disturb the microdroplets. The plates were incubated at 37° C. in a humidified (7.5% $CO_2$: 95% air) incubator for about 48 hours.

Migration was assessed visually and the distance of migration was measured back to the edge of the agar droplet. A migratory inhibitory $IC_{50}$ was derived by plotting the mean migration measurement against test compound concentration.

(g) In Vivo A549 Xenograft Growth Assay

This test measures the ability of compounds to inhibit the growth of the A549 human carcinoma grown as a tumour in athymic nude mice (Alderley Park nu/nu strain). A total of about $5 \times 10^6$ A549 cells in matrigel (Beckton Dickinson Catalogue No. 40234) were injected subcutaneously into the left flank of each test mouse and the resultant tumours were allowed to grow for about 14 days. Tumour size was measured twice weekly using callipers and a theoretical volume was calculated. Animals were selected to provide control and treatment groups of approximately equal average tumour volume. Test compounds were prepared as a ball-milled suspension in 1% polysorbate vehicle and dosed orally once daily for a period of about 28 days. The effect on tumour growth was assessed.

Although the pharmacological properties of the compounds of the Formula I vary with structural change as expected, in general activity possessed by compounds of the Formula I, may be demonstrated at the following concentrations or doses in one or more of the above tests (a) to (g):

| | |
|---|---|
| Test (a):- | $IC_{50}$ in the range, for example, less than 4 µM; |
| Test (b):- | activity was observed in this screen; |
| Test (c):- | $IC_{50}$ in the range, for example, less than 30 µM. |
| Test (d):- | $IC_{50}$ in the range, for example, 0.001-10 µM; |
| Test (d):- | $IC_{50}$ in the range, for example, 0.01-20 µM; |
| Test (f):- | activity in the range, for example, 0.1-25 µM; |

Test (g): activity in the range, for example, 1-200 mg/kg/day;

No physiologically-unacceptable toxicity was observed in Test (g) at the effective dose for compounds tested of the present invention. Accordingly no untoward toxicological effects are expected when a compound of Formula I, or a pharmaceutically-acceptable salt thereof, as defined hereinbefore is administered at the dosage ranges defined hereinafter.

According to a further aspect of the invention there is provided a pharmaceutical composition which comprises a quinazoline derivative of the Formula I, or a pharmaceutically-acceptable salt thereof, as defined hereinbefore in association with, a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

According to a further aspect of the invention there is provided a quinazoline derivative of the Formula I, or a pharmaceutically-acceptable salt thereof, as defined hereinbefore for use in a method of treatment of the human or animal body by therapy.

According to a further aspect of the invention there is provided a quinazoline derivative of the Formula I or a pharmaceutically acceptable salt thereof, as defined hereinbefore for use in the treatment of cancer.

As stated above we have found that the quinazoline derivatives of the present invention of Formula I possess potent anti-tumour activity which it is believed is obtained by way of inhibition of one or more of the MEK enzymes that are involved in the MAPK pathway.

Accordingly, the quinazoline derivatives of Formula I are of value as anti-proliferative agents in the containment and/or treatment of solid tumour disease. Particularly, the compounds of Formula I are expected to be useful in the prevention or treatment of those tumours which are sensitive to inhibition of one or more of the MEK enzymes that are involved in the MAPK pathway. Further, the compounds of Formula I are expected to be useful in the prevention or treatment of those tumours which are mediated alone or in part by inhibition of the MEK enzymes i.e. the compounds may be used to produce a MEK enzyme inhibitory effect in a warm-blooded animal in need of such treatment. Specifically, the compounds of Formula I are expected to be useful in the prevention or treatment of solid tumour disease.

Thus, according to this aspect of the invention there is provided of a quinazoline derivative of the Formula I, or a pharmaceutically-acceptable salt thereof, as defined hereinbefore for use as an anti-proliferative agent in the containment and/or treatment of solid tumour disease.

According to a further aspect of the invention there is provided the use of a quinazoline derivative of the Formula I, or a pharmaceutically-acceptable salt thereof, as defined hereinbefore in the manufacture of a medicament for use as an anti-proliferative agent in the containment and/or treatment of solid tumour disease.

According to a further feature of the invention there is provided a method for producing an anti-proliferative effect by the containment and/or treatment of solid tumour disease in a warm-blooded animal, such as man, in need of such treatment which comprises administering to said animal an effective amount of a quinazoline derivative of the Formula I, or a pharmaceutically-acceptable salt thereof, as defined hereinbefore.

According to a further aspect of the invention there is provided the use of a quinazoline derivative of the Formula I, or a pharmaceutically-acceptable salt thereof, as defined hereinbefore in the manufacture of a medicament for use in the prevention or treatment of solid tumour disease in a warm-blooded animals such as man.

According to a further feature of this aspect of the invention there is provided a method for the prevention or treatment of solid tumour disease in a warm-blooded animal, such as man, in need of such treatment which comprises administering to said animal an effective amount of a quinazoline derivative of the Formula 1, or a pharmaceutically-acceptable salt thereof, as defined hereinbefore.

According to a further aspect of the invention there is provided the use of a quinazoline derivative of the Formula I, or a pharmaceutically-acceptable salt thereof, as defined hereinbefore in the manufacture of a medicament for use in the prevention or treatment of those tumours which are sensitive to inhibition of MEK enzymes that are involved in the MAPK pathway. Particular enzymes that the tumours may be sensitive to are MEK 1, MEK 2 and MEK 5.

According to a further feature of this aspect of the invention there is provided a method for the prevention or treatment of those tumours which are sensitive to inhibition of MEK enzymes that are involved in the MAPK pathway which comprises administering to said animal an effective amount of a quinazoline derivative of the Formula I, or a pharmaceutically-acceptable salt thereof, as defined hereinbefore.

According to a further aspect of the invention there is provided the use of a quinazoline derivative of the Formula I, or a pharmaceutically-acceptable salt thereof, as defined hereinbefore in the manufacture of a medicament for use in providing a MEK enzyme inhibitory effect.

According to a further feature of this aspect of the invention there is provided a method for providing a MEK enzyme inhibitory effect which comprises administering to said animal an effective amount of a quinazoline derivative of the Formula I, or a pharmaceutically-acceptable salt thereof, as defined hereinbefore.

We have also found that the quinazoline derivatives of the present invention possess potent anti-tumour activity which it is believed is obtained by way of inhibition of one or more of the non-receptor tyrosine-specific protein kinases such as c-Src kinase that are involved in the signal transduction steps which lead to the invasiveness and migratory ability of metastasising tumour cells.

Particularly, the quinazoline derivatives of the present invention are of value as anti-invasive agents in the containment and/or treatment of solid tumour disease. Particularly, the compounds of the present invention: are expected to be useful in the prevention or treatment of those tumours which are sensitive to inhibition of one or more of the multiple non-receptor tyrosine kinases such as c-Src kinase that are involved in the signal transduction steps which lead to the invasiveness and migratory ability of metastasising tumour cells. Further, the compounds of the present invention are expected to be useful in the prevention or treatment of those tumours which are mediated alone or in part by inhibition of the enzyme c-Src, i.e. the compounds may be used to produce a c-Src enzyme inhibitory effect in a warm-blooded animal in need of such treatment. Specifically, the compounds of the present invention are expected to be useful in the prevention or treatment of solid tumour disease.

According to this aspect of the invention there is provided a quinazoline derivative of the Formula I, or a pharmaceutically-acceptable salt thereof, as defined hereinbefore for use as an anti-invasive agent in the containment and/or treatment of solid tumour disease.

According to a further feature of this aspect of the invention there is provided the use of a quinazoline derivative of the Formula I, or a pharmaceutically-acceptable salt thereof, as defined hereinbefore in the manufacture of a medicament for use as an anti-invasive agent in the containment and/or treatment of solid tumour disease.

According to a further feature of this aspect of the invention there is provided a method for producing an anti-invasive effect by the containment and/or treatment of solid tumour disease in a warm-blooded animal, such as man, in need of such treatment which comprises administering to said animal an effective amount of a quinazoline derivative of the Formula I, or a pharmaceutically-acceptable salt thereof, as defined hereinbefore.

According to a further aspect of the invention there is provided the use of a quinazoline derivative of the Formula I, or a pharmaceutically-acceptable salt thereof, as defined hereinbefore in the manufacture of a medicament for use in the prevention or treatment of those tumours which are sensitive to inhibition of non-receptor tyrosine kinases such as c-Src kinase that are involved in the signal transduction steps which lead to the invasiveness and migratory ability of metastasising tumour cells.

According to a further feature of this aspect of the invention there is provided a method for the prevention or treatment of those tumours which are sensitive to inhibition of non-receptor tyrosine kinases such as c-Src kinase that are involved in the signal transduction steps which lead to the invasiveness and migratory ability of metastasising tumour cells which comprises administering to said animal an effective amount of a quinazoline derivative of the Formula I, or a pharmaceutically-acceptable salt thereof, as defined hereinbefore.

According to a further aspect of the invention there is provided the use of a quinazoline derivative of the Formula I, or a pharmaceutically-acceptable salt thereof, as defined hereinbefore in the manufacture of a medicament for use in providing a c-Src kinase inhibitory effect.

According to a further feature of this aspect of the invention there is provided a method for providing a c-Src kinase inhibitory effect which comprises administering to said animal an effective amount of a quinazoline derivative of the Formula I, or a pharmaceutically-acceptable salt thereof, as defined hereinbefore.

The anti-proliferative and anti-invasive treatment defined hereinbefore may be applied as a sole therapy or may involve, in addition to the quinazoline derivative of the invention, conventional surgery or radiotherapy or chemotherapy. Such chemotherapy may include one or more of the following categories of anti-tumour agents:

(i) other anti-invasion agents (for example metalloproteinase inhibitors like marimastat and inhibitors of urokinase plasminogen activator receptor function);

(ii) other anti-proliferative or antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea, or, for example, one of the preferred antimetabolites disclosed in European Patent Application No. 562734 such as (2S)-2-{o-fluoro-p-[N-{2,7-dimethyl-4-oxo-3,4-dihydroquinazolin-6-ylmethyl}N-(prop-2-ynyl)amino]benzamido}-4-(tetrazol-5-yl)butyric acid); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(iii) cytostatic agents such as antioestrogens (for example tamoxifen, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrazole, vorazole and exemestane) and inhibitors of 5 α-reductase such as finasteride;

(iv) inhibitors of growth factor function, for example such inhibitors include growth factor antibodies, growth factor receptor antibodies, farnesyl transferase inhibitors, tyrosine kinase inhibitors and serine/threonine kinase inhibitors, for example inhibitors of the epidermal growth factor family (for example the EGFR tyrosine kinase inhibitors N-(3-chloro-4-fluorophenyl)-7-methoxy-6-(3-morpholino propoxy)quinazolin-4-amine (ZD1839), N-(3-ethynylphenyl)-6,7-bis(2-methoxyethoxy)quinazolin-4-amine (CP 358774) and 6-acrylamido-N-(3-chloro-4-fluorophenyl)-7-(3-morpholinopropoxy) quinazolin-4-amine (CI 1033)), for example inhibitors of the platelet-derived growth factor family and for example inhibitors of the hepatocyte growth factor family;

(v) antiangiogenic agents such as those which inhibit vascular endothelial growth factor such as the compounds disclosed in International Patent Applications WO 97/22596; WO 97/30035, WO 97/32856 and WO 98/13354 and those that work by other mechanisms (for example linomide, inhibitors of integrin αvβ3 function and angiostatin);

(vi) antisense therapies, for example those which are directed to the targets listed above, such as ISIS 2503, an anti-ras antisense;

(vii) gene therapy approaches, including for example approaches to replace aberrant genes such as aberrant p53 or aberrant BRCA1, GDEPT (gene-directed enzyme prodrug therapy) approaches such as those using cytosine deaminase, thymidine kinase or a bacterial nitroreductase enzyme and approaches to increase patient tolerance to chemotherapy or radiotherapy such as multi-drug resistance gene therapy; and (viii) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinazoline derivative of the formula I as defined hereinbefore and an additional anti-tumour agent as defined hereinbefore for the conjoint treatment of cancer.

Although the compounds of the Formula I are primarily of value as therapeutic agents for use in warm-blooded animals (including man), they are also useful whenever it is required to inhibit the effects of the MEK enzymes that are involved in the MAPK kinase pathway or the effects of c Src. Thus, they are useful as pharmacological standards for use in the development of new biological tests and in the search for new pharmacological agents.

The invention will now be illustrated in the following Examples in which, generally:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields, where present, are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Jeol JNM E 400 spectrometer operating at a field strength of 400 MHz, Varian Gemini 2000 spectrometer operating at a field strength of 300 Mz or a Bruker AM300 spectrometer operating at a field strength of 300 MHz]; the following abbreviations have been used: s, singlet; d, doublet; t, triplet; q, quartet; m, multiplet; br, broad;

(vi) intermediates were not generally fully characterised and purity was assessed by thin layer chromatograpbic, HPLC, infra-red (IR) and/or NMR analysis;

(vii) melting points are uncorrected and were determined using a Mettler SP62 automatic melting point apparatus or an oil-bath apparatus; melting points for the end-products

47 of the Formula I were determined after crystallisation from a conventional organic solvent such as ethanol, methanol, acetone, ether or hexane, alone or in admixture;
(viii) the following abbreviations have been used:

| DMF | N,N-dimethylformamide |
| DMSO | dimethylsulphoxide |
| THF | tetrahydrofuran |
| DMA | N,N-dimethylacetamide |

EXAMPLE 1

6-methoxy-N-[7-(3-methoxyprop-1-ynyl)-1,3-benzodioxol-4-yl]-7-(3-morpholin-4-ylpropoxy)quinazolin-4-amine Bis(Triphenyl-phosphine)palladium(II) chloride (94 mg), copper iodide (19 mg) and diisopropylamine (68 mg) were added to a stirred solution of N-(7-iodo-1,3-benzodioxol-4-yl)-6-methoxy-7-(3-morpholin-4-ylpropoxy)quinazolin-4-amine (200 mg) and methyl propargyl ether (47 mg) in ethyl acetate (5 mls) at −20° C. The reaction was allowed to warm to ambient temperature and stirred over 16 hours. The reaction mixture was partitioned between ethyl acetate and saturated NaHCO$_3$. The organic layer was washed with water and saturated brine and dried over magnesium sulfate. The product was purified by column chromatography on silica using a gradient of 0-10% methanol/methylene chloride as eluent. The resultant yellow gum was dissolved in minimal methylene chloride, diluted with diethyl ether and precipitated as an HCl salt by the addition of 1.0 M ethereal hydrogen chloride. The resultant solid was centrifuged and washed with diethyl ether (3 times) and dried to give the title compound as a yellow solid (55 mg); NMR Spectrum: DMSOd$_6$) 2.29-2.36 (m, 2H); 3.03-3.14 (m, 2H); 3.24 -3.31 (m, 2H), 3.32 (s, 3H), 3.43-3.54 (m, 2H), 3.76-3.86 (m, 2H), 3.94 -4.00 (m, 5H), 4.31 (t, 2H), 4.35 (s, 2H), 6.13 (s, 2H), 6.98 (d, 1H), 7.02 (d, 1H), 7.40 (s, 1H), 8.27 (s, 1H), 8.80 (s, 1H); Mass Spectrum: M+H$^+$ 507.11

The N-(7-iodo-1,3-benzodioxol-4-yl)-6-methoxy-7-(3-morpholin-4-ylpropoxy)quinazolin-4-amine used as a starting material was prepared as follows;

a) Preparation of 1,3-benzodioxol-4-amine

A mixture of 2,3-dihydroxybenzoic acid (5 g), methanol (50 ml) and concentrated sulphuric acid (10 drops) was stirred and heated to 60° C. for 24 hours. The mixture was evaporated and the residue was taken up in ethyl acetate. The organic solution was washed with a saturated solution of sodium bicarbonate, dried over magnesium sulphate and evaporated to give methyl 2,3-dihydroxybenzoate (2.19 g); NMR Spectrum: (CDCl$_3$) 3.95 (s, 3H), 5.7 (s, 1H), 6.8 (t, 1H), 7.15 (d, H), 7.35 (d, H).

After repetition of the previous reaction, a mixture of methyl 2,3-dihydroxybenzoate (2.8 g), potassium fluoride (4.8 g) and DMF (45 ml) was stirred at ambient temperature for 30 minutes. Dibromomethane (1.28 ml) was added and the mixture was heated to 120° C. for 3 hours. The mixture was cooled to ambient temperature, poured into water and extracted with diethyl ether. The organic phase was washed with water and with brine, dried over magnesium sulphate and evaporated. The residue was purified by column chromatography using a 9:1 mixture of petroleum ether (b.p. 40-60° C.) and ethyl acetate as eluent. There was thus obtained

48 methyl 2,3-methylenedioxybenzoate (2.3 g) as a solid; NMR Spectrum: (CDCl$_3$) 3.95 (s, 3H), 6.1 (s, 2H), 6.85 (t, 1H), 7.0 (d, 1H), 7.45 (d, 1H).

A mixture of the material so obtained, a 2N aqueous potassium hydroxide solution (15.5 ml) and methanol (40 ml) was stirred at ambient temperature for 2 hours. The solution was concentrated to about one quarter of the original volume and cooled in an ice bath. The mixture was acidified to pH 3.5 by the addition of a 2N aqueous hydrochloric acid solution. The resultant precipitate was collected by filtration and washed in turn with water and diethyl ether. There was thus obtained 2,3-methylenedioxybenzoic acid (1.87 g); NMR Spectrum: (DMSOd$_6$) 6.1 (s, 1H), 6.9 (t, 1H), 7.15 (d, 1H), 7.3 (d, 1H), 13.0 (br s, 1H).

The material so obtained was suspended in anhydrous dioxane (30 ml) and anhydrous diphenylphosphoryl azide (2.45 ml), triethylamine (1.6 ml) and tert-butanol (9 ml) were added. The mixture was heated to reflux for 5 hours. The mixture was cooled to ambient temperature, concentrated by evaporation and diluted with ethyl acetate. The organic phase was washed in turn with a 5% aqueous citric acid solution, water, an aqueous sodium bicarbonate solution and brine and dried over magnesium sulphate. The solvent was evaporated and the residue was purified by column chromatography on silica using a 19:1 mixture of petroleum ether (b.p. 40-60° C.) and ethyl acetate as eluent. There was thus obtained tert-butyl 2,3-methylenedioxyphenylcarbamate (1.98 g) as a solid; NMR Spectrum: (CDCl$_3$) 1.55 (s, 9H), 5.95 (s, 2H), 6.4 (br s, 1H), 6.55 (d, 1H), 6.8 (t, 1H), 7.45 (d, 1H).

A 5N aqueous hydrochloric acid solution (30 ml) was added to a solution of tert-butyl 2,3-methylenedioxyphenylcarbamate (1.9 g) in ethanol (38 ml) and the reaction mixture was stirred at ambient temperature for 20 hours. The ethanol was evaporated and the residual aqueous phase was washed with diethyl ether and neutralised to pH7 by the addition of solid potassium hydroxide. The resultant mixture was filtered and the aqueous phase was extracted with diethyl ether. The organic phase was washed with brine, dried over magnesium sulphate and evaporated. There was thus obtained 1,3-benzodioxol-4-amine (1.0 g) as an oil; NMR Spectrum: (CDCl$_3$) 3.0 (br s, 2H), 5.9 (s, 2H), 6.3 (m, 2H), 7.25 (t, 1H).

b) Preparation of 7-iodo-1,3-benzodioxol-4-amine

Benzyltrimethylammonium dichloroiodate (2.8 g) was added portionwise over 10 minutes to a stirred mixture of 1,3-benzodioxol-4-amine (1 g), calcium carbonate (0.95 g) in methanol (5 ml) and dichloromethane (10 ml). The reaction mixture was stirred at ambient temperature for 1.5 hours. The reaction mixture was diluted with water and extracted with dichloromethane. The organics were washed with water saturated brine and dried over magnesium sulfate. The residue was purified by column chromatography on silica using a gradient of an 8:1 mixture of dichloromethane/isohexane to Dichloromethane as eluent. There was thus obtained 7-iodo-1,3-benzodioxol-4-amine as a beige crystalline solid (1.1 g); NMR Spectrum: (DMSOd$_6$) 5.04 (bs, 2H); 5.94 (s, 2H); 6.13 (d, 1H), 6.80 (d, 1H).

c) Preparation of 4-chloro-6-methoxy-7-(3-morpholin-4-ylpropoxy)quinazoline

A mixture of 2-amino-4-benzyloxy-5-methoxybenzamide (*J. Med. Chem.*, 1977, 20, 146-149; 10 g), (3-dimethylamino-2-azaprop-2-en-1-ylidene)dimethylammonium chloride (Gold's reagent, 7.4 g) and dioxane (100 ml) was stirred and heated to reflux for 24 hours. Sodium acetate (3.02 g) and acetic acid (1.65 ml) were added and the reaction mixture was heated for a further 3 hours. The mixture was evaporated and water was added to the residue. The resultant solid was collected by filtration, washed with water and dried. The material was recrystallised from acetic acid to give 7-benzyloxy-6-methoxy-3,4-dihydroquinazolin-4-one (8.7 g).

After repetition of the reaction so described, a mixture of 7-benzyloxy-6-methoxy-3,4-dihydroquinazolin-4-one (35 g), thionyl chloride (440 ml) and DMF (1.75 ml) was heated to reflux for 4 hours. The thionyl chloride was evaporated under vacuum and the residue was azeotroped with toluene three times. The residue was dissolved in N-methylpyrrolidin-2-one (250 ml) to give a solution of 7-benzyloxy-4-chloro-6-methoxyquinazoline.

Phenol (29.05 g) was dissolved in N-methylpyrrolidin-2-one (210 ml) and sodium hydride (60% dispersion in mineral oil; 11.025 g) was added in portions with cooling. The resultant mixture was stirred at ambient temperature for 3 hours. The resultant viscous suspension was diluted with N-methylpyrrolidin-2-one (180 ml) and stirred overnight. The above-mentioned solution of 7-benzyloxy-4-chloro-6-methoxyquinazoline was added and the resultant suspension was stirred and heated to 100° C. for 2.5 hours. The mixture was allowed to cool to ambient temperature and poured into water (1.5 L) with vigorous stirring. The precipitate was collected by filtration, washed with water and dried under vacuum. The material so obtained was dissolved in methylene chloride and the solution was washed with brine and filtered through phase separating paper. The solution was evaporated under vacuum and the resultant residue was triturated under diethyl ether. There was thus obtained 7-benzyloxy-6-methoxy-4-phenoxyquinazoline (87.8 g); NMR Spectrum: (CDCl$_3$) 4.09 (s, 3H), 5.34 (s, 2H), 7.42 (m, 12), 7.63 (s, 1H).

A mixture of a portion (36.95 g) of the material so obtained and trifluoroacetic acid (420 ml) was heated to reflux for 3 hours. The reaction mixture was allowed to cool and evaporated under vacuum. The residue was stirred mechanically under water, basified by the addition of a saturated aqueous sodium bicarbonate solution and stirred overnight. The water was decanted and the residual solid was suspended in acetone. After stirring, the white solid was collected by filtration, washed with acetone and dried to give 7-hydroxy-6-methoxy-4-phenoxyquinazoline (26.61 g); NMR Spectrum: (DMSOd$_6$) 3.97 (s, 3H), 7.22 (s, 1H), 7.3 (m, 3H), 7.47 (t, 2H), 7.56 (s, 1H), 8.47 (s, 1H), 10.7 (s, 1H).

A mixture of 7-hydroxy-6-methoxy-4-phenoxyquinazoline (25.27 g), 3-morpholinopropyl chloride (18.48 g), potassium carbonate (39.1 g) and DMF (750 ml) was stirred and heated to 90° C. for 3 hours. The mixture was allowed to cool to ambient temperature and filtered. The filtrate was evaporated and the residue was triturated under ethyl acetate. There was thus obtained 6-methoxy-7-(3-morpholin-4-ylpropoxy)-4-phenoxyquinazoline (31.4 g); NMR Spectrum: (DMSOd$_6$) 1.97 (m, 2H), 2.39 (t, 4H), 2.47 (t, 2H), 3.58 (t, 4), 3.95 (s, 3H), 4.23 (t, 2H), 7.31 (m, 3H), 7.36 (s, 1H), 7.49 (t, 2H), 7.55 (s, 1H), 8.52 (s, 1H).

A mixture of the material so obtained and 6N aqueous hydrochloric acid solution (800 ml) was stirred and heated to reflux for 1.5 hours. The reaction mixture was decanted and concentrated to a volume of 250 ml. The mixture was basified to pH9 by the addition of a saturated aqueous sodium bicarbonate solution and extracted with methylene chloride (4×400 ml). The combined extracts were filtered through phase separating paper and the filtrate was evaporated. The resultant solid was triturated under ethyl acetate to give 6-methoxy-7-(3-morpholin-4-ylpropoxy)-3,4-dihydroquinazolin-4-one (23.9 g); NMR Spectrum: (DMSOd$_6$) 1.91 (m, 2H), 2.34 (t, 4H), 2.42 (t, 2H), 3.56 (t, 4H), 3.85 (s, 3H), 4.12 (t, 2), 7.11 (s, 1H), 7.42 (s, 1H), 7.96 (s, 1H), 12.01 (s, 1H).

A mixture of the material so obtained, thionyl chloride (210 ml) and DMF (1.8 ml) was heated to reflux for 1.5 hours. The thionyl chloride was removed by evaporation under vacuum and the residue was azeotroped with toluene three times. The residue was taken up in water and basified to pH8 by the addition of a saturated aqueous sodium bicarbonate solution. The resultant aqueous layer was extracted with methylene chloride (4×400 ml). The combined extracts were washed with water and with brine and dried over magnesium sulphate. The solution was filtered and evaporated. The resultant solid was triturated under ethyl acetate to give 4-chloro-6-methoxy-7-(3-morpholin-4-ylpropoxy)quinazoline (17.39 g); NMR Spectrum: (CDCl$_3$) 2.1-2.16 (m, 2H), 2.48 (br s, 4H), 2.57 (t, 2H), 3.73 (t, 4H), 4.05 (s, 3H), 4.29 (t, 2H), 7.36 (s, 1H), 7.39 (s, 1H), 8.86 (s, 1H).

The 3-morpholinopropyl chloride used as a reagent was obtained as follows:

A mixture of morpholine (52.2 ml), 1-bromo-3-chloropropane (30 ml) and toluene (180 ml) was heated to 70° C. for 3 hours. The solid was removed by filtration and the filtrate was evaporated under vacuum. The resultant oil was decanted from the additional solid which was deposited and the oil was purified by vacuum distillation to yield 3-morpholinopropyl chloride (37.91 g); NMR Spectrum: (DMSOd$_6$) 1.85 (m, 2H), 2.3 (t, 4H), 2.38 (t, 2H), 3.53 (t, 4H), 3.65 (t, 2H).

4.0M HCl in Dioxane (0.37 ml) was added to a stirred suspension of 4-chloro-6-methoxy-7-(3-morpholin-4-ylpropoxy)quinazoline (500 mg) and 7-iodo-1,3-benzodioxol-4-amine (0.39 g) in DMA (1 ml). The resultant mixture was stirred and heated to 80° C. for 10 mins. A grey precipitate was formed which was filtered and washed with further DMA followed by diethyl ether and dried to give N-(7-iodo-1,3-benzodioxol-4-yl)-6-methoxy-7-(3-morpholin-4-ylpropoxy)quinazolin-4-amine as a beige solid (0.59 g); NMR Spectrum: (DMSOd$_6$) 2.29-2.37 (m, 2H); 3.03-3.14 (m, 2H); 3.22-3.30 (m, 2H), 3.40-3.51 (m, 2H), 3.78-3.88 (m, 2H), 3.94-4.00 (m, 5H), 4.31 (t, 2H), 6.11 (s, 2H), 6.80 (d, 1H), 7.27 (d, 1H), 7.41 (s, 1H), 8.29 (s, 1H), 8.78 (s, 1H); Mass Spectrum: M+H$^+$ 562.9.

EXAMPLE 2

N-[5-chloro-7-(3-methoxyprop-1-ynyl)-1,3-benzodioxol-4-yl]-6-methoxy-7-(3-morpholin-4-ylpropoxy)quinazolin-4-amine Sodium hexamethyldisilazane (1M solution in THF; 1.0 ml) was added to a mixture of 4-chloro-6-methoxy-7-(3-morpholin-4-ylpropoxy)quinazoline (0.16 g) and 5-chloro-7-(3-methoxyprop-1-ynyl)-1,3-benzodioxol-4-amine (0.12 g) in DMA (5 ml) that was cooled to 0° C. The resultant mixture was stirred and allowed to warm to ambient temperature for 2 hours. The reaction mixture was reduced in vacuo and partitioned between ethylacetate and water. The organic layers were washed with water and brine and the product was purified column chromatography on silica using a gradient of 0-10% methanol/methylene chloride as eluent. The resultant yellow gum was dissolved in minimal methylene chloride, diluted with diethyl ether and precipitated as an HCl salt by the addition of 1.0M ethereal HCl. The resultant solid was centrifuged and washed with diethyl ether (3 times) and dried to give the title compound as a yellow solid (185 mg); NMR Spectrum: (DMSOd$_6$+CD$_3$CO$_2$D at 100° C.) 2.33-2.40 (m, 2H), 3.30-3.40 (m, 9H), 3.93-3.98 (m, 4H), 4.03 (s, 3H), 4.38-4.41 (m, 4H), 6.19 (s, 2H), 7.15 (s, 1H), 7.41 (s, 1H), 8.16 (s, 1H), 8.66 (s, 1H); Mass Spectrum: M+H+ 541.5.

The starting material were prepared as follows:

a) 4-chloro-6-methoxy-7-(3-morpholin-4-ylpropoxy) quinazoline was prepared as described in example 1 above b) Preparation of 5-chloro-7-(3-methoxyprop-1-ynyl)-1,3-benzodioxol-4-amine Sulphuryl chloride (72.5 ml) was added dropwise during 1.7 hours to a stirred mixture of benzodioxole (100 g), aluminium trichloride (0.43 g) and diphenyl sulphide (0.55 ml). Once the reaction started with the evolution of sulphur dioxide, the reaction mixture was cooled in a water bath to a temperature of approximately 22° C. After completion of the addition, the reaction mixture was stirred at ambient temperature for 45 minutes. The reaction mixture was degassed under vacuum and filtered and the filtrate was distilled at atmospheric pressure using a Vigreux distillation column. There was thus obtained 5-chloro-1,3-benzodioxole; b.p. 185-187° C.; NMR Spectrum: (CDCl$_3$) 6.0 (s, 2H); 6.7 (d, 1H); 6.75-6.9 (m, 2H).

A mixture of diisopropylamine (4.92 ml) and THF (100 ml) was cooled to −78° C. and n-butyllithium (2.5 M in hexane, 14 ml) was added dropwise. The mixture was stirred at −78° C. for 15 minutes. 5-Chloro-1,3-benzodioxole (3.73 ml) was added dropwise and the reaction mixture was stirred at −78° C. for 30 minutes. Dry carbon dioxide gas was bubbled into the reaction mixture for 30 minutes. The resultant reaction mixture was allowed to warm to ambient temperature and was stirred for a further hour. Water was added and the organic solvent was evaporated. The residue was acidified to pH2 by the addition of 2N aqueous hydrochloric acid solution. The resultant solid was isolated and washed in turn with water and diethyl ether. There was thus obtained 5-chloro-1,3-benzodioxole-4-carboxylic acid (5.4 g); NMR Spectrum: DMSOd$_6$) 6.15 (s, 2H), 7.0 (m, 2H), 13.7 (br s, 1H).

A portion (1 g) of the material so obtained was dissolved in 1,4dioxane (15 ml) and anhydrous tert-butanol (4 ml), diphenylphosphoryl azide (1.12 ml) and triethylamine (0.73 ml) were added in turn. The resultant mixture was stirred and heated to 100° C. for 4 hours. The mixture was evaporated and the residue was partitioned between ethyl acetate and a 5% aqueous citric acid solution. The organic phase was washed in turn with water, a saturated aqueous sodium bicarbonate solution and brine, dried over magnesium sulphate and evaporated. The residue was purified by column chromatography on silica using a 9:1 mixture of petroleum ether (b.p. 40-60° C.) and ethyl acetate as eluent. There was thus obtained tert-butyl 5-chloro-1,3-benzodioxol-4-ylcarbamate (1.1 g); NMR Spectrum: (DMSOd$_6$) 1.45 (s, 9H), 6.1 (s, 2H), 6.85 (d, 1H), 6.95 (d, 1H), 8.75 (s, 1H).

A mixture of the material so obtained (1.1 g), trifluoroacetic acid (6 ml) and methylene chloride (20 ml) was stirred at ambient temperature for 3 hours. The solvent was evaporated and the residue was partitioned between ethyl acetate and a saturated aqueous sodium bicarbonate solution. The organic phase was-washed with brine, dried over magnesium sulphate and evaporated. There was thus obtained 5-chloro-1,3-benzodioxol-4amine (0.642 g); NMR Spectrum: (DMSOd$_6$) 5.15 (s, 2H), 6.0 (s, 2H), 6.25 (d, 1H), 6.75 (d, 1H).

Benzyltrimethylammonium dichloroiodate (6.7 g) was added portionwise over 10 minutes to a stirred mixture of 5-chloro-1,3-benzodioxol-4-amine (3 g), calcium carbonate (2.28 g) in methanol (15 ml) and dichloromethane (30 ml). The reaction mixture was stirred at ambient temperature for 1.5 hours. The reaction mixture was diluted with water and extracted with dichloromethane. The organics were washed with water, saturated brine and dried over magnesium sulfate. The residue was purified by column chromatography on silica using a gradient of an 8:1 mixture of dichloromethane/isohexane to dichloromethane as eluent. There was thus obtained 5-chloro-7-iodo-1,3-benzodioxol-4-amine as a black crystalline solid (4.82 g); NMR Spectrum: (DMSOd$_6$) 6.04 (s, 2H), 7.00 (s, 1H).

Bis(Triphenyl-phosphine)palladium(II) chloride (472 mg), copper iodide (192 mg) and diisopropylamine (680 mg) were added to a stirred solution of 5-chloro-7-iodo-1,3-benzodioxol-4-amine (1000 mg) and methyl propargyl ether (471 mg) in ethyl acetate (10 mls) at −20° C. The reaction was allowed to warm to ambient temperature over 16 hours. The reaction mixture was partitioned between Ethyl acetate and saturated NaHCO3. The organics were washed with water and saturated brine and dried over magnesium sulfate. The product was purified by column chromatography on silica using a gradient of 80-100% Dichloromethane/isohexane as eluent. The 5-chloro-7-(3-methoxyprop-1-ynyl)-1,3-benzodioxol-4-amine product was thus obtained as a tan crystalline solid (200 mg); NMR Spectrum: (DMSOd$_6$) 3.28 (s, 3H), 4.26 (s, 2H), 5.52 (s, 2H), 6.05 (s, 2H), 6.93 (s, 1H).

EXAMPLE 3

6-methoxy-N-[5-chloro-7-(3-methoxyprop-1-ynyl)-1,3-benzodioxol-4-yl]-7-[3-(4-methylpiperazin-1-yl)propoxy]quinazolin-4-amine A solution of sodium bis(trimethylsilyl)amide (1.33 ml) in tetrahydrofuran (1.0 Mol/L, 1.33 mmol) was added to a solution of 4-chloro-6-methoxy-7-(3-(4-methylpiperazin-1-yl)propoxy)quinazoline (0.212 g) and 5-chloro-7-(3-methoxyprop-1-ynyl)-1,3-benzodioxol-4-amine (0.16 g) in DMF (3 ml) cooled to 0° C. under a nitrogen atmosphere. The reaction mixture was stirred for 1.5 hours. The reaction mixture was diluted with a saturated solution of ammonium chloride and extracted twice with ethyl acetate. The organic phases were combined and dried over magnesium sulfate and evaporated in vacuo. The residue was purified by column chromatography on silica using increasingly polar mixtures of dichloromethane and methanol as the eluent to give the title compound as a light brown solid (0.22 g). NMR Spectrum: 1.93 (m, 2H), 2.12 (s, 3H), 2.22-2.50 (m, 10H), 3.36 (s, 3H), 3.93 (s, 3H), 4.17 (t, 2H), 4.35 (s, 2H), 6.14 (s, 2H), 7.14 (s, 1H), 7.15 (s, 1H), 7.80 (s, 1H), 8.29 (s, 1H), 9.49 (s, 1H); Mass Spectrum: M+H+ 554, M+H− 552.

The starting materials were prepared as follows:

a) 5-chloro-7-(3-methoxyprop-1-ynyl)-1,3-benzodioxol-4-amine was prepared as described in example 2 b) Preparation of 4-chloro-6-methoxy-7-(3-(4-methylpiperazin-1-yl)propoxy)quinazoline 3-(4-Methylpiperazin-1-yl)propyl 4-toluenesulphonate was prepared as follows:

A mixture of 3-bromopropanol (20 ml), N-methylpiperazine (29 ml), potassium carbonate (83 g) and ethanol (200 ml)was stirred and heated to reflux for 20 hours. The mixture was cooled to ambient temperature and filtered. The filtrate was evaporated and the residue was triturated under diethyl ether. The resultant mixture was filtered and the filtrate was evaporated. The residue was purified by distillation at about 60-70° C. under about 0.2 mm Hg to give 1-(3-hydroxypropyl)-4-methylpiperazine (17 g); NMR Spectrum: (CDCl$_3$) 1.72 (m, 2H), 2.3 (s, 3H), 2.2-2.8 (m, 8H), 2.6 (t, 2H), 3.8 (t, 2H), 5.3 (br s, 1H).

4-Toluenesulphonyl chloride (3.2 g) was added to a stirred mixture of 1-(3-hydroxypropyl)-4-methylpiperazine (2.4 g), triethylamine (4.6 ml) and methylene chloride (60 ml) and the resultant mixture was stirred at ambient temperature for 2 hours. The solution was washed in turn with a saturated aqueous sodium bicarbonate solution and with water and filtered through phase separating paper. The organic filtrate was evaporated to give 3-(4-methylpiperazin-1-yl)propyl 4-toluenesulphonate as an oil which crystallised on standing (3.7 g); Mass Spectrum: M+H$^+$ 313.

The trifluoroacetic acid salt of 4-(4-chloro-2-fluorophenoxy)-7-hydroxy-6-methoxyquinazoline was prepared as follows:

A mixture of 2-amino-4-benzyloxy-5-methoxybenzamide (*J. Med. Chem.*, 1977, 20, 146-149; 10 g), (3-dimethylamino-2-azaprop-2-en-1-ylidene)dimethylammonium chloride (Gold's reagent, 7.4 g) and dioxane (100 ml) was stirred and heated to reflux for 24 hours. Sodium acetate (3.02 g) and acetic acid (1.65 ml) were added and the reaction mixture was heated for a further 3 hours. The mixture was evaporated and water was added to the residue. The resultant solid was collected by filtration, washed with water and dried. The material was recrystallised from acetic acid to give 7-benzyloxy-6-methoxy-3,4-dihydroquinazolin-4-one (8.7 g).

After repetition of the reaction so described, a mixture of 7-benzyloxy-6-methoxy-3,4-dihydroquinazolin-4-one (20.3 g), thionyl chloride (440 ml) and DMF (1.75 ml) was heated to reflux for 4 hours. The thionyl chloride was evaporated under vacuum and the residue was azeotroped with toluene three times to give 7-benzyloxy-4-chloro-6-methoxyquinazoline.

A mixture of the 7-benzyloxy-4-chloro-6-methoxyquinazoline so obtained, potassium carbonate (50 g) and 4-chloro-2-fluorophenol (8.8 ml) and DMF (500 ml) was stirred and heated to 100° C. for 5 hours. The mixture was allowed to cool to ambient temperature, poured into water (2 L) and stirred at ambient temperature for a few minutes. The resultant solid was isolated and washed with water. The solid was dissolved in methylene chloride and the solution was filtered and treated with decolourising charcoal. The resultant solution was filtered and evaporated to give a solid which was triturated under diethyl ether. There was thus obtained 7-benzyloxy-4-(4chloro-2-fluorophenoxy)-6-methoxyquinazoline (23.2 g); NMR Spectrum: (DMSOd$_6$) 3.98 (s, 3H), 5.34 (s, 2H), 7.42 (m, 9H), 7.69 (m, 1H), 8.55 (s, 1H).

A mixture of the material so obtained and trifluoroacetic acid (15 ml) was heated to reflux for 3 hours. The reaction mixture was allowed to cool, toluene was added and the mixture was evaporated. The residue was triturated under diethyl ether and then under acetone. The resultant precipitate was isolated and dried to give 4-(4-chloro-2-fluorophenoxy)-7-hydroxy-6-methoxyquinazoline trifluoroacetate salt (21.8 g) which was used without further purification.

Thereafter, a mixture of the trifluoroacetic acid salt of 4-(4-chloro-2-fluorophenoxy)-7-hydroxy-6-methoxyquinazoline (3.2 g), 3-(4-methylpiperazin-1-yl)propyl 4-toluenesulphonate (3.0 g), potassium carbonate (6.1 g) and DMF (60 ml) was stirred at 90° C. for 5 hours. The resultant mixture was cooled to ambient temperature, poured into water (700 ml) and extracted with ethyl acetate (5 times). The combined extracts were washed in turn with water, a saturated aqueous sodium bicarbonate solution, water and brine. The ethyl acetate solution was dried over magnesium sulphate and evaporated. The residue was purified by column chromatography on silica using a 100: 8:1 mixture of methylene chloride, methanol and a concentrated aqueous ammonium hydroxide solution (0.880 g/ml) as eluent. The material so obtained was triturated under diethyl ether. There was thus obtained 4-(4-chloro-2-fluorophenoxy)-6-methoxy-7-[3-(4-methylpiperazin-1-yl)propoxy]quinazoline (1.64 g); NMR Spectrum: (DMSOd$_6$) 1.95 (m, 2H), 2.14 (s, 3H), 2.35 (m, 8H), 2.44 (t, 2H), 3.96 (s, 3H), 4.22 (t, 2H), 7.38 (s, 1H), 7.4 (m, 1H), 7.54 (m, 2), 7.68 (m, 1H), 8.55 (s, 1H).

After repetition of the previous reaction, a mixture of 4-(4-chloro-2-fluorophenoxy)-6-methoxy-7-[3-(4-methylpiperazin-1-yl)propoxy]quinazoline (2.6 g) and 2N aqueous hydrochloric acid solution (45 ml) was stirred and heated to 95° C. for 2 hours. The mixture was cooled to ambient temperature and basified by the addition of solid sodium bicarbonate The mixture was evaporated and the residue was purified by column chromatography on silica using a 50: 8:1 mixture of methylene chloride, methanol and a concentrated aqueous ammonium hydroxide solution (0.880 g/ml) as eluent. There was thus obtained 6-methoxy-7-[3-(4-methylpiperazin-1-yl)propoxy]-3,4-dihydroquinazolin-4-one (1.8 g,); Mass Spectrum: M+H$^+$ 333.

After repetition of the previous reaction, a mixture of 6-methoxy-7-[3-(4-methylpiperazin-1-yl)propoxy]-3,4-dihydroquinazolin-4-one (2.15 g), thionyl chloride (25 ml) and DMF (0.18 ml) was stirred and heated to reflux for 2 hours. The thionyl chloride was evaporated under vacuum and the residue azeotroped twice with toluene. The residue was taken up in water, basified by the addition of a saturated aqueous sodium bicarbonate solution and extracted with methylene chloride (4 times). The combined extracts were washed in turn with water and brine and filtered through phase separating paper. The filtrate was evaporated under vacuum and the residue was purified by column chromatography on silica using a 100: 8:1 mixture of methylene chloride, methanol and a concentrated aqueous ammonium hydroxide solution (0.880 g/ml) as eluent. The solid so obtained was triturated under acetone, filtered and dried to give 4-chloro-6-methoxy-7-[3-(4-methylpiperazin-1-yl)propoxy]quinazoline (1.2 g); Mass Spectrum: M+H$^+$ 351.

EXAMPLE 4

N-[5-fluoro-7-(3-methoxyprop-1-yn-1-yl)-1,3-benzodioxol-4-yl]-6-methoxy-7-(3-morpholin-4-ylpropoxy)quinazolin-4-amine 4-Chloro-6-methoxy-7-(3-morpholin-4ylpropoxy) quinazoline (201 mg, 0.60 mmol) and 5-fluoro-7-(3-methoxyprop-1-yn-1-yl)-1,3-benzodioxol-4-amine (140 mg, 0.63 mmol) in DMF (3 ml) were cooled in an ice-water bath then treated dropwise, under an atmosphere of nitrogen, with a solution of sodium bis(trimethylsilyl)amide (1.0 M in THF, 1.25 ml). The resulting mixture was stirred at ice temperature for a further 90 minutes before quenching in dilute aqueous ammonium chloride solution and extracting with dichloromethane (containing a small percentage of methanol). The extract was washed with saturated brine, dried over magnesium sulphate and evaporated to an orange oil. The residue was purified by column chromatography on silica using increasing concentrations of methanol in dichloromethane as eluent. There was thus obtained the title compound (245 mg, 78%) as a colourless solid; NMR Spectrum: (DMSOd$_6$) 1.97 (quintet, 2), 2.40 (m, 4H), 2.47 (t, 2H), 3.36 (s, 3H), 3.59 (m, 4H), 3.95 (s, 3H), 4.20 (t, 2H), 4.37 (s, 2H), 6.16 (s, 2H), 6.91 (d, 1H), 7.19 (s, 1H), 7.81 (s, 1H), 8.36 (s, 1H), 9.52 (s, 1H); Mass Spectrum: M+H$^+$ 525.

The starting materials were prepared as follows:

a) 4-Chloro-6-methoxy-7-(3-morpholin-4-ylpropoxy) quinazoline was prepared as described in example 1 above b) 5-fluoro-7-(3-methoxyprop-1-yn-1-yl)-1,3-benzodioxole-4-amine was prepared as follows 5-Fluoro-1,3-benzodioxol-4-amine was prepared as described in WO0308409.

5-Fluoro-1,3-benzodioxol-4-amine (1.1 g, 7.10 mmol), benzyltrimethylammonium dichloroiodate (2.7 g, 7.76 mmol) and calcium carbonate (0.92 g, 9.2 mmol) in a mixture of dichloromethane (10 ml) and methanol (5 ml) were stirred at room temperature for 3 hr. The mixture was filtered through Celite and then evaporated to a dark brown solid. The residue was purified by column chromatography on silica using a 1:1 mixture of methyl tert-butyl ether and iso-hexane as eluent to give 4-amino-5-fluoro-7-iodo-1,3-benzodioxole (1.14 g, 57%) as a pale brown solid; NMR Spectrum: (CDCl$_3$) 3.61 (s, 2H), 6.00 (s, 2H), 6.81 (d, 1H).

5-Fluoro-7-iodo-1,3-benzodioxol-4-amine (800 mg, 2.85 mmol) and methyl propargyl ether (398 mg, 5.68 mmol) in ethyl acetate (10 ml) were cooled in ice-methanol, under an atmosphere of nitrogen, and then treated with bis(triphenylphosphine) palladium(II) dichloride (200 mg, 10 mol %) followed by copper(I) iodide (54 mg, 10 mol %) and diisopropylamine (575 mg, 5.69 mmol). The reaction mixture was allowed to warm to room temperature and stirred for 16 hr. The mixture was filtered through Celite and the filtrate was purified by column chromatography on silica using a 1:1 mixture of methyl tert-butyl ether and iso-hexane as eluent to give 5-fluoro-7-(3-methoxyprop-1-yn-1-)yl-1,3-benzodioxole-4-amine (524 mg, 82%) as a pale brown solid; NM Spectrum: (CDCl$_3$) 3.42 (s, 3H), 3.73 (s, 2H), 4.31 (s, 2H), 5.99 (s, 2H), 6.60 (d, 1H).

EXAMPLE 5

7-[3-(1,1-dioxidothiomorpholin-4-yl)propoxy]-N-[5-fluoro-7-(3-methoxyprop-1-yn-1-yl)-1,3-benzo-dioxol-4-yl]-6-methoxyquinazolin-4-amine This was prepared using the method described in example 4 using 4-chloro-7-[3-(1,1-dioxidothiomorpholin-4-yl)propoxy]-6-methoxyquinazoline (150 mg, 0.39 mmol), 5-fluoro-7-(3-methoxyprop-1-yn-1-yl)-1,3-benzodioxola-mine (91 mg, 0.41 mmol) and a solution of sodium bis(trimethylsilyl)amide (1.0M in THF, 0.82 ml) in DMF (2.5 ml). The crude product was purified by column chromatography on silica using increasing concentrations of methanol in dichloromethane as eluent. There was thus obtained the title compound (194 mg, 87%) as a colourless solid; NMR Spectrum:DMSOd$_6$) 1.98 (quintet, 2H), 2.66 (t, 2H), 2.92 (m, 4H), 3.21 (m, 4H), 3.36 (s, 3H), 3.94 (s, 3H), 4.20 (t, 2H), 4.37 (s, 2H), 6.16 (s, 2H), 6.91 (d, 1H), 7.23 (s, 1H), 7.81 (s, 1H), 8.36 (s, 1H), 9.52 (s, 1H); Mass Spectrum: M+H$^+$ 573.

4-Chloro-7-[3-(1,1-dioxidothiomorpholin-4-yl)propoxy]-6-methoxyquinazoline used as a starting materials was prepared as described in WO 0047212.

EXAMPLE 6

7-[3-(4-acetylpiperazin-1-yl)propoxy]-N-[5-fluoro-7-(3-methoxyprop-1-yn-1-yl)-1,3-benzodioxol-4-yl]-6-methoxyquinazolin-4-amine This was prepared using the, method described in the example 4 using 7-[3-(4-acetylpiperazin-1-yl)propoxy]-4-chloro-6-methoxyquinazoline (150 mg, 0.40 mmol), 5-fluoro-7-(3-methoxyprop-1-yn-1-yl)-1,3-benzodioxol-4-amine (97 mg, 0.43 mmol) and a solution of sodium bis(trimethylsilyl)amide (1.0M in THF, 0.83 ml) in DMF (2.5 ml). The crude product was purified by column chromatography on silica using increasing concentrations of methanol in dichloromethane as eluent. There was thus obtained the title compound (162 mg, 72%) as a pale yellow solid; NMR Spectrum:(DMSOd$_6$) 1.98 (quintet, 2H), 1.99 (s, 3H), 2.34 (m, 2H), 2.40 (m, 2H), 2.50 (t, 2H), 3.37 (s, 3H), 3.44 (m, 4H), 3.94 (s, 3H), 4.20 (t, 2H), 4.37 (s, 2H), 6.16 (s, 2H), 6.91 (d, 1H), 7.19 (s, 1H), 7.81 (s, 1H), 8.36 (s, 1H), 9.52 (s, 1H); Mass Spectrum: M+H$^+$ 566.

7-[3-(4-Acetylpiperazin-1-yl)propoxy]-4-chloro-6-methoxyquinazoline used as a starting material was prepared as follows:

4-chloro-6-methoxyquinazolin-7-ol (6.0 g, 28.5 mmol) was suspended in dichloromethane (300 mL). Triphenylphosphine (10.47 g, 40 mmol) and 3-(4-acetylpiperazin-1-yl)propan-1-ol (6.36 g, 34 mmol) were added. Diisopropyl azadicarboxylate (6.75 mL, 34 mmol) was then added dropwise. The reaction mixture was stirred for 3.5 hours at room temperature and then concentrated in vacuo. The residue was suspended in acetone (200 mL), stirred at room temperature for 30 minutes then filtered and washed with more acetone (50+30 mL). The filtercake was then dried to give clean product (7.24 g, 67%). NMR Spectrum: (DMSOd$_6$) 1.95 (3H, s), 1.95 (2H, m), 2.30 (2H, m), 2.35 (2H, m), 2.45 (2H, m), 3.40 (4H), m), 4.00 (3H, s), 4.30 (2H, t), 7.35 (1H, s), 7.40 (1H, s), 8.85 (1H, s), Mass Spectrum (M$^+$H) 379/381.

4-chloro-6-methoxyquinazolin-7-ol was prepared as described in WO0020402.

EXAMPLE 7

N-[5-chloro-7-(4-methoxybut-1-yn-1-yl)-1,3-benzo-dioxol-4-yl]-6-methoxy-7-(3-morpholin-4-ylpropoxy)quinazolin-4-amine This was prepared using the method described in example 4 using 4-chloro-6-methoxy-7-(3-morpholin-4-ylpropoxy)quinazoline (200 mg, 0.59 mmol), 5-chloro-7-(4-methoxybut-1-yn-1-yl)-1,3-benzodioxol-4-amine (165 mg, 0.65 mmol) and a solution of sodium bis(trimethylsilyl)amide (1.0M in THF, 1.24 ml) in DMF (3 ml). The crude product was purified by column chromatography on silica using increasing concentrations of methanol in dichloromethane as eluent. There was thus obtained the title compound (109 mg, 33%) as a pale yellow solid; NMR Spectrum:(DMSOd$_6$) 1.96 (quintet, 2H), 2.40 (m, 4H), 2.47 (t, 2H), 2.72 (t, 2H), 3.35 (s, 3), 3.55 (t, 2H), 3.60 (m, 4H), 3.94 (s, 3H), 4.20 (t, 2H), 6.14 (s, 2H), 7.07 (s, 1H), 7.19 (s, 1H), 7.83 (s, 1H), 8.32 (s, 1H), 9.48 (s, 1H); Mass Spectrum: M+H$^+$ 555/557.

5-chloro-7-(4-methoxybut-1-yn-1-yl)-1,3-benzodioxol-4-amine used as a starting material was prepared as follows:

5-Chloro-7-iodo-1,3-benzodioxol-4-amine was prepared as described in example 2.

A solution of 5-chloro-7-iodo-1,3-benzodioxol-4-amine (1.0 g, 3.36 mmol) and 4-methoxybut-1-yne (564 mg, 6.7 mmol) in ethyl acetate (12 ml) was cooled in ice-methanol, under an atmosphere of nitrogen, then treated with bis(triphenylphosphine) palladium(II) dichloride (236 mg, 10 mol %) followed by copper(I) iodide (64 mg, 10 mol %) and diisopropylamine (681 mg, 6.7 mmol). The reaction was allowed to warm to room temperature and stirred for 3 hr. The mixture was filtered through Celite and the filtrate was then purified by column chromatography on silica using a 1:1 mixture of methyl tert-butyl ether and iso-hexane as eluent to give 5-chloro-7-(4-methoxybut-1-yn-1-)yl-1,3-benzodioxol-4- amine (524 mg, 82%) as a pale brown solid; NMR Spectrum: (CDCl$_3$) 2.69 (t, 2H), 3.38 (s, 3H), 3.58 (t, 2H), 3.99 (s, 2H), 6.00 (s, 2H), 6.84 (s, 1H).

4-Methoxybut-1-yne was prepared as described in Aust. J. Chem. 1988, 41(2), 251 261.

EXAMPLE 8

N-[5-fluoro-7-(4-methoxybut-1-yn-1-yl)-1,3-benzodioxol-4-yl]-6-methoxy-7-(3-morpholin-4-ylpropoxy)quinazolin-4-amine This was prepared using the method described in example 4 using 4-chloro-6-methoxy-7-(3-morpholin-4-ylpropoxy)quinazoline (200 mg, 0.59 mmol), 5-fluoro-7-(4-methoxybut-1-yn-1-yl)-1,3-benzodioxol-4-amine (154 mg, 0.65 mmol) and a solution of sodium bis(trimethylsilyl)amide (1.0M in THF, 1.25 ml) in DMF (3 ml). The crude product was purified by column chromatography on silica using increasing concentrations of methanol in dichloromethane as eluent. There was thus obtained the title compound (183 mg, 57%) as a pale brown solid; NMR Spectrum:(DMSOd$_6$) 1.96 (quintet, 2H), 2.39 (m, 4H), 2.46 (t, 2H), 2.72 (t, 2H), 3.33 (s, 3H), 3.52 (t, 2H), 3.60 (m, 4H), 3.93 (s, 3H), 4.19 (t, 2H), 6.14 (s, 2H), 6.84 (d, 1H), 7.19 (s, 1H), 7.81 (s, 1H), 8.36 (s, 1H), 9.51 (s, 1H); Mass Spectrum: M+H$^+$ 539.

5-fluoro-7-(4methoxybut-1-yn-1-yl)-1,3-benzodioxol-4-amine used as starting material was prepared as follows:

5-fluoro-7-iodo-1,3-benzodioxol-4-amine was made as described in example 4.

4-Methoxybut-1-yne was prepared as described in Aust. J. Chem. 1988, 41(2), 251 261.

5-fluoro-7-iodo-1,3-benzodioxol-4-amine (320 mg, 1.14 mmol) and 4-methoxybut-1-yne (191 mg, 2.27 mmol) in ethyl acetate (5 ml) were cooled in ice-methanol, under an atmosphere of nitrogen and then treated with bis(triphenylphosphine) palladium(II) dichloride (80 mg, 10 mol %) followed by copper(I) iodide (22 mg, 10 mol %) and diisopropylamine (231 mg, 2.28 mmol). The reaction was allowed to warm to room temperature and stirred for 4 hr. The mixture was filtered through Celite and the filtrate was then purified by column chromatography on silica using a 1:1 mixture of methyl tert-butyl ether and iso-hexane as eluent to give 5-fluoro-7-(4-methoxybut-1-yn-1-)yl-1,3-benzodioxol-4-amine (524 mg, 82%) as a dark orange oil; solidified on standing; NMR Spectrum: (CDCl$_3$) 2.70 (t, 2H), 3.38 (s, 3H), 3.58 (t, 2H), 3.67 (s, 2H), 6.00 (s, 2H), 6.56 (d, 1H).

EXAMPLE 9

N-[5-chloro-7-(3-ethoxyprop-1-yn-1-yl)-1,3-benzodioxol-4-yl]-6-methoxy-7-(3-morpholin-4-ylpropoxy)quinazolin-4-amine This was prepared using the method described in example 4 using 4-chloro-6-methoxy-7-(3-morpholin-4-ylpropoxy)quinazoline (200 mg, 0.59 mmol), 5-chloro-7-(3-ethoxyprop-1-yn-1-yl)-1,3-benzodioxol-4-amine (165 mg, 0.65 mmol) and a solution of sodium bis(trimethylsilyl)amide (1.0M in THF, 1.24 ml) in DMF (3 ml). The crude product was purified by column chromatography on silica using increasing concentrations of methanol in dichloromethane as eluent. There was thus obtained the title compound (261 mg, 79%) as a pale yellow solid; NMR Spectrum:(DMSOd$_6$) 1.17 (t, 3H), 1.96 (quintet, 2H), 2.39 (m, 4H), 2.46 (t, 2H), 3.60 (m, 6H), 3.93 (s, 3H), 4.19 (t, 2H), 4.40 (s, 2H), 6.17 (s, 2H), 7.17 (s, 1H), 7.20 (s, 1H), 7.82 (s, 1H), 8.33 (s, 1H), 9.54 (s, 1H); Mass Spectrum: M+H$^+$ 555/557.

5-chloro-7-(3-ethoxyprop-1-yn-1-yl)-1,3-benzodioxol-4-amine used as starting material was prepared as follows:

5-Chloro-7-iodo-1,3-benzodioxol-4-amine was prepared as described in example 2.

3-Ethoxyprop-1-yne was prepared as described in Zh. Org. Khim. 1991, 27(8), 1600-4; C.A. 116, 128130

5-chloro-7-iodo-1,3-benzodioxol-4-amine (1.0 g, 3.36 mmol) and 3-ethoxyprop-1-yne (560 mg, 6.67 mmol) in ethyl acetate (12 ml) were cooled in ice-methanol, under an atmosphere of nitrogen and then treated with bis(triphenylphosphine) palladium(II) dichloride (236 mg, 10 mol %) followed by copper(I) iodide (64 mg, 10 mol %) and diisopropylamine (681 mg, 6.7 mmol). The reaction mixture was allowed to warm to room temperature and stirred for 2.5 hr and then filtered through Celite. The filtrate was purified by column chromatography on silica using a 1:1 mixture of methyl tert-butyl ether and iso-hexane as eluent to give 5-chloro-7-(3-ethoxyprop-1-yn-1-)yl-1,3-benzodioxole-4-amine (610 mg, 72%) as a dark orange oil which solidified on standing; NMR Spectrum: (CDCl$_3$) 1.25 (t, 3H), 3.62 (q, 2H), 4.04 (s, 2H), 4.36 (s, 3H), 6.02 (s, 2H), 6.89 (s, 1H).

EXAMPLE 10

N-{5-chloro-7-[3-(2methoxyethoxy)prop-1-yn-1-yl]-1,3-benzodioxol-4-yl}-6-methoxy-7-(3-morpholin-4-ylpropoxy)quinazolin-4-amine This was prepared using the method described in example 4 using 4-chloro-6-methoxy-7-(3-morpholin-4-ylpropoxy)quinazoline (200 mg, 0.59 mmol), 5-chloro-7-[3-(2-methoxyethoxy)prop-1-yn-1-yl]-1,3-benzodioxol-4-amine (185 mg, 0.65 mmol) and a solution of sodium bis(trimethylsilyl)amide (1.0M in THF, 1.24 ml) in DMF (3 ml). The crude product was purified by column chromatography on silica using increasing concentrations of methanol in dichloromethane as eluent. There was thus obtained the title compound (268 mg, 77%) as a pale yellow solid; NMR Spectrum: (DMSOd$_6$) 1.99 (quintet, 2H), 2.40 (m, 4H), 2.49 (t, 2H), 3.30 (s,3H), 3.52 (m, 2H), 3.59 (m, 4H), 3.65 (m, 2H), 3.93 (s, 3H), 4.20 (t, 2H), 4.44 (s, 2H), 6.16 (s, 2H), 7.16 (s, 1H), 7.19 (s, 1H), 7.82 (s, 1H), 8.32 (s, 1H), 9.5 (s, 1H); Mass Spectrum: M+H$^+$ 585/587.

5-chloro-7-[3-(2-methoxyethoxy)prop-1-yn-1-yl]-1,3-benzodioxol-4amine used as a starting material was prepared as follows:

5-Chloro-7-iodo-1,3-benzodioxol-4-amine was prepared as described in example 2.

3-(2-Methoxyethoxy)prop-1-yne was prepared as described in J. Med. Chem. 2001, 44(17), 2719-34.

5-Chloro-7-iodo-1,3-benzodioxol-4-amine (1.0 g, 3.36 mmol) and 3-(2-methoxyethoxy)prop-1-yne (766 mg, 6.72 mmol) in ethyl acetate (12 ml) were cooled in ice-methanol, under an atmosphere of nitrogen, and then treated with bis(triphenylphosphine) palladium(II) dichloride (236 mg, 10 mol %) followed by copper(I) iodide (64 mg, 10 mol %) and diisopropylamine (681 mg, 6.74 mmol). The reaction mixture was allowed to warm to room temperature and stirred for 2.5 hours and then filtered through Celite. The filtrate was purified by column chromatography on silica using a 1:1 mixture of methyl tert-butyl ether and iso-hexane as eluent to give 5-chloro-7-[3-(2-methoxyethoxy)prop-1-yn-1-yl]-1,3-benzodioxol-4-amine (816 mg, 86%) as a dark orange oil; solidified on standing; NMR Spectrum: (CDCl$_3$) 3.40 (s, 3H), 3.58 (m, 2H), 3.74 (m, 2H), 4.06 (s, 2H), 4.42 (s, 2H), 6.01 (s, 2H), 6.88 (s, 1H).

EXAMPLE 11

N-[5-Chloro-7-(3-isopropoxyprop-1-yn-1-yl)-1,3-benzodioxol-4-yl]-6-methoxy-7-(3-morpholin-4-ylpropoxy)quinazolin-4-amine This was prepared using the method described in example 4 using 4-chloro-6-methoxy-7-(3-morpholin-4-ylpropoxy)quinazoline (200 mg, 0.59 mmol), 5-chloro-7-(3-isopropoxyprop-1-yn-1-yl)-1,3-benzodioxol-4-amine (174 mg, 0.65 mmol) and a solution of sodium bis(trimethylsilyl)amide (1.0M in THF, 1.24 ml) in DMF (3 ml). The crude product was purified by column chromatography on silica using increasing concentrations of methanol in dichloromethane as eluent. There was thus obtained the title compound (222 mg, 66%) as a pale yellow solid; NMR Spectrum: (DMSOd$_6$) 1.15 (d, 6H), 1.97 (quintet, 2H), 2.39 (m, 4H), 2.47 (t, 2H), 3.59 (m, 4H), 3.80 (m, 1H), 3.93 (s, 3H), 4.20 (t, 2H), 4.40 (s, 2H), 6.16 (s, 2H), 7.14 (s, 1H), 7.19 (s, 1H), 7.82 (s, 1H), 8.32 (s, 1H), 9.50 (s, 1H); Mass Spectrum: M+H$^+$ 569/571

5-chloro-7-(3-isopropoxyprop-1-yn-1-yl)-1,3-benzodioxol-4-amine used as starting material was prepared as follows:

3-Isopropoxyprop-1-yne was prepared as described in *Macromolecules* 1995, 28(4), 866-9.

5-Chloro-7-iodo-1,3-benzodioxol-4-amine was prepared as described in example 2.

5-Chloro-7-iodo-1,3-benzodioxol-4-amine (1.0 g, 3.36 mmol) and 3-isopropoxyprop-1-yne (502 mg, 5.12 mmol) in ethyl acetate (12 ml) were cooled in ice-methanol, under an atmosphere of nitrogen, and then treated with bis(triphenylphosphine) palladium(II) dichloride (236 mg, 10 mol %) followed by copper(I) iodide (64 mg, 10 mol %) and diisopropylamine (681 mg, 6.74 mmol). The reaction mixture was allowed to warm to room temperature and stirred for 2.5 hours and then filtered through Celite. The filtrate was purified by column chromatography on silica using 40% methyl tert-butyl ether in iso-hexane as eluent to give 5-chloro-7-(3-isopropoxyprop-1-yn-1-yl)-1,3-benzodioxo-4-amine (660 mg, 73%) as a dark orange oil; NMR Spectrum: (CDCl$_3$) 1.20 (d, 6H), 3.86 (sept, 1H), 4.03 (s, 2H), 4.37 (s, 2H), 6.00 (s, 2H), 6.89 (s, 1H).

EXAMPLE 12

N-{5chloro-7-[3-(cyclopropylmethoxy)prop-1-yn-1-yl]-1,3-benzodioxol-4-yl}-6-methoxy-7-(3-morpholin-4-ylpropoxy)quinazolin-4-amine This was prepared using the method described in example 4 using 4-chloro-6-methoxy-7-(3-morpholin-4-ylpropoxy)quinazoline (200 mg, 0.59 mmol), 5-chloro-7-[3-(cyclopropylmethoxy)prop-1-yn-1-yl]-1,3-benzodioxol-4-amine (182 mg, 0.65 mmol) and a solution of sodium bis(trimethylsilyl)amide (1.0M in THF, 1.24 ml) in DMF (3 ml). The crude product was purified by column chromatography on silica using increasing concentrations of methanol in dichloromethane as eluent. There was thus obtained the title compound (247 mg, 72%) as a pale yellow solid; NMR Spectrum: (DMSOd$_6$) 0.23 (m, 2H), 0.51 (m, 2H), 1.04 (m, 1H), 1.96 (quintet, 2H), 2.38 (m, 4H), 2.46 (t, 2H), 3.37 (d, 2H), 3.59 (m, 4H), 3.93 (s, 3H), 4.20 (t, 2H), 4.42 (s, 2H), 6.16 (s, 2H), 7.15 (s, 1H), 7.19 (s, 1H), 7.84 (s, 1H), 8.34 (s, 1H), 9.52 (s, 1H); Mass Spectrum: M+H$^+$ 581/583.

5-chloro-7-[3-(cyclopropylmethoxy)prop-1-yn-1-yl]-1,3-benzodioxol-4-amine used as starting material was prepared as follows:

Sodium hydride (1.3 g of a 60% dispersion in oil, 32 mmol) in DMF (30 ml) was cooled, under an atmosphere of nitrogen, in an ice-water bath and then treated dropwise with cyclopropylmethanol (2.0 g, 28 mmol). The resulting mixture was stirred at ice temperature for 1 hr and then treated dropwise with propargyl bromide (3.1 ml of an 80% solution in toluene, 28 mmol). The reaction mixture was allowed to warm slowly to room temperature and then stirred for 16 hours before quenching in dilute aqueous ammonium chloride solution and extracting with iso-hexane. The extract was washed with saturated brine, dried over magnesium sulphate and evaporated to a yellow oil which was purified by column chromatography on silica using 10% methyl tert-butyl ether in iso-hexane as eluent to give [(prop-2-yn-1-yloxy)methyl]cyclopropane (1.07 g, 35%) as a pale yellow oil; NMR Spectrum: (CDCl$_3$) 0.26 (m, 2H), 0.55 (m, 2H), 1.10 (m, 1H), 2.42 (t, 1H), 3.40 (d, 2H), 4.20 (d, 2H).

5-Chloro-7-iodo-1,3-benzodioxol-4-amine was prepared as described in example 2.

5-Chloro-7-iodo-1,3-benzodioxol-4-amine (1.0 g, 3.36 mmol) and [(prop-2-yn-1-yloxy)methyl]cyclopropane (739 mg, 6.72 mmol) in ethyl acetate (12 ml) were cooled in ice-methanol, under an atmosphere of nitrogen, then treated with bis(triphenylphosphine) palladium(II) dichloride (236 mg, 10 mol %) followed by copper(I) iodide (64 mg, 10 mol %) and diisopropylamine (681 mg, 6.74 mmol). The reaction was allowed to warm to room temperature and stirred for 4 hours and then filtered through Celite. The filtrate was purified by column chromatography on silica using 40% methyl tert-butyl ether in iso-hexane as eluent to give 5-chloro-7-[3-(cyclopropylmethoxy)prop-1-yn-1-yl]-1,3-benzodioxol-4-amine (850 mg, 90%) as a dark orange oil; NMR Spectrum: (CDCl$_3$) 0.25 (m, 2H), 0.56 (m, 2H), 1.08 (m, 1H), 3.40 (d, 2H), 4.03 (s, 2H), 4.40 (s, 2H), 6.00 (s, 2H), 6.88 (s, 1H).

EXAMPLE 13

7-[3-(4-acetylpiperazin-1-yl)propoxy]-N-[5-chloro-7-(4-methoxybut-1-yn-1-yl)-1,3-benzodioxol-4-yl]-6-methoxyquinazolin-4-amine N-[5-Chloro-7-(4-methoxybut-1-yn-1-yl)-1,3-benzodioxol-4-yl]-7-(3-chloropropoxy)-6-methoxyquinazolin-4-amine (192 mg, 0.38 mmol) and 1-acetylpiperazine (244 mg, 1.9 mmol) in 2-methoxyethanol (4 ml) were stirred and heated at 100° for 12 hr. then quenched in water and extracted with dichloromethane. The combined extracts were washed with saturated brine, dried over magnesium sulphate and evaporated to an orange oil. This was then purified by column chromatography on silica using increasing concentrations of methanol in dichloromethane as eluent. There was thus obtained the title compound (187 mg, 82%) as a pale yellow solid; NMR Spectrum:(DMSOd$_6$) 1.98 (quintet, 2H), 1.99 (s, 3H), 2.33 (m, 2H), 2.40 (m, 2H), 2.48 (t, 2H), 2.72 (t, 2H), 3.31 (s, 3H), 3.43 (m, 4H), 3.53 (t, 2H), 3.93 (s, 3H), 4.21 (t, 2H), 6.13 (s, 2H), 7.07 (s, 1H), 7.18 (s, 1H), 7.81 (s, 1H), 8.32 (s, 1H), 9.50 (s, 1H); Mass Spectrum: M+H$^+$ 596/598.

The starting material, N-[5-Chloro-7-(4-methoxybut-1-yn-1-yl)-1,3-benzodioxol-4-yl]-7-(3-chloropropoxy)-6-methoxyquinazolin-4-amine was prepared as follows:

5-chloro-7-(4-methoxybut-1-yn-1-yl)-1,3-benzodioxole-4-amine was made by the method described in example 7.

4-chloro-7-(3-chloropropoxy)-6-methoxyquinazoline was prepared as described in WO 0121597.

4-chloro-7-(3-chloropropoxy)-6-methoxyquinazoline (320 mg, 1.11 mmol), 5-chloro-7-(4-methoxybut-1-yn-1-yl)-1,3-benzodioxol-4-amine (311 mg, 1.23 mmol) and a solution of sodium bis(trimethylsilyl)amide (1.0M in THF, 2.34 ml) in DMF (4 ml) were reacted together according to the method described in example 4. The crude product was purified by column chromatography on silica using ethyl acetate as eluent. There was thus obtained the starting material (389 mg, 69%) as a pale yellow solid; NMR Spectrum: (CDCl$_3$) 2.36 (quintet, 2H), 2.75 (t, 2H), 3.40 (s, 3H), 3.60 (t, 2H), 3.80 (t, 2H), 3.97 (s, 3H), 4.32 (t, 2H), 6.06 (s, 2H), 6.93 (s, 1H), 7.03 (s, 1H), 7.10 (s, 1H), 7.29 (s, 1H), 8.62 (s, 1H).

EXAMPLE 14

(1-{3-[(4-{[5-chloro-7-(4-methoxybut-1-yn-1-yl)-1,3-benzodioxol-4-yl]amino}-6-methoxyquinazolin-7-yl)oxy]propyl}piperidin-4-yl)methanol This was prepared using the method described in example 13 using N-[5-chloro-7-(4-methoxybut-1-yn-1-yl)-1,3-benzodioxol-4-yl]-7-(3-chloropropoxy)-6-methoxyquinazolin-4-amine (192 mg, 0.38 mmol) and 4-piperidinemethanol (220 mg, 1.9 mmol) in 2-methoxyethanol (4 ml). The crude product was purified by column chromatography on silica using increasing concentrations of methanolic ammonia in dichloromethane as eluent. There was thus obtained the title compound (177 mg, 80%) as a pale yellow solid; NMR Spectrum: (DMSOd$_6$) 1.10-1.20 (m, 2H), 1.35 (m, 1H), 1.64 (d, 2H), 1.88 (t, 2H), 1.95 (quintet, 2H), 2.45 (t, 2H), 2.72 (t, 2H), 2.89 (d, 2H), 3.26 (t, 2H), 3.32 (s, 3H), 3.53 (t, 2H), 3.94 (s, 3H), 4.18 (t, 2H), 4.37 (t, 1H), 6.14 (s, 2H), 7.07 (s, 1H), 7.17 (s, 1H), 7.82 (s, 1H), 8.32 (s, 1H), 9.48 (s, 1H); Mass Spectrum: M+H$^+$ 583/585.

EXAMPLE 15

N-[3-(6-chloro-7-{[6-methoxy-7-(3-morpholin-4-ylpropoxy)quinazolin-4-yl]amino}-1,3-benzodioxol-4-yl)prop-2-yn-1-yl]morpholine-4-carboxamide This was prepared by the method described in example 4 using 4-chloro-6-methoxy-7-(3-morpholin-4-ylpropoxy)quinazoline (200 mg, 0.59 mmol), N-[3-(7-amino-6-chloro-1,3-benzodioxol-4-yl)prop-2-yn-1-yl]morpholine-4-carboxamide (220 mg, 0.65 mmol) and a solution of sodium bis(trimethylsilyl)amide (1.0M in THF, 1.24 ml) in DMF (3 ml). The crude product was purified by column chromatography on silica using 10% methanol in dichloromethane as eluent. There was thus obtained the title compound (272 mg, 72%) as a pale brown solid; NMR Spectrum:(DMSOd$_6$) 1.96 (quintet, 2H), 2.39 (m, 4H), 2.47 (t, 2H), 2.50 (m, 4H), 3.55-3.62 (m, 8H), 3.94 (s, 3H), 4.14 (d, 2H), 4.20 (t, 2H), 6.15 (s, 2H), 7.10 (m, 2H), 7.20 (s, 1H), 7.82 (s, 1H), 8.34 (s, 1H), 9.50 (s, 1H); Mass Spectrum: M+H$^+$ 639/641.

The starting material, N-[3-(7-Amino-6-chloro-1,3-benzodioxol-4-yl)prop-2-yn-1-yl]morpholine-4-carboxamide, was prepared as follows:

5-Chloro-7-iodo-1,3-benzodioxol-4amine was prepared as described in example 2

4-Nitrophenyl prop-2-yn-1-ylcarbamate was prepared as described in WO 0226723.

Morpholine (510 mg, 5.86 mmol) and 4-nitrophenyl prop-2-yn-1-ylcarbamate (800 mg (80% purity), 2.91 mmol) in dichloromethane (10 ml) were stirred at room temperature for 4 hours and then the reaction solution was purified directly by chromatography on silica using ethyl acetate as eluent to give N-prop-2-yn-1-ylmorpholine-4-carboxamide (453 mg, 92%) as a pale yellow solid; NMR Spectrum: (CDCl$_3$) 2.24 (t, 1H), 3.37 (m, 4H), 3.69 (m, 4H), 4.05 (m, 2H), 4.65 (s, 1H).

5-Chloro-7-iodo-1,3-benzodioxol-4-amine (600 mg, 2.02 mmol) and N-prop-2-yn-1-ylmorpholine-4-carboxamide (406 mg, 2.42 mmol) in ethyl acetate (10 ml) were cooled in ice-methanol, under an atmosphere of nitrogen, and then treated with bis(triphenylphosphine) palladium(II) dichloride (140 mg, 10 mol %) followed by copper(I) iodide (38 mg, 10 mol %) and diisopropylamine (407 mg, 4.03 mmol). The reaction was allowed to warm to room temperature and stirred for 3 hours and then filtered through Celite. The filtrate was purified by column chromatography on silica using ethyl acetate as eluent to give N-[3-(7-amino-6-chloro-1,3-benzodioxol-4-yl)prop-2-yn-1-yl]morpholine-4-carboxamide (529 mg, 78%) as a pale brown solid; NMR Spectrum:(DMSOd$_6$) 3.28 (m, 4H), 3.54 (m, 4H), 4.05 (d, 2H), 5.47 (s, 2H), 6.05 (s, 2H), 6.78 (s, 1H), 7.01 (t, 1H); Mass Spectrum: M+H$^+$ 338/340.

EXAMPLE 16

N'-[3-(6-chloro-7-{[6-methoxy-7-(3-morpholin-4-ylpropoxy)quinazolin-4-yl]amino}-1,3-benzodioxol-4-yl)prop-2-yn-1-yl]-N,N-dimethylurea This was prepared by the method described in example 4 using 4-chloro-6-methoxy-7-(3-morpholin-4-ylpropoxy)quinazoline (200 mg, 0.59 mmol), N'-[3-(7-amino-6-chloro-1,3-benzodioxol-4-yl)prop-2-yn-1-yl]-N,N-dimethylurea (193 mg, 0.65 mmol) and a solution of sodium bis(trimethylsilyl)amide (1.0M in THF, 1.24 ml) in DMF (3 ml). The crude product was purified by column chromatography on silica using 10% methanol in dichloromethane as eluent. There was thus obtained the title compound (254 mg, 72%) as a pale brown solid; NMR Spectrum:(DMSOd$_6$) 1.96 (quintet, 2H), 2.39 (m, 4H), 2.45 (t, 2H), 3.81 (s, 6H), 3.60 (m, 4H), 3.94 (s, 3H), 4.10 (d, 2H), 4.20 (t, 2H), 6.15 (s, 2H), 6.84 (t, 1H), 7.08 (s, 1H), 7.20 (s, 1H), 7.82 (s, 1H), 8.34 (s, 1H), 9.50 (s, 1H); Mass Spectrum: M+H$^+$ 597/599.

The starting material, N'-[3-(7-amino-6-chloro-1,3-benzodioxol-4-yl)prop-2-yn-1-yl]-N,N-dimethylurea, was prepared as follows:

4-Nitrophenyl prop-2-yn-1-ylcarbamate was prepared as described in WO 0226723.

5-Chloro-7-iodo-1,3-benzodioxol-4-amine was prepared as described in example 2

Dimethylamine (3.0 ml of a 2.0M solution in THF, 6.0 mmol) and 4-nitrophenyl prop-2-yn-1-ylcarbamate (800 mg (80% purity), 2.91 mmol) in dichloromethane (7 ml) were stirred at room temperature for 4 hr. then the reaction solution purified by chromatography on silica using ethyl acetate as eluent to give N,N-dimethyl-N'-prop-2-yn-1-ylurea (289 mg, 79%) as a colourless solid.

5-Chloro-7-iodo-1,3-benzodioxol-5-amine (682 mg, 2.29 mmol) and N,N-dimethyl-N'-prop-2-yn-1-ylurea (289 mg, 2.29 mmol) in ethyl acetate (10 ml) were cooled in ice-methanol, under an atmosphere of nitrogen, then treated with bis(triphenylphosphine) palladium(II) dichloride (161 mg, 10 mol %) followed by copper(I) iodide (43 mg, 10 mol %) and diisopropylamine (463 mg, 4.03 mmol). The reaction was allowed to warm to room temperature and stirred 3 hr. then filtered through Celite. The filtrate was purified by column chromatography on silica using ethyl acetate as eluent to give N'-[3-(7-amino-6-chloro-1,3-benzodioxol-4-yl)prop-2-yn-1-yl]-N,N-dimethylurea (463 mg, 68%) as an off-white solid;

NMR Spectrum:(DMSOd$_6$) 2.79 (s, 6H), 4.01 (d, 2H), 5.50 (s, 2H), 6.05 (s, 2H), 6.78 (t, 1H), 6.79 (s, 1H).

EXAMPLE 17

N-[3-(6-chloro-7-{[6-methoxy-7-(3-morpholin-4-ylpropoxy)quinazolin-4-yl]amino}-1,3-benzodioxol-4-yl)prop-2-yn-1-yl]-N'-methylurea This was prepared by the method described in example 4 using 4-chloro-6-methoxy-7-(3-morpholin-4-ylpropoxy)quinazoline (200 mg, 0.59 mmol), N-[3-(7-amino-6-chloro-1,3-benzodioxol-4-yl)prop-2-yn-1-yl]-N'-methylurea (170 mg, 0.60 mmol) and sodium bis(trimethylsilyl)amide (1.0M in THF, 1.24 ml) in DMF (3 ml). The crude product was purified by column chromatography on silica using 10% methanol in dichloromethane as eluent. There was thus obtained the title compound (209 mg, 61%) as a yellow solid; NMR Spectrum:(DMSOd$_6$) 1.96 (quintet, 2H), 2.39 (m, 4H), 2.45 (t, 2H), 2.57 (d, 3H), 3.60 (m, 4H), 3.94 (s, 3H), 4.08 (d, 2H), 4.20 (t, 2H), 5.91 (q, 1H), 6.15 (s, 2H), 6.38 (t, 1H), 7.09 (s, 1H), 7.19 (s, 1H), 7.81 (s, 1H), 8.32 (s, 1H), 9.51 (s, 1H); Mass Spectrum: M+H$^+$ 583/585.

N-[3-(7-amino-6-chloro-1,3-benzodioxol-4-yl)prop-2-yn-1-yl]-N'-methylurea used as starting material was prepared as follows:

4-Nitrophenyl prop-2-yn-1-ylcarbamate was prepared as described in WO 0226723.

5-Chloro-7-iodo-1,3-benzodioxol-4-amine was prepared as described in example 2

Methylamine (4.0 ml of a 2.0M solution in THF, 8.0 mmol) and 4-nitrophenyl prop-2-yn-1-ylcarbamate (800 mg (80% purity), 2.91 mmol) in dichloromethane (6 ml) were stirred at room temperature for 18 hr. then the reaction solution purified by chromatography on silica using ethyl acetate as eluent to give N-methyl-N'-prop-2-yn-1-ylurea (500 mg) as a pale yellow solid (contains some 4-nitrophenol).

5-Chloro-7-iodo-1,3-benzodioxol-4-amine (500 mg, 1.68 mmol) and N-methyl-N'-prop-2-yn-1-ylurea (226 mg, 2.02 mmol) in ethyl acetate (10 ml) were cooled in ice-methanol, under an atmosphere of nitrogen, then treated with bis(triphenylphosphine) palladium(II) dichloride (118 mg, 10 mol %) followed by copper(I) iodide (32 mg, 10 mol %) and diisopropylamine (339 mg, 4.03 mmol). The reaction was allowed to warm to room temperature and stirred 3 hr. then filtered through Celite. The filtrate was purified by column chromatography on silica using ethyl acetate as eluent to give N-[3-(7-amino-6-chloro-1,3-benzodioxol-4-yl)prop-2-yn-1-yl]-N'-methylurea (177 mg, 37%) as an colourless solid; NMR Spectrum:(DMSOd$_6$) 2.55 (d, 3), 4.00 (d, 2H), 5.52 (s, 2H), 5.84 (q, 1H), 6.05 (s, 2H), 6.27 (t, 1H), 6.78 (s, 1H).

EXAMPLE 18

N-[5-chloro-7-(4-methoxybut-1-yn-1-yl)-1,3-benzodioxol-4-yl]-6-methoxy-7-[3-(4-methylpiperazin-1-yl)propoxy]quinazolin-4-amine This was prepared by the method described in example 13 using N-[5-Chloro-7-(4-methoxybut-1-yn-1-yl)-1,3-benzodioxol-4-yl]-7-(3-chloropropoxy)-6-methoxyquinazolin-4-amine (200 mg, 0.40 mmol) and 1-methylpiperazine (198 mg, 1.98 mmol) in 2-methoxyethanol (4 ml). The crude product was purified by column chromatography on silica using increasing concentrations of methanolic ammonia in dichloromethane as eluent. There was thus obtained the title compound (154 mg, 68%) as a pale brown solid; NMR Spectrum: (DMSOd$_6$) 1.95 (quintet, 2H), 2.14 (s, 3), 2.2-2.6 (m, 8H), 2.47 (t, 2H), 2.72 (t, 2H), 3.31 (s, 3H), 3.53 (t, 2H), 3.92 (s, 3H), 4.18 (s, 2H), 6.14 (s, 2H), 7.08 (s, 1H), 7.16 (s, 1H), 7.82 (s, 1H), 8.32 (s, 1H), 9.50 (s, 1H); Mass Spectrum: M+H$^+$ 568/570.

EXAMPLE 19

N-[5-chloro-7-(4-methoxybut-1-yn-1-yl)-1,3-benzodioxol-4-yl]-7-[3-(dimethylamino)propoxy]-6-methoxyquinazolin-4-amine N-[5-Chloro-7-(4-methoxybut-1-yn-1-yl)-1,3-benzodioxol-4-yl]-7-(3-chloropropoxy)-6-methoxyquinazolin-4-amine (200 mg, 0.40 mmol) and dimethylamine (5 ml of a 33% solution in ethanol) were stirred and heated under reflux at 90° for 30 min. before evaporating the solution. A further 5 ml of dimethylamine solution were added to the residue and the solution heated for a further 90 min. then evaporated. Again a further 5 ml of dimethylamine solution were added to the residue and the solution heated for 1 hr. before quenching in water and extracting with dichloromethane. The extract was washed with saturated brine, dried over magnesium sulphate and evaporated to an orange oil. It was then purified by column chromatography on silica using increasing concentrations of methanolic ammonia in dichloromethane as eluent. There was thus obtained the title compound (156 mg, 77%) as a pale orange solid; NMR Spectrum:(DMSOd$_6$) 1.95 (quintet, 2H), 2.17 (s, 6H), 2.38 (t, 2H), 2.71 (t, 2H), 3.30 (s, 3H), 3.52 (t, 2H), 3.92 (s, 3H), 4.17 (t, 2H), 6.14 (s, 2H), 7.07 (s, 1H), 7.17 (s, 1H), 7.81 (s, 1H), 8.31 (s, 1H), 9.50 (s, 1H); Mass Spectrum: M+H$^+$ 513/515.

EXAMPLE 20

7-{3-[bis(2-methoxyethyl)amino]propoxy}-N-[5-chloro-7-(4-methoxybut-1-yn-1-yl)-1,3-benzodioxol-4-yl]-6-methoxyquinazolin-4-amine This was prepared using the method described in example 13 using N-[5-chloro-7-(4-methoxybut-1-yn-1-yl)-1,3-benzodioxol-4-yl]-7-(3-chloropropoxy)-6-methoxyquinazolin-4-amine (200 mg, 0.40 mmol) and bis(2-methoxyethyl)amine (264 ml, 1.98 mmol) in 2-methoxyethanol (4 ml). The crude product was purified by column chromatography on silica using increasing concentrations of methanol in dichloromethane as eluent. There was thus obtained the title compound (147 mg, 66%) as a pale brown solid; NMR Spectrum: (DMSOd$_6$) 1.91 (quintet, 2H), 2.65 (m, 6H), 2.72 (t, 2), 3.21 (s, 6H), 3.30 (s, 3H), 3.38 (t, 4H), 3.53 (t, 2H), 3.94 (s, 3H), 4.19 (t, 2H), 6.14 (s, 2H), 7.07 (s, 1H), 7.17 (s, 1H), 7.81 (s, 1H), 8.32 (s, 1H), 9.49 (s, 1H); Mass Spectrum: M+H$^+$ 601/603.

EXAMPLE 21

4-{3-[(4-{[5-chloro-7-(4-methoxybut-1-yn-1-yl)-1,3-benzodioxol-4-yl]amino}-6-methoxyquinazolin-7-yl)oxy]propyl}piperazine-1-carbaldehyde This was prepared using the method described in example 13 using N-[5-chloro-7-(4-methoxybut-1-yn-1-yl)-1,3-benzodioxol-4-yl]-7-(3-chloropropoxy)-6-methoxyquinazolin-4-amine (200 mg, 0.40 mmol) and 1-formylpiperazine (226 mg, 1.98 mmol) in 2-methoxyethanol (4 ml). The crude product was purified by column chromatography on silica using increasing concentrations of methanol in dichloromethane as eluent. There was thus obtained the title compound (148 mg, 64%) as a pale brown solid; NMR Spectum:(DMSOd$_6$) 1.96 (quintet, 2H), 2.36 (m, 2H), 2.41 (m, 2H), 2.50 (t, 2H), 2.71 (t, 2H), 3.31 (s, 3H), 3.39 (m, 4H), 3.52 (t, 2H), 3.93 (s, 3H), 4.20 (t, 2H), 6.14 (s, 2H), 7.07 (s, 1H), 7.20 (s, 1H), 7.82 (s, 1H), 8.00 (s, 1H), 8.32 (s, 1H), 9.48 (s, 1H); Mass Spectrum: M+H$^+$ 582/584.

EXAMPLE 22

N-[5-chloro-7-(4-methoxybut-1-yn-1-yl)-1,3-benzo-dioxol-4-yl]-7-{3-[4-(2-fluoroethyl)piperazin-1-yl]propoxy}-6-methoxyquinazolin-4-amine This was prepared by the method described in example 4 using 4-chloro-7-{3-[4-(2-fluoroethyl)piperazin-1-yl]propoxy}-6-methoxyquinazoline (200 mg, 0.52 mmol), 5-chloro-7-(4-methoxybut-1-yn-1-yl)-1,3-benzodioxol-4-amine (146 mg, 0.57 mmol) and sodium bis(trimethylsilyl)amide (1.0M in THF, 1.10 ml) in DMF (3 ml). The crude product was purified by column chromatography on silica using increasing concentrations of methanol in dichloromethane as eluent. There was thus obtained the title compound (187 mg, 60%) as colourless solid, NMR Spectrum: (CDCl$_3$) 2.10 (quintet, 2H), 2.57 (m, 8H), 2.67 & 2.72 (dt, 2H), 2.74 (t, 2H), 3.41 (s, 3H), 3.60 (t, 2H), 3.98 (s, 3H), 4.23 (t, 2H), 4.51 & 4.63 (dt, 2H), 6.06 (s, 2H), 6.85 (s, 1H), 7.04 (s, 1H), 7.08 (s, 1H), 7.28 (s, 1H), 8.61 (s, 1H); Mass Spectrum: M+H$^+$ 600/602

The starting materials used were prepared as follows:
a) 5-chloro-7-(4-methoxybut-1-yn-1-yl)-1,3-benzodioxol-4-amine was prepared as described in example 7
b) 4-chloro-7-{3-[4-(2-fluoroethyl)piperazin-1-yl]propoxy}-6-methoxyquinazoline used as starting material was prepared as follows:

Diisopropylazodicarboxylate (921 mg, 4.56 mmol) was added portionwise, at room temperature, to a stirred suspension of 4-chloro-6-methoxyquinazolin-7-ol (800 mg, 3.80 mmol), 3-[4-(2-fluoroethyl)piperazin-1-yl]propan-1-ol (794 mg, 4.18 mmol) and triphenylphosphine (1.4 g, 5.34 mmol) in THF (20 ml). The reaction was stirred 1 hr. before adding triphenylphosphine (1.4 g), di-tert-butylazodicarboxylate (1.05 g, 4.56 mmol) and dichloromethane (10 ml). The reaction was stirred for a further 1 hr. then evaporated and purified by column chromatography on silica using increasing concentrations of methanol in dichloromethane as eluent then on alumina (neutral) using 10% methanol in dichloromethane as eluent to give 4chloro-7-{3-[4-(2-fluoroethyl)piperazin-1-yl]propoxy}-6-methoxyquinazoline (696 mg, 48%) as a colourless solid; NMR Spectrum:(CDCl$_3$) 2.13 (quintet, 2H), 2.55 (m, 10H), 2.67 & 2.76 (dt, 2), 4.06 (s, 3H), 4.30 (t, 2H), 4.53 & 4.64 (dt, 2H), 7.36 (s, 1H), 7.38 (s, 1H), 8.86 (s, 1H).

3-[4-(2-fluoroethyl)piperazin-1-yl]propan-1-ol used as starting material was prepared as follows:

Potassium carbonate (1.85 g, 13.4 mmol) and 1-bromo-2-fluoroethane (440 μl, 5.9 mmol) were added to a solution of tert-butyl-1-piperazinecarboxylate (1 g, 5.4 mmol) in acetonitrile (12 ml). The reaction mixture was stirred at 65?C for 3.5 hours after which time more 1-bromo-2-fluoroethane (160 μl, 2.1 mmol) was added. The reaction was heated for a further 3 hours then filtered to remove the inorganic solids. The filtrate was concentrated and the crude product was purified using column chromatography eluting with ethyl acetate to give 4-(2-fluoroethyl)-piperazine-1-carboxylic acid tert-butyl ester (714 mg, 57%). NMR Spectrum: (CDCl$_3$) 1.46 (s, 9H); 2.50 (t, 4H); 2.70 (dt, 2H); 3.45 (t, 4H); 3.45 (t, 4H); 4.57 (dt, 2H) MS-ESI: 233 [MH]$^+$ Trifluoroacetic acid (3 ml, 17.5 mmol) was added to a solution of 4-(2-fluoroethyl)-piperazine-1-carboxylic acid tert-butyl ester (350 mg, 1.5 mmol) in methylene chloride (12 ml). The reaction mixture was stirred at ambient temperature for 40 minutes, before the solvent was evaporated under high vacuum. The residue was azeotroped with toluene to give 1-(2-fluoroethyl)-piperazine diTFA salt (377 mg, 96%). NMR Spectrum: (DMSOd$_6$) 3.06 (s, 4H); 3.17 (m, 2H); 3.25 (m, 4H); 4.67 (dt, 2H); 9.03 (br s, 1H). MS-EI: 133 [MH]$^+$ 3-Bromopropan-1-ol (581 mg, 4.18 mmol) and potassium carbonate (2.88 g, 20.9 mmol) were added to a solution of 1-(2-fluoroethyl)-piperazine diTFA salt (1.5 g, 4.18 mmol) in acetonitrile (11 ml). The reaction mixture was stirred at 85° C. for 4 hours and then loaded directly onto a column and eluted with a mixture of methanol in methylene chloride (7/93) to give 3-[4-(2-fluoroethyl)piperazin-1-yl]propan-1-ol (721 mg, 91%). NMR Spectrum: (CDCl$_3$) 1.72 (m, 2H); 2.58(m, 8H) 2.62 (m, 2H); 2.73 (t, 2H); 3.79 (t, 2H); 4.55 (dt, 2H). MS-EI: 191 [MH]$^+$

EXAMPLE 23

N-[5-chloro-7-(4-methoxybut-1-yn-1-yl)-1,3-benzo-dioxol-4-yl]-6-methoxy-7-[3-(4-methoxypiperidin-1-yl)propoxy]quinazolin-4-amine This was prepared using the method described in example 13 using N-[5-chloro-7-(4-methoxybut-1-yn-1-yl)-1,3-benzodioxol-4-yl]-7-(3-chloropropoxy)-6-methoxyquinazolin-4-amine (200 mg, 0.40 mmol) and 4-methoxypiperidine (246 mg, 2.14 mmol) in 2-methoxyethanol (4 ml). The crude product was purified by column chromatography on silica using increasing concentrations of methanolic ammonia in dichloromethane as eluent. There was thus obtained the title compound (184 mg, 80%) as a pale yellow solid; NMR Spectrum: (CDCl$_3$) 1.55-1.70 (m, 2H), 1.85-2.00 (m, 2H), 2.10 (quintet, 2H), 2.24 (m, 2H), 2.56 (t, 2H), 2.72 (t, 2), 2.78 (m, 2H), 3.24 (m, 1H), 3.34 (s, 3H), 3.42 (s, 3H), 3.62 (t, 2H), 3.98 (s, 3H), 4.24 (t, 2H), 6.05 (s, 2H), 6.90 (s, 1H), 7.04 (s, 1H), 7.09 (s, 1H), 7.28 (s, 1H), 8.61 (s, 1H); Mass Spectrum: M+H$^+$ 583/585.

4-Methoxypiperidine was prepared as described in *J. Med. Chem.* 1992, 35(10), 1722-34.

EXAMPLE 24

N'-(3-{6-chloro-7-[(6,7-dimethoxyquinazolin-4-yl)amino]-1,3-benzodioxol-4-yl}prop-2-yn-1-yl)-N,N-dimethylurea This was prepared using the method described in example 4 using 4-chloro-6,7-dimethoxyquinazoline (160 mg, 0.71 mmol), N'-[3-(7-amino-6-chloro-1,3-benzodioxol-4-yl)prop-2-yn-1-yl]-N,N-dimethylurea (232 mg, 0.78 mmol) and sodium bis(trimethylsilyl)amide (1.0M in THF, 1.5 ml) in DMF (3 ml). The crude product was purified by column chromatography on silica using increasing concentrations of methanol in dichloromethane as eluent. There was thus obtained the title compound (265 mg, 77%) as a pale brown solid; NMR Spectrum:DMSOd$_6$) 2.81 (s, 6H), 3.91 (s, 3H), 3.92 (s, 3H), 4.09 (d, 2H), 6.14 (s, 2H), 6.82 (t, 1H), 7.07 (s, 1H), 7.18 (s, 1H), 7.82 (s, 1H), 8.33 (s, 1H), 9.47 (s, 1H); Mass Spectrum: M+H$^+$ 484/486.

The starting materials were prepared as follows:
a) N'-[3-(7-amino-6-chloro-1,3-benzodioxol-4-yl)prop-2-yn-1-yl]-N,N-dimethylurea was prepared as described in example 16 b) 4-chloro-6,7-dimethoxyquinazoline was prepared as described in EP 566226 A1.

EXAMPLE 25

4-{3-[(4-{[5-chloro-7-(4-methoxybut-1-yn-1-yl)-1,3-benzodioxol-4-yl]amino}-6-methoxyquinazolin-7-yl)oxy]propyl}-1-methylpiperazin-2-one This was prepared by the method described in example 13 using N-[5-Chloro-7-(4-methoxybut-1-yn-1-yl)-1,3-benzodioxol-4-yl]-7-(3-chloropropoxy)-6-methoxyquinazolin-4-amine (200 mg, 0.40 mmol) and 1-methylpiperazin-2-one (226 mg, 1.98 mmol) in 2-methoxyethanol (4 ml). The crude product was purified by column chromatography on silica using increasing concentrations of methanol in dichloromethane as eluent. There was thus obtained the title compound (166 mg, 72%) as a pale brown solid; NMR Spectrum: (CDCl$_3$) 2.10 (quintet, 2H), 2.61 (t,2H), 2.72 (m, 4H), 2.95 (s, 3H), 3.15 (s, 2H), 3.31 (t, 2H), 3.40 (s, 3H), 3.61 (t, 2H), 3.98 (s, 3H), 4.25 (t, 2H), 6.06 (s, 2H), 6.96 (s, 1H), 7.03 (s, 1H), 7.12 (s, 1H), 7.26 (s, 1H), 8.60 (s, 1H); Mass Spectrum: M+H$^+$ 582/584.

1-Methylpiperazin-2-one was prepared as described in WO 9727188

EXAMPLE 26

1-[3-(6-chloro-7-{[6-methoxy-7-(3-morpholin-4-ylpropoxy)quinazolin-4-yl]amino}-1,3-benzodioxol-4-yl)prop-2-yn-1-yl]pyrrolidin-2-one N-(5-chloro-7-iodo-1,3-benzodioxol-4-yl)-6-methoxy-7-(3-morpholin-4ylpropoxy)quinazolin-4-amine (250 mg, 0.42 mmol) and 1-prop-2-yn-1-ylpyrrolidin-2-one (103 mg, 0.84 mmol) in ethyl acetate (8 ml) were cooled in ice-methanol, under an atmosphere of nitrogen, then treated with bis(triphenylphosphine) palladium(II) dichloride (30 mg, 10 mol %) followed by copper(I) iodide (8 mg, 10 mol %) and diisopropylamine (84 mg, 0.84 mmol). The reaction was allowed to warm to room temperature and stirred 46 hr. then filtered through Celite and evaporated. The residue was partitioned between dichloromethane and dilute aqueous ammonium chloride solution, the organic layer separated, dried over magnesium sulphate and evaporated then purified by chromatography on silica using increasing concentrations of methanol in dichloromethane as eluent to give the title compound (98 mg, 40%) as a pale brown solid; NMR Spectrum: (CDCl$_3$) 2.12 (m, 4H), 2.44 (t, 2H), 2.49 (m, 4H), 2.57 (t, 2H), 3.55 (t, 2H), 3.72 (m, 4H), 4.00 (s,3H), 4.25 (t,2H), 4.35 (s,2H), 6.08 (s,2H), 7.03 (s,1H), 7.10 (s, 1H), 7.17 (s, 1H), 7.30 (s, 1H), 8.60 (s, 1H); Mass Spectrum: M+H$^+$ 594/596.

The starting materials were prepared as follows:

a) 1-Prop-2-yn-1-ylpyrrolidin-2-one was prepared as described in *J. Med. Chem.* 1990, 33(2), 580-4.

b) N-(5-chloro-7-iodo-1,3-benzodioxol-4-yl)-6-methoxy-7-(3-morpholin-4ylpropoxy)quinazolin-4-amine was prepared as follows 5-Chloro-7-iodo-1,3-benzodioxol-4-amine was prepared as described in example 2.

N-(5-chloro-7-iodo-1,3-benzodioxol-4-yl)-6-methoxy-7-(3-morpholin-4-ylpropoxy)quinazolin-4-amine was prepared using the method described in example 4 using 4-chloro-6-methoxy-7-(3-morpholin-4-ylpropoxy)quinazoline (1.0 g, 2.96 mmol), 5-chloro-7-iodo-1,3-benzodioxol-4-amine (0.97 g, 3.26 mmol) and sodium bis(trimethylsilyl)amide (1.0M in THF, 6.2 ml) in DMF (15 ml). The crude product was obtained as a pale bown solid (1.71 g, 97%) by quenching the reaction mixture with dilute aqueous ammonium chloride solution; Mass Spectrum: M+H$^+$ 599/601.

EXAMPLE 27

N-[3-(6-chloro-7-{[6-methoxy-7-(3-morpholin-4-ylpropoxy)quinazolin-4-yl]amino}-1,3-benzodioxol-4-yl)prop-2-yn-1-yl]-N,N',N'-trimethylurea This was prepared using the method described in example 26 but it was carried out at room temperature over 3 hr using N-(5-chloro-7-iodo-1,3-benzodioxol-4-yl)-6-methoxy-7-(3-morpholin-4ylpropoxy)quinazolin-4-amine (310 mg, 0.52 mmol), N,N,N'-trimethyl-N'-prop-2-yn-1-ylurea (145 mg, 1.04 mmol), bis(triphenylphosphine) palladium(II) dichloride (36 mg, 10 mol %), copper(I) iodide (10 mg, 10 mol %) and diisopropylamine (105 mg, 1.04 mmol) in ethyl acetate (10 ml). The crude product was purified by column chromatography on silica using increasing concentrations of methanol in dichloromethane as eluent to give the title compound (218 mg, 69%) as a pale brown solid; NMR Spectrum: (CDCl$_3$) 2;11 (quintet, 2H), 2.48 (m, 4H), 2.56 (t, 2H), 2.87 (s, 6H), 2.92 (s, 3H), 3.72 (m, 4H), 4.00 (s, 3H), 4.15 (s, 2H), 4.25 (t, 2H), 6.06 (s, 2H), 7.03 (s, 1H), 7.10-7.30 (s(broad), 1H), 7.20 (s, 1H), 7.31 (s, 1H), 8.60 (s, 1H); Mass Spectrum: M+H$^+$ 611/613.

The N,N,N'-trimethyl-N'-prop-2-yn-1-ylurea used as starting material was prepared as follows:

N-Methylpropargylamine (600 mg, 8.70 mmol) and triethylamine (878 mg, 8.68 mmol) in dichloromethane (10 ml) were added dropwise, with ice cooling, to a stirred solution of 4-nitrophenyl chloroformate (1.75 g, 8.68 mmol) in dichloromethane (10 ml). The reaction was stirred at ice temperature for 3 hr. then the resulting solution purified by column chromatography on silica using 25% ethyl acetate in isohexane as eluent. Thus was obtained 4-nitrophenyl methyl (prop-2-yn-1-yl)carbamate (1.80 g, 89%) as a colourless oil. Dimethylamine (3.0 ml of a 2.0M solution in THF, 6.0 mmol) and 4-nitrophenyl methyl(prop-2-yn-1-yl)carbamate (600 mg, 2.56 mmol), in dichloromethane (7 ml) were stirred at room temperature for 6 days then the reaction solution purified by chromatography on silica using ethyl acetate as eluent to give N,N,N'-trimethyl-N'-prop-2-yn-1-ylurea (164 mg, 46%) as a colourless oil.

EXAMPLE 28

4-{3-[(4-{[5-Chloro-7-(3-methoxyprop-1-yn-1-yl)-1,3-benzodioxol-4-yl]amino}-6-methoxyquinazolin-7-yl)oxy]propyl}-1-methylpiperazin-2-one This was prepared using the method described in example 13 using N-[5-chloro-7-(3-methoxyprop-1-yn-1-yl)-1,3-benzodioxol-4-yl]-7-(3-chloropropoxy)-6-methoxyquinazolin-4-amine (250 mg, 0.51 mmol) and 1-methylpiperazin-2-one (290 mg, 2.54 mmol) in 2-methoxyethanol (4 ml). The crude product was purified by column chromatography on silica using increasing concentrations of methanol in dichloromethane as eluent. There was thus obtained the title compound (229 mg, 79%) as a pale brown solid; NMR Spectrum: ()MSOd$_6$) 1.98 (quintet, 2H), 2.56 (t, 2H), 2.69 (t, 2H), 2.82 (s, 3H), 3.01 (s, 2H), 3.30 (t, 2H), 3.35 (s, 3H), 3.93 (s, 3H), 4.19 (t, 2H), 4.37 (s, 2H), 6.16 (s, 2H), 7.15 (s, 1H), 7.18 (s, 1H), 7.81 (s, 1H), 8.32 (s, 1H), 9.52 (s, 1H); Mass Spectrum: M+H$^+$ 566/568.

The starting materials were prepared as follows:
a) 1-Methylpiperazin-2-one was prepared as described in WO 9727188
b) N-[5-chloro-7-(3-methoxyprop-1-yn-1-yl)-1,3-benzodioxol-4-yl]-7-(3-chloropropoxy)-6-methoxyquinazolin-4-amine was prepared as described in example 77.

EXAMPLE 29

N-[5-Chloro-7-(3-methoxyprop-1-yn-1-yl)-1,3-benzodioxol-4-yl]-7-(3-chloropropoxy)-6-methoxyquinazolin-4-amine This was prepared using the method described in example 4 using 4-chloro-7-(3-chloropropoxy)-6-methoxyquinazoline (400 mg, 1.39 mmol), 5-chloro-7-(3-methoxyprop-1-yn-1-yl)-1,3-benzodioxol-4-amine (367 mg, 1.53 mmol) and sodium bis(trimethylsilyl)amide (1.0M in THF, 2.90 ml) in DMF (3 ml). The crude product was purified by column chromatography on silica using ethyl acetate as eluent. There was thus obtained the title compound (454 mg, 66%) as a pale yellow solid; NMR Spectrum:(CDCl$_3$) 2.39 (quintet, 2H), 3.46 (s, 3H), 3.79 (t, 2H), 3.98 (s, 3H), 4.33 (t, 2H), 4.35 (s, 2H), 6.07 (s, 2H), 6.94 (s, 1H), 7.07 (s, 1H), 7.10 (s, 1H), 7.29 (s, 1H), 8.63 (s, 1H); Mass Spectrum: M+H$^+$ 490.

The starting materials were prepared as follows
a) 5-chloro-7-(3-methoxyprop-1-yn-1-yl)-1,3-benzodioxol-4-amine was prepared as described in example 2
b) 4-chloro-7-(3-chloropropoxy)-6-methoxyquinazoline was prepared as described in example 13.

EXAMPLE 30

N'-{3-[6-Chloro-7-({6-methoxy-7-[3-(4-methyl-3-oxopiperazin-1-yl)propoxy]quinazolin-4-yl}amino)-1,3-benzodioxol-4-yl]prop-2-yn-1-yl}-N,N-dimethylurea 4-[3-({4-[(5-Chloro-7-iodo-1,3-benzodioxol-4-yl)amino]-6-methoxyquinazolin-7-yl}oxy)propyl]-1-methylpiperazin-2-one (250 mg, 0.40 mmol) and N,N-dimethyl-N'-prop-2-yn-1-ylurea (60 mg, 0.48 mmol) in ethyl acetate (8 ml) stirred at room temperature, under an atmosphere of nitrogen, and treated with bis(triphenylphosphine)palladium (II) dichloride (28 mg, 10 mol %) followed by copper(I) iodide (8 mg, 10 mol %) and diisopropylamine (81 mg, 0.80 mmol). The reaction was stirred 6 hr then DMF (3 ml) added and reaction heated at 60° for 3 hr. A further 60 mg N,N-dimethyl-N'-prop-2-yn-1-ylurea was added and heating continued for 3 hr. The mixture was then evaporated and the residue partitioned between water and dichloromethane. The organic layer was separated, washed with brine, dried over magnesium sulphate and evaporated to an orange oil. This was purified by column chromatography on silica using increasing concentrations of methanol in dichloromethane as eluent to give the title compound (164 mg, 66%) as a pale brown solid; NMR Spectrum:(DMSOd$_6$) 1.99 (quintet, 2H), 2.54 (t, 2H), 2.66 (t, 2H), 2.81 (s, 9H), 3.00 (s, 2H), 3.28 (t, 2H), 3.93 (s, 3H), 4.10 (d, 2H), 4.20 (t, 2H), 6.14 (s, 2H), 6.82 (t, 1H), 7.07 (s, 1H), 7.23 (s(broad), 1H), 7.85 (s, 1H), 8.40 (s(br), 1H), 9.50 (s, 1H); Mass Spectrum: M+H$^+$ 624/626.

The starting materials were prepared as follows:
a) N,N-dimethyl-N'-prop-2-yn-1-ylurea was prepared as described in example 16
b) 4-[3-({4-[(5-Chloro-7-iodo-1,3-benzodioxol-4-yl)amino]-6-methoxyquinazolin-7-yl}oxy)propyl]-1-methylpiperazin-2-one was follows 1-methylpiperazin-2-one was prepared as described in example 28.

N-(5-chloro-7-iodo-1,3-benzodioxol-4-yl)-7-(3-chloropropoxy)-6-methoxyquinazolin-4-amine was prepared as follows:

A solution of sodium bis(trimethylsilyl)amide (11 ml) in tetrahydrofuran (1.0M, 11 mmol) was added dropwise to an ice-cold solution of 4-chloro-7-(3-chloropropoxy)-6-methoxyquinazoline (1.3 g, 4.5 mmol) and 5-chloro-7-iodo-1,3-benzodioxol-4amine (1.5 g, 5 mmol) in dimethylformamide (15 ml). The mixture was allowed to warm to room temperature over 1.5 hours. A saturated solution of ammonium chloride was added and the mixture was partitioned between water and ethyl acetate. The organic layer was separated, dried over magnesium sulfate and evaporated under reduced pressure. Flash chromatography on silica eluting with a mixture of 30-70% ethyl acetate in hexane gave the product as a solid (2.17 g, 88%). NMR Spectrum: (DMSOd6) 2.38 (m, 2H), 3.95 (t, 2H), 4.06 (s, 3H), 4.38 (t, 2H), 6.26 (s, 2H), 7.34 (s, 1H), 7.53 (s, 1H), 7.95 (s, 1H), 8.43 (s, 1H), 9.60 (s, 1H). Mass Spectrum: M+H$^+$ 548 and M+H$^-$ 546.

5-chloro-7-iodo-1,3-benzodioxol-4amine was prepared as described in example 2.

4-[3-({4-[(5-Chloro-7-iodo-1,3-benzodioxol-4-yl)amino]-6-methoxyquinazolin-7-yl}oxy)propyl]-1-methylpiperazin-2-one was prepared by the method described in example 13 using N-(5-chloro-7-iodo-1,3-benzodioxol-4-yl)-7-(3-chloropropoxy)-6-methoxyquinazolin-4-amine (800 mg, 1.46 mmol) and 1-methylpiperazin-2-one (830 mg, 7.28 mmol) in 2-methoxyethanol (12 ml). The crude product was purified by column chromatography on silica using increasing concentrations of methanol in dichloromethane as eluent. There was thus obtained the title compound (752 mg, 82%) as a pale orange solid; NMR Spectrum:(CDCl$_3$) 2.10 (quintet, 2H), 2.62 (t, 2H), 2.72 (t, 2H), 2.95 (s, 3H), 3.16 (s, 2H), 3.32 (t, 2H), 3.98 (s, 3H), 4.24 (t, 2H), 6.07 (s, 2H), 7.02 (s, 1H), 7.15 (s, 1H), 7.27 (s, 1H), 7.31 (s, 1H), 8.60 (s, 1H); Mass Spectrum: M+H$^+$ 626/628.

EXAMPLE 31

1-{3-[(4-{[5-Chloro-7-(3-methoxyprop-1-yn-1-yl)-1,3-benzodioxol-4-yl]amino}-6-methoxyquinazolin-7-yl)oxy]propyl}-4-methylpiperazin-2-one This was prepared by the method described in example 4 using 1-{3-[(4-chloro-6-methoxyquinazolin-7-yl)oxy]propyl}-4-methylpiperazin-2-one (200 mg, 0.55 mmol), 5-chloro-7-(3-methoxyprop-1-yn-1-yl)-1,3-benzodioxol-4-amine (145 mg, 0.60 mmol) and sodium bis(trimethylsilyl)amide (1.0M in THF, 1.15 ml) in DMF (3 ml). The crude product was purified by column chromatography on silica using ethyl acetate as eluent. There was thus obtained the title compound (237 mg, 76%) as a pale yellow solid; NMR Spectrum:(DMSOd$_6$) 2.05 (quintet, 2H), 2.20 (s, 3H), 2.58 (t, 2H), 2.92 (s, 2H), 3.33 (t, 2H), 3.36 (s, 3H), 3.48 (t, 2H), 3.94 (s, 3H), 4.13 (t, 2H), 4.37 (s, 2H), 6.15 (s, 2H), 7.15 (s, 2H), 7.82 (s, 1H), 8.34 (s, 1H), 9.51 (s, 1H); Mass Spectrum: M+H$^+$ 568/570.

The starting materials were prepared as follows:
a) 5-chloro-7-(3-methoxyprop-1-yn-1-yl)-1,3-benzodioxol-4-amine was prepared as described in example 2
b) 1-{3-[(4-chloro-6-methoxyquinazolin-7-yl)oxy]propyl}-4-methylpiperazin-2-one was prepared as follows:
(3-Bromopropoxy)-tert-butyldimethylsilane (2.53 g, 0.01 mol) in THF (10 ml) was added dropwise at room temperature to a stirred mixture of tert-butyl 3-oxopiperazine-1-carboxylate (2.0 g, 0.01 mol), powdered potassium hydroxide (0.67 g, 0.012 mol) and tetra-n-butylammonium bromide (0.63 g, 0.002 mol) in THF (15 ml). The reaction was stirred 2 hr then filtered and evaporated. The residue was purified by column chromatography on silica using ethyl acetate as eluent to give tert-butyl 4-(3-{[tert-butyl(dimethyl)silyl]oxy}propyl)-3-oxopiperazine-1-carboxylate (2.98 g, 80%) as a colourless oil; NMR Spectrum:(CDCl$_3$) 0.02 (s, 6H), 0.87 (s, 9H), 1.43 (s, 9H), 1.76 (quintet, 2H), 3.35 (m, 2H), 3.45 (t, 2H), 3.60 (m, 4H), 4.03 (s, 2H)

Tert-butyl 4-(3-{[tert-butyl(dimethyl)silyl]oxy}propyl)-3-oxopiperazine-1-carboxylate (2.90 g, 7.8 mmol) in 1,4-dioxane (10 ml) was treated at room temperature with a 4N solution of HCl in 1,4-dioxane (15 ml) and the resulting solution stirred 4 hr then evaporated. The residue was taken up in a 10% methanol in dichloromethane solution (30 ml) and basified with a 7N solution of ammonia in methanol then filtered and the filtrate evaporated. The residue was purified by column chromatography on silica using increasing concentrations of methanolic ammonia in dichloromethane as eluent to give 1-(3-hydroxypropyl)piperazin-2-one (708 mg, 57%) as a colourless oil; NMR Soectrum:(CDCl$_3$) 1.77 (quintet, 2H), 2.72 (s(br), 2H), 3.09 (t, 2H), 3.32 (t, 2H), 3.55 (m, 6H).

1-(3-Hydroxypropyl)piperazin-2-one (700 mg, 4.43 mmol) in formic acid (10 ml) and 37/40% aqueous formaldehyde solution (5 ml) was stirred and heated at 95° for 2 hr then the resulting solution evaporated in vacuo. The residue was taken up in 5% methanol in dichloromethane (20 ml), basified with a 7N solution of ammonia in methanol and stirred 4.5 hr at room temperature. The mixture was filtered and the filtrate purified by column chromatography on silica using increasing concentrations of methanolic ammonia in dichloromethane as eluent to give 1-(3-hydroxypropyl)-4-methylpiperazin-2-one (710 mg, 93%) as a colourless oil; NMR Spectrum:(CDCl$_3$) 1.73 (quintet, 2H), 2.34 (s, 3H), 2.66 (t, 2H), 3.13 (s, 2H), 3.33 (t, 2H), 3.53 (m, 4H), 3.80 (s(broad, 1H).

4-chloro-6-methoxyquinazolin-7-ol was prepared as described in WO0020402.

Di-tert-butylazodicarboxylate (393 mg, 1.71 mmol) was added portionwise, at room temperature, to a stirred suspension of 4-chloro-6-methoxyquinazolin-7-ol, (300 mg, 1.42 mmol), 1-(3-hydroxypropyl)-4-methylpiperazin-2-one (270 mg, 1.57 mmol) and triphenylphosphine (522 mg, 1.99 mmol) in dichloromethane (10 ml). The reaction was stirred 1 hr before adding further di-tert-butylazodicarboxylate (393 mg) and triphenylphosphine (522 mg) and stirring for a further 1 hr. The resulting reaction solution was purified by column chromatography on silica using increasing concentrations of methanol in dichloromethane as eluent to give 1-{3-[(4-chloro-6-methoxyquinazolin-7-yl)oxy]propyl}-4-methylpiperazin-2-one (260 mg, 50%) as a pale yellow solid; NMR Spectrum:(DMSOd$_6$) 2.06 (quintet, 2H), 2.20 (s, 3H), 2.60 (t, 2H), 2.91 (s, 2H), 3.33 (t, 2H), 3.48 (t, 2H), 4.00 (s, 3H), 4.22 (t, 2H), 7.40 (s, 1H), 7.41 (s, 1H), 8.87 (s, 1H); Mass Spectrum: M+H$^+$ 365/367.

EXAMPLE 32

1-{3-[(4-{[5-Chloro-7-(4-methoxybut-1-yn-1-yl)-1,3-benzodioxol-4-yl]amino}-6-methoxyquinazolin-7-yl)oxy]propyl}-4-methylpiperazin-2-one This was prepared by the method described in example 4 but using 1-{3-[(4-chloro-6-methoxyquinazolin-7-yl)oxy]propyl}-4-methylpiperazin-2-one (140 mg, 0.38 mmol), 5-chloro-7-(4-methoxybut-1-yn-1-yl)-1,3-benzodioxol-4-amine (107 mg, 0.42 mmol) and sodium bis(trimethylsilyl)amide (1.0M in THF, 0.81 ml) in DMF (2 ml). The crude product was purified by column chromatography on silica using increasing concentrations of methanol in dichloromethane as eluent. There was thus obtained the title compound (150 mg, 67%) as a pale orange solid; NMR Spectrum: (DMSOd$_6$) 2.04 (quintet, 2H), 2.20 (s, 3H), 2.59 (t, 2H), 2.72 (t, 2H), 2.91 (s, 2H), 3.30 (s, 3H), 3.32 (t, 2H), 3.47 (t, 2H), 3.53 (t, 2H), 3.94 (s, 3H), 4.14 (t, 2H), 6.14 (s, 2H), 7.07 (s, 1H), 7.15 (s, 1H), 7.83 (s, 1H), 8.32 (s, 1H), 9.49 (s, 1H); Mass Spectrum: M+H$^+$ 582/584.

The starting materials were prepared as follows:
a) 5-chloro-7-(4-methoxybut-1-yn-1-yl)-1,3-benzodioxol-4-amine was prepared as described in example 7
b) 1-{3-[(4-chloro-6-methoxyquinazolin-7-yl)oxy]propyl}-4-methylpiperazin-2-one was prepared as described in example 31.

EXAMPLE 33

N'-{3-[6-Chloro-7-({6-methoxy-7-[3-(4-methyl-2-oxopiperazin-1-yl)propoxy]quinazolin-4-yl}amino)-1,3-benzodioxol-4-yl]prop-2-yn-1-yl}-N,N-dimethylurea This was prepared by the method described in example 4 but using 1-{3-[(4-chloro-6-methoxyquinazolin-7-yl)oxy]propyl}-4-methylpiperazin-2-one (140 mg, 0.38 mmol), N'-[3-(7-amino-6-chloro-1,3-benzodioxol-4-yl)prop-2-yn-1-yl]-N,N-dimethylurea (125 mg, 0.42 mmol) and sodium bis(trimethylsilyl)amide (1.0M in THF, 0.81 ml) in DMF (2 ml). The crude product was purified by column chromatography on silica using increasing concentrations of methanolic ammonia in dichloromethane as eluent. There was thus obtained the title compound (193 mg, 81%) as a pale yellow solid; NMR Spectrum:(DMSOd$_6$) 2.03 (quintet, 2H), 2.20 (s, 3H), 2.59 (t, 2H), 2.81 (s, 6H), 2.91 (s, 2H), 3.33 (t, 2H), 3.48 (t, 2H), 3.94 (s, 3H), 4.10 (d, 2H), 4.14 (t, 2H), 6.14 (s, 2H), 6.82 (t, 1H), 7.07 (s, 1H), 7.16 (s, 1H), 7.82 (s, 1H), 8.32 (s, 1H), 9.49 (s, 1H); Mass Spectrum: M+H$^+$ 624/626.

The starting materials were prepared as follows:
a) 1-{3-[(4-chloro-6-methoxyquinazolin-7-yl)oxy]propyl}-4-methylpiperazin-2-one was prepared as described in example 31.
b) N'-[3-(7-amino-6-chloro-1,3-benzodioxol-4-yl)prop-2-yn-1-yl]-N,N-dimethylurea was prepared as described in example 16.

EXAMPLE 34

N-[5-Chloro-7-(4-methoxypent-1-yn-1-yl)-1,3-benzodioxol-4-yl]-6-methoxy-7-(3-morpholin-4-ylpropoxy)quinazolin-4-amine This was prepared by the method described in example 4 but using 4-chloro-6-methoxy-7-(3-morpholin-4-ylpropoxy)quinazoline (200 mg, 0.59 mmol), 5-chloro-7-(4-methoxypent-1-yn-1-yl)-1,3-benzodioxole-4-amine (174 mg, 0.65 mmol) and sodium bis(trimethylsilyl)amide (1.0M in THF, 1.24 ml) in DMF (3 ml). The crude product was purified by column chromatography on silica using increasing concentrations of methanol in dichloromethane as eluent. There was thus obtained the title compound (216 mg, 64%) as an off-white solid; NMR Spectrum:(CDCl$_3$) 1.33 (d, 3H), 2.12 (quintet, 2H), 2.47 (m, 4H), 2.55 (m, 3H), 2.74 (dd, 1H), 3.40 (s, 3H), 3.58 (m, 1H), 3.71 (m, 4H), 3.98 (s, 3H), 4.25 (t, 2H), 6.07 (s, 2H), 6.90 (s, 1H), 7.03 (s, 1H), 7.09 (s, 1H), 7.30 (s, 1H ), 8.62 (s, 1H); Mass Spectrum: M+H$^+$ 569/571.

The 5-chloro-7-(4-methoxypent-1-yn-1-yl)-1,3-benzodioxol-4-amine used as starting material was prepared as follows:

4-Pentyn-2-ol (3.2 g, 0.038 mol) in DMF (15 ml) was added dropwise, under an atmosphere of nitrogen, to a stirred suspension of sodium hydride (1.7 g of a 60% dispersion in oil, 0.042 mol) in DMF (15 ml) under ice-water cooling. The mixture was stirred at ice temperature for a further 1 hr then treated dropwise with iodomethane (3.8 ml, 0.061 mol). The reaction was allowed to warn to room temperature and stirred for 4 hr before quenching in water (100 ml) and extracting with diethyl ether. The extract was washed with water (3×) and saturated brine, dried over magnesium sulphate and filtered. The filtrate was distilled at atmospheric pressure to remove diethyl ether and leave crude 4-methoxypent-1-yne (2.5 g) as a colourless oil; NMR Spectrum:(CDCl$_3$) 1.25 (d, 3H), 2.00 (t, 1H), 2.33 (dd, 1H), 2.46 (dd, 1H), 3.36 (s, 3H), 3.50 (m, 1H).

5-chloro-7-iodo-1,3-benzodioxol-4-amine was prepared as described in example 2.

5-chloro-7-iodo-1,3-benzodioxol-4-amine (600 mg, 2.02 mmol) and 4-methoxypent-1-yne (500 mg, 5.10 mmol) in ethyl acetate (8 ml) were cooled in ice-methanol, under an atmosphere of nitrogen, then treated with bis(triphenylphosphine)palladium(II) dichloride (141 mg, 10 mol %) followed by copper(I) iodide (38 mg, 10 mol %) and diisopropylamine (407 mg, 5.69 mmol). The reaction was allowed to warn to room temperature and stirred 90 min then filtered through Celite. The filtrate was purified by column chromatography on silica using a 1:1 mixture of methyl tert-butyl ether and iso-hexane as eluent to give 5-chloro-7-(4-methoxypent-1-yn-1-yl)-1,3-benzodioxol-4-amine (495 mg, 92%) as a dark brown oil;

NMR Spectrum:(CDCl$_3$) 1.30 (d, 3H), 2.50 (dd, 1H), 2.71 (dd, 1H), 3.38 (s, 3H), 3.54 (m, 1H), 3.98 (s, 2H), 6.00 (s, 2H), 6.84 9s, 1H).

EXAMPLE 35

4-{3-[(4-{[5-Chloro-7-(4-methoxypent-1-yn-1-yl)-1,3-benzodioxol-4-yl]amino}-6-methoxyquinazolin-7-yl)oxy]propyl}-1-methylpiperazin-2-one 4-[3-({4-[(5-Chloro-7-iodo-1,3-benzodioxol-4-yl) amino]-6-methoxyquinazolin-7-yl}oxy)propyl]-1-methylpiperazin-2-one (250 mg, 0.40 mmol) and 4-methoxypent-1-yne (120 mg, 1.2 mmol) in ethyl acetate (8 ml) stirred at room temperature, under an atmosphere of nitrogen, and treated with bis(triphenylphosphine)palladium(II) dichloride (28 mg, 10 mol %) followed by copper(I) iodide (8 mg, 10 mol %) and diisopropylamine (82 mg, 0.81 mmol). The reaction was stirred 2 hr then DMF (3 ml) added followed by a further 120 mg 4-methoxypent-1-yne. The mixture was stirred for 1 hr then evaporated and the residue partitioned between water and dichloromethane. The organic layer was separated, washed with brine, dried over magnesium sulphate and evaporated to an orange oil. Purified by column chromatography on silica using increasing concentrations of methanol in dichloromethane as eluent to give the title compound (174 mg, 73%) as a pale yellow solid; NMR Spectrum:(DMSOd$_6$) 1.23 (d, 3H), 1.98 (quintet, 2H), 2.54 (t, 2H), 2.61 (dd, 1H), 2.65-2.75 (m, 3H), 2.82 (s, 3H), 3.01 (s, 2H), 3.27 (t, 2H), 3.30 (s, 3H), 3.53 (m, 1H), 3.92 (s, 3H), 4.18 (t, 2H), 6.13 (s, 2H), 7.06 (s, 1H), 7.22 (s(broad), 1H), 7.84 (s, 1H), 8.38 (s(broad), 1H), 9.49 (s, 1H); Mass Spectrum: M+H$^+$ 596/598.

The starting materials were prepared as follows:
a) 4-[3-({4-[(5-Chloro-7-iodo-1,3-benzodioxol-4-yl) amino]-6-methoxyquinazolin-7-yl}oxy)propyl]-1-methylpiperazin-2-one was prepared as described in example 30
b) 4-methoxypent-1-yne was prepared as described in example 34.

EXAMPLE 36

1-{3-[(4-{[5-Chloro-7-(pyridin-2-ylethynyl)-1,3-benzodioxol-4-yl]amino}-6-methoxyquinazolin-7-yl)oxy]propyl}-4-methylpiperazin-2-one This was prepared by the method described in example 4 but using 1-{3-[(4-chloro-6-methoxyquinazolin-7-yl)oxy]propyl}-4-methylpiperazin-2-one (137 mg, 0.37 mmol), 5-chloro-7-(pyridin-2-ylethynyl)-1,3-benzodioxol-4-amine (113 mg, 0.41 mmol) and sodium bis(trimethylsilyl)amide (1.0M in THF, 0.8 ml) in DMF (2 ml). The crude product was purified by column chromatography on silica using 10% methanol in dichloromethane as eluent. There was thus obtained the title compound (181 mg, 80%) as a pale yellow solid; NMR Spectrum:(DMSOd$_6$) 2.21 (quintet, 2H), 2.31 (s, 3H), 2.63 (t, 2H), 3.09 (s, 2H), 3.38 (t, 2H), 3.61 (t, 2H), 3.97 (s, 3H), 4.20 (t, 2H), 6.08 (s, 2H), 7.18 (d, 2H), 7.25 (m, 3H), 7.54 (d, 1H), 7.70 (t, 1H), 8.62 (m, 2H); Mass Spectrum: M+H$^+$ 601/603.

The starting materials were prepared as follows:
a) 1-{3-[(4-chloro-6-methoxyquinazolin-7-yl)oxy]propyl}-4-methylpiperazin-2-one was prepared as described in example 31.
b) 5-chloro-7-(pyridin-2-ylethynyl)-1,3-benzodioxol-4-amine was prepared as described in example 52.

EXAMPLE 37

N'-{3-[6-Chloro-7-({7-[3-(cis-2,6-dimethylmorpholin-4-yl)propoxy]-6-methoxyquinazolin-4-yl}amino)-1,3-benzodioxol-4-yl]prop-2-yn-1-yl}-N, N-dimethylurea N-(5-Chloro-7-iodo-1,3-benzodioxol-4-yl)-7-[3-(cis-2,6-dimethylmorpholin-4-yl)propoxy]-6-methoxyquinazolin-4-amine (250 mg, 0.40 mmol) and N,N-dimethyl-N'-prop-2-yn-1-ylurea (100 mg, 0.79 mmol) in ethyl acetate (8 ml) stirred at room temperature, under an atmosphere of nitrogen, and treated with bis(triphenylphosphine)palladium(II) dichloride (28 mg, 10 mol %) followed by copper(I) iodide (8 mg, 10 mol %) and diisopropylamnine (81 mg, 0.81 mmol). The reaction was stirred 1 hr then DMF (4 ml) added and the reaction stirred for a further 1 hr. The resulting orange solution was evaporated in vacuo then treated with dilute aqueous sodium bicarbonate solution and extracted with dichloromethane. The extract was dried over magnesium sulphate and evaporated to an orange oil. Purification was by column chromatography on silica using increasing concentrations of methanolic ammonia in dichloromethane as eluent gave the title compound (211 mg, 85%) as a pale orange solid;

NMR Spectrum:(CDCl$_3$) 1.16 (d, 6H), 1.73 (t, 2H), 2.12 (quintet, 2H), 2.52 (t, 2H), 2.75 (d, 2H), 2.93 (s, 6H), 3.68 (m, 2H), 3.99 (s, 3H), 4.23 (t, 2H), 4.29 (d, 2H), 4.67 (t, 1H), 6.06 (s, 2H), 7.00 (s, 1H), 7.20 (s(broad), 2H), 7.30 (s, 1H), 8.59 (s, 1H); Mass Spectrum: M+H$^+$ 625/627.

The starting materials were prepared as follows:
a) N,N-dimethyl-N'-prop-2-yn-1-ylurea was prepared as described in example 16.

b) N-(5-Chloro-7-iodo-1,3-benzodioxol-4-yl)-7-[3-(cis-2,6-dimethylmorpholin-4-yl)propoxy]-6-methoxyquinazolin-4-amine was prepared as follows N-(5-chloro-7-iodo-1,3-benzodioxol-4-yl)-7-(3-chloropropoxy)-6-methoxyquinazolin-4-amine was prepared as described in example 30.

N-(5-Chloro-7-iodo-1,3-benzodioxol-4-yl)-7-[3-(cis-2,6-dimethylmorpholin-4-yl)propoxy]-6-methoxyquinazolin-4-amine was prepared by the method described in example 13 using N-(5-chloro-7-iodo-1,3-benzodioxol-4-yl)-7-(3-chloropropoxy)-6-methoxyquinazolin-4-amine (600 mg, 1.09 mmol) and cis-2,6-dimethylmorpholine (1.0 g, 8.69 mmol) in 2-methoxyethanol (12 ml). The crude product was purified by column chromatography on silica using increasing concentrations of methanol in dichloromethane as eluent. There was thus obtained the title compound (332 mg, 48%) as a pale orange solid;

NMR Spectrum:(CDCl$_3$) 1.17 (d, 6H), 1.75 (t, 2H), 2.11 (quintet, 2H), 2.54 (t, 2H), 2.76 (d, 2H), 3.68 (m, 2H), 3.99 (s, 3H), 4.25 (t, 2H), 6.08 (s, 2H), 6.82 (s, 1H), 7.08 (s, 1H), 7.30 (s, 1H), 7.31 (s, 1H), 8.62 (s, 1H); Mass Spectrum: M+H$^+$ 627/629.

EXAMPLE 38

N-[5-chloro-7-(3-methoxyprop-1-1-yl)-1,3-benzodioxol-4-yl]-6-methoxy-7-[(1-methylpiperdin-4-yl)methoxy]quinazolin-4-amine A solution of sodium bis(trimethylsilyl)amide (1.7 ml) in tetrahydrofuran (1.0M, 1.7 mmol) was added dropwise to an ice-cold solution of 4-chloro-6-methoxy-7-[(1-methylpiperidin-4-yl)methoxy]quinazoline (0.25 g, 0.78 mmol) and 5-chloro-7-(3-methoxyprop-1-yn-1-yl)-1,3-benzodioxol-4-amine (0.223 g, 0.93 mmol) in dimethylformamide (5 ml). The mixture was allowed to warm to room temperature over 1.5 hours. A saturated solution of ammonium chloride was added and the mixture was partitioned between water and dichloromethane. The organic layer was separated, dried over magnesium sulfate and evaporated under reduced pressure. Flash chromatography on silica eluting with a mixture of 2-11% methanol in dichloromethane gave the product as a solid (0.092 g, 23%). NMR Spectrum: (CDCl$_3$) 1.42-1.60 (t, 2H), 1.78-2.09 (m, 5H), 2.34 (s, 3H), 2.92 (d, 2H), 3.48 (s, 3H), 4.00 (s, 3H), 4.04 (d, 2H), 4.39 (s, 2H), 6.07 (s, 2H), 6.82 (s(broad), 1H), 7.07 (s, 2H), 7.25 (s, 1H), 8.62 (s, 1H). Mass Spectrum: M+H$^+$ 525 and M+H$^-$ 523.

The starting materials were prepared as follows:
a) 4-chloro-6-methoxy-7-[(1-methylpiperidin-4-yl)methoxy]quinazoline was prepared as described in WO 0285895
b) 5-chloro-7-(3-methoxyprop-1-yn-1-yl)-1,3-benzodioxol-4-amine was prepared as described in example 2.

EXAMPLE 39

N-[5-chloro-7-(3-methoxyprop-1-yn-1-yl)-1,3-benzodioxol-4-yl]-6-methoxy-7-(2-morpholin-4-ylethoxy)quinazolin-4-amine A solution of sodium bis(trimethylsilyl)amide (1.63 ml) in tetrahydrofuran (1.0M, 1.63 mmol) was added dropwise to an ice-cold solution of 6-methoxy-7-(2-morpholin-4-ylethoxy)-4-(pentafluorophenoxy)quinazoline (0.35 g, 0.74 mmol) and 5-chloro-7-(3-methoxyprop-1-yn-1-yl)-1,3-benzodioxol-4-amine (0.213 g, 0.89 mmol) in dimethylformamide (4 ml). The mixture was allowed to warm to room temperature over 3 hours. A saturated solution of ammonium chloride was added and the mixture was partitioned between water and dichloromethane. The organic layer was separated, dried over magnesium sulfate and evaporated under reduced pressure. Flash chromatography on silica eluting with a mixture of 2-11% methanol in dichloromethane gave the product as a solid (0.029 g, 8%). NMR Spectrum: (CDCl$_3$) 2.63 (m, 4H), 2.92 (t, 2H), 3.48 (s, 3H), 3.72 (m, 4H), 4.00 (s, 3H), 4.32 (t, 2H), 4.37 (s, 2H), 6.07 (s, 2H), 7.02 (s(broad), 1H), 7.07 (s, 1H), 7.12 (s, 1H), 7.25 (s, 1H), 8.62 (s, 1H). Mass Spectrum: M+H$^+$ 525 and 527.

The starting materials were prepared as follows:
a) 6-methoxy-7-(2-morpholin-4-ylethoxy)-4-(pentafluorophenoxy)quinazoline was prepared as described in WO 0020402
b) 5-chloro-7-(3-methoxyprop-1-yn-1-yl)-1,3-benzodioxol-4-amine was prepared as described in example 2.

EXAMPLE 40

N-[5-chloro-7-(3-methoxyprop-1-yn-1-yl)-1,3-benzodioxol-4-yl]-7-ethoxy-6-methoxyquinazolin-4-amine A solution of sodium bis(trimethylsilyl)amide (2.2 ml) in tetrahydrofuran (1.0M, 2.2 mmol) was added dropwise to an ice-cold solution of 4-chloro-7-ethoxy-6-methoxyquinazoline (0.24 g, 1.0 mmol) and 5-chloro-7-(3-methoxyprop-1-yn-1-yl)-1,3-benzodioxol-4-amine (0.266 g, 1.1 mmol) in dimethylformamide (4 ml). The mixture was allowed to warm to room temperature over 3 hours. A saturated solution of ammonium chloride was added and the mixture was partitioned between water and dichloromethane. The organic layer was separated, washed with a saturated solution of sodium chloride, dried over magnesium sulfate and evaporated under reduced pressure. Flash chromatography on silica eluting with a mixture of 30%-70% ethyl acetate in hexane gave the product as an off white solid (0.159 g, 36%). NMR Spectrum: (DMSOd6) 1.4 (t, 3H), 3.36 (s, 3H), 3.92 (s, 3H), 4.19 (q, 2H), 4.37 (s, 2H), 6.16 (s, 2H), 7.14 (s, 1H), 7.16 (s, 1H), 7.80 (s, 1H), 8.25 (s, 1H), 9.49 (s, 1H). Mass Spectrum: M+H$^+$ 442 and M+H$^-$ 440.

The starting materials were prepared as follows
a) 4-chloro-7-ethoxy-6-methoxyquinazoline
4chloro-6-methoxyquinazolin-7-ol was prepared as described in WO 0020402

A suspension of 4-chloro-6-methoxyquinazolin-7-ol (0.4 g, 1.9 mmol), ethyl bromide (1.42 ml, 19.0 mmol), potassium carbonate (0.787 g, 5.7 mmol) in dimethylformamide (10 ml) was warmed at 60 C over 1.5 hours. The reaction was allowed to cool, filtered and then evaporated. Flash chromatography on silica eluting with a mixture of 30%-70% ethyl acetate in hexane gave the product as-an off white solid (0.26 g, 57%). NMR Spectrum: (CDCl$_3$) 1.58 (t, 3H), 4.08 (s, 3H), 4.30 (q, 2H), 7.27 (s, 1H), 7.40 (s, 1H), 8.86 (s, 1H). Mass Spectrum: M+H$^+$ 239.

b) 5-chloro-7-(3-methoxyprop-1-yn-1-yl)-1,3-benzodioxol-4-amine was prepared as described in example 2.

EXAMPLES 41-43

These examples were made in an analogous procedure to that described in example 40.

TABLE 1

| Example | Product | Intermediate | Notes & data |
|---|---|---|---|
| 41 | (structure) | (structure) | Intermediate formed in analogous procedure to example 40 but using 2 bromopropane as the reagent. NMR Spectrum: (CDCl₃)1.50(d, 6H), 4.05 (s, 3H), 4.82(m, 1H), 7.27(s, 1H), 7.40 (s, 1H), 8.83(s, 1H). Mass Spectrum: M+H⁺ 253. Product purified by flash chromatography eluting with a mixture 1%-9% methanol in dichloromethane. NMR Spectrum: (CDCl₃)1.50(d, 6H), 3.48(s, 3H), 4.02(s, 3H), 4.34(s, 2H), 4.80(m, 1H), 6.08(s, 2H), 6.75(Brs, 1H), 7.05(s, 1H), 7.06(s, 1H), 7.27(s, 1H), 8.63(s, 1H). Mass Spectrum: M + H⁺ 456 and M + H⁻ 454. |
| 42 | (structure) | (structure) | Intermediate formed in analogous procedure to example 40 but using 2-bromoethyl methyl ether as the reagent. NMR Spectrum: (CDCl₃)3.48(s, 3H), 3.90(t, 2H), 4.05(s, 3H), 4.37(t, 2H), 7.36(s, 1H), 7.39(s, 1H), 8.84(s, 1H). Mass Spectrum: M+H⁺ 269. Product purified by flash chromatograpy eluting with a mixture 1%-9% methanol in dichloromethane. NMR Spectrum: (CDCl₃)3.43(s, 3H), 3.46(s, 3H), 3.90(t, 2H), 4.02(s, 3H), 4.33(t, 2H), 4.37(s, 2H), 6.08(s, 2H), 6.76(s, 1H), 7.04(s, 1H), 7.06(s, 1H), 7.27(s, 1H), 8.63(s, 1H). Mass Spectrum: M+H⁺ 472 and M+H⁻ 470. |
| 43 | (structure) | (structure) | Intermediate formed in analogous procedure to example 40 but using 1-bromo-2-methylpropane as the reagent. The reaction was heated to 90 C. for 1.5 hour. NMR Spectrum: (CDCl₃)1.02(d, 6H), 2.13(m, 1H), 4.01(s, 3H), 4.01(d, 2H), 7.36(s, 1H), 7.40(s, 1H), 8.84(s, 1H). Mass Spectrum: M+H⁺ 267. Product purified by flash chromatography eluting with a mixture 30%-100% ethyl acetate in hexane. NMR Spectrum: (CDCl₃)1.08(d, 6H), 2.14(m, 1H), 3.44(s, 3H), 3.95(d, 2H), 4.01(s, 3H), 4.36(s, 2H), 6.08(s, 2H), 6.78(s, 1H), 7.04(s, 1H), 7.05(s, 1H), 7.25(s, 1H), 8.63(s, 1H). Mass Spectrum: M+H⁺ 470 and M+H⁺ 468. |

EXAMPLE 44

N-[5-chloro-7-(3-methoxyprop-1-yn-1-yl)-1,3-benzodioxol-4-yl]-6-methoxy-7-(4-morpholin-4-ylbutoxy)quinazolin-4-amine 7-(4-chlorobutoxy)-N-[5-chloro-7-(3-methoxyprop-1-yn-1-yl)-1,3-benzodioxol-4-yl]-6-methoxyquinazolin-4-amine (0.23 g, 0.4 mmol) was dissolved in morpholine (3 ml) and warmed to 50 C for 12 hours. The solvent was evaporated under reduced pressure and the residue was purified by flash chromatography on silica eluting with a mixture of 2-10% methanol in dichloromethane to give the product as an orange solid (0.16 g, 72%). NMR Spectrum: (CDCl₃) 1.74 (m, 2H), 1.98 (m, 2H), 2.46 (m, 6H), 3.48 (s, 3H), 3.72 (m, 4H), 4.00 (s, 3H), 4.22 (t, 2H), 4.37 (s, 2H), 6.07 (s, 2H), 6.83 (s(broad), 1H), 7.12 (s, 2H), 7.25 (s, 1H), 8.64 (s, 1H). Mass Spectrum: M+H⁺ 555 and M+H⁻ 553.

The starting materials were prepared as follows:

a) 7-(4-chlorobutoxy)-N-[5-chloro-7-(3-methoxyprop-1-yn-1-yl)-1,3-benzodioxol-4-yl]-6-methoxyquinazolin-4-amine 4-chloro-6-methoxyquinazolin-7-ol was prepared as described in WO 0020402.

A suspension of 4-chloro-6-methoxyquinazolin-7-ol (0.6 g, 2.86 mmol), 1 bromo 4 chlorobutane (0.63 g, 3.7 mmol), potassium carbonate (1.19 g, 8.6 mmol) and dimethylformamide (10 ml) were heated to 95 C for 1.5 hours. The excess potassium carbonate was filtered off and the reaction evaporated under reduced pressure. The residue was purified by flash chromatography on silica eluting with a mixture of 60-100% dichloromethane in hexane and 30-50% ethyl acetate in hexane to give 4-chloro-7-(4-chlorobutoxy)-6-methoxyquinazoline as a solid (0.4 g, 47%)

NMR Spectrum: (CDCl₃) 2.10 (m, 4H), 3.66 (t, 2H), 4.06 (s, 3H), 4.26 (t, 2H), 7.34 (s, 1H), 7.39 (s, 1H), 8.87 (s, 1H). Mass Spectrum: M+H⁺ 301.

5-chloro-7-(3-methoxyprop-1-yn-1-yl)-1,3-benzodioxol-4-amine was prepared as described in example 2.

A solution of sodium bis(trimethylsilyl)amide (2.66 ml) in tetrahydrofuran (1.0M, 2.66 mmol) was added dropwise to an ice-cold solution of 4-chloro-7-(4-chlorobutoxy)-6-methoxyquinazoline (0.4 g, 1.33 mmol) and 5-chloro-7-(3-methoxyprop-1-yn-1-yl)-1,3-benzodioxol-4-amine (0.35 g, 1.47 mmol) in dimethylformamide (4 ml). The mixture was allowed to warm to room temperature over 1 hour. A saturated solution of ammonium chloride was added and the mixture was partitioned between water and dichloromethane. The organic layer was separated, dried over magnesium sulfate and evaporated under reduced pressure to give 7-(4-chlorobutoxy)-N-[5-chloro-7-(3-methoxyprop-1-yn-1-yl)-1,3-benzodioxol-4-yl]-6-methoxyquinazolin-4-amine as a gum (0.493 g, 73%). NMR Spectrum: (CDCl$_3$) 2.05 (m, 4H), 3.48 (s, 3H), 3.65 (t, 2H), 3.98 (s, 3H), 4.23 (t, 2H), 4.37 (s, 2H), 6.08 (s, 2H), 6.88 (s, 1H), 7.07 (s, 1H), 7.09 (s, 1H), 7.25 (s, 1H), 8.63 (s, 1H). Mass Spectrum: M+H$^+$ 504 and M+H$^-$ 502.

EXAMPLE 45

7-[4-(4-acetylpiperazin-1-yl)butoxy]-N-[5-chloro-7-(3-methoxyprop-1-yn-1-yl)-1,3-benzodioxol-4-yl]-6-methoxyquinazolin-4-amine A mixture of 7-(4-chlorobutoxy)-N-[5-chloro-7-(3-methoxyprop-1-yn-1-yl)-1,3-benzodioxol-4-yl]-6-methoxyquinazolin-4-amine (0.23 g, 0.4 mmol), triethylamine (0.22 ml, 1.6 mmol), N-acetyl piperazine (0.205 g, 1.6 mmol) in 2 methoxyethanol (2 ml) was heated to 80 C for 12 hours and then at 100 C for 7 hours. The solvent was evaporated under reduced pressure and the residue was partitioned between ethyl acetate and water. The organic layer was separated, dried over magnesium sulfate and evaporated under reduced pressure. Flash chromatography on silica eluting with a mixture of 2-10% methanol in dichloromethane gave the product as a light orange solid (0.041 g, 17%). NMR Spectrum: (DMSOd6 at 373k+d4 acetic acid) 1.73 (m, 2H), 1.88 (m, 2H), 1.98 (s, 3H), 2.67 (t, 4H), 3.09 (t, 2H), 3.37 (s, 3H), 3.55 (t, 4H), 3.96 (s, 3H), 4.18 (t, 2H), 4.32 (s, 2H), 6.09 (s, 2H), 7.05 (s, 1H), 7.21 (s, 1H), 7.80 (s, 1H), 8.25 (s, 1H). Mass Spectrum: M+H$^+$ 596 and M+H$^-$ 594.

7-(4-chlorobutoxy)-N-[5-chloro-7-(3-methoxyprop-1-yn-1-yl)-1,3-benzodioxol-4-yl]-6-methoxyquinazolin-4-amine was prepared as described in example 44.

EXAMPLE 46

N-[5-chloro-7-(3-methoxyprop-1-yn-1-yl)-1,3-benzodioxol-4-yl]-7-{cis-2,6-dimethylmorpholin-4-yl]propoxy}-6-methoxyquinazolin-4-amine 7-(4-Chloropropoxy)-N-[5-chloro-7-(3-methoxyprop-1-yn-1-yl)-1,3-benzodioxol-4-yl]-6-methoxyquinazolin-4-amine (0 15 g, 0.307 mmol) was dissolved in 2,6 dimethylmorpholine (2 ml) and warmed to 50 C for 12 hours. The solvent was evaporated under reduced pressure and the residue was purified first by flash chromatography on silica eluting with a mixture of 0-10% methanol in dichloromethane and then further by reversed phase chromatography to give the product as solid (0.026 g, 15%). NMR Spectrum: (DMSOd6) 1.05 (d, 6H), 1.57 (t, 2H), 1.94 (m, 2H), 2.42 (t, 2H), 2.74 (d, 2H), 3.32 (s, 3H), 3.54 (m, 2H), 3.90 (s, 3H), 4.17 (t, 2H), 4.36(s, 2H), 6.12 (s, 2H), 7.11 (s, 1H), 7.14 (s, 1H), 7.79 (s, 1H), 8.31 (s, 1H), 9.48 (s, 1H). Mass Spectrum: M+H$^+$ 569 and M+H$^-$ 567.

7-(4-Chloropropoxy)-N-[5-chloro-7-(3-methoxyprop-1-yn-1-yl)-1,3-benzodioxol-4-yl]-6-methoxyquinazolin-4-amine was made as described in example 44.

EXAMPLE 47

3-({2-[(4-{[5-chloro-7-(3-methoxyprop-1-yn-1-yl)-1,3-benzodioxol-4-yl]amino}-6-methoxyquinazolin-7-yl)oxy]ethyl}amino)propan-1-ol A mixture of 7-(2-chloroethoxy)-N-[5-chloro-7-(3-methoxyprop-1-yn-1-yl)-1,3-benzodioxol-4-yl]-6-methoxyquinazolin-4-amine (0.15 g, 0.31 mmol), triethylamine (0.22 ml, 1.6 mmol), 3-aminopropanol (0.12 ml, 1.6 mmol) and 2 methoxyethanol (2 ml) was heated at 110 C for 12 hours. The solvent was evaporated under reduced pressure and the residue was then partitioned between ethyl acetate and water. The organic layer was separated, dried over magnesium sulfate and evaporated under reduced pressure. Flash chromatography on silica eluting with a mixture of 2-10% methanol in dichloromethane gave the product as a light orange solid (0.051 g, 32%). NMR Spectrum: (DMSOd6) 1.62 (m, 2H), 2.70 (t, 2H), 2.96 (t, 2H), 3.35 (s, 3H), 3.53 (t, 2H), 3.96 (s, 3H), 4.19 (t, 2H), 4.38 (s, 2H), 6.18 (s, 2H), 7.18 (s, 1H), 7.21 (s, 1H), 7.85 (s, 1H), 8.33 (s, 1H), 9.55 (s, 1H). Mass Spectrum: M+H$^+$ 515 and M+H$^-$ 513.

7-(2-chloroethoxy)-N-[5-chloro-7-(3-methoxyprop-1-yn-1-yl)-1,3-benzodioxol-4-yl]-6-methoxyquinazolin-4-amine was prepared as follows 4-chloro-6-methoxyquinazolin-7-ol was prepared as described in WO0020402.

A suspension of 4-chloro-6-methoxyquinazolin-7-ol (1.2 g, 5.8 mmol), 1 bromo 2 chloroethane (5.69 ml, 6.8 mmol), potassium carbonate (2.36 g, 17.4 mmol) and dimethylformamide (15 ml) were heated to 90 C for 1.5 hours. The excess potassium carbonate was filtered off and the reaction evaporated under reduced pressure. The residue was purified by flash chromatography on silica eluting with a mixture of 60-100% dichlormethane in hexane and 30-50% ethyl acetate in hexane to give 4-chloro-7-(2-chloroethoxy)-6-methoxyquinazoline as a solid (0.89 g, 57%). NMR Spectrum: (CDCl$_3$) 3.98 (t, 2H), 4.08 (s, 3H), 4.47 (t, 2H), 7.36 (s, 1H), 7.42 (s, 1H), 8.87 (s, 1H). Mass Spectrum: M+H$^+$ 273.

5-chloro-7-(3-methoxyprop-1-yn-1-yl)-1,3-benzodioxol-4-amine was prepared as described in example 2.

A solution of sodium bis(trimethylsilyl)amide (5.6 ml) in tetrahydrofuran (1.0M, 5.6 mmol) was added dropwise to an ice-cold solution of 4-chloro-7-(2-chloroethoxy)-6-methoxyquinazoline (0.7 g, 2.6 mmol) and 5-chloro-7-(3-methoxyprop-1-yn-1-yl)-1,3-benzodioxol-4-amine (0.675 g, 2.8 mmol) in dimethylformamide (8 ml). The mixture was allowed to warm to room temperature over 3 hours. A saturated solution of ammonium chloride was added and the mixture was partitioned between water and dichloromethane. The organic layer was separated, dried over magnesium sulfate and evaporated under reduced pressure. Flash chromatography on silica eluting with a mixture of 30-100% ethyl acetate in hexane gave the product as a solid. (0.608 g, 49%).
Mass Spectrum: M+H$^+$ 476 and M+H$^-$ 474.

EXAMPLE 48

N-[5-chloro-7-(3-methoxyprop-1-yn-1-yl)-1,3-benzodioxol-4-yl]-6-methoxy-7-[2-(4-methylpiperazin-1-yl)ethoxy]quinazolin-4-amine 7-(2-Chloroethoxy)-N-[5-chloro-7-(3-methoxyprop-1-yn-1-yl)-1,3-benzodioxol-4-yl]-6-methoxyquinazolin-4-amine (0.2 g, 0.4 mmol) was dissolved in 1-methylpiperazine (4 ml) and heated at 50 C for 12 hours. The solvent was evaporated under reduced pressure and the residue purified by flash chromatography on alumina eluting with a mixture of 0-10%, methanol in dichloromethane to give the product as a white solid (0.037 g, 17%). NMR Spectrum: (CDCl$_3$) 2.28 (s, 3H), 2.50 (s(broad), 4H), 2.63 (s(broad), 4H), 2.94 (t, 2H), 3.44 (s, 3H), 4.01 (s, 3H), 4.33 (t, 2H), 4.36 (s, 2H), 6.08 (s, 2H), 6.78 (s, 1H), 7.04 (s, 1H), 7.05 (s, 1H), 7.25 (s, 1H), 8.63 (s, 1H). Mass Spectrum: M+H$^+$ 540 and M+H$^-$]538.

7-(2-Chloroethoxy)-N-[5-chloro-7-(3-methoxyprop-1-yn-1-yl)-1,3-benzodioxol-4-yl]-6-methoxyquinazolin-4-amine was prepared as described in example 47.

EXAMPLE 49

N-[5-chloro-7-(3-methoxyprop-1-yn-1-yl)-1,3-benzodioxol-4-yl]-6,7-dimethoxyquinazolin-4-amine A solution of sodium bis(trimethylsilyl)amide (1.5 ml) in tetrahydrofuran (1.0M, 1.5 mmol) was added dropwise to an ice-cold solution of 4-chloro-6,7-dimethoxyquinazoline (0.15 g, 0.7 mmol) and 5-chloro-7-(3-methoxyprop-1-yn-1-yl)-1,3-benzodioxol-4-amine (0.176 g, 0.7 mmol) in dimethylformamide (4 ml). The mixture was allowed to warm to room temperature over 2 hours. A saturated solution of ammonium chloride was added and the mixture was partitioned between water and dichloromethane. The organic layer was separated, washed with a saturated solution of sodium chloride, dried over magnesium sulfate and evaporated under reduced pressure. Flash chromatography on silica eluting with a mixture of 3-10% methanol in dichloromethane gave the product as a solid (0.118 g, 60%).

NMR Spectrum: (CDCl$_3$) 3.48 (s, 3H), 4.03 (s, 6H), 4.38 (s, 2H), 6.08 (s, 2H), 6.78 (s, 1H), 7.08 (s, 2H), 7.30 (s, 1H), 8.64 (s, 1H). Mass Spectrum: M+H$^+$ 428 and M+H$^-$ 426.

The starting materials were prepared as follows:
a) 4-chloro-6,7-dimethoxyquinazoline was prepared as described in example 24.
b) 5-chloro-7-(3-methoxyprop-1-yn-1-yl)-1,3-benzodioxol-4-amine was prepared as described in example 2.

EXAMPLE 50

3-(6-chloro-7-{[6-methoxy-7-(3-morpholin-4-ylpropoxy)quinazolin-4-yl]amino}-1,3-benzodioxol-4-yl)prop-2-yn-1-ol A solution of N-(5-chloro-7-iodo-1,3-benzodioxol-4-yl)-6-methoxy-7-(3-morpholin-4-ylpropoxy)quinazolin-4-amine (0.35 g, 0.59 mmol) propargyl alcohol (0.075 ml, 1.3 mmol) and diisopropylamine (0.18 ml, 1.3 mmol) in ethyl acetate (10 ml) was cooled to −20 C under a nitrogen atmosphere. To this was added copper (I) iodide (0.034 g, 0.12 mmol) and bis(triphenylphospine)palladium (II) chloride (0.082 g, 0.17 mmol). The reaction was allowed to warm to ambient temperature and then stirred overnight. The reaction was filtered through Celite and the filtrate was then evaporated under reduced pressure. The residue was purified by flash chromatography on silica eluting with a mixture of 0-10% methanol in dichloromethane to give the product as a solid (0.16 g, 51%). NMR Spectrum: (DMSOd6) 1.95 (m, 2H), 2.5 (s(broad), 4H), 2.61 (t, 2H), 3.61 (t, 4H), 3.92 (s, 3H), 4.21 (t, 2H), 4.37 (s, 2H), 5.02 (s(broad), 1H), 6.06 (s, 2H), 7.07 (s, 1H), 7.17 (s, 1H), 7.83 (s, 1H), 8.25 (s(broad), 1H), 9.18 (s(broad), 1H). Mass Spectrum: M+H$^+$ 527 and M+H$^-$ 525.

N-(5-chloro-7-iodo-1,3-benzodioxol-4-yl)-6-methoxy-7-(3-morpholin-4-ylpropoxy)quinazolin-4-amine was prepared as described in example 26.

EXAMPLE 51

N-[5-chloro-7-(phenylethynyl)-1,3-benzodioxol-4-yl]-6-methoxy-7-(3-morpholin-4-ylpropoxy)quinazolin-4-amine A mixture of N-(5-chloro-7-iodo-1,3-benzodioxol-4-yl)-6-methoxy-7-(3-morpholin-4-ylpropoxy)quinazolin-4-amine (0.17 g, 0.285 mmol), phenyl acetylene (0.07 ml, 0.63 mmol) and diisopropylamine (0.088 ml, 0.63 mmol) in ethyl acetate (4 ml) was cooled to −20 C under a nitrogen atmosphere. To this was added copper (I) iodide (0.016 g, 0.085 mmol) and bis(triphenylphospine)palladium (II) chloride (0.04 g, 0.057 mmol). The mixture was allowed to warm to ambient temperature and then stirred overnight. The mixture was filtered and the filtrate was evaporated under reduced pressure. The residue was purified by flash chromatography on silica eluting with a mixture of 0-10% methanol in dichloromethane gave the product as a solid (0.108 g, 66%). NMR Spectrum: (DMSOd6 at 373k+d4 acetic acid) 2.10 (m, 2H), 2.76 (t, 4H), 2.83 (t, 2H), 3.69 (t, 4H), 3.97 (s, 3H), 4.24 (t, 2H), 6.12 (s, 2H), 7.15 (s, 1H), 7.30 (s(broad), 1H), 7.42 (m, 3H), 7.54 (m, 2H), 7.95 (s, 1H), 8.63 (s(broad), 1H). Mass Spectrum: M+H$^+$ 573 and M+H$^-$ 571.

N-(5-chloro-7-iodo-1,3-benzodioxol-4-yl)-6-methoxy-7-(3-morpholin-4-ylpropoxy)quinazolin-4-amine was prepared as described in example 26.

EXAMPLE 52

N-[5-chloro-7-(pyridin-2-ylethynyl)-1,3-benzodioxol-4-yl]-6-methoxy-7-(3-morpholin-4-ylpropoxy)quinazolin-4-amine A solution of sodium bis(trimethylsilyl)amide (1.6 ml) in tetrahydrofuran (1.0M, 1.6 mmol) was added dropwise to an ice-cold solution of 4-chloro-6-methoxy-7-(3-morpholin-4-ylpropoxy)quinazoline (0.272 g, 0.73 mmol) and 5-chloro-7-(pyridin-2-ylethynyl)-1,3-benzodioxol-4-amine (0.2 g, 0.81 mmol) in dimethylformamide (4 ml). The mixture was allowed to warm to room temperature over 1.5 hours. A saturated solution of ammonium chloride was added and the mixture was partitioned between water and ethyl acetate. The organic layer was separated, dried over magnesium sulfate and evaporated under reduced pressure. Flash chromatography on silica eluting with a mixture of 0-10% methanol in dichloromethane gave the product as a solid (0.135 g, 32%). NMR Spectrum: (CDCl$_3$) 2.12 (m, 2H), 2.52 (t, 4H), 2.59 (t, 2H), 3.72 (t, 2H), 4.04(s, 3H), 4.28 (t, 2H), 6.12 (s, 2H), 6.87 (s, 1H), 7.10 (s, 1H), 7.22 (s, 1H), 7.30 (m, 1H) partially obscured by CDCl$_3$ peak, 7.34 (s, 1H), 7.57 (d, 1H), 7.72 (t, 1H), 8.68 (d, 1H), 8.70 (s, 1H). Mass Spectrum: M+H$^+$ 574 and M+H$^-$ 572.

The starting materials were prepared as follows:
a) 4-chloro-6-methoxy-7-(3-morpholin-4-ylpropoxy) quinazoline was prepared as described in example 1
b) 5-Chloro-7-(pyridin-2-ylethynyl)-1,3-benzodioxol-4-yl-amine was prepared as follows:
5-chloro-7-iodo-1,3-benzodioxol-4-amine was prepared as described in example 2.

A mixture of 5-chloro-7-iodo-1,3-benzodioxol-4-amine (0.6 g, 2.02 mmol), 2-ethynylpyridine (0.407 ml, 4.04 mmol) and diisopropylamine (0.564 ml, 4.04 mmol) in ethyl acetate (10 ml) was cooled to −10 C under a nitrogen atmosphere. To this was added copper (I) iodide (0.038 g, 0.2 mmol) and bis(triphenylphospine)palladium (II) chloride (0.141 g, 0.2 mmol). The reaction mixture was allowed to warm to ambient temperature and then stirred overnight. The reaction mixture was filtered and the filtrate was evaporated under reduced pressure. The residue was purified by flash chromatography on silica eluting with a mixture of 100-0% hexane in ethyl acetate gave the product as a solid (0.312 g, 57%). NMR Spectrum: (CDCl$_3$) 4.10 (s, 2H), 6.06 (s, 2H), 7.02 (s, 1H), 7.20 (q, 1H), 7.49 (d, 1H), 7.64 (m, 1H), 8.60 (d, 1H). Mass Spectrum: M+H$^+$ 273.

EXAMPLE 53

N-{5-chloro-7-[3-(cyclopentylmethoxy)prop-1-yn-1-yl]-1,3-benzodioxol-4-yl}-6-methoxy-7-(3-morpholin-4-ylpropoxy)quinazolin-4-amine A mixture of N-(5-chloro-7-iodo-1,3-benzodioxol-4-yl)-6-methoxy-7-(3-morpholin-4-ylpropoxy)quinazolin-4-amine (0.14 g, 0.235 mmol), [(prop-2-yn-1-yloxy)methyl]cyclopentane (0.071 g, 0.52 mmol) and diisopropylamine (0.073 ml, 0.52 mmol) in ethyl acetate (3 ml) was cooled to −20 C under a nitrogen atmosphere. To this was added copper (I) iodide (0.014 g, 0.071 mmol) and bis(triphenylphospine) palladium (II) chloride (0.033 g, 0.041 mmol). The reaction mixture was allowed to warm to ambient temperature and then stirred overnight. The mixture was filtered and the filtrate was evaporated under reduced pressure. The residue was purified by flash chromatography on silica eluting with a mixture of 0-8% methanol in dichloromethane to give the product as a solid (0.132 g, 90%). NMR Spectrum: (DMSOd6) 1.28 (m, 2H), 1.45-1.62 (m, 4H), 1.70 (m, 2H), 1.97 (s(broad), 2H), 2.12 (m, 1H), 2.40 (t, 2H), 2.50(s, 4H under DMSO), 3.38 (d, 2H), 3.61 (s, 4H), 3.91 (s, 3H), 4.19 (t, 2H), 4.39 (s, 2H), 6.14 (s, 2H), 7.10 (s, 1H), 7.84 (s(broad), 1H), 8.00 (s(broad), 1H), 9.58 (s(broad), 1H).

Mass Spectrum: M+H$^+$ 609 and M+H$^-$ 607.

The starting materials were prepared as follows:
a) N-(5-chloro-7-iodo-1,3-benzodioxol-4-yl)-6-methoxy-7-(3-morpholin-4-ylpropoxy)quinazolin-4-amine was prepared as described in example 26.
b) [(prop-2-yn-1-yloxy)methyl]cyclopentane was prepared as follows:

Sodium hydride (60% dispersion in oil, 0.82 g, 20.4 mmol) was taken into dimethylformamide (30 ml) and cooled in an ice bath under an inert atmosphere. To this was added cyclopentanemethanol (2 ml, 18.5 mmol) and the mixture was allowed to stir for 1 hour. Propargyl bromide (2.24 ml, 20.4 mmol) in toluene (80% wt/solution, 20.4 mmol) was added dropwise and the reaction mixture was allowed to warm to ambient temperature and then stirred for 12 hours. A saturated solution of ammonium chloride was added and the mixture was partitioned between water and ethyl acetate. The organic layer was separated, dried over magnesium sulfate and evaporated under reduced pressure. The residue was purified by flash chromatography on silica eluting with a mixture of 8040% hexane in dichloromethane gave the product as an oil (1.14 g, 32%). NMR Spectrum: (CDCl$_3$) 1.24 (m, 2H), 1.55 (m, 4H), 1.77 (m, 2H), 2.17 (m, 1H), 2.40 (m, 1H), 3.37 (d, 2H), 4.15 (s, 2H).

EXAMPLES 54-56

These were made in an analogous procedure to that described in example 53.

TABLE 2

| Example | Product | Intermediate | Notes & data |
| --- | --- | --- | --- |
| 54 | | | Intermediate formed in analogous procedure to example 53 using 3 hydroxytetrahydrofuran. NMR Spectrum: (CDCl$_3$)2.04(m, 2H), 2.42 (s, 1H), 3.78-3.96(m, 4H), 4.18(s, 2H), 4.39(m, 1H). Product purified by flash chromatography eluting with a mixture 0-10% methanol in dichloromethane. NMR Spectrum: (DMSOd6)1.89-2.11 (m, 4H), 2.72(s, 4H), 2.78(t, 2H), 3.68 (t, 4H), 3.77(m, 4H), 3.95(s, 3H), 4.24 (t, 2H), 4.37(m, 1H), 4.41(s, 2H), 6.08 (s, 2H), 7.05(s, 1H), 7.29(s(broad), 1H), 7.88(s, 1H), 8.53 (s(broad), 1H). Mass Spectrum: M+H$^+$ 597 and M+H$^-$ 595. |

TABLE 2-continued

| Example | Product | Intermediate | Notes & data |
|---|---|---|---|
| 55 | | | Intermediate formed in analogous procedure to example 53 using tetrahydro-3-furanmethanol. NMR Spectrum: (CDCl$_3$)1.55-1.71(m, 1H), 1.93-2.08(m, 1H), 2.43(m, 1H), 2.46-2.63(m, 1H), 3.38-3.62(m, 3H), 3.71(q, 1H), 3.87(m, 2H), 4.16(d, 2H). Product purified by flash chromatography eluting with a mixture 0-10% methanol in dichloromethane. NMR Spectrum: (DMSOd6 at 373k+d4 acetic acid) 1.59(m, 1H), 1.96(m, 1H), 2.04(m, 2H), 2.48(m, 1H) obscured by DMSO peak, 2.58(t, 4H), 2.67(t, 2H), 3.43-3.55(m, 3H), 3.65(m, 5H), 3.73 (m, 2H), 3.94(s, 3H), 4.22(t, 2H), 4.38 (s, 2H), 6.08(s, 2H), 7.05(s, 1H), 7.20 (s, 1H), 7.81(s, 1H), 8.25(s, 1H). Mass Spectrum: M+H$^+$ 611 and M+H$^-$ 609. |
| 56 | | | Intermediate formed in analogous procedure to example 53 using 2 bromomethyl-1,3-dioxolane. NMR Spectrum: (CDCl$_3$)2.43(t, 1H), 3.63(d, 2H), 3.87-4.03(m, 4H), 4.26(d, 2H), 5.09(t, 1H). Product purified by flash chromatography eluting with a mixture 0-10% methanol in dichloromethane. NMR Spectrum: (DMSOd6 at 373k+d4 acetic acid) 2.05(m, 2H), 2.70(t, 4H), 2.78(t, 2H), 3.58(d, 2H), 3.67(t, 4H), 3.79(m, 2H), 3.90(m, 2H), 3.93(s, 3H), 4.23(t, 2H), 4.48(s, 2H), 4.99(t, 1H), 6.08(s, 2H), 7.05(s, 1H), 7.24(s(broad), 1H), 7.84(s, 1H), 8.46(s(broad), 1H). Mass Spectrum: M+H$^+$ 613 and M+H$^-$ 611. |

EXAMPLE 57

N-{5-chloro-7-[3-dimethylaminoprop-1-yn-1-yl]-1,3-benzodioxol-4-yl}-6-methoxy-7-(3-morpholin-4-ylpropoxy)quinazolin-4-amine A mixture of N-(5-chloro-7-iodo-1,3-benzodioxol-4-yl)-6-methoxy-7-(3-morpholin-4-ylpropoxy)quinazolin-4-amine (0.25 g, 0.42 mmol), 1-dimethylamino-2-propyne (0.088 ml, 0.84 mmol) and diisopropylamine (0.12 ml, 0.84 mmol) in ethyl acetate (4 ml) was cooled to −10 C under a nitrogen atmosphere. To this was added copper (I) iodide (0.023 g, 0.12 mmol) and bis(triphenylphospine)palladium (II) chloride (0.06 g, 0.084 mmol). The reaction mixture was allowed to warm to ambient temperature and then stirred overnight. The reaction mixture was filtered and the filtrate was evaporated under reduced pressure. The residue was purified by flash chromatography on silica eluting with a mixture of 0-10% methanol in dichloromethane gave the product as a solid (0.129 mg, 55%).

NMR Spectrum: (DMSOd6) 1.97 (m, 2H), 2.28 (s, 6H), 2.42 (s(broad), 4H), 2.50 (t, 2H) obscured by DMSO peak, 3.53 (s, 2H), 3.62 (s, 4H), 3.95 (s, 3H), 4.21 (t, 2H), 6.14 (s, 2H), 7.15 (s, 1H), 7.22 (s, 1H), 7.84 (s, 1H), 8.35 (s, 1H), 9.51 (s, 1H). Mass Spectrum: M+H$^+$ 554 and M+H$^-$ 552.

N-(5-chloro-7-iodo-1,3-benzodioxol-4-yl)-6-methoxy-7-(3-morpholin-4-ylpropoxy)quinazolin-4-amine was prepared as described in example 26.

EXAMPLE 58

N-[5-chloro-7-(pyridin-3-ylethynyl)-1,3-benzodioxol-4-yl]-6-methoxy-7-(3-morpholin-4-ylpropoxy)quinazolin-4-amine A solution of sodium bis(trimethylsilyl)amide (0.48 ml) in tetrahydrofuran (1.0M, 0.48 mmol) was added dropwise to an ice-cold solution of 4-chloro-6-methoxy-7-(3-morpholin-4-ylpropoxy)quinazoline (0.074 g, 0.22 mmol) and 5-chloro-7-(pyridin-3-ylethynyl)-1,3-benzodioxol-4-amine (0.06 g, 0.22 mmol) in dimethylformamide (2 ml). The mixture was allowed to warm to room temperature over 2 hours. A saturated solution of ammonium chloride was added and the mixture was partitioned between water and ethyl acetate. The organic layer was separated, dried over magnesium sulfate and evaporated under reduced pressure. Flash chromatography on silica eluting with a mixture of 0-10% methanol in dichloromethane gave the product as a solid (0.036 g, 29%). NMR Spectrum: (DMSOd6) 1.96 (m, 2H), 2.40 (s(broad), 4H), 2.50 (t, 2H) partially obscured by DMSO peak, 3.59 (s(broad), 4H), 3.94 (s, 3H), 4.19 (t, 2H), 6.12 (s, 2H), 7.19 (s, 1H), 7.28 (s, 1H), 7.48 (m, 1H), 7.80 (s, 1H), 7.97 (d, 1H), 8.32 (s, 1H), 8.62 (d, 1H), 8.78 (s, 1H), 9.56 (s, 1H). Mass Spectrum: M+H$^+$ 574 and M+H$^-$ 572.

The starting materials were prepared as follows:

a) 4-chloro-6-methoxy-7-(3-morpholin-4-ylpropoxy) quinazoline was prepared as described in example 1 b) 5-Chloro-7-(pyridin-3-ylethynyl)-1,3-benzodioxol-4-amine was prepared as follows:

i) Preparation of 5-Chloro-7-[(trimethylsilyl)ethynyl]-1,3-benzodioxol-4-amine

A solution of 5-chloro-7-iodo-1,3-benzodioxol-4-amine (example 2) (3 g, 10.0 mmol), trimethylsilylacetylene (2.8 ml, 20.0 mmol) and diisopropylamine (2.8 ml, 20.0 mmol) in ethyl acetate (60 ml) was cooled to −20 C under a nitrogen atmosphere. To this was added copper (I) iodide (0.58 g, 3.0 mmol) and bis(triphenylphospine)palladium (II) chloride (1.4 g, 2.0 mmol). The reaction mixture was allowed to warm to ambient temperature and then stirred overnight. The reaction mixture was filtered and the filtrate was evaporated under reduced pressure. The residue was purified by flash chromatography on silica eluting with a mixture of 80-20% hexane in dichloromethane to give the product as an oil (2.44 g, 91%). NMR Spectrum: (CDCl$_3$) 0.0 (s, 9H), 3.81 (s, 2H), 5.79 (s, 2H), 6.64 (s, 1H).

ii) Preparation of 5-Chloro-7-ethynyl-1,3-benzodioxol-4-amine

A solution of 5-chloro-7-[(trimethylsilyl)ethynyl]-1,3-benzodioxol-4-amine (2.44 g, 9.12 mmol), potassium carbonate (3.78 g, 27.4 mmol) in methanol (30 ml) and water (6 ml) was warmed to 35 C for 3 hours. The mixture was cooled, filtered and the filtrate was then evaporated under reduced pressure. The residue was purified by flash chromatography on silica eluting with a mixture of 80-0% hexane in dichloromethane to give the product as a fawn solid (1.41 g, 79%). NMR Spectrum: (CDCl$_3$) 3.17 (s, 1H), 4.05 (s, 2H), 6.04 (s, 2H), 6.96 (s, 1H).

iii) Preparation of 5-Chloro-7-(pyridin-3-ylethynyl)-1,3-benzodioxol-4-amine

A solution of 5-chloro-7-ethynyl-1,3-benzodioxol-4-amine (0.08 g, 0.41 mmol), 3 iodopyridine (0.084 g, 0.41 mmol) and diisopropylamine (0.115 ml, 0.82 mmol) in ethyl acetate (3 ml) was cooled to −20 C under a nitrogen atmosphere. To this was added copper (I) iodide (0.023 g, 0.123 mmol) and bis(triphenylphospine)palladium (II) chloride (0.057 g, 0.08 mmol). The reaction mixture was allowed to warm to ambient temperature and then stirred overnight. The reaction mixture was filtered and then evaporated under reduced pressure. The residue was purified by flash chromatography on silica eluting with dichloromethane and then a mixture of 70-30% hexane in ethyl acetate to give the product as an oil (0.065 g, 58%). NMR Spectrum: (CDCl$_3$) 4.11 (s, 2H), 6.08 (s, 2H), 6.99 (s, 1H), 7.26 (dd, 1H) partially obscured by CHCl$_3$ peak, 7.77 (m, 1H), 8.51(d, 1H), 8.73 (s, 1H). Mass Spectrum: M+H$^+$ 273.

EXAMPLE 59

N-[5-chloro-7-(pyrazin-2-ylethynyl)-1,3-benzodioxol-4-yl]-6-methoxy-7-(3-morpholin-4-ylpropoxy)quinazolin-4-amine A solution of N-(5-chloro-7-ethynyl-1,3-benzodioxol-4-yl)-6-methoxy-7-(3-morpholin-4-ylpropoxy)quinazolin-4-amine (0.12 g, 0.24 mmol), 3-iodopyrazine (0.1 g, 0.48 mmol) and diisopropylamine (0.066 ml, 0.48 mmol) in ethyl acetate (3 ml) was cooled to −20 C under a nitrogen atmosphere. To this was added copper (I) iodide (0.014 g, 0.072 mmol) and bis(triphenylphospine)palladium (II) chloride (0.034 g, 0.048 mmol). The reaction mixture was allowed to warm to ambient temperature and then stirred overnight. The mixture was filtered and the filtrate was evaporated under reduced pressure. The residue was purified by flash chromatography on silica eluting with a mixture of 0-10% methanol in dichloromethane to give the product as a light yellow solid (0.052 g, 38%). NMR Spectrum: (DMSOd6) 1.99 (t, 2H), 2.40 (brs, 4H), 2.50 (t, 2H) partially obscured by DMSO peak, 3.59 (s, 4H), 3.97 (s, 3H), 4.23 (t, 2H), 6.27(s, 2H), 7.19 (s, 1H), 7.35 (s, 1H), 7.89 (s, 1H), 8.42 (s, 1H), 8.74 )s, 1H), 8.78 (s, 1H), 8.96 (s, 1H), 9.66 (s, 1H). Mass Spectrum: M+H$^+$ 575 and M+H 573.

N-(5-chloro-7-ethynyl-1,3-benzodioxol-4-yl)-6-methoxy-7-(3-morpholin-4-ylpropoxy)quinazolin-4-amine was as follows i) Preparation of 5-chloro-7-[(trimethylsilyl)ethynyl]-1,3-benzodioxol-4-amine 5-chloro-7-iodo-1,3-benzodioxol-4-amine was prepared as described in example 2.

Bis(triphenylphosphine)palladium(II) chloride (0.283 g), cuprous iodide (0.115 g) and diisopropylamine (0.57 ml) were added to a stirred solution of 5-chloro-7-iodo-1,3-benzodioxol-4-amine (0.600 g) and trimethylsilylacetylene (0.57 ml) in ethyl acetate (10 ml) cooled to −20° C. under a nitrogen atmosphere. The mixture was stirred for 4 hr at ambient temperature. The reaction mixture was filtered through Celite and the crude product in solution was then absorbed onto silica and purified by column chromatography using 20% dichloromethane in isohexane as eluent. There was thus obtained the title compound as an oil (0.560 g). NMR Spectrum: (CDCl$_3$) 0.24 (s 9H), 4.03 (s, 2H), 6.02 (s, 2H), 6.91 (s, 1H); Mass Spectrum: M+H$^+$ 268 and 270.

ii) Preparation of N-(5-chloro-7-ethynyl-1,3-benzodioxol-4-yl)-6-methoxy-7-(3-morpholin-4-ylpropoxy)quinazolin-4-amine 4-chloro-6-methoxy-7-(3-morpholin-4-ylpropoxy) quinazoline was prepared as described in example 1.

A solution of sodium bis(trimethylsilyl)amide (0.91 ml) in tetrahydrofuran (1.0M, 0.91 mmol) was added over 5 min. to a stirred mixture of {5-chloro-7-[(trimethylsilyl)ethynyl]-1,3-benzodioxol-4-yl}amine (0.122 g) and 4-chloro-6-methoxy-7-(3-morpholin-4-ylpropoxy)quinazoline (0.140 g) in DMF (4 ml) cooled to 0° C. under a nitrogen atmosphere and the mixture was stirred for 1 hr at ambient temperature. The mixture was diluted with saturated aqueous ammonium chloride (40 ml) and extracted with ethyl acetate (3×20 ml). The organic extracts were washed with brine (20 ml), dried over sodium sulphate and then evaporated. The residue was purified by column chromatography on silica using increasingly polar mixtures of methanol and dichloromethane as eluent. There was thus obtained the title compound as a solid (0.120 g). NMR Spectrum: (DMSOd$_6$) 1.95 (m, 2H), 2.37 (m, 4H), 2.45 (t, 2H), 3.57 (m, 4H), 3.92 (s, 3H), 4.17 (t, 2H), 4.50 (s, 1H), 6.15 (s, 2H), 7.15 (s, 1H), 7.17 (s, 1H), 7.82 (s, 1H), 8.32 (s, 1H), 9.50 (s, 1H); Mass Spectrum: M+H$^+$ 497 and 499.

EXAMPLE 60

N-[5-chloro-7-(pyrimidin-2-ylethynyl)-1,3-benzodioxol-4-yl]-6-methoxy-7-(3-morpholin-4-ylpropoxy)quinazolin-4-amine A solution of N-(5-chloro-7-ethynyl-1,3-benzodioxol-4-yl)-6-methoxy-7-(3-morpholin-4-ylpropoxy)quinazolin-4-amine (0.12 g, 0.24 mmol), 2 bromopyrimidine (0.076 g, 0.48 mmol) and diisopropylamine (0.066 ml, 0.48 mmol) in ethyl acetate (3 ml) was cooled to −20 C under a nitrogen atmosphere. To this was added copper (I) iodide (0.014 g, 0.072 mmol) and bis(triphenylphospine)palladium (II) chloride (0.034 g, 0.048 mmol). The reaction mixture was allowed to warm to ambient temperature and then stirred overnight. The mixture was filtered and the filtrate was then evaporated under reduced pressure. The residue was purified by flash chromatography on silica eluting with a mixture of 0-10% methanol in dichloromethane gave the product as a light yellow solid (0.026 g, 19%). NMR Spectrum: (DMSOd6) 1.99 (t, 2H), 2.40 (s(broad), 4H), 2.50 (t, 2H) partially obscured by DMSO peak, 3.59 (s, 4H), 3.97 (s, 3H), 4.23 (t, 2H), 6.27(s, 2H), 7.23 (s, 1H), 7.35 (s, 1H), 7.89 (s, 1H), 8.40 (s, 1H), 9.08 (s(broad), 1H), 9.08 (s, 1H), 9.30 (s, 1H), 9.62 (s, 1H). Mass Spectrum: M+H$^+$ 575 and M+H$^-$ 573.

N-(5-chloro-7-ethynyl-1,3-benzodioxol-4-yl)-6-methoxy-7-(3-morpholin-4-ylpropoxy)quinazolin-4-amine was prepared as described in example 59.

EXAMPLE 61

N-[5-chloro-7-(1H-pyrazol-4-ylethynyl)-1,3-benzodioxol-4-yl]-6-methoxy-7-(3-morpholin-4-ylpropoxy)quinazolin-4-amine A solution of N-(5-chloro-7-ethynyl-1,3-benzodioxol-4-yl)-6-methoxy-7-(3-morpholin-4-ylpropoxy)quinazolin-4-amine (0.15 g, 0.30 mmol), 1-acetyl-4-iodo-1H-pyrazole (0.142 g, 0.6 mmol) and diisopropylamine (0.082 ml, 0.6 mmol) in ethyl acetate (5 ml) was cooled to −20 C under a nitrogen atmosphere. To this was added copper (I) iodide (0.018 g, 0.091 mmol) and bis(triphenylphospine)palladium (II) chloride (0.043 g, 0.06 mmol). The reaction mixture was allowed to warm to ambient temperature and then stirred overnight. The mixture was filtered and the filtrate was evaporated under reduced pressure. The residue was purified by flash chromatography on silica eluting with a mixture of 0-10% methanol in dichloromethane gave the product as a cream solid (0.017 g, 10%). NMR Spectrum: (DMSOd6) 1.99 (t, 2H), 2.40 (s(broad), 4H), 2.50 (t, 2H) partially obscured by DMSO peak, 3.59 (s, 4H), 3.97 (s, 3H), 4.23 (t, 2H), 6.27(s, 2H), 7.23 (s, 1H), 7.35 (s, 1H), 7.89 (s, 1H), 8.40 (s, 1H), 9.08 (s(broad), 1H), 9.08 (s, 1H), 9.30 (s, 1H), 9.62 (s, 1H). Mass Spectrum: M+H$^+$ 575 and M+H$^-$ 573.

N-(5-chloro-7-ethynyl-1,3-benzodioxol-4-yl)-6-methoxy-7-(3-morpholin-4-ylpropoxy)quinazolin-4-amine was prepared as described in example 59.

EXAMPLE 62

N-[5-chloro-7-(pyridin-2-ylethynyl)-1,3-benzodioxol-4-yl]-7-[3-(cis-2,6dimethylmorpholin-4-yl]propoxy)]-6-methoxyquinazolin-4-amine A solution of 7-(3-chloropropoxy)-N-[5-chloro-7-(pyridin-2-ylethynyl)-1,3-benzodioxol-4-yl]-6-methoxyquinazolin-4-amine (0.39 g, 0.75 mmol) was dissolved in cis-2,6 dimethylmorpholine (2 ml) and warmed to 40 C for 12 hours. The solvent was evaporated under reduced pressure and the residue was partitioned between dichloromethane and water. The organic layer was separated, dried over magnesium sulfate and evaporated under reduced pressure. Flash chromatography on silica eluting with a mixture of 0-10% methanol in dichloromethane gave the product as a cream solid (0.096 g, 22%). NMR Spectrum: (DMSOd6 at 373K) 1.11 (d, 6H), 1.69 (t, 2H), 1.98 (m, 2H), 2.42 (t, 2H), 2.74 (d, 2H), 3.63 (m, 2H), 3.95 (s, 3H), 4.22 (t, 2H), 6.17 (s, 2H), 7.15 (s, 1H), 7.22 (s, 1H), 7.42 (m, 1H), 7.63 (d, 1H), 7.86 (s, 1H), 7.88 (d, 1H), 8.30 (s, 1H), 8.65 (d, 1H), 9.38 (s(broad), 1H). Mass Spectrum: M+H$^+$ 602 and M+H$^-$ 600.

7-(3-Chloropropoxy)-N-[5-chloro-7-(pyridin-2-ylethynyl)-1,3-benzodioxol-4-yl]-6-methoxyquinazolin-4-amine was prepared as follows:

4-Chloro-7-(3-chloropropoxy)-6-methoxyquinazoline was prepared as described in example 13

5-chloro-7-(pyridin-2-ylethynyl)-1,3-benzodioxol-4-amine was prepared as described in example 52.

A solution of sodium bis(trimethylsilyl)amide (1.8 ml) in tetrahydrofuran (1.0M, 1.8 mmol) was added dropwise to an ice-cold solution of 4-chloro-7-(3chloropropoxy)-6-methoxyquinazoline (0.23 g, 0.83 mmol) and 5-chloro-7-(pyridin-2-ylethynyl)-1,3-benzodioxol-4-amine (0.25 g, 0.91 mmol) in dimethylformamide (5 ml). The mixture was allowed to warm to room temperature over 1.5 hours. A saturated solution of ammonium chloride was added and the mixture was partitioned between water and dichloromethane. The organic layer was separated, dried over magnesium sulfate and evaporated under reduced pressure. Flash chromatography on silica eluting with a mixture of 0-100% ethyl acetate in dichloromethane gave the product as a solid (0.40 g, 92%). NMR Spectrum: DMSOd6) 2.38 (m, 2H), 3.95 (t, 2H), 4.08 (s, 3H), 4.40 (t, 2H), 6.37 (s, 2H), 7.34 (s, 1H), 7.57 (m, 1H), 7.78 (d, 1H), 7.98 (s, 1H), 8.01 (m, 1H), 8.07 (s, 1H), 8.48 (s, 1H), 8.76 (d, 1H), 9.68 (s, 1H). Mass Spectrum: M+H$^+$ 523 and M+H$^-$ 521.

EXAMPLE 63

N-(5-chloro-7-(pyridin-2-ylethynyl)-1,3-benzodioxol-4-yl)-6,7-dimethoxyquinazolin-4-amine A mixture of N-(5-chloro-7-iodo-1,3-benzodioxol-4-yl)-6,7-dimethoxyquinazolin-4-amine (0.131 g, 0.27 mmol), 2 ethynyl pyridine (0.056 g, 0.54 mmol) and diisopropylamine (0.075 ml, 0.54 mmol) in ethyl acetate (5 ml) was cooled to −20 C under a nitrogen atmosphere. To this was added copper (I) iodide (0.016 g, 0.081 mmol) and bis(triphenylphospine) palladium (II) chloride (0.038 g, 0.054 mmol). The reaction mixture was allowed to warm to ambient temperature and then stirred overnight. The reaction mixture was filtered and the filtrate was then evaporated under reduced pressure. The residue was purified by flash chromatography on silica eluting with a mixture of 0-3% methanol in dichloromethane to give the product as a light brown solid (0.075 g, 60%). NMR Spectrum: (DMSOd6) 3.99 (s, 6H), 6.28 (s, 2H), 7.26 (s, 1H), 7.34 (s, 1H), 7.52 (m, 1H), 7.72 (d, 1H), 7.92 (m, 2H), 8.43 (s, 1H), 8.66 (d, 1H), 9.62 (s, 1H). Mass Spectrum: M+H$^+$ 461 and M+H$^-$ 459.

N-(5-chloro-7-iodo-1,3-benzodioxol-4-yl)-6,7-dimethoxyquinazolin-4-amine was prepared as follows:

4-chloro-6,7-dimethoxyquinazoline was prepared as described in example 24

5-chloro-7-iodo-1,3-benzodioxol-4-amine was prepared as described in example 2.

A solution of sodium bis(trimethylsilyl)amide (7 ml) in tetrahydrofuran (1.0M, 7.0 mmol) was added dropwise to an ice-cold solution of 4-chloro-6,7-dimethoxyquinazoline (0.72 g, 3.2 mmol) and 5-chloro-7-iodo-1,3-benzodioxol-4-amine (1.0 g, 3.4 mmol) in dimethylformamide (14 ml). The mixture was allowed to warm to room temperature over 2 hours. A saturated solution of ammonium chloride was added and the mixture was partitioned between water and ethyl acetate. The organic layer was separated, dried over magnesium sulfate and evaporated under reduced pressure. Flash chromatography on silica eluting with a mixture of 20-80% ethyl acetate in hexane gave the product as a solid (0.93 g, 60%). NMR Spectrum: (DMSOd6) 3.42 (s, 3H), 4.04 (s, 3H), 6.26 (s, 2H), 7.30(s, 1H), 7.53 (s, 1H), 7.93 (s, 1H), 8.42(s, 1H), 9.59 (s, 1H). Mass Spectrum: M+H$^+$ 486 and M+H$^-$ 484.

EXAMPLE 64

4-{3-[(4-{[5-Chloro-7-(3-isopropoxyprop-1-yn-1-yl)-1,3-benzodioxol-4-yl]amino}-6-methoxyquinazolin-7-yl)oxy]propyl}-1-methylpiperazin-2-one A mixture of N-[5-chloro-7-(3-isopropoxyprop-1-yn-1-yl)-1,3-benzodioxol-4-yl]-7-(3-chloropropoxy)-6-methoxyquinazolin-4-amine (0.22 g, 0.43 mmol), triethylamine (0.29 ml, 2.13 mmol), 1-methylpiperazin-2-one (0.24 g, 2.13 mmol) in 2-methoxyethanol (3 ml) was heated to 80 C for 12 hours and then at 100 C for 7 hours. The solvent was removed under reduced pressure and the residue was partitioned between dichloromethane and water. The organic layer was separated, dried over magnesium sulfate and evaporated under reduced pressure. The residue was purified by flash chromatography on silica eluting with a mixture of 2-8% methanol in dichloromethane to give the product as an light orange solid (0.129 g, 51%). NMR Spectrum: (DMSOd6) 1.18 (d, 6H), 1.98 (m, 2H), 2.52 (t, 2H under DMSO), 2.72 (t, 2H), 2.88 (s, 3H), 3.04 (s, 2H), 3.34 (t, 2H under H2O), 3.83 (m, 1H), 3.97 (s, 3H), 4.22 (t, 2H), 4.42 (s, 2H), 6.17 (s, 2H), 7.15 (s, 1H), 7.21 (s, 1H), 7.83 (s, 1H), 8.34 (s, 1H), 9.52 (s, 1H). Mass Spectrum: M+H$^+$ 596 and M+H$^-$ 594.

N-[5-chloro-7-(3-isopropoxyprop-1-yn-1-yl)-1,3-benzodioxol-4yl]-7-(3-chloropropoxy)-6-methoxyquinazolin-4-amine was prepared as follows:

1-Methylpiperazin-2-one was prepared as described in WO 9727188.

5-Chloro-7-(3-isopropoxyprop-1-yn-1-yl)-1,3-benzodioxol-4amine was prepared as described in example 11.

4-chloro-7-(3-chloropropoxy)-6-methoxyquinazoline was prepared as described in example 13.

A solution of sodium bis(trimethylsilyl)amide (1.5 ml) in tetrahydrofuran (1.0M, 1.5 mmol) was added dropwise to an ice-cold solution of 4-chloro-7-(3-chloropropoxy)-6-methoxyquinazoline (0.196 g, 0.68 mmol) and 5-chloro-7-(3-isopropoxyprop-1-yn-1-yl)-1,3-benzodioxol-4-yl-amine (0.20 g, 0.75 mmol) in dimethylformamide (3 ml). The mixture was allowed to warm to room temperature over 1.5 hours. A saturated solution of ammonium chloride was added and the mixture was partitioned between water and dichloromethane. The organic layer was separated, dried over magnesium sulfate and evaporated under reduced pressure. The residue was purified by flash chromatography on silica eluting first with dichloromethane and then with a mixture of 20-70% ethyl acetate in hexane to give the product as a brown oil (0.265 g, 75%). NMR Spectrum: (DMSOd6) 1.25 (d, 6H), 2.37 (m, 2H), 3.79 (t, 4.08), 3.86 (m, 1H), 3.98 (s, 3H), 4.35 (t, 2H), 4.40 (s, 3H), 6.07 (s, 2H), 7.04 (s, 1H), 7.15 (s, 1H), 7.30 (s, 1H), 8.62 (s, 1H). Mass Spectrum: M+H$^+$ 518 and M+H$^-$ 516.

EXAMPLE 65

N-[5-chloro-7-(1H-pyrazol-5-ylethynyl)-1,3-benzodioxol-4-yl]-6-methoxy-7-(3-morpholin-4-ylpropoxy)quinazolin-4-amine A solution of N-[5-chloro-7-({1-[(4-methylphenyl)sulfonyl]-1H-pyrazol-5-yl}ethynyl)-1,3-benzodioxol-4-yl]-6-methoxy-7-(3-morpholin-4-ylpropoxy)quinazolin-4-amine (0.098 g, 0.137 mmol), sodium hydroxide (0.5 ml of 1M soln, 0.5 mmol) and methanol (3 ml) were stirred at ambient temperature for 1 hour. A saturated solution of ammonium chloride was added and the mixture was partitioned between water and ethyl acetate. The organic layer was separated, dried over magnesium sulfate and evaporated under reduced pressure. The residue was purified by flash chromatography on silica eluting with a mixture of 0-10% methanol in dichloromethane to give the product as a solid (0.023 g, 30%). NMR Spectrum: (DMSOd6) 2.02 (m, 2H), 2.42 (s, 4H), 2.52 (t, 2H under DMSO), 3.62 (s, 4H), 3.99 (s, 3H), 4.24 (d, 2H), 6.24 (s, 2H), 6.63 (s, 1H), 7.23 (s, 1H), 7.27 (s, 1H), 7.86 (s, 1H), 7.88 (s, 1H), 8.37 (s, 1H), 9.57 (s, 1H), 13.31(s, 1H). Mass Spectrum: M+H$^+$ 518 and M+H$^-$ 516.

N-[5-chloro-7-({1-[(4-methylphenyl)sulfonyl]-1H-pyrazol-5-yl}ethynyl)-1,3-benzodioxol-4-yl]-6-methoxy-7-(3-morpholin-4-ylpropoxy)quinazolin-4-amine was prepared as follows:

i) Preparation of 1-[(4-methylphenyl)sulfonyl]-1H-pyrazole:

To a solution of pyrazole (2 g, 29.0 mmol), dichloromethane (20 ml) and pyridine (5 ml) was added 4 toluene sulphonyl chloride (6.89 g, 36 mmol) and the reaction mixture stirred at ambient temperature for 1 hour. The reaction mixture was partitioned between dichlormethane and an aqueous solution of sodium bicarbonate. The organic layer was separated, dried over magnesium sulfate and evaporated under reduced pressure. The residue as purified by flash chromatography on silica eluting with a mixture of 70-100% dichloromethane in hexane and then 10% ethyl acetate in dichloromethane to give the product as a white solid (4.9 g, 76%). NMR Spectrum: (CDCl3) 2.43 (s, 3H), 6.39 (m, 1H), 7.34 (d, 2H), 7.72 (d, 1H), 7.89 (d, 2H), 8.10 (d, 1H). Mass Spectrum: M+H$^+$ 223 and M+H$^-$ 221.

ii) Preparation of 5-iodo-1-[(4-methylphenyl)sulfonyl]-1H-pyrazole

A solution of 1-[(4-methylphenyl)sulfonyl]-1H-pyrazole (2.0 g, 9.0 mmol) in THF (50 ml) was cooled to −78 C under a nitrogen atmosphere. To this was added tert butyl lithium (5.9 ml) in pentane (1.7M, 10 mmol). After 10 minutes iodine (2.53 g, 10 mmol) in THF (10 ml) was added and the reaction mixture was stirred for a further 30 minutes before allowing to warm to ambient temperature followed by stirring for 12 hours. A saturated solution of ammonium chloride was added and the mixture was partitioned between water and ethyl acetate. The organic layer was separated, dried over magnesium sulfate and evaporated under reduced pressure. The residue was purified by flash chromatography on silica eluting with a mixture of 20-100% dichloromethane in hexane to give the product as a solid (0.96 g, 30%).

NMR Spectrum: (DMSOd6) 2.44 (s, 3H), 6.97 (d, 1H), 7.62 (d, 2H), 7.98 (d, 2H), 8.51 (d, 1H). Mass Spectrum: M+H$^+$ 349 and M+H$^-$ 347.

iii) Preparation of N-[5-chloro-7-({1-[(4-methylphenyl)sulfonyl]-1H-pyrazol-5-yl}ethynyl)-1,3-benzodioxol-4-yl]-6-methoxy-7-(3-morpholin-4-ylpropoxy)quinazolin-4-amine N-(5-chloro-7-ethynyl-1,3-benzodioxol-4-yl)-6-methoxy-7-(3-morpholin-4-ylpropoxy)quinazolin-4-amine was prepared as described in example 59

A solution of N-(5-chloro-7-ethynyl-1,3-benzodioxol-4-yl)-6-methoxy-7-(3-morpholin-4-ylpropoxy)quinazolin-4-amine (0.140 g, 0.28 mmol ), 5-iodo-1-[(4-methylphenyl)sulfonyl)-1H-pyrazole (0.147 g, 0.42 mmol) and diisopropylamine (0.078 ml, 0.56 mmol) in ethyl acetate (5 ml) was cooled to −20 C under a nitrogen atmosphere. To this mixture was added copper (I) iodide (0.016 g, 0.084 mmol)

and bis(triphenylphospine)palladium (II) chloride (0.039 g, 0.056 mmol). The reaction mixture was allowed to warm to ambient temperature and then stirred overnight. The reaction mixture was filtered and then evaporated under reduced pressure. The residue was purified by flash chromatography on silica eluting with a mixture of 0-8% methanol in dichloromethane to give the product as a yellow solid (0.103 g, 51%). Mass Spectrum: M+H$^+$ 717 and M+H$^-$ 715.

EXAMPLE 66

4-{3-[(4-{[5-chloro-7-(pyridin-2-ylethynyl)-1,3-benzodioxol-4-yl]amino}-6-methoxyquinazolin-7-yl)oxy]propyl}-1-methylpiperazin-2-one A solution of 4-[3-({4-[(5-chloro-7-iodo-1,3-benzodioxol-4-yl)amino]-6-methoxyquinazolin-7-yl}oxy)propyl]-1-methylpiperazin-2-one (0.17 g, 0.27 mmol), 2-ethynyl pyridine (0.056 g, 0.54 mmol) and diisopropylamine (0.075 ml, 0.54 mmol) in ethyl acetate (5 ml) was cooled to −20 C under a nitrogen atmosphere. To this was added copper (I) iodide (0.016 g, 0.081 mmol) and bis(triphenylphospine)palladium (II) chloride (0.038 g, 0.054 mmol). The reaction mixture was allowed to warm to ambient temperature and then stirred overnight. The reaction mixture was partitioned between ethyl acetate and water. The organic layer was separated, dried over magnesium sulfate and evaporated under reduced pressure. The residue was purified by flash chromatography on silica eluting with a mixture of 0-8% methanol in dichloromethane to give the product as a light brown solid (0.056 g, 35%). NMR Spectrum: (DMSOd6) 2.02 (m, 2H), 2.50 (t, 2H under DMSO), 2.72 (t, 2H), 2.84 (s, 3H), 3.01 (s, 2H), 3.28 (t, 2H under H2O), 3.94 (s, 3H), 4.20 (t, 2H), 6.23 (s, 2H), 7.21 (s, 1H), 7.32 (s, 1H), 7.45 (dd, 1H), 7.68 (d, 1H), 7.86 (m, 2H), 8.35 (s, 1H), 8.64 (d, 1H), 9.54 (s, 1H). Mass Spectrum: M+H$^+$ 601 and M+H$^-$ 599.

4-[3-({4-[(5-chloro-7-iodo-1,3-benzodioxol-4-yl)amino]-6-methoxyquinazolin-7-yl}oxy)propyl]-1-methylpiperazin-2-one was prepared as described in example 30.

EXAMPLE 67

4-{6-chloro-7-[(6,7-dimethoxyquinazolin-4-yl)amino]-1,3-benzodioxol-4-yl}-2-methylbut-3-yn-2-ol A solution of sodium bis(trimethylsilyl)amide (1.5 ml) in tetrahydrofuran (1.0M, 1.5 mmol) was added over 5 min. to a stirred mixture of 4-(7-amino-6-chloro-1,3-benzodioxol-4yl)-2-methylbut-3-yn-2-ol (0.186 g) and 4-chloro-6,7-dimethoxyquinazoline (0.150 g) in DMF (6.5 ml) cooled to 0° C. under a nitrogen atmosphere. The mixture was stirred for 1 hr at ambient temperature. The reaction mixture was diluted with saturated aqueous ammonium chloride (70 ml) and extracted with ethyl acetate (3×30 ml). The organic extracts were washed with brine (20 ml), dried over sodium sulphate and then evaporated. The residue was purified by column chromatography on silica using increasingly polar mixtures of ethyl acetate and isohexane as eluent. There was thus obtained the title compound as a solid (0.150 g). NMR Spectrum: (DMSOd$_6$) 1.47 (s, 6H), 3.90 (s, 3H), 3.91 (s, 3H), 5.50 (s, 1H), 6.13 (s, 2H), 7.04 (s, 1H), 7.17 (s, 1H), 7.80 (s, 1H), 8.31 (s, 1H), 9.48 (s, 1H); Mass Spectrum: M+H$^+$ 442 and 444.

The starting materials were prepared as follows:
a) 4-chloro-6,7-dimethoxyquinazoline was prepared as described in example 24.

b) 4-(7-amino-6-chloro-1,3-benzodioxol-4-yl)-2-methylbut-3-yn-2-ol was prepared as follows:

Bis(triphenylphosphine)palladium(II) chloride (0.236 g), cuprous iodide (0.096 g) and diisopropylamine (0.47 ml) were added to a stirred solution of 5-chloro-7-iodo-1,3-benzodioxol-4-amine (0.500 g) and 2-methyl-3-butyn-2-ol (0.33 ml) in ethyl acetate (8 ml) cooled to −20° C. under a nitrogen atmosphere. The mixture was stirred for 3 hr at ambient temperature. The reaction mixture was filtered through Celite, diluted with ethyl acetate (12 ml) and then washed with saturated aqueous sodium bicarbonate (20 ml). The aqueous layer was re-extracted with ethyl acetate (20 ml). The organic extracts were washed with brine (10 ml), dried with sodium sulphate and then evaporated. The residue was purified by column chromatography using 25% ethyl acetate in isohexane as eluent. There was thus obtained the title compound as a solid (0.475 g). NMR Spectrum: (CDCl$_3$) 1.54 (s, 1H), 1.61 (s, 6H), 4.02 (s, 2H), 6.02 (s, 2H), 6.87 (s, 1H); Mass Spectrum: M+H$^+$ 254 and 256.

EXAMPLE 68

2-[(3-{6-chloro-7-[(6,7-dimethoxyquinazolin-4-yl)amino]-1,3-benzodioxol-4-yl}prop-2-yn-1-yl)oxy]-N-methylacetamide A solution of sodium bis(trimethylsilyl)amide (1.23 ml) in tetrahydrofuran (1.0M, 1.23 mmol) was added over 5 min. to a stirred mixture of 2-{[3-(7-amino-6-chloro-1,3-benzodioxol-4-yl)prop-2-yn-1-yl]oxy}-N-methylacetamide (0.182 g) and 4chloro-6,7-dimethoxyquinazoline (0.125 g) in DMF (6.0 ml) cooled to 0° C. under a nitrogen atmosphere; the mixture was stirred for 1.25 hr at ambient temperature. The reaction mixture was diluted with saturated aqueous ammonium chloride (60 ml) and extracted with ethyl acetate (3×30 ml). The organic extracts were washed with brine (30 ml), dried over sodium sulphate and then evaporated. The residue was purified by column chromatography on silica using increasingly polar mixtures of methanol and dichloromethane as eluent. There was thus obtained the title compound as a solid (0.106 g). NMR Spectrum: (DMSOd$_6$) 2.62 (d, 3H), 3.91 (s, 6H), 3.98 (s, 2H), 4.50 (s, 2H), 6.15 (s, 2H), 7.15 (s, 1H), 7.17 (s, 1H), 7.76 (s, 1H), 7.80 (s, 1H), 8.31 (s, 1H), 9.52 (s, 1H); Mass Spectrum: M+H$^+$ 485 and 487.

The starting materials were prepared as follows:
a) 4-chloro-6,7-dimethoxyquinazoline was prepared as described in example 24
b) 2-{[3-(7-amino-6-chloro-1,3-benzodioxol-4-yl)prop-2-yn-1-yl]oxy}-N-methylacetamide was prepared as follows:
  i) Preparation of N-methyl-2-(prop-2-yn-1-yloxy)acetamide was prepared as follows:

Prop-2-ynyloxyacetyl chloride was prepared as described in Teresa M. V. D. Pinhoe Melo et al, J. Chem. Soc., Perkins Trans. 1, 1999, 1219-1223.

Prop-2-ynyloxyacetyl chloride (1.74 g) in tetrahydrofuran (20 ml) was added dropwise over 5 minutes to a stirred solution of 2M methylamine in tetrahydrofuran (26 ml) at ambient temperature. After 30 minutes the solvent was evaporated and the residue partitioned between saturated aqueous sodium bicarbonate (20 ml) and ethyl acetate (30 ml). The aqueous layer separated and then re-extracted with ethyl acetate (20 ml). The combined ethyl acetate extracts were washed with brine (20 ml), dried over sodium sulphate and then evaporated. There was thus obtained the title compound as a liquid (0.912 g). NMR Spectrum: (CDCl₃) 2.51 (t, 1H), 2.87 (d, 3H), 4.06 (s, 2H), 4.24 (d, 2H), 6.48 (s(broad), 1H); Mass Spectrum: M+H⁺ 128.

ii) Preparation of 2-{[3-(7-amino-6-chloro-1,3-benzodioxol-4-yl)prop-2-yn-1-yl]oxy}-N-methylacetamide 5-chloro-7-iodo-1,3-benzodioxol-4-amine was prepared as described in example 2.

Bis(triphenylphosphine)palladium(II) chloride (0.236 g), cuprous iodide (0.096 g) and diisopropylamine (0.47 ml) were added to a stirred solution of 5-chloro-7-iodo-1,3-benzodioxol-4-amine (0.500 g) and N-methyl-2-(prop-2-yn-1-yloxy)acetamide (0.427 g) in ethyl acetate (8 ml) cooled to −20° C. under a nitrogen atmosphere; the resultant mixture was stirred for 4 hr at ambient temperature. The reaction mixture was filtered through Celite, ethyl acetate (12 ml) was added and the resultant solution was washed with saturated aqueous sodium bicarbonate (20 ml). The aqueous layer was re-extracted with ethyl acetate (20 ml). The combined organic extracts were washed with brine (10 ml), dried with sodium sulphate and then evaporated. The residue was purified by column chromatography on silica using ethyl acetate as eluent. There was thus obtained the title compound as a solid (0.380 g). NMR Spectrum: (CDCl₃) 2.86 (d, 3H), 4.08 (s, 2H), 4.10 (s, 2H), 4.44 (s, 2H), 6.03 (s, 2H), 6.53 (s(broad), 1H), 6.88 (s, 1H); Mass Spectrum: M+H⁺ 297 and 299.

EXAMPLE 69

2-[(3-{6-chloro-7-[(6,7-dimethoxyquinazolin-4-yl)amino]-1,3-benzodioxol-4-yl}prop-2-yn-1-yl)oxy]-N,N-dimethylacetamide A solution of sodium bis(trimethylsilyl)amide (1.3 ml) in tetrahydrofuran (1.0M, 1.3 mmol) was added over 5 minutes to a stirred mixture of 2-{[3-(7-amino-6-chloro-1,3-benzodioxol-4-yl)prop-2-yn-1-yl]oxy}-N,N-dimethylacetamide (0.200 g) and 4-chloro-6,7-dimethoxyquinazoline (0.132 g) in DMF (5.7 ml) cooled to 0° C. under a nitrogen atmosphere; the resultant mixture was stirred for 1.5 hr at ambient temperature. The reaction mixture was diluted with saturated aqueous ammonium chloride (60 ml) and extracted with ethyl acetate (3×30 ml). The organic extracts were washed with brine (20 ml), dried over sodium sulphate and then evaporated. The residue was purified by column chromatography on silica using increasingly polar mixtures of methanol and dichloromethane as eluent. There was thus obtained the title compound as a solid (0.102 g). NMR Spectrum: (DMSOd₆) 2.82 (s, 3H), 2.92 (s, 3H), 3.92 (s, 6H), 4.26 (s, 2H), 4.51 (s, 2H), 6.15 (s, 2H), 7.16 (s, 1H), 7.18 (s, 1H), 7.82 (s, 1H), 8.32 (s, 1H), 9.52 (s, 1H); Mass Spectrum: M+H⁺ 499 and 501.

4-chloro-6,7-dimethoxyquinazoline was prepared as described in example 24.

2-{[3-(7-amino-6-chloro-1,3-benzodioxol-4-yl)prop-2-yn-1-yl]oxy}-N,N-dimethylacetamide was prepared as follows:

i) Preparation of N,N-dimethyl-2-(prop-2-yn-1-yloxy)acetamide

Prop-2-ynyloxyacetyl chloride was prepared as described in example 68.

Prop-2-ynyloxyacetyl chloride (1.74 g) in tetrahydrofuran (20 ml) was added dropwise over 5 min. to a stirred solution of dimethylamine (12 ml of 33% solution in ethanol) in tetrahydrofuran (15 ml) at ambient temperature. After 30 minutes the solvent was evaporated and the residue was partitioned between saturated aqueous sodium bicarbonate (20 ml) and ethyl acetate (30 ml). The aqueous layer was separated and then re-extracted with ethyl acetate (20 ml). The combined ethyl acetate extracts were washed with brine (20 ml), dried over sodium sulphate and then evaporated. There was thus obtained the title compound as a liquid (1.15 g). NMR Spectrum: (CDCl₃) 2.47 (t, 1H), 2.96 (s, 3H), 3.02 (s, 3H), 4.27 (s, 2H), 4.33 (d, 2M); Mass Spectrum: M+H⁺ 142.

ii) Preparation of 2-{[3-(7-amino-6-chloro-1,3-benzodioxol-4-yl)prop-2-yn-1-yl]oxy}-N,N-dimethylacetamide:

5-chloro-7-iodo-1,3-benzodioxol-4-amine was prepared as described in example 2.

Bis(triphenylphosphine)palladium(II) chloride (0.236 g), cuprous iodide (0.96 g) and diisopropylamine (0.47 ml) were added to a stirred solution of 5-chloro-7-iodo-1,3-benzodioxol-4-amine (0.500 g) and N,N-dimethyl-2-(prop-2-yn-1-yloxy)acetamide (0.474 g) in ethyl acetate (8 ml) cooled to −20° C. under a nitrogen atmosphere; the resultant mixture was stirred for 4 hr at ambient temperature. The reaction mixture was filtered through Celite, ethyl acetate (12 ml) was then added and the resultant solution washed with saturated aqueous sodium bicarbonate (20 ml). The aqueous layer was re-extracted with ethyl acetate (20 ml). The combined organic extracts were washed with brine (20 ml), dried over sodium sulphate and then evaporated. The residue was purified by column chromatography on silica using ethyl acetate as eluent. There was thus obtained the title compound as a solid (0.428 g). NMR Spectrum: (CDCl₃) 2.96 (s, 3H), 3.02 (s, 3H), 4.06 (s, 2H), 4.31 (s, 2H), 4.52 (s, 2H), 6.02 (s, 2H), 6.89 (s, 1H); Mass Spectrum: M+H⁺ 311 and 313.

EXAMPLE 70

N-[5-chloro-7-(3-methoxybut-1-yn-1-yl)-1,3-benzodioxol-4-yl]-6,7-dimethoxyquinazolin-4-amine A solution of sodium bis(trimethylsilyl)amide (1.7 ml) in tetrahydrofuran (1.0M, 1.7 mmol) was added over 5 minutes to a stirred mixture of 5-chloro-7-(3-methoxybut-1-yn-1-yl)-1,3-benzodioxol-4-amine (0.211 g) and 4-chloro-6,7-dimethoxyquinazoline (0.170 g) in DMF (7.0 ml) cooled to 0° C. under a nitrogen atmosphere; the resultant mixture was stirred for 1 hr at ambient temperature. The reaction mixture was diluted with saturated aqueous ammonium chloride (70 ml) and extracted with ethyl acetate (3×30 ml). The organic extracts were washed with brine (20 ml), dried over sodium sulphate and then evaporated. The residue was purified by column chromatography on silica using increasingly polar mixtures of ethyl acetate and isohexane as eluent. There was thus obtained the title compound as a racemate and in a solid form (0.200 g). NMR Spectrum: (DMSOd₆) 1.41 (d, 3H), 3.35 (s, 3H), 3.92 (s, 6H), 4.39 (q, 1H), 6.15 (s, 2H), 7.13 (s, 1H), 7.18 (s, 1H), 7.82 (s, 1H), 8.32 (s, 1H), 9.50 (s, 1H);

Mass Spectrum: M+H⁺ 442 and 444.

The starting materials were prepare as follows:

a) 4-chloro-6,7-dimethoxyquinazoline was prepared as described in example 24 b) 5-chloro-7-(3-methoxybut-1-yn-1-yl)-1,3-benzodioxol-4-amine was prepared as follows:

i) Preparation of 3-methoxybut-1-yne:

A solution of 3-butyn-2-ol (7.8 ml) in DMF (20 ml) was added over 30 minutes to a stirred slurry of sodium hydride (6.0 g of a 60% dispersion) in DMF (100 ml) cooled to 0° C. under a nitrogen atmosphere. After 30 minutes dimethyl sulphate (14.2 ml) was added over 30 minutes at 0° C. After the addition the reaction mixture was stirred for 30 minutes at ambient temperature, and then acetic acid (6 ml) was added slowly. The product was distilled directly from the reaction mixture. There was thus obtained 3-methoxybut-1-yne as a liquid (3.37 g, bp 80-84° C.; 77% pure). NMR Spectrum: (CDCl$_3$) 1.45 (d, 3H), 2.43 (d, 1H), 3.41 (s, 3H), 4.07 (m, 1H).
  ii) 5-chloro-7-iodo-1,3-benzodioxol-4-amine was prepared as described in example 2
  iii) Preparation of 5-chloro-7-(3-methoxybut-1-yn-1-yl)-1,3-benzodioxol-4-amine Bis(triphenylphosphine)palladium(II) chloride (0.236 g), cuprous iodide (0.096 g) and diisopropylamine (0.47 ml) were added to a stirred solution of 5-chloro-7-iodo-1,3-benzodioxol-4-amine (0.500 g) and 3-methoxybut-1-yne (0.370 g) in ethyl acetate (8 ml) cooled to −20° C. under a nitrogen atmosphere; the resultant mixture was stirred for 3.5 hr at ambient temperature. The reaction mixture was filtered through Celite, ethyl acetate (12 ml) was added and the resultant solution washed with saturated aqueous sodium bicarbonate (20 ml). The aqueous was separated and re-extracted with ethyl acetate (20 ml). The combined organic extracts were washed with brine (20 ml), dried over sodium sulphate and then evaporated. The residue was purified by column chromatography on silica using 20% ethyl acetate in isohexane as eluent. There was thus obtained the title compound as a solid (0.454 g). NMR Spectrum: (CDCl$_3$) 1.50 (d, 3H), 3.45 (s, 3H), 4.03 (s, 2H), 4.30 (q, 1H), 6.02 (s, 2H), 6.89 (s, 1H); Mass Spectrum: M$^+$ 253 and 255.

EXAMPLE 71

N-[5-chloro-7-(3-methoxybut-1-yn-1-yl)-1,3-benzodioxol-4-yl]-6-methoxy-7-(3-morpholin-4-ylpropoxy)quinazolin-4-amine A solution of sodium bis(trimethylsilyl)amide (1.5 ml) in tetrahydrofuran (1.0M, 1.5 mmol) was added over 5 min. to a stirred mixture of 5-chloro-7-(3-methoxybut-1-yn-1-yl)-1,3-benzodioxol-4-yl-amine (0.190 g) and 4-chloro-6-methoxy-7-(3-morpholin-4-ylpropoxy)quinazoline (0.230 g) in DMF (6.5 ml) cooled to 0° C. under a nitrogen atmosphere; the resultant mixture was stirred for 1 hr at ambient temperature. The reaction mixture was diluted with saturated aqueous ammonium chloride (70 ml) and extracted with ethyl acetate (3×25 ml). The organic extracts were washed with brine (25 ml), dried over sodium sulphate and then evaporated. The residue was purified by column chromatography on silica using increasingly polar mixtures of methanol in dichloromethane as eluent. There was thus obtained the title compound as a racemate and in the form of a solid (0.314 g). NMR Spectrum: (DMSOd$_6$) 1.42 (d, 3H), 1.95 (m, 2H), 2.37 (m, 4H), 2.45 (t, 2H), 3.35 (s, 3H), 3.57 (m, 4H), 3.92 (s, 3H), 4.18 (t, 2H), 4.39 (q, 1H), 6.15 (s, 2H), 7.13 (s, 1H), 7.18 (s, 1H), 7.82 (s, 1H), 8.32 (s, 1H), 9.50 (s, 1H); Mass Spectrum: M+H$^+$ 555 and 557.

The starting materials were prepared as follows:
a) 5-chloro-7-(3-methoxybut-1-yn-1-yl)-1,3-benzodioxol-4-yl-amine was prepared as described in example 70.
b)   4-chloro-6-methoxy-7-(3-morpholin-4-ylpropoxy)quinazoline was prepared as described in example 1.

EXAMPLE 72

N-[5-bromo-7-(3-methoxyprop-1-yn-1-yl)-1,3-benzodioxol-4-yl]-6-methoxy-7-(3-morpholin-4-ylpropoxy)quinazolin-4-amine A solution of sodium bis(trimethylsilyl)amide (1.0 ml) in tetrahydrofuran (1.0M, 1.0 mmol) was added dropwise to an ice-cold solution of [5-bromo-7-(3-methoxyprop-1-yn-1-yl)-1,3-benzodioxol-4-yl]amine (0.137 g, 0.48 mmol) and 4-chloro-6-methoxy-7-(3-morpholin-4-ylpropoxy)quinazoline (0.163 g, 0.48 mmol) in dimethylformamide (5 ml). The mixture was allowed to warm to room temperature over 2 hours. A saturated solution of ammonium chloride (10 ml) was added and the mixture was partitioned between water (50 ml) and ethyl acetate (50 ml). The organic layer was separated, washed with a saturated solution of sodium chloride (50 ml), dried over magnesium sulfate and evaporated under reduced pressure to leave a brown oil. Flash chromatography on silica eluting with a mixture of 24% methanol (containing 7N ammonia) in dichloromethane gave the product as a light yellow solid (0.175 g, 62%). NMR Spectrum: (CDCl$_3$) 2.07-2.14 (m, 2H), 2.46-2.48 (m, 4H), 2.56 (t, 2H), 3.46 (s, 3H), 3.71-3.73 (m, 4H), 4.00 (s, 3H), 4.26 (t, 2H), 4.36 (s, 2H), 6.07 (s, 2H), 6.82 (s(broad), 1H), 7.07 (s, 1H), 7.25 (s, 1H), 7.30 (s, 1H), 8.63 (s, 1H). Mass Spectrum: M+H$^+$ 585 and 587.

The starting materials were prepared as follows:
a)   4-chloro-6-methoxy-7-(3-morpholin-4-ylpropoxy)quinazoline was prepared as described in example 1.
b) Preparation of 5-bromo-7-(3-methoxyprop-1-yn-1-yl)-1,3-benzodioxol-4-yl]amine
  i) 5-bromo-7-iodo-1,3-benzodioxol-4-amine was prepared as follows:
  5-bromo-1,3-benzodioxol-4-amine was prepared as described in WO 0216352.

Benzyltrimethylammonium dichloroiodate (2.2 g, 6.3 mmol) was added in one portion to a mixture of 5-bromo-1,3-benzodioxol-4-amine (1.3 g, 5.8 mmol) and calcium carbonate (0.75 g, 7.5 mmol) in dichloromethane (30 ml) and methanol (15 ml). The mixture was stirred at room temperature for 1 hour and then diluted with dichloromethane (20 ml) and washed first with water (50 ml) and then with a saturated solution of sodium chloride (50 ml). The organic layer was dried over magnesium sulfate and evaporated under reduced pressure to leave a brown oil. Flash chromatography on silica eluting with a 3:1 mixture of iso-hexane and ethyl acetate gave the product as a yellow solid (1.5 g, 76%). NMR Spectrum: (CDCl$_3$) 3.95 (s(broad), 2H), 6.02 (s, 2H), 7.21 (s, 1H).
  ii) Preparation of 5-bromo-7-(3-methoxyprop-1-yn-1-yl)-1,3-benzodioxol-4-yl]amine Dichlorobis(triphenylphosphine)palladium (II) (0.111 g, 0.16 mmol) and copper(I) iodide (0.045 g, 0.24 mmol) were added to a solution of 5-bromo-7-iodo-1,3-benzodioxol-4-amine (0.27 g, 0.79 mmol), methyl propargyl ether (0.11 g, 1.6 mmol) and di-iso-propylamine (0.22 ml, 1.6 mmol) in ethyl acetate (5 ml) cooled to −20 C. The mixture was allowed to warm to room temperature over 1 hour and then stirred for 2 hours. The mixture was absorbed onto silica and purified by flash chromatography on silica eluting with a 3:1 to 2:1 mixture of iso-hexane and ethyl acetate to give the product as a dark brown oil (0.165 g, 74%). NMR Spectrum: (CDCl$_3$) 3.43 (s, 3H), 4.07 (s(broad), 2H), 4.31 (s, 2H), 6.02 (s, 2H), 7.05 (s, 1H).

EXAMPLE 73

N-[5-chloro-7-(3-methoxyprop-1-yn-1-yl)-1,3-benzodioxol-4-yl]-7-[3-(dimethylamino)propoxyl-6-methoxyquinazolin-4-amine N-[5-chloro-7-(3-methoxyprop-1-yn-1-yl)-1,3-benzodioxol-4-yl]-7-(3-chloropropoxy)-6-methoxyquinazolin-4-amine (0.153 g, 0.31 mmol) was added to a solution of dimethylamine in ethanol (33%, 10 ml) and the mixture was heated at 100 C for 2 hours. A further portion of dimethylamine solution (10 ml) was added and the mixture heated at 100 C for a further 2 hours. The solvent was evaporated under reduced pressure and the residue was partitioned between a solution of sodium hydroxide (1N, 25 ml) and ethyl acetate (25 ml). The organic layer was separated, washed with a saturated solution of sodium chloride and dried over magnesium sulfate and then evaporated under reduced pressure to leave a pale yellow solid. Flash chromatography on silica eluting with a mixture of 24% methanol (containing 7N ammonia) in dichloromethane gave the product as a light yellow solid (0.069 g, 45%). NMR Spectrum: (CDCl$_3$) 2.06-2.13 (m, 2H), 2.26 (s, 6H), 2.49 (t, 2H), 3.46 (s, 3H), 4.00 (s, 3H), 4.24 (t, 2H), 4.36 (s, 2H), 6.08 (s, 2H), 6.90 (s(broad), 1H), 7.07 (s, 1H), 7.09 (s, 1H), 7.29 (s, 1H), 8.63 (s, 1H). Mass Spectrum: M+H$^+$ 499 and 501.

N-[5-chloro-7-(3-methoxyprop-1-yn-1-yl)-1,3-benzodioxol-4-yl]-7-(3-chloropropoxy)-6-methoxyquinazolin-4-amine was prepared as described in example 77.

EXAMPLE 74

4-{3-[(4-{[5-bromo-7-(3-methoxybut-1-yn-1-yl)-1,3-benzodioxol-4-yl]amino}-6-methoxyquinazolin-7-yl)oxy]propyl}-1-methylpiperazin-2-one A solution of N-[5-bromo-7-(3-methoxybut-1-yn-1-yl)-1,3-benzodioxol-4-yl]-7-(3-chloropropoxy)-6-methoxyquinazolin-4-amine (0.12 g, 0.22 mmol), 1-methylpiperazin-2-one (0.125 g, 1.1 mmol) and triethylamine (0.15 ml, 1.1 mmol) in 2-methoxyethanol (2 ml) was heated to 80 C overnight followed by heating to 100 C for a further 24 hours. The solvent was evaporated under reduced pressure and the residue was partitioned between dichloromethane and water. The organic layer was separated, dried over magnesium sulfate and evaporated under reduced pressure. Flash chromatography on silica eluting with increasingly polar solutions of methanol (0-8%) in dichloromethane followed by trituration with diethyl ether gave the product as a racemate and in the form of a cream coloured solid (0.052 g). NMR Spectrum: (d$_6$DMSO) 1.43 (d, 3H), 1.96-1.99 (m, 2H), 2.50-2.55 (m, 2H), 2.64-2.69 (m, 2H), 2.82 (s, 3H), 3.01 (s, 2H), 3.25-3.29 (m, 2H), 3.36 (s, 3H), 3.94 (s, 3H), 4.16-4.21 (m, 2H), 4.40 (q, 1H), 6.16 (s, 2H), 7.19 (s, 1H), 7.29 (s, 1H), 7.84 (s, 1H), 8.32 (s, 1H), 9.50 (s, 1H).

Mass Spectrum: M+H$^+$ 626/628.

The starting materials were prepared as follows:
a) Preparation of 5-bromo-7-(3-methoxybut-1-yn-1-yl)-1,3-benzodioxol-4-amine 5-bromo-7-iodo-1,3-benzodioxol-4-amine was prepared as described in example 72

Dichlorobis(triphenylphosphine)palladium (II) (0.99 g, 0.14 mmol) and copper(I) iodide (0.040 g, 0.21 mmol) were added to a solution of 5-bromo-7-iodo-1,3-benzodioxol-4-amine (0.24 g, 0.70 mmol), 3-methoxybut-1-yne (0.197 g, 1.76 mmol) and di-iso-propylamine (0.25 ml, 1.8 mmol) in ethyl acetate (5 ml) cooled to −20 C. The mixture was allowed to warm to room temperature over 1 hour and then stirred for 2 hours. The mixture was absorbed onto silica and purified by flash chromatography on silica eluting with a 3:1 mixture of iso-hexane and ethylacetate to give the product as a brown oil (0.23 g). Mass Spectrum: M+H$^+$ 298 and 200.
b) Preparation of N-[5-bromo-7-(3-methoxybut-1-yn-1-yl)-1,3-benzodioxol-4-yl]-7-(3-chloropropoxy)-6-methoxyquinazolin-4-amine 4-chloro-7-(3-chloropropoxy)-6-methoxyquinazoline was prepared as described in example 13.

A solution of sodium bis(trimethylsilyl)amide (1.4 ml) in tetrahydrofuran (1.0M, 1.4 mmol) was added dropwise to an ice-cold solution of 5-bromo-7-(3-methoxybut-1-yn-1-yl)-1,3-benzodioxol-4-amine (0.208 g, 0.70 mmol) and 4-chloro-7-(3-chloropropoxy)-6-methoxyquinazoline (0.201 g, 0.70 mmol) in dimethylformamide (10 ml). The mixture was allowed to warm to room temperature over 2 hours and then stirred at room temperature overnight. A saturated solution of ammonium chloride (25 ml) was added and the mixture was then extracted with ethyl acetate (25 ml). The organic layer was separated, washed with a saturated solution of sodium chloride (25 ml), dried over magnesium sulfate and evaporated under reduced pressure to leave a brown oil. Flash chromatography on silica eluting with a 1:1 to 3:1 mixture of ethyl acetate and iso-hexane gave the product as a brown gum (0.245 g).

Mass Spectrum: M+H$^+$ 548/550/552.

EXAMPLE 75

N-[5-bromo-7-(3-methoxybut-1-yn-1-yl)-1,3-benzodioxol-4-yl]-6-methoxy-7-(3-morpholin-4-ylpropoxy)quinazolin-4-amine A mixture of N-[5-bromo-7-(3-methoxybut-1-yn-1-yl)-1,3-benzodioxol-4-yl]-7-(3-chloropropoxy)-6-methoxyquinazolin-4-amine (0.12 g, 0.22 mmol) in morpholine (2 ml) was heated at 40 C for 5 hours and then stirred at room temperature overnight. The solvent was removed under reduced pressure and the residue purified directly by flash chromatography on silica eluting with increasingly polar solutions of methanol 0-8% in dichloromethane followed by trituration with diethyl ether to give the product as a racemate and in the form of a pale yellow solid (0.040 g). NMR Spectrum: (d$_6$DMSO) 1.54 (d, 3H), 2.02-2.13 (m, 2H), 2.46-2.53 (m, 4H), 2.54-2.60 (m, 2H), 3.47 (s, 3H), 3.67-3.73 (m, 4H), 4.04 (s, 3H), 4.27-4.33 (m, 2H), 4.51 (q, 1H), 6.27 (s, 2H), 7.30 (s, 1H), 7.40 (s, 1H), 7.94 (s, 1H), 8.43 (s, 1H), 9.62 (s(broad), 1H). Mass Spectrum: M+H$^+$ 599/601.

N-[5-bromo-7-(3-methoxybut-1-yn-1-yl)-1,3-benzodioxol-4-yl]-7-(3-chloropropoxy)-6-methoxyquinazolin-4-amine was prepared as described in example 74.

EXAMPLE 76

4-{3-[(4-{[5-bromo-7-(3-methoxyprop-1-yn-1-yl)-1,3-benzodioxol-4-yl]amino}-6-methoxyquinazolin-7-yl)oxy]propyl}-1-methylpiperazin-2-one A solution of N-[5-bromo-7-(3-methoxyprop-1-yn-1-yl)-1,3-benzodioxol-4-yl]-7-(3-chloropropoxy)-6-methoxyquinazolin-4-amine (0.14 g, 0.26 mmol), 1-methylpiperazin-2-one (0.15 g, 1.3 mmol) and triethylamine (0.18 ml, 1.3 mmol) in 2-methoxy ethanol (2 ml) was heated at 80 C overnight and then further heated at 100 C for 24 hours. The solvent was evaporated under reduced pressure and the residue was partitioned between dichloromethane and water. The organic layer was separated, dried over magnesium sulfate and evaporated under reduced pressure. Flash chromatography on silica eluting with increasingly polar solutions of methanol (0-8%) in dichloromethane followed by trituration with diethyl ether gave the product as a cream coloured solid (042 g). NMR Spectrum: (d$_6$DMSO) 1.93-2.03 (m, 2H), 2.50-2.57 (m, 2H), 2.63-2.70 (m, 2H), 2.82 (s, 3H), 3.01 (s, 2H), 3.25-3.29 (m, 2H), 3.35 (s, 3H), 3.94 (s, 3H), 4.16-4.22 (m, 2H), 4.37 (s, 2H), 6.16 (s, 2H), 7.19 (s, 1H), 7.30 (s, 1H), 7.84 (s, 1H), 8.32 (s, 1H), 9.50 (s, 1H). Mass Spectrum: M+H$^+$ 612/614.

N-[5-bromo-7-(3-methoxyprop-1-yn-1-yl)-1,3-benzodioxol-4-yl]-7-(3-chloropropoxy)-6-methoxyquinazolin-4-amine was made as follows:

5-bromo-7-(3-methoxyprop-1-yn-1-yl)-1,3-benzodioxol-4-amine was prepared as described in example 72.

4-chloro-7-(3-chloropropoxy)-6-methoxyquinazoline was prepared as described in example 13.

A solution of sodium bis(trimethylsilyl)amide (0.5 ml) in tetrahydrofuran (1.0M, 0.5 mmol) was added dropwise to an ice-cold solution of [5-bromo-7-(3-methoxyprop-1-yn-1-yl)-1,3-benzodioxol-4-yl]amine (0.073 g, 0.25 mmol) and 4-chloro-7-(3-chloropropoxy)-6-methoxyquinazoline (0.076 g, 0.26 mmol) in dimethylformamide (5 ml). The mixture was allowed to warm to room temperature over 2 hours and then stirred at room temperature overnight. A saturated solution of ammonium chloride (15 ml) was added and the mixture was extracted with ethyl acetate (15 ml). The organic layer was separated, washed with a saturated solution of sodium chloride (25 ml), dried over magnesium sulfate and evaporated under reduced pressure to leave a brown oil. Flash chromatography on silica eluting with a mixture of 1:1 to 3:1 ethyl acetate and iso-hexane gave the product as a brown gum (0.066 g). Mass Spectrum: M+H$^+$ 534/536/538.

EXAMPLE 77

7-[3-(4-acetylpiperazin-1-yl)propoxy-N-[5-chloro-7-(3-methoxyprop-1-yn-1-yl)-1,3-benzodioxol-4-yl]-6-methoxyquinazolin-4-amine N-[5-chloro-7-(3-methoxyprop-1-yn-1-yl)-1,3-benzodioxol-4-yl]-7-(3-chloropropoxy)-6-methoxyquinazolin-4-amine (0.158 g) was dissolved in 2-methoxyethanol (5 ml) and then N-acetylpiperazine (0.600 g) was added and the mixture heated to 105° C. A small amount of sodium iodide was added to the reaction mixture, and heating continued for a total of 2½ hours. The reaction mixture was cooled to room temperature and then diluted with dichloromethane. The mixture was washed with a water/brine (5/1) mixture followed by brine and then dried over magnesium sulfate and evaporated. The residue was purified by column chromatography on silica using increasingly polar mixtures of dichloromethane and methanol as eluent. There was thus obtained the title compound (0.136 g) as a pale yellow foam. NMR Spectrum: (CDCl$_3$) 2.10 (quin, 2H), 2.43 (m, 2H), 2.47 (m, 2H), 2.57 (t, 2H), 3.46 (s, 3H), 3.47 (m, 2H), 3.49 (s, 3H), 3.62 (t, 3H), 3.98 (s, 3H), 4.25 (t, 2H), 4.35 (s, 2H), 6.08 (s, 2H), 7.06 (s, 1H), 7.20 (s, 1H), 7.28 (s, 2H), 8.62 (s, 1H); Mass Spectrum: M+H$^+$ 582/584.

N-[5-chloro-7-(3-methoxyprop-1-yn-1-yl)-1,3-benzodioxol-4-yl]-7-(3-chloropropoxy)-6-methoxyquinazolin-4-amine used as a starting material was prepared as follows:

5-chloro-7-(3-methoxyprop-1-yn-1-yl)-1,3-benzodioxol-4-amine was prepared as described in example 2.

4-chloro-7-(3-chloropropoxy)-6-methoxyquinazoline was prepared as described in example 13.

A solution of sodium bis(trimethylsilyl)amide (6.96 ml) in tetrahydrofuran (1.0M, 6.96 mmol) was added to a solution of 5-chloro-7-(3-methoxyprop-1-yn-1-yl)-1,3-benzodioxol-4-amine (0.834 g) and 4-chloro-7-(3-chloropropoxy)-6-methoxyquinazoline (1.00 g) in DMF (5 ml) that had been cooled to −10° C. and the mixture was stirred for 10 minutes and then allowed to warm to room temperature for 90 minutes. The reaction mixture was quenched into water and saturated ammonium chloride solution was added. The resulting solid material was filtered off and then dissolved in dichloromethane, dried over magnesium sulfate and then evaporated. The residue was purified by column chromatography on silica using increasingly polar mixtures of dichloromethane and methanol as eluent. There was thus obtained N-[5-chloro-7-(3-methoxyprop-1-yn-1-yl)-1,3-benzodioxol-4-yl]-7-(3-chloropropoxy)-6-methoxyquinazolin-4-amine (1.346 g) as an orange foam; NMR Spectrum: (CDCl$_3$) 2.36 (quin, 2H), 3.45 (s, 3H), 3.78 (t, 2H), 3.96 (s, 3H), 4.31 (t, 2H), 4.35 (s, 2H), 6.07 (s, 2H), 7.06 (s, 1H), 7.09 (s, 1H), 7.14 (s, 1H), 7.28 (s, 1H), 8.63 (s, 1H); Mass Spectrum: M+H$^+$ 490/492.

EXAMPLE 78

N-[5-chloro-7-(3-methoxyprop-1-yn-1-yl)-1,3-benzodioxol-4-yl]-6-methoxy-7-[3-(4-hydroxypiperidin-1-yl)propoxyl-quinazolin-4-amine N-[5-chloro-7-(3-methoxyprop-1-yn-1-yl)-1,3-benzodioxol-4-yl]-7-(3-chloropropoxy)-6-methoxyquinazolin-4-amine (0.265 g) was dissolved in 2-methoxyethanol (7 ml) then 4-hydroxypiperidine (0.818 g) was added and the mixture heated to 105° C. for 50 minutes. The reaction mixture was cooled to room temperature then diluted with dichloromethane, washed with water then brine then dried over magnesium sulfate and evaporated. The residue was purified by column chromatography on silica using increasingly polar mixtures of dichloromethane and methanol with methanolic ammonia as eluent. There was thus obtained the title compound (0.341 g) as a pale yellow gum; NMR Spectrum: (CDCl$_3$) 1.61 (m, 2H), 1.90 (m, 2H), 2.11 (quin, 2H), 2.20 (m, 2H), 2.56 (t, 2H), 2.80 (m, 2H), 3.46 (s, 3H), 3.71 (m, 1H), 3.98 (s, 3H), 4.24 (t, 2H), 4.35 (s, 2H), 6.07 (s, 2H), 6.92 (s, 1H), 7.07 (s, 1H), 7.09 (s, 1H), 7.28 (s, 1H), 8.63 (s, 1H) Mass Spectrum: M+H$^+$ 555/557.

N-[5-chloro-7-(3-methoxyprop-1-yn-1-yl)-1,3-benzodioxol-4-yl]-7-(3-chloropropoxy)-6-methoxyquinazolin-4-amine was prepared as described in example 77.

EXAMPLE 79

((2R)-1-{3-[(4-{[5-chloro-7-(3-methoxyprop-1-yn-1-yl)-1,3-benzodioxol-4-yl]amino}-6-methoxyquinazolin-7-yl)oxy]propyl}pyrrolidin-2-yl)methanol N-[5-chloro-7-(3-methoxyprop-1-yn-1-yl)-1,3-benzodioxol-4-yl]-7-(3-chloropropoxy)-6-methoxyquinazolin-4-amine (0.165 g) was dissolved in 2-methoxyethanol (5 ml) then (R)-(−)-2-pyrrolidinemethanol (0.516 g) was added and the mixture heated to 110° C. for 50 minutes. The reaction mixture was cooled to room temperature and diluted with dichloromethane, washed with water and brine, dried over magnesium sulfate and then evaporated. The residue was purified by column chromatography on silica using increasingly polar mixtures of dichloromethane and methanol with methanolic ammonia as eluent. There was thus obtained the title compound (0.341 g) as a pale yellow gum; NMR Spectrum: (CDCl$_3$) 1.761 (m, 3H), 1.88 (m, 1H), 2.12 (m, 2H), 2.30 (m, 1H), 2.48 (m, 1H), 2.63 (m, 1H), 3.04 (m, 1H), 3.21 (m, 1H), 3.39 (dd, 1H), 3.46 (s, 3H), 3.64 (dd, 1H), 3.98 (s, 3H), 4.25 (m, 2H), 4.35 (s, 2H), 6.07 (s, 2H), 7.01 (s, 1H), 7.06 (s, 1H), 7.12 (s, 1H), 7.28 (s, 1H), 8.62 (s, 1H). Mass Spectrum: M+H$^+$ 555/557.

N-[5-chloro-7-(3-methoxyprop-1-yn-1-yl)-1,3-benzodioxol-4-yl]-7-(3-chloropropoxy)-6-methoxyquinazolin-4-amine was prepared as described in example 77.

EXAMPLE 80

N-[5-chloro-7-(3-methoxyprop-1-yn-1-yl)-1,3-benzodioxol-4-yl]-6-methoxy-7-[3-piperazin-1-ylpropoxy]-quinazolin-4-amine N-[5-chloro-7-(3-methoxyprop-1-yn-1-yl)-1,3-benzodioxol-4-yl]-7-(3-chloropropoxy)-6-methoxyquinazolin-4-amine (0.165 g) was dissolved in 2-methoxyethanol (5 ml) and piperazine (0.586 g) was then added and the mixture heated to 110° C. for 45 minutes. The reaction mixture was cooled to room temperature, diluted with dichloromethane, washed with water and brine, dried over magnesium sulfate and then evaporated. The residue was purified by column chromatography on silica using increasingly polar mixtures of dichloromethane and methanol with methanolic ammonia as eluent. There was thus obtained the title compound (0.126 g) as a clear gum; NMR Spectrum: (CDCl$_3$) 2.09 (quin, 2H), 2.46 (s(broad), 4H), 2.54 (t, 2H), 2.91 (t, 4H), 3.45 (s, 3H), 3.47 (s, 1H), 3.96 (s, 3H), 4.23 (t, 2H), 4.35 (s, 2H), 6.06 (s, 2H), 7.06 (s, 1H), 7.13 (s, 1H), 7.28 (s, 2H), 8.62 (s, 1H); Mass Spectrum: M+H$^+$ 540/542.

N-[5-chloro-7-(3-methoxyprop-1-yn-1-yl)-1,3-benzodioxol-4-yl]-7-(3-chloropropoxy)-6-methoxyquinazolin-4-amine was prepared as described in example 77.

EXAMPLE 81

4-{3-[(4-{[5-chloro-7-(3-methoxyprop-1-yn-1-yl)-1,3-benzodioxol-4-yl]amino}-6-methoxyquinazolin-7-yl)oxy]propyl}piperazin-2-one N-[5-chloro-7-(3-methoxyprop-1-yn-1-yl)-1,3-benzodioxol-4-yl]-7-(3-chloropropoxy)-6-methoxyquinazolin-4-amine (0.200 g) was dissolved in 2-methoxyethanol (6 ml) and piperazine-2-one (0.821 g) was then added and the mixture heated to 110° C. for 3 hours. The reaction mixture was cooled to room temperature, diluted with dichloromethane, washed with water and brine, dried over magnesium sulfate and then evaporated. The residue was purified by column chromatography on silica using increasingly polar mixtures of dichloromethane and methanol as eluent. There was thus obtained the title compound (0.162 g) as a white powder, NMR Spectrum: (d$_6$-DMSO) 2.10 (quin, 2H), 2.66 (m, 4H), 3.12 (s, 2H), 3.33 (m, 2H), 3.44 (s, 3H), 4.01 (s, 3H), 4.24 (t, 2H), 4.34 (s, 2H), 6.09 (s, 2H), 7.04 (, 1H), 7.06 (s, 1H), 7.19 (s, 1H), 7.77 (s, 1H), 8.46 (s, 1H), 9.04 (s, 1H); Mass Spectrum: M+H$^+$ 554/556.

N-[5-chloro-7-(3-methoxyprop-1-yn-1-yl)-1,3-benzodioxol-4-yl]-7-(3-chloropropoxy)-6-methoxyquinazolin-4-amine was prepared as described in example 77.

EXAMPLE 82

N-[5-chloro-7-(3-methoxyprop-1-yn-1-yl)-1,3-benzodioxol-4-yl]-7-{3-[4-(2-fluoroethyl)piperazin-1-yl]propoxy}-6-methoxyquinazolin-4-amine N-[5-chloro-7-(3-methoxyprop-1-yn-1-yl)-1,3-benzodioxol-4-yl]-7-(3-chloropropoxy)-6-methoxyquinazolin-4-amine (0.165 g) was dissolved in 2-methoxyethanol (5 ml) and then fluoroethyl piperazine (0.821 g) was added followed by diisopropylethylamine (0.83 ml) and the mixture heated to 110° C. for 15 hours. The reaction mixture was cooled to room temperature, diluted with dichloromethane, washed with water and brine, dried over magnesium sulfate and then evaporated. The residue was purified by column chromatography on silica using increasingly polar mixtures of dichloromethane and methanol with methanolic ammonia as eluent. There was thus obtained the title compound (0.092 g) as a white powder, contaminated with approximately 5 wt. % diisopropylethylamine; NMR Spectrum: (CDCl$_3$) 2.15 (quin, 2H), 2.63 (m(broad), 12H, ), 2.69 (t, 1H), 2.76 (t, 1H), 3.46 (s, 3H), 3.99 (s, 3H), 4.35 (s, 2H), 4.52 (t, 1H), 4.64 (t, 1H), 6.07 (s, 2H), 6.96 (s, 1H), 7.07 (s, 1H), 7.12 (s, 1H), 7.28 (s, 1H), 8.62 (s, 1H); Mass Spectrum: M+H$^+$ 586/588.

N-[5-chloro-7-(3-methoxyprop-1-yn-1-yl)-1,3-benzodioxol-4-yl]-7-(3-chloropropoxy)-6-methoxyquinazolin-4-amine was prepared as described in example 77.

EXAMPLE 83

N-[5-chloro-7-(3-methoxyprop-1-yn-1-yl)-1,3-benzodioxol-4-yl]-7-(3-morpholin-4-ylpropoxy)-5-(tetrahydro-2H-pyran-4-yloxy)quinazolin-4-amine A solution of sodium bis(trimethylsilyl)amide (1.28 ml) in tetrahydrofuran (1.0M, 1.28 mmol) was added to a suspension of 5-chloro-7-(3-methoxyprop-1-yn-1-yl)-1,3-benzodioxol-4-amine (0.153 g) and 4-chloro-7-(3-morpholin-4-ylpropoxy)-5-(tetrahydro-2H-pyran-4-yloxy)quinazoline (0.260 g) in DMF (4 ml) that had been cooled to −10° C. and the mixture was stirred for 90 minutes. A further portion of sodium bis(trimethylsilyl)amide (0.64 ml) in tetrahydrofuran (1.0M, 0.64 mmol) was added and the reaction was allowed to warm to room temperature and then stirred for a further 2 hours. The reaction mixture was quenched into water and saturated ammonium chloride solution was added. This was then extracted into dichloromethane and the organic portion was then washed with brine, dried over magnesium sulfate and evaporated. The residue was purified by column chromatography on silica using increasingly polar mixtures of dichloromethane and methanol as eluent. The product material gathered after chromatography as a foam was triturated with diethyl ether giving an off-white solid. This was then re-dissolved into dichloromethane and then evaporated under reduced pressure. The resulting solid was triturated with diethyl ether and air-dried. There was thus obtained the title compound (0.141 g) as a white solid; NMR Spectrum: (CDCl$_3$) 2.00 (m, 4H), 2.23 (m, 2H), 2.48 (m, 4H), 2.54 (t, 2H), 3.46 (s, 3H), 3.63 (dq, 2H), 3.73 (t, 4H), 4.02 (dt, 2H), 4.16 (t, 2H), 4.35 (s, 2H), 4.76 (tt, 1H), 6.11 (s, 2H), 6.51 (d, 1H), 6.85 (d, 1H), 7.06 (s, 1H), 8.52 (s, 1H), 9.26 (s, 1H); Mass Spectrum: M+H$^+$ 611/613.

The starting materials were prepared as follows:
a) 5-chloro-7-(3-methoxyprop-1-yn-1-yl)-1,3-benzodioxol-4-amine was prepared as described in example 2.
b) 4-Chloro-7-(3-morpholin-4-ylpropoxy)-5-(tetrahydro-2H-pyran-4-yloxy)quinazoline was prepared as follows:
 i) 4-oxo-5-(tetrahydro-2H-pyran-4-yloxy)-3,4-dihydroquinazolin-7-yl acetate was prepared as described in WO 01/94341.
 ii) Preparation of 4-chloro-5-(tetrahydro-2H-pyran-4-yloxy)quinazolin-7-ol Carbon tetrachloride (1.76 ml) was added to a suspension of 4-oxo-5-(tetrahydro-2H-pyran-4-yloxy)-3,4-dihydroquinazolin-7-yl acetate (1.842 g) and triphenylphosphine (3.333 g) in 1,2-dichloroethane (150 ml) and the reaction mixture was heated to 70° C. for 2 hours. The reaction mixture was cooled to room temperature and the solvent evaporated under reduced pressure. The residue was purified by column chromatography on silica using dichloromethane: ethyl acetate (9:1) as eluent. There was thus obtained the crude product (2.516 g) as a white solid, in an intimate mixture with triphenylphosphine. This material was dissolved in 7N methanolic ammonia (40 ml) and diluted with dichloromethane (40 ml) and the whole was stirred for 20 minutes at room temperature. Evaporation of solvents under reduced pressure gave an off-white solid material that was triturated with dichloromethane. The resulting white precipitate was filtered off and air-dried under suction, giving the title compound (0.580 g) as a white solid; NMR Spectrum: ($d_6$-DMSO) 1.77 (m, 2H), 2.06 (m, 2H), 3.58 (dq, 2H), 3.89 (dq, 2H), 4.87 (m, 1H), 6.84 (s, 2H), 8.71 (s, 1H), 10.99 (s(broad), 1H); Mass Spectrum: M+H$^+$ 281/283.

iii) Preparation of 4-Chloro-7-(3-morpholin-4-ylpropoxy)-5-(tetrahydro-2H-pyran-4-yloxy)quinazoline 4-Chloro-5-(tetrahydro-2H-pyran-4-yloxy)quinazolin-7-ol (0.200 g) and triphenylphosphine (0.260 g) were suspended in dichloromethane (7 ml). To this was added 3-morpholin-4-yl-propan-1-ol (0.1 ml) followed by diisopropylazodicarboxylate (0.17 ml). The reaction mixture was allowed to stir at room temperature for 18 hours before evaporation of solvents under reduced pressure to a volume of approximately 2 ml. This residue was purified by column chromatography on silica using increasingly polar mixtures of dichloromethane and methanol as eluent. There was thus obtained the title compound (0.265 g) as an off-white solid; NMR Spectrum: (CDCl$_3$) 2.00 (m, 4H), 2.13 (m, 2H), 2.48 (t, 4H), 2.54 (t, 2H), 3.70 (m, 6H), 4.06 (dq, 2H), 4.19 (t, 2H), 4.75 (tt, 1H,) 6.59 (d, 1H), 6.96 (d, 1H), 8.80 (s, 1H); Mass Spectrum: M+H$^+$ 408/410.

EXAMPLE 84

N-[5-chloro-7-(3-methoxyprop-1-yn-1-yl)-1,3-benzodioxol-4-yl]-7-methoxy-5-(tetrahydro-2H-pyran-4-yloxy)quinazolin-4-amine 7-Methoxy-5-(tetrahydro-2H-pyran-4-yloxy)quinazolin-4(3H)-one (0.800 g) and triphenylphosphine (1.592 g) were suspended in 1,2-dichloroethane (60 ml) and then carbon tetrachloride (0.84 ml) was added. The reaction mixture was heated to 80° C. for 3 hours. The solvents were evaporated under reduced pressure to give a thick gum which underwent purification by column chromatography on silica gel using methyl tert-butyl ether as eluent. This afforded 4-chloro-7-methoxy-5-(tetrahydro-2H-pyran-4-yloxy)quinazoline (1.524 g) as a 1:2 wt.:wt. mixture with triphenylphosphine oxide. A portion of this mixture (0.556 g) was transferred to a reaction vessel and to this was added a solution of 5-chloro-7-(3-methoxyprop-1-yn-1-yl)-1,3-benzodioxol-4-amine (0.152 g) in N,N-dimethylformamide (4 ml). The reaction mixture was then cooled to −10° C. before the addition of a solution of sodium bis(trimethylsilyl)amide (1.26 ml) in tetrahydrofuran (1.0M, 1.26 mmol). The reaction mixture was warmed to room temperature and left to stir for 3 hours. The reaction mixture was then poured into water and saturated ammonium chloride was added. The mixture was stirred for 10 minutes, extracted into dichloromethane, washed with brine, dried over magnesium sulfate and evaporated. The residue was purified by column chromatography on silica using increasingly polar mixtures of methanol in dichloromethane as eluent. There was thus obtained the title compound (0.193 g) as a white foam; NMR Spectrum: (CDCl$_3$) 1.97 (m, 2H), 2.22 (m, 2H), 3.46 (s, 3H), 3.62 (ddd, 2H), 3.92 (s, 3H), 4.02 (dt, 2H), 4.35 (s, 2H), 4.76 (sept, 1H), 6.11 (s, 2H), 6.52 (d, 1H), 6.86 (d, 1H), 7.06 (s, 1H), 8.53 (s, 1H), 9.27 (s, 1H); Mass Spectrum: M+H$^+$ 498/500.

7-Methoxy-5-(tetrahydro-2H-pyran-4-yloxy)quinazolin-4(3H)-one was prepared as described in WO 0194341.

5-chloro-7-(3-methoxyprop-1-yn-1-yl)-1,3-benzodioxol-4-amine was prepared as described in example 2.

EXAMPLE 85

N-[5-chloro-7-(4-methoxybut-1-yn-1-yl)-1,3-benzodioxol-4-yl]-7-(3-morpholin-4-ylpropoxy)-5-(tetrahydro-2H-pyran-4-yloxy)quinazolin-4-amine A solution of sodium bis(trimethylsilyl)amide (1.10 ml) in tetrahydrofuran (1.0M, 1.10 mmol) was added to a suspension of 5-chloro-7-(4-methoxybut-1-yn-1-yl)-1,3-benzodioxol-4-yl-amine (0.139 g) and 4-chloro-7-(3-morpholin-4-ylpropoxy)-5-(tetrahydro-2H-pyran-4-yloxy)quinazoline (0.223 g) in DMF (5 ml) that had been cooled to −10° C. and the mixture was stirred for 90 minutes then the reaction was allowed to warm to room temperature and stirred for a further 2 hours. The reaction mixture was quenched into water and saturated ammonium chloride solution was added. This was then extracted into dichloromethane and the organic portion was washed with brine, dried over magnesium sulfate and evaporated. The residue was purified by column chromatography on silica using increasingly polar mixtures of dichloromethane and methanol as eluent. The product material gathered after chromatography as a foam was triturated with diethyl ether and air-dried giving an off-white solid. There was thus obtained the title compound (0.216 g) as a grey solid; NMR Spectrum: (CDCl$_3$) 2.00 (m, 4H), 2.23 (m, 2H), 2.48 (m, 4H), 2.54 (t, 2H), 2.73 (t, 2H), 3.42 (s, 3H), 3.61 (m, 6H), 3.73 (t, 2H), 4.02 (m, 2H), 4.15 (t, 2H), 4.76 (tt, 1H), 6.09 (s, 2H), 6.51 (s, 1H), 6.85 (s, 1H), 7.03 (s, 1H), 8.51 (s, 1H), 9.24 (s, 1H);

Mass Spectrum: M+H$^+$ 625/627.

5-chloro-7-(4-methoxybut-1-yn-1-yl)-1,3-benzodioxol-4-yl-amine was prepared as described in example 7.

4-chloro-7-(3-morpholin-4-ylpropoxy)-5-(tetrahydro-2H-pyran-4-yloxy)quinazoline was prepared as described in example 83.

EXAMPLE 86

N-[5-chloro-7-(4-methoxybut-1-1-yl)-1,3benzodioxol-4-yl]-7-(3-morpholin-4-ylpropoxy)-5-isopropoxyquinazolin-4-amine A mixture of N-(5-chloro-7-iodo-1,3-benzodioxol-4-yl)-5-isopropoxy-7-(3-morpholin-4-ylpropoxy)quinazolin-4-amine (0.262 g), 4-methoxy-but-1-yne (0.070 g), palladium (II) bis-triphenylphosphine dichloride (0.030 g) and copper (I) iodide (0.008 g) was taken up into ethyl acetate (5 ml) and cooled to −10° C. The was set to stir rapidly, then diisopropylamine (0.12 ml) was added and the reaction was allowed to warm to room temperature and left to stir for 3 hours. The reaction mixture was filtered through Celite and then the filtrate was evaporated under reduced pressure to leave a brown gum which was then purified by column chromatography on silica using increasingly polar mixtures of methanol in dichloromethane as eluent. There was thus obtained the title compound (0.239 g) as a pale yellow foam; NMR Spectrum: (CDCl$_3$) 1.53 (d, 6H), 2.03 (quin, 2H), 2.49 (m, 4H), 2.56 (t, 2H), 2.73 (t, 2H), 3.41 (s, 3H), 3.61 (t, 2H), 3.73 (t, 4H), 4.16 (t, 2H), 4.82 (sept, 1H), 6.08 (s, 2H), 6.49 (s, 1H), 7.00 (s, 1H), 7.02 (s, 1H), 8.55 (s, 1H), 9.42 (s, 1H); Mass Spectrum: M+H$^+$ 583/585.

4-Methoxybut-1-yne was prepared as described in example 7.

N-(5-chloro-7-iodo-1,3-benzodioxol-4-yl)-5-isopropoxy-7-(3-morpholin-4-ylpropoxy)quinazolin-4famine was prepared as follows:

7-Benzyloxy-5-hydroxy-3-pivaloyloxymethyl-3,4-dihydroquinazolin-4-one was prepared as described in WO 0194341.

i) Preparation of 7-benzyloxy-5-isopropoxy-3,4-dihydroquinazolin-4-one

To a solution of 7-benzyloxy-5-hydroxy-3-pivaloyloxymethyl-3,4-dihydroquinazolin-4-one (6.500 g) and triphenylphosphine (6.242 g) in dichloromethane (300 ml), cooled to −10° C., was added isopropyl alcohol (1.45 ml), followed by dropwise addition over 30 minutes of a solution of di-tert-butylazodicarboxylate (4.698 g) in dichloromethane (25 ml). The resulting yellow solution was allowed to stir cold for a further 1 hour and then warmed to room temperature and stirred for 30 minutes. The solvents were evaporated under reduced pressure leave a yellow gum. This was then dissolved in 7N methanolic ammonia (250 ml) and left to stir for 18 hours at room temperature. Evaporation of solvents under reduced pressure gave a clear oil which was triturated with diethyl ether and air dried to give the title compound (3.477 g) as a white solid; NMR Spectrum: (CDCl$_3$) 1.45 (d, 6H), 4.62 (sept, 1H), 5.15 (s, 2H), 6.58 (d, 1H), 6.83 (d, 1H), 7.40 (m, 5H), 7.95 (s, 1H), 11.34 (s, 1H).

ii) Preparation of 7-hydroxy-5-isopropoxy-3,4-dihydroquinazolin-4-one

7-Benzyloxy-5-isopropoxy-3,4-dihydroquinazolin-4-one (3.461 g) was suspended in N,N-dimethylformamide (46 ml). To this was added 10% palladium on charcoal (0.408 g) and the mixture was set to stir rapidly. There was then added ammonium formate (7.031 g) and the mixture was left to stir for 2 hours at room temperature before being filtered through Celite under suction (the Celite being further washed with N,N-dimethylformamide (25 ml)). The combined filtrate solution was evaporated to dryness under reduced pressure and the resulting white gum was suspended in water and pH was adjusted to 7. The resulting white solid precipitate was gathered by filtration and air-dried. There was thus obtained the title compound (2.357 g) as a white solid; NMR Spectrum: (d$_6$-DMSO) 1.30 (d, 6H), 4.55 (sept, 1H), 6.42 (d, 1H), 6.50 (d, 1H), 7.81 (s, 1H), 10.30 (s, 1H), 11.48 (s, 1H); Mass Spectrum: M+H$^+$ 221.

iii) Preparation of 7-acetoxy-5-isopropoxy-3,4-dihydroquinazolin-4-one

7-Hydroxy-5-isopropoxy-3,4-dihydroquinazolin-4-one (2.329 g) was suspended in a mixture of acetic anhydride (5 ml) and pyridine (0.09 ml). This was then heated to 75° C. for 20 minutes, giving a clear solution. The solvents were then evaporated under reduced pressure to give a white solid which was suspended in water (50 ml) and heated to 70° C. with occasional manual agitation for 45 minutes. The resulting white precipitate was gathered by filtration under suction and air-dried. There was thus obtained the title compound (2.769 g) as a white solid; NMR Spectrum: (CDCl$_3$) 1.47 (d, 6H), 2.34 (s, 3H), 4.64 (sept, 1H), 6.71 (d, 1H), 7.05 (d, 1H), 8.00 (s, 1H), 11.33. (s, 1H); Mass Spectrum: M+H$^+$ 263.

iv) Preparation of 4-[(5-chloro-7-iodo-1,3-benzodioxol-4-yl)amino]-5-isopropoxyquinazolin-7-ol 5-chloro-7-iodo-1,3-benzodioxol-4-amine was prepared as described in example 2.

7-Acetoxy-5-isopropoxy-3,4-dihydroquinazolin-4-one (2.297 g) was suspended in 1,2-dichloroethane (100 ml) and to this was added, with stirring, diisopropylethylamine (12.2 ml) followed by phosphorous oxychloride (3.3 ml). Upon heating to 80° C. the solution turned clear, and deep red in colour. The reaction was left to stir at 80° C. for 3 hours before being cooled to room temperature. Evaporation of solvents under reduced pressure gave the crude chloroquinazoline intermediate as a dark brown gum. This was transferred to a new reaction vessel, and to this was added 5chloro-7-iodo-1,3-benzodioxol-4-amine (2.737 g) followed by isopropyl alcohol (70 ml) and the rapidly stirring brown solution was heated to 80° C. Heating of the reaction was maintained for 1 hour and then the reaction was cooled to room temperature and the solvents were evaporated under reduced pressure to leave a dark brown gum. The gum was dissolved in 7N methanolic ammonia (80 ml) and stirred for 2 hours at room temperature before evaporation of solvents under reduced pressure to leave a brown gum. The gum was then dissolved in dichloromethane (50 ml) and the insoluble salts were filtered off. The filtrate was concentrated to a small volume under reduced pressure and purified by column chromatography on silica using increasingly polar mixtures of dichloromethane and methanol as eluent. There was thus obtained the title compound (1.566 g) as a brown foam, shown to be a mixture with approximately 8 mol. % acetamide; NMR Spectrum: (d$_6$-DMSO) 1.47 (d, 6H), 4.92 (sept, 1H), 6.16 (s, 2H), 6.74 (s(broad), 3H), 7.40 (s, 1H), 8.27 (s, 1H), 9.23 (s, 1H); Mass Spectrum : M+H$^+$ 500/502.

v) Preparation of N-(5-chloro-7-iodo-1,3-benzodioxol-4-amino)-7-(3-chloropropoxy)-5-isopropoxyquinazolin-4-amine 4-[(5-chloro-7-iodo-1,3-benzodioxol-4-yl)amino]-5-isopropoxyquinazolin-7-ol (1.533 g) and triphenylphosphine (2.256 g) were suspended in dichloromethane (58 ml) and 3-chloropropan-1-ol (0.70 ml) was added before the stirred suspension was cooled to −5° C. To this was added, in a dropwise fashion, a solution of di-tert-butylazodicarboxylate (1.768 g) in dichloromethane (7 ml) and the reaction was left to stir for 1 hour. Evaporation of the solvents under reduced pressure gave a thick brown oil which was purified by column chromatography on silica using diethyl ether as eluent, giving 2 batches of product containing material. The first batch of material was shown to contain the desired N-(5-chloro-7-iodo-1,3-benzodioxol-4-amino)-7-(3-chloropropoxy)-5-isopropoxyquinazolin-4-amine (2.500 g) as a white solid, but as a 1:1 wt.:wt. mixture with triphenylphosphine oxide. The second batch of material was further purified by column chromatography on silica using 3:1 methyl-tert-butyl ether: iso-hexane as eluent. There was thus obtained the desired N-(5-chloro-7-iodo-1,3-benzodioxol-4amino)-7-(3-chloropropoxy)-5-isopropoxyquinazolin-4-amine (0.206 g) as a white crystalline solid; NMR Spectrum: (CDCl$_3$) 1.53 (d, 6H), 2.30 (quin, 2H), 3.76 (t, 2H), 4.25 (t, 2H), 4.82 (sept, 1H), 6.10 (s, 2H), 6.50 (d, 1H), 6.83 (d, 1H), 7.29 (s, 1H), 8.51 (s, 1H), 9.34 (s, 1H); Mass Spectrum: M+H$^+$ 576/578/580.

vi) Preparation of N-(5-chloro-7-iodo-1,3-benzodioxol-4-yl)-5-isopropoxy-7-(3-morpholin-4-ylpropoxy)quinazolin-4-amine N-(5-chloro-7-iodo-1,3-benzodioxol-4-yl)-7-(3-chloropropoxy)-5-isopropoxyquinazolin-4-amine (0.188 g) was dissolved in 2-methoxyethanol (5 ml) then morpholine (0.71 ml) and sodium iodide (0.049 g) were added and the mixture heated to 110° C. for 90 minutes. The reaction mixture was cooled to room temperature and evaporated to dryness under reduced pressure. The residue was purified by column chromatography on silica using increasingly polar mixtures of dichloromethane and methanol as eluent. The product containing fractions were combined and solvents evaporated under reduced pressure to give a brown gum which was dissolved in dichloromethane and washed with water and brine, dried over magnesium sulfate and then evaporated to dryness under reduced pressure. There was thus obtained (0.179 g) as a white foam; NMR Spectrum: (CDCl$_3$) 1.52 (d, 6H), 2.02 (t, 2H), 2.48 (m, 4H), 2.54 (t, 2H), 3.73 (m, 4H), 4.15 (t, 2H), 4.82 (m, 1H), 6.10 (s, 2H), 6.49 (s, 1H), 6.82 (s, 1H), 7.29 (s, 1H), 8.50 (s, 1H), 9.34 (s, 1H); Mass Spectrum: M+H$^+$ 627/629.

EXAMPLE 87

N-[5-chloro-7-(4-methoxyprop-1-yn-1-yl)-1,3-benzodioxol-4-yl]-7-(3-morpholin-4-ylpropoxy)-5-isopropoxyquinazolin-4-amine A mixture of N-(5-chloro-7-iodo-1,3-benzodioxol-4-yl)-5-isopropoxy-7-(3-morpholin-4-ylpropoxy)quinazolin-4-amine (0.228 g), 3-methoxy-prop-1-yne (0.067 ml), palladium(II) bis-triphenylphosphine dichloride (0.025 g) and copper (I) iodide (0.007 g) was taken up into ethyl acetate (5 ml) and cooled to −10° C. This was set to stir rapidly and then diisopropylamine (0.1 ml) was added and the reaction was allowed to warm to room temperature and left to stir for 3 hours. The reaction mixture was filtered through Celite under suction (washing the Celite with a further portion of ethyl acetate) and the combined filtrate solutions were evaporated under reduced pressure to give a brown gum. The gum was then purified by column chromatography on silica using increasingly polar mixtures of methanol in dichloromethane as eluent. There was thus obtained the title compound (0.129 g) as a pale yellow foam; NMR Spectrum: (CDCl$_3$) 1.53 (d, 6H), 2.02 (quin, 2H), 2.48 (m, 4H), 2.54 (t, 2H), 3.46 (s, 3H), 3.73 (t, 4H), 4.15 (t, 2H), 4.35 (s, 2M), 4.83 (sept, 1H), 6.10 (s, 2H), 6.49 (s, 1H), 6.83 (s, 1H, 7.06 (s, 1H), 8.51 (s, 1H), 9.41 (s, 1H); Mass Spectrum: M+H$^+$ 569/571.

N-(5-chloro-7-iodo-1,3-benzodioxol-4yl)-5-isopropoxy-7-(3-morpholin-4-ylpropoxy)quinazolin-4-amine was prepared as described in example 86.

EXAMPLE 88

7-[3-(4-acetylpiperazin-1-yl)propoxyl-N-[5-chloro-7-(3-methoxyprop-1-yn-1-yl)-1,3-benzodioxol-4-yl]-5-isopropoxyquinazolin-4-amine A mixture of N-[5-chloro-7-(3-methoxyprop-1-yn-1-yl)-1,3-benzodioxol-4-yl]-7-(3-chloropropoxy)-5-isopropoxyquinazolin-4-amine (0.253 g, as a 1:1.3 wt.:wt. mixture with triphenylphosphine) and N-acetyl piperazine (0.538 g) was dissolved in 2-methoxyethanol. Sodium iodide (0.031 g) was added and the reaction mixture was heated at 110° C. with stirring for 4 hours. The reaction mixture was cooled to room temperature, diluted with dichloromethane (150 ml), washed with water and brine, dried over magnesium sulfate and evaporated under reduced pressure. The residue was purified by column chromatography on silica using increasingly polar mixtures of methanol in dichloromethane as eluent. There was thus obtained the title compound (0.105 g) as a white foam; NMR Spectrum: (CDCl$_3$) 1.53 (d, 6H), 2.03 (quin, 2H), 2.09 (s, 3H), 2.46 (m, 4H), 2.56 (t, 2H), 3.46 (s, 3H), 3.48 (t, 2H), 3.63 (t, 2H), 4.16 (t, 2H), 4.35 (s, 2H), 4.82 (sept, 1H), 6.10 (s, 2H), 6.49 (d, 1H), 6.83 (d, 1H), 7.06 (s, 1H), 8.51 (s, 1H), 9.41 (s, 1H); Mass Spectrum: M+H$^+$ 610/612.

N-[5-chloro-7-(3-methoxyprop-1-yn-1-yl)-1,3-benzodioxol-4-yl]-7-(3-chloropropoxy)-5-isopropoxyquinazolin-4-amine was prepared as follows A mixture N-(5-chloro-7-iodo-1,3-benzodioxol-4yl)-7-(3-chloropropoxy)-5-isopropoxyquinazolin-4-amine (1.313 g, 1:1 wt.:wt. mixture with triphenylphosphine), 3-methoxyprop-1-yne (0.19 ml), palladium(II) bis-triphenylphosphine dichloride (0.080 g) and copper (I) iodide (0.022 g) was taken up into ethyl acetate (15 ml) and cooled to −10° C. This was set to stir rapidly and then diisopropylamine (0.32 ml) was added and the reaction was stirred cold for 45 minutes before being warmed to room temperature and left to stir for a further 90 minutes. The reaction mixture was then filtered through Celite under suction (washing the Celite with a further portion of ethyl acetate) then the combined filtrate solutions were evaporated under reduced pressure to leave a brown gum. The gum was then purified by column chromatography on silica using diethyl ether as eluent. There was thus obtained the title compound (as a 1:1.3 wt.:wt. mixture with triphenylphosphine) (1.056 g) as a yellow solid; NMR Spectrum: (CDCl$_3$) 1.53 (d, 6H), 2.30 (quin, 2H), 3.45 (s, 3H), 3.76 (t, 2H), 4.25 (t, 2H), 4.35 (s, 2H), 4.83 (sept, 1H), 6.10 (s, 2H), 6.49 (d, 1H), 6.85 (d, 1H), 7.06 (s, 1H), 8.52 (s, 1H), 9.42 (s, 1H)—triphenylphosphine 7.46 (m, 6H), 7.54 (m, 3H), 7.67 (m, 6H); Mass Spectrum: M+H$^+$ 518/520.

N-(5-chloro-7-iodo-1,3-benzodioxol-4-yl)-7-(3-chloropropoxy)-5-isopropoxyquinazolin-4-amine was prepared as described in example 86.

EXAMPLE 89

N-[5-chloro-7-(pyridin-2-ylethynyl)-1,3-benzodioxol-4-yl]-5-isopropoxy-7-(3-morpholin-4-ylpropoxy)quinazolin-4-amine N-(5-chloro-7-iodo-1,3-benzodioxol-4-yl)-5-isopropoxy-7-(3-morpholin-4-ylpropoxy)quinazolin-4-amine (0.162 g), 2-ethynyl pyridine (0.03 ml), palladium(II) bis-triphenylphosphine dichloride (0.020 g) and copper (I) iodide (0.006 g) was taken up into ethyl acetate (5 ml) and cooled to −10° C. This was set to stir rapidly, then diisopropylamine (0.047 ml) was added and the reaction was stirred cold for 30 minutes before being warmed to room temperature and left to stir for 18 hours. The reaction mixture was then filtered through Celite under suction (washing the Celite with a further portion of ethyl acetate) then the combined filtrate solutions were evaporated under reduced pressure to give a brown gum. This was then purified by column chromatography on silica using increasingly polar mixtures of methanol in dichloromethane as eluent. There was thus obtained the title compound (0.090 g) as a pale brown foam; NMR Spectrum: (CDCl$_3$) 1.54 (d, 6H), 2.04 (quin, 2H), 2.50 (m, 4H), 2.56 (t, 2H), 3.74 (t, 4H), 4.16 (t, 2H), 4.83 (sept, 1H), 6.14 (s, 2H), 6.50 (d, 1H), 6.84 (d, 1H), 7.19 (s, 1H), 7.25 (m, 1H), 7.54 (d, 1H), 7.68 (td, 1H), 8.53 (s, 1H), 8.63 (dd, 1H), 9.46 (s, 1H); Mass Spectrum: M+H$^+$ 602/604.

N-(5-chloro-7-iodo-1,3-benzodioxol-4-yl)-5-isopropoxy-7-(3-morpholin-4-ylpropoxy)quinazolin-4-amine was prepared as described in example 86.

EXAMPLE 90

4-{3-[(4-{[5-chloro-7-(3-methoxyprop-1-yn-1-yl)-1,3-benzodioxol-4-yl]amino}-5-isopropoxyquinazolin-7-yl)oxy]propyl}piperazine-1-carbaldehyde A mixture N-[5-chloro-7-(3-methoxyprop-1-yn-1-yl)-1,3-benzodioxol-4-yl]-7-(3-chloropropoxy)-5-isopropoxyquinazolin-4-amine (0.320 g, as a 1:1.3 wt.:wt. mixture with triphenylphosphine) and N-formyl piperazine (0.69 ml) was dissolved in 2-methoxyethanol (7 ml), then sodium iodide (0.040 g) was added and the reaction mixture was then heated at 110° C. with stirring for 24 hours. The reaction mixture was then cooled to room temperature, diluted with dichloromethane (70 ml) and washed with water:brine (1:1) then water then brine and dried over magnesium sulfate before filtration and evaporation of solvents under reduced pressure. The residues so resulting were then purified by column chromatography on silica using increasingly polar mixtures of methanol in dichloromethane as eluent. There was thus obtained the title compound (0.086 g) as a white foam; NMR Spectrum: (CDCl$_3$) 1.53 (d, 6H), 2.03 (quin, 2H), 2.47 (dt, 4H), 2.58 (t, 2H), 3.40 (t, 2H), 3.45 (s, 3H), 3.58 (t, 2H), 4.16 (t, 2H), 4.35 (s, 2H), 4.82 (sept, 1H), 6.10 (s, 2H), 6.49 (d, 1H), 6.83 (d, 1H), 7.06 (s, 1H), 8.03 (s, 1H), 8.51 (s, 1H), 9.41 (s, 1H); Mass Spectrum: M+H$^+$ 596/598.

N-[S-chloro-7-(3-methoxyprop-1-yn-1-yl)-1,3-benzodioxol-4-yl]-7-(3-chloropropoxy)-5-isopropoxyquinazolin-4-amine was prepared as described in example 88.

EXAMPLE 91

4-{3-[(4-{[5-chloro-7-(3-methoxyprop-1-yn-1-yl)-1,3-benzodioxol-4-yl]amino}-5-isopropoxyquinazolin-7-yl)oxy]propyl}-1-methylpiperazin-2-one A mixture N-[5-chloro-7-(3-methoxyprop-1-yn-1-yl)-1,3-benzodioxol-4-yl]-7-(3-chloropropoxy)-5-isopropoxyquinazolin-4-amine (0.320 g, as a 1:1.3 wt.:wt. mixture with triphenylphosphine) and 1-methylpiperazin-2-one (0.280 g) was dissolved in 2-methoxyethanol (7 ml), then sodium iodide (0.040 g) was added and the reaction mixture was then heated at 110° C. with stirring for 24 hours. The reaction mixture was then cooled to room temperature, diluted with dichloromethane (70 ml) and washed with water:brine (1:1) then water then brine and dried over magnesium sulfate before filtration and evaporation of solvents under reduced pressure. The residues so resulting were then purified by column chromatography on silica using increasingly polar mixtures of methanol in dichloromethane as eluent. There was thus obtained 4-(3-{4-[5-chloro-7-(3-methoxy-prop-1-ynyl)-benzo[1,3]dioxol-4-ylamino]-5-isopropoxy-quinazolin-7-yloxy}-propoxy)-1-methyl-piperazin-2-one (0.086 g) as a white foam; NMR Spectrum: (CDCl$_3$) 1.53 (d, 6H), 2.02 (quin, 2H), 2.61 (t, 2H), 2.72 (t, 2H), 2.96 (s, 3H), 3.18 (s, 2H), 3.33 (t, 2H), 3.45 (s, 3H), 4.15 (t, 2H), 4.35 (s, 2H), 4.83 (sept, 1H), 6.10 (s, 2H), 6.49 (d, 1H), 6.82 (d, 1H), 7.05 (s, 1H), 8.51 (s, 1H), 9.41 (s, 1H); Mass Spectrum: M+H$^+$ 596/598.

N-[5-chloro-7-(3-methoxyprop-1-yn-1-yl)-1,3-benzodioxol-4-yl]-7-(3-chloropropoxy)-5-isopropoxyquinazolin-4-amine was prepared as described in example 88.

1-Methylpiperazin-2-one was prepared as described in example 25.

EXAMPLE 92

N-[5-chloro-7-(3-methoxy-3-methylbut-1-yn-1-yl)-1,3-benzodioxol-4-yl]-6-methoxy-7-(3-morpholin-4-ylpropoxy)quinazolin-4-amine A solution of sodium bis(trimethylsilyl)amide (1.12 ml) in tetrahydrofuran (1.0M, 1.12 mmol) was added to a solution 4-chloro-6-methoxy-7-(3-morpholin-4-ylpropoxy)quinazoline (0.189 g) and 5-chloro-7-(3-methoxy-3-methylbut-1-yn-1-yl)-1,3-benzodioxol-4-amine (0.150 g) in DMF (6 ml) that had been cooled to −15° C. and the mixture was stirred for 3 hours then the reaction was allowed to warm to room temperature. The reaction mixture was quenched into water and saturated ammonium chloride solution was added. The resulting white precipitate was filtered under suction, washing with water, giving a pale tan paste. This was then extracted into dichloromethane, dried over magnesium sulfate and solvents evaporated under reduced pressure to give a tan foam. This was triturated with diethyl ether, giving a white solid. The resulting solid was then gathered by filtration and air-dried. There was thus the title compound (0.225 g) as an off-white solid; NMR Spectrum: (CDCl$_3$) 1.55 (s, 6H), 2.11 (quin, 2H), 2.47 (s(broad), 4H), 2.56 (t, 2H), 3.43 (s, 3H), 3.72 (t, 4H), 4.00 (s, 3H), 4.26 (t, 2H), 6.07 (s, 2H), 6.83 (s, 1H), 7.05 (s, 1H), 7.08 (s, 1H), 7.30 (s, 1H), 8.62 (s, 1H); Mass Spectrum: M+H$^+$ 569/571.

4-chloro-6-methoxy-7-(3-morpholin-4-ylpropoxy) quinazoline was prepared as described in example 1.

5-chloro-7-(3-methoxy-3-methylbut-1-yn-1-yl)-1,3-benzodioxol-4-amine was prepared as described in example 67.

The invention claimed is:
1. A quinazoline derivative of the Formula I

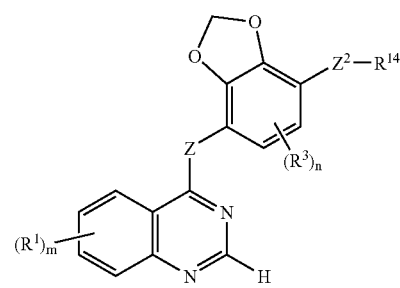

wherein Z is an O, S, SO, SO$_2$, N(R$^2$) or C(R$^2$)$_2$ group, wherein each R$^2$ group, which may be the same or different, is hydrogen or (1-6C)alkyl;

m is 1 or 2;

each R$^1$ group, which may be the same or different, is selected from halogeno, trifluoromethyl, hydroxy, amino, carbamoyl, (1-6C)alkyl, (2-8C)alkenyl, (2-8C) alkynyl, (1-6C)alkoxy, (2-6C)alkenyloxy, (2-6C)alkenyloxy, (2-6C)alkynyloxy, or from a group of the formula:

Q$^1$-X$^1$— wherein X$^1$ is a direct bond or is O and Q$^1$ is heterocyclyl or heterocyclyl-(1-6C)alkyl, and wherein adjacent carbon atoms in any (2-6C)alkylene chain within a R$^1$ substituent are optionally separated by the insertion into the chain of an O, and wherein any CH$_2$ or CH$_3$ group within a R$^1$ substituent optionally bears on each said CH$_2$ or CH$_3$ group one or more halogeno groups or a group selected from amino, (1-6C)alkylamino, di-[(1-6C)alkyl]amino, (1-6C) alkoxyalkylamino di-[(1-6C)alkoxyalkyl]amino or hydroxy(1-6C)alkylamino, and wherein any heterocyclyl group within a substituent on R$^1$ optionally bears 1, 2 or 3 substituents, which may be the same or different, selected from halogeno, halogeno (1-6C) alkyl, (1-6C)alkyl, (1-6C)alkoxy, formyl, (2-6C) alkanoyl, hydroxy and hydroxy(1-6C)alkyl, and wherein any heterocyclyl group within a substituent on R$^1$ optionally bears 1 or 2 oxo substituents;

n is 0, 1 or 2; and

R$^3$ is selected from halogeno, trifluoromethyl, cyano, nitro, hydroxy, amino, carboxy, carbamoyl, (1-6C)alkyl, (2-8C)alkenyl, (2-8C)alkynyl, (1 -6C)alkoxy, (2-6C)

alkenyl (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino or from a group of the formula:

—$X^6$—$R^{11}$ wherein $X^6$ is a direct bond or is selected from O and N($R^{12}$), wherein $R^{12}$ is hydrogen or (1-6C)alkyl, and $R^{11}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl;

$Z^2$ is a C≡C or C($R^{13}$)=C($R^{13}$) group, wherein each $R^{13}$ group, which maybe the same or different, is hydrogen or (1-6C)alkyl; and $R^{14}$ is selected from hydroxy-(1-6C)alkyl, (1-6C)alkoxy-(1-6C)alkyl, (1-6C)alkylamino-(1-6C)alkyl, di-[(1-6C)alkyl]amino-(1-6C)alkyl, from a group of formula:

($CH_2$)$_x$—N($R^c$)—(O)—N$R^a R^b$ wherein x is 0, 1, 2 or 3, $R^3$ is hydrogen or (1-6C)alkyl and $R^a$ and $R^b$ are each independently selected from hydrogen and (1-6C)alkyl or $R^a$ and $R^b$ together with the nitrogen to which they are attached form morpholino
or from a group of the formula:

—$X^7$-$Q^5$ wherein $X^7$ is a direct bond and $Q^5$ is aryl, heteroaryl, heterocyclyl, heterocyclyl-(1-6C)alkyl or heterocyclyloxy-(1-6C)alkyl, and wherein any CH, $CH_2$ or $CH_3$ group within a $R^{14}$ substituent optionally bears on each said CH, $CH_2$ or $CH_3$ group one or more halogeno, (1-6C)alkyl, (1-6C)alkoxy, carbamoyl, (1-6C)alkoxy, N-(1-6C)alkylcarbamoyl, N,N-di-[(1-6C)alkyl]carbamoyl or from a group of the formula:

—$X^8$-$Q^6$ wherein $X^8$ is a direct bond or O and $Q^6$ is aryl, (3-7C)cycloalkyl, (3-7C)cycloalkyl-(1-6C)alkyl, heterocyclyl or heterocyclyl-(1-6C)alkyl, and wherein any aryl, cycloalkyl or heterocyclyl group within a substituent on $R^{14}$ optionally bears 1, 2 or 3 substituents, which may be the same or different, selected from halogeno, hydroxyl, amino, (1-6C)alkyl or (1-6C)alkanoyl, and wherein any heterocyclyl group within a substituent on $R^{14}$ optionally bears 1 or 2 oxo or thioxo substituents;

or a pharmaceutically-acceptable salt thereof.

2. The quinazoline derivative of the Formula I according to claim 1 wherein

Z is O or NH m is 1 and the $R^1$ group is located at the 5-, 6-, or 7-position or m is 2 and each $R^1$ group, which may be the same or different, is located at the 5- and 7-positions or at the 6- and 7-positions and $R^1$ is selected from methoxy, ethoxy, propoxy, isopropoxy, 2-methylpropoxy, or from a group of the formula:

$Q^1$-$X^1$— wherein $X^1$ is O and $Q^1$ is piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, tetrahydro-2H-pyran-4-yl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, piperidin-4-ylmethyl, 2-piperidin-3-ylethyl, 3-piperidin-1-ylpropyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein adjacent carbon atoms in any (2-6C)alkylene chain within a $R^1$ substituent are optionally separated by the insertion into the chain of a O, and wherein any $CH_2$ or $CH_3$ group within a $R^1$ substituent optionally bears on each said $CH_2$ or $CH_3$ group one or more fluoro, chloro or bromo groups or a substituent selected from amino, methylamino, dimethylamino, methoxyethylamino, di-(methoxyethyl)amino, or hydroxypropylamino, and wherein any heterocyclyl group within a substituent on $R^1$ optionally bears 1, 2 or 3 substituents, which may be the same or different, selected from methyl, ethyl, methoxy, ethoxy, formyl, acetyl, hydroxyl, hydroxymethyl, fluoroethyl or hydroxypropylamino, and wherein any heterocyclyl group within a substituent on $R^1$ optionally bears 1 or 2 oxo substituents;

n is 0 or 1 and $R^3$ group, if present, is located at the 5- or 6-position of the 1,3-benzodioxol-4-yl group and is selected from fluoro, chloro, bromo, trifluoromethyl, cyano, hydroxy, methyl, ethyl, methoxy and ethoxy;

$Z^2$ is a C≡C or CH=CH group; and $R^{14}$ is selected from hydroxy-(1-6C)alkyl, (1-6C)alkoxy-(1-6C)alkyl, (1-6C)alkylamino-(1-6C)alkyl, di-[(1-6C)alkyl]amino-(1-6C)alkyl, from a group of formula:

($CH_2$)$_x$—N($R^c$)—C(O)—N$R^a R^b$ wherein x is 0, 1, 2 or 3, $R^c$ is hydrogen or (1-6C)alkyl and $R^a$ and $R^b$ are each independently selected from hydrogen and (1-6C)alkyl or $R^a$ and $R^b$ together with the nitrogen to which they are attached form morpholino
or from a group of the formula:

—$X^7$-$Q^5$ wherein $X^7$ is a direct bond and $Q^5$ is aryl, heteroaryl, heterocyclyl, heterocyclyl-(1-6C)alkyl or heterocyclyloxy-(1-6C)alkyl, and wherein any CH, $CH_2$ or $CH_3$ group within a $R^{14}$ substituent optionally bears on each said CH, $CH_2$ or $CH_3$ group one or more halogeno, (1-6C)alkyl, (1-6C)alkoxy, carbamoyl, (1-6C)alkoxy, N-(1-6C)alkylcarbamoyl, N,N-di-[(1-6C)alkyl]carbamoyl or from a group of the formula:

—$X^8$-$Q^6$ wherein $X^8$ is a direct bond or O and $Q^6$ is aryl, (3-7C)cycloalkyl, (3-7C)cycloalkyl-(1-6C)alkyl, heterocyclyl or heterocyclyl-(1-6C)alkyl, and wherein any aryl, cycloalkyl or heterocyclyl group within a substituent on $R^{14}$ optionally bears 1, 2 or 3 substituents, which may be the same or different, selected from halogeno, hydroxyl, amino, (1-6C)alkyl or (1-6C)alkanoyl, and wherein any heterocyclyl group within a substituent on $R^{14}$ optionally bears 1 or 2 oxo or thioxo substituents;

or a pharmaceutically acceptable acid addition salt thereof.

3. The quinazoline derivative of the Formula I, or a pharmaceutically acceptable salt thereof, according to claim 1 wherein $R^1, R^2, R^3, R^{14}, Z^2$, m and n have any of the meanings defined in claim 1 and Z is NH.

4. The quinazoline derivative of the Formula I according to claim 1 wherein

Z is NH m is 2, and the first $R^1$ group is a 6-methoxy group and the second $R^1$ group is located at the 7-position and is selected from methoxy, 2-methoxyethoxy, 2-fluoroethoxy, 3-chloroethoxy, isopropoxy, isopropylmethoxy, 3-dimethylaminopropoxy, 2-dimethylaminoethoxy, dimethylaminoisopropoxy, 2-[3-(hydroxy)propylamino]ethoxy, 3-[bis(2-methoxyethyl)amino]propoxy, 2-(2-methoxyethoxy)ethoxy, 3-chloropropoxy, 2-(2-chloroethoxy)ethoxy, 3-piperazin-1-ylpropoxy, 2-piperazin-1-ylethoxy, 4-piperazin-1-ylbutoxy, 2-(4-methylpiperazin-1-yl)ethoxy, 3-(4-methylpiperazin-1-yl) propoxy, 4-(4-methylpiperazin-1-yl)butoxy, 3-[4-(2-fluoroethyl)piperazin-1-yl]propoxy, 2-[4-(2-fluoroethyl)piperazin-1-yl]ethoxy, 4-[4-(2-fluoroethyl)piperazin-1-yl]butoxy, 3-(4-acetylpiperazin-1-yl) propoxy, 2-(4-acetylpiperazin-1-yl)ethoxy, 4-(4-acetylpiperazin-1-yl)butoxy, 3-(4-formylpiperazin-1-yl)propoxy, 2-(4-formylpiperazin-1-yl)ethoxy, 4-(4-formylpiperazin-1-yl)butoxy, 3-morpholinopropoxy, 2-morpholin-4-ylethoxy, 4-morpholin-4-ylbutoxy, 3-(2,6-dimethylmorpholin-4-yl)propoxy, 2-(2,6-dimethylmorpholin-4-yl)ethoxy, 4-(2,6-dimethylmorpholin-4-yl)butoxy, 3-(1,1-dioxotetrahydro-4H-1,4-thiazin-4-yl)propoxy, 3-[2-(hydroxymethyl)pyrrolidin-1-yl]propoxy, 4-[2-(hydroxymethyl)pyrrolidin-1-yl]butoxy, 2-[2-(hydroxymethyl)pyrrolidin-1-yl] ethoxy, 3-(4-hydroxypiperidin-1-yl)propoxy, 2-(4-hydroxypiperidin-1-yl)ethoxy, 4-(4-hydroxypiperidin-1-yl)butoxy, 1-methylpiperidin-4-ylmethoxy, 3-(1-methylpiperidin-4-yl)propoxy, 3-(4-methoxypiperidin-1-yl)propoxy, 3-(4-methoxypiperidin-1-yl)ethoxy or 4-(4-methoxypiperidin-1-yl)butoxy and wherein any heterocyclyl group within a substituent on $R^1$ optionally bears 1 or 2 oxo substituents;

n is 0 or 1 and $R^3$ group, if present, is located at the 5-position of the 1,3-benzodioxol-yl group and is selected from fluoro, chloro, bromo, trifluoromethyl, cyano, hydroxy, methyl, ethyl, methoxy and ethoxy;

$Z^2$ is a C≡C or CH=CH group; and $R^{14}$ is selected from (1-6C)alkoxy-(1-6C)alkyl, di-[(1-6C)alkyl]amino-(1-6C)alkyl, hydroxyl-(1-6C)alkyl or from a group of formula:

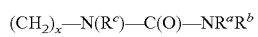

$(CH_2)_x$—$N(R^c)$—$C(O)$—$NR^aR^b$ wherein x is 0, 1, 2 or 3, $R^c$ is hydrogen or (1-6C)alkyl and $R^a$ and $R^b$ are each independently selected from hydrogen and (1-6C)alkyl or $R^a$ and $R^b$ together with the nitrogen to which they are attached form morpholino, or from a group of the formula:

—$X^7$-$Q^5$ wherein $X^7$ is a direct bond and $Q^5$ is aryl, heteroaryl, heterocyclyl, heterocyclyl-(1-6C)alkyl, or heterocyclyloxy-(1-6C) alkyl, and wherein any CH, $CH_2$ or $CH_3$ group within a $R^{14}$ substituent optionally bears on each said CH, $CH_2$ or $CH_3$ group a substituent selected from (1-6C)alkoxy, carbamoyl, N-(1-6C)alkylcarbamoyl or a group of the formula:

—$X^8$-$Q^6$ wherein $X^8$ is a direct bond or O and $Q^6$ is (3-7C)cycloalkyl or heterocyclyl and wherein any heterocyclyl group within a substituent on $R^{14}$ optionally bears 1 oxo substituent;

or a pharmaceutically acceptable acid addition salt thereof.

5. The quinazoline derivative of the Formula I, or a pharmaceutically acceptable acid addition salt thereof, according to claim 1 wherein $R^1, R^2, R^3, Z, Z^2$, m and n have any of the meanings defined in claim 1 and $R^{14}$ is a group of the formula:

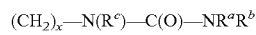

$(CH_2)_x$—$N(R^c)$—$C(O)$—$NR^aR^b$ wherein x is 1, $R^c$ is hydrogen or (1-3C)alkyl and $R^a$ and $R^b$ are each independently selected from hydrogen and (1-3C) alkyl.

6. The quinazoline derivative of the Formula I according to claim 1 wherein

Z is NH m is 2, and the first $R^1$ group is a 6-methoxy group and the second $R^1$ group is located at the 7-position and is selected from methoxy, 2-methoxyethoxy, isopropoxy, isopropylmethoxy, 3-dimethylaminopropoxy, dimethylaminoisopropoxy, 2-[3-(hydroxy)propylamino]ethoxy, 3-[bis(2-methoxyethyl)amino]propoxy, 2-(4-methylpiperazin-1-yl)ethoxy, 3-(3-oxo-4-methylpiperazin-1-yl)propoxy, 3-(2-oxo-4-methylpiperazin-1-yl)propoxy, 3-morpholinopropoxy, 2-morpholin-4-ylethoxy, 4-morpholin-4-ylbutoxy, 3-(2,6-dimethylmorpholin-4-yl)propoxy, 3-(1,1-dioxotetrahydro-4H-1,4-thiazin-4-yl)propoxy, 2-fluoroethoxy, 3-[4-(2-fluoroethyl)piperazin-1-yl]propoxy, 3-(4-acetylpiperazin-1-yl)propoxy, 3-(4-formylpiperazin-1-yl)propoxy, 3-piperazin-1-ylpropoxy, 3-(4-hydroxypiperidin-1-yl) propoxy, 3-[2-(hydroxymethyl)pyrrolidin-1-yl]propoxy, 2-(2-methoxyethoxy)ethoxy, 3-chloropropoxy, 2-(2-chloroethoxy)ethoxy, 1-methylpiperidin-4-ylmethoxy, 3-(4-methoxypiperidin-1-yl)propoxy or 3-(4-hydroxypiperidin-1-yl)propoxy, n is 1 and $R^3$ group, if present, is located at the 6 position of the 1,3-benzodioxol group and is selected from fluoro, chloro or bromo;

$Z^2$ is a C≡C or CH=CH group; and $R^{14}$ is selected from methoxymethyl, 1-methoxyethyl, 2-methoxyethyl, methoxyisopropyl, 2-methoxypropyl, ethoxymethyl, methoxyethoxymethyl, hydroxymethyl, carbamoylmethoxymethyl, methylcarbamoylmethoxymethyl, isopropoxymethyl, di-(methylamino) methyl, hydroxyisopropyl, (cyclopropylmethoxy)methyl, (cyclopentylmethoxy)methyl from a group of formula:

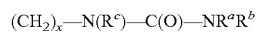

$(CH_2)_x$—$N(R^c)$—$C(O)$—$NR^aR^b$ wherein x is 1, $R^c$ is hydrogen and $R^a$ and $R^b$ are each independently selected from hydrogen, and methyl or $R^a$ and $R^b$ together with the nitrogen to which they are attached form morpholino, or x is 1 and $R^a$, $R^b$ and $R^c$ are all methyl, or is selected from 2-oxo-pyrrolidin-1-ylmethyl, pyridin-2-yl, (tetrahydrofuran-3-ylmethoxy)methyl, (tetrahydrofuran-3-yloxy)methyl, [(1,3-dioxolan-2-yl)methoxy]methyl, phenyl, pyridin-3-yl, pyrazin-3-yl, pyrimidin-2-yl, 1H-pyrazol-4-yl or 1H-pyrazol-5-yl;

7. The quinazoline derivative of the Formula I according to claim 1 wherein

Z is NH m is 2 and each $R^1$ group, which may be the same or different, is located at the 5- and 7-positions and $R^1$ is selected from methoxy, ethoxy, propoxy, isopropoxy, 2-methylpropoxy, vinyloxy, or from a group of the formula:

$$Q^1\text{-}X^1\text{—}$$

wherein $X^1$ is O and $Q^1$ is 1-, 2-, or 3-pyrrolidinyl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, tetrahydro-2$\underline{H}$-pyran-4-yl, 2-(1,1-dioxotetrahydro-4$\underline{H}$-1,4-thiazin-4-yl)ethyl, 3-(1,1-dioxotetrahydro-4$\underline{H}$-1,4-thiazin-4-yl)propyl, 2-piperidinoethyl, 3-piperidinopropyl, 4-piperidinobutyl, 2-piperidin-3-ylethyl, piperidin-4-ylmethyl, 3-piperidin-1-ylpropyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein any $CH_2$ or $CH_3$ group within a $R^1$ substituent optionally bears on each said $CH_2$ or $CH_3$ group one or more fluoro or chloro groups or a substituent selected from amino, methylamino, methoxy, dimethylamino, methoxyethylamino, di-(methoxyethyl)amino or hydroxypropylamino, and wherein any heterocyclyl group within a substituent on $R^1$ optionally bears 1, 2 or 3 substituents, which may be the same or different, selected from methyl, ethyl, methoxy, ethoxy, formyl, acetyl, hydroxyl, hydroxymethyl, fluoroethyl or hydroxypropylamino, and wherein any heterocyclyl group within a substituent on $R^1$ optionally bears 1 or 2 oxo substituents;

n is 0 or 1 and $R^3$ group, if present, is located at the 5 position of the 1,3-benzodioxol group and is selected from fluoro or chloro;

$Z^2$ is a C≡C or CH=CH group; and $R^{14}$ is selected from (1-6C)alkoxy-(1-6C)alkyl, di-[(1-6C)alkyl]amino-(1-6C)alkyl, hydroxyl-(1-6C)alkyl or from a group of formula:

$$(CH_2)_x\text{—}N(R^c)\text{—}C(O)\text{—}NR^aR^b$$

wherein x is 0, 1, 2 or 3, $R^c$ is hydrogen or (1-6C)alkyl and $R^a$ and $R^b$ are each independently selected from hydrogen and (1-6C)alkyl or $R^a$ and $R^b$ together with the nitrogen to which they are attached form morpholino, or from a group of the formula:

$$\text{—}X^7\text{-}Q^5$$

wherein $X^7$ is a direct bond and $Q^5$ is aryl, heteroaryl, heterocyclyl, heterocyclyl-(1-6C)alkyl, or heterocyclyloxy-(1-6C)alkyl, and wherein any CH, $CH_2$ or $CH_3$ group within a $R^{14}$ substituent optionally bears on each said CH, $CH_2$ or $CH_3$ group a substituent selected from (1-6C)alkoxy, carbamoyl, $\underline{N}$-(1-6C)alkylcarbamoyl or a group of the formula:

$$\text{—}X^8\text{-}Q^6$$

wherein $X^8$ is a direct bond or O and $Q^6$ is (3-7C)cycloalkyl or heterocyclyl and wherein any heterocyclyl group within a substituent on $R^{14}$ optionally bears 1 oxo substituent;

or a pharmaceutically acceptable acid addition salt thereof.

8. The quinazoline derivative of the Formula I according to claim 1 wherein

Z is NH m is 2 and the first $R^1$ group is at the 5-position and is selected from isopropoxy, tetrahydro-2$\underline{H}$-pyran-4-yloxy and the second $R^1$ group is at the 7-position and is selected from methoxy, 3-morpholin-4-ylpropoxy, 3-(4-acetylpiperazin-1-yl)propoxy, 3-(4-formylacetylpiperazin-1-yl)propoxy and 3-(3-oxo-4-methyl-piperazin-1-yl)propyoxy n is 1 and $R^3$ group is located at the 5-position of the 1,3-benzodioxol-4-yl group and is chloro;

$Z^2$ is a C≡C or CH=CH group; and $R^{14}$ is selected from-methoxymethyl, 2-methoxyethyl, methoxyisopropyl and pyridin-2-yl, or a pharmaceutically acceptable acid addition salt thereof.

9. The quinazoline derivative of the Formula I according to claim 1 and selected from N-[5-chloro-7-(3-methoxyprop-1-ynyl)-1,3-benzodioxol-4-yl]-6-methoxy-7-(3-morpholin-4-ylpropoxy) quinazolin-4-amine, N-[5-chloro-7-(4-methoxybut-1-yn-1-yl)-1,3-benzodioxol-4-yl]-6-methoxy-7-(3-morpholin-4-ylpropoxy) quinazolin-4-amine, N-[5-chloro-7-(3-ethoxyprop-1-yn-1-yl)-1,3-benzodioxol-4-yl]-6-methoxy-7-(3-morpholin-4-ylpropoxy) quinazolin-4-amine, N-[5-chloro-7-(3-isopropoxyprop-1-yn-1-yl)-1,3-benzodioxol-4-yl]-6-methoxy-7-(3-morpholin-4ylpropoxy) quinazolin-4-amine, N-{5-chloro-7-[3-(cyclopropylmethoxy)prop-1-yn-1-yl]-1,3-benzodioxol-4-yl}-6-methoxy-7-(3-morpholin-4-ylpropoxy)quinazolin-4-amine, (1-{3-[(4-{[5-chloro-7-(4-methoxybut-1-yn-1-yl)-1,3-benzodioxol-4-yl]amino}-6-methoxyquinazolin-7-yl) oxy]propyl}piperidin4-yl)methanol, N'-[3-(6-chloro-7-{[6-methoxy-7-(3-morpholin-4-ylpropoxy)quinazolin-4-yl]amino}-1,3-benzodioxol-4-yl) prop-2-yn-1-yl]-N,N-dimethylurea, 7-{3-[bis(2-methoxyethyl)amino]propoxy}-N-[5-chloro-7-(4-methoxybut-1-yn-1-yl)-1,3-benzodioxol-4-yl3-6-methoxyquinazolin-4-amine, 4-{3-[(4-{[5-chloro-7-(4-methoxybut-1-yn-1-yl)-1,3-benzodioxol-4-yl]amino}-6-methoxyquinazolin-7-yl) oxy]propyl}piperazine-1-carbaldehyde, N-[5-chloro-7-(4-methoxybut-1-yn-1-yl)-1,3-benzodioxol-4-yl]-7-{3-[4-(2-fluoroethyl)piperazin-1-yl] propoxy}-6-methoxyquinazolin-4-amine, N-[5-chloro-7-(4-methoxybut-1-yn-1-yl)-1,3-benzodioxol-4-yl]-6-methoxy-7-[3-(4-methoxypiperidin-1-yl)propoxy]quinazolin-4-amine, 4-{3-[(4-{[5-chloro-7-(4-methoxybut-1-yn-1-yl)-1,3-benzodioxol-4-yl]amino}-6-methoxyquinazolin-7-yl) oxy]propyl}-1-methylpiperazin-2-one, 4-{3-[(4-{[5-chloro-7-(3-methoxyprop-1-yn-1-yl)-1,3-benzodioxol-4-yl]amino}-6-methoxyquinazolin-7-yl) oxy]propyl}-1-methylpiperazin-2-one, N'-{3-[6-chloro-7-({6-methoxy-7-[3-(4-methyl-3-oxopiperazin-1-yl)propoxy]quinazolin-4-yl}amino)-1,3-benzodioxol-4-yl]prop-2-yn-1-yl]-N,N-dimethylurea, 1-{3-[(4-{[5-chloro-7-(pyridin-2-ylethynyl)-1,3-benzodioxol-4-yl]amino}-6-methoxyquinazolin-7-yl)oxy] propyl}-4-methylpiperazin-2-one, N'-{3-[6-chloro-7-({7-[3-(cis-2,6-dimethylmorpholin-4-yl)propoxy]-6-methoxyquinazolin-4-yl}amino)-1,3-benzodioxol-4-yl]prop-2-yn-1-yl}-N,N-dimethylurea,
N-[5-chloro-7-(3-methoxyprop-1-yn-1-yl)-1,3-benzodioxol-4-yl]-6-methoxy-7-(4-morpholin-4-ylbutoxy)quinazolin-4-amine,
N-[5-chloro-7-(pyridin-2-ylethynyl)-1,3-benzodioxol-4-yl]-6-methoxy-7-(3-morpholin-4-ylpropoxy)quinazolin-4-amine,
N-[5-chloro-7-(3-methoxyprop-1-yn-1-yl)-1,3-benzodioxol-4-yl]-7-{3-(cis-2,6-dimethylmorpholin-4-yl]propoxy}-6-methoxyquinazolin-4-amine,
N-[5-chloro-7-[(tetrahydrofuran-3-ylmethoxy)methyl]-1,3-benzodioxol-4-yl]-6-methoxy-7-(3-morpholin-4-ylpropoxy)quinazolin-4-amine,
N-[5-chloro-7-{[(1,3-dioxolan-2-yl)methoxy]methyl}-1,3-benzodioxol-4-yl]-6-methoxy-7-(3-morpholin-4-ylpropoxy)quinazolin-4-amine,
N-[5-chloro-7-[(tetrahydrofuran-3-yloxy)methyl]-1,3-benzodioxol-4-yl]-6-methoxy-7-(3-morpholin-4-ylpropoxy)quinazolin-4-amine,
N-[5-chloro-7-(pyridin-3-ylethynyl)-1,3-benzodioxol-4-yl]-6-methoxy-7-(3-morpholin-4-ylpropoxy)quinazolin-4-amine,
N-[5-chloro-7-(1H-pyrazol-4-ylethynyl)-1,3-benzodioxol-4-yl]-6-methoxy-7-(3-morpholin-4-ylpropoxy)quinazolin-4-amine,
4-{3-[(4-{[5-chloro-7-(3-methoxybut-1-yn-1-yl)-1,3-benzodioxol-4-yl]amino}-6-methoxyquinazolin-7-yl)oxy]propyl}-1-methylpiperazin-2-one,
N-[5-bromo-7-(3-methoxybut-1-yn-1-yl)-1,3-benzodioxol-4-yl]-6-methoxy-7-(3-morpholin-4-ylpropoxy)quinazolin-4-amine,
4-{3-[(4-{[5-bromo-7-(3-methoxyprop-1-yn-1-yl)-1,3-benzodioxol-4yl]amino}-6-methoxyquinazolin-7-yl)oxy]propyl}-1-methylpiperazin-2-one,
N-[5-chloro-7-(pyridin-2-ylethynyl)-1,3-benzodioxol-4-yl]-7-[3-(cis-2,6dimethylmorpholin-4-yl]propoxy)]-6-methoxyquinazolin-4-amine,
4-{3-[(4-{[5-Chloro-7-(3-isopropoxyprop-1-yn-1-yl)-1,3-benzodioxol-4-yl]amino}-6-methoxyquinazolin-7-yl)oxy]propyl}-1-methylpiperazin-2-one,
N-[5-chloro-7-(1H-pyrazol-5-ylethynyl)-1,3-benzodioxol-4-yl]-6-methoxy-7-(3-morpholin-4-ylpropoxy)quinazolin-4-amine,
4-{3-[(4-{[5-chloro-7-(pyridin-2-ylethynyl)-1,3-benzodioxol-4-yl]amino}-6-methoxyquinazolin-7-yl)oxy]propyl}-1-methylpiperazin-2-one,
N-[5-chloro-7-(3-methoxyprop-1-yn-1-yl)-1,3-benzodioxol-4-yl]-6-methoxy-7-[3-(4-hydroxypiperidin-1-yl)propoxy]-quinazolin-4-amine,
((2R)-1-{3-[(4-{[5-chloro-7-(3-methoxyprop-1-yn-1-yl)-1,3-benzodioxol-4-yl]amino}-6-methoxyquinazolin-7-yl)oxy]propyl}pyrrolidin-2-yl)methanol,
4-{3-[(4-{[5-chloro-7-(3-methoxyprop-1-yn-1-yl)-1,3-benzodioxol-4-yl]amino}-6-methoxyquinazolin-7-yl)oxy]propyl}piperazin-2-one,
N-[5-chloro-7-(3-methoxyprop-1-yn-1-yl)-1,3-benzodioxol-4-yl]-7-{3-[4-(2-fluoroethyl)piperazin-1-yl]propoxy}-6-methoxyquinazolin-4-amine,
N-[5-chloro-7-(4-methoxybut-1-yn-1-yl)-1,3-benzodioxol-4-yl]-7-(3-morpholin-4-ylpropoxy)-5-(tetrahydro-2H-pyran-4-yloxy)quinazolin-4-amine,
N-[5-chloro-7-(4-methoxyprop-1-yn-1-yl)-1,3-benzodioxol-4-yl]-7-(3-morpholin-4-ylpropoxy)-5-isopropoxyquinazolin-4-amine,
7-[3-(4-acetylpiperazin-1-yl)propoxy]-N-[5-chloro-7-(3-methoxyprop-1-yn-1-yl)-1,3-benzodioxol-4-yl]-5-isopropoxyquinazolin-4-amine,
N-[5-chloro-7-(pyridin-2-ylethynyl)-1,3-benzodioxol-4-yl]-5-isopropoxy-7-(3-morpholin-4-ylpropoxy)quinazolin-4-amine,
4-{3-[(4-{[5-chloro-7-(3-methoxyprop-1-yn-1-yl)-1,3-benzodioxol-4-yl]amino}-5-isopropoxyquinazolin-7-yl)oxy]propyl}piperazine-1-carbaldehyde,
4-{3-[(4-{[5-chloro-7-(3-methoxyprop-1-yn-1-yl)-1,3-benzodioxol-4-yl]amino}-5-isopropoxyquinazolin-7-yl)oxy]propyl}-1-methylpiperazin-2-one,
N-[5-chloro-7-(3-methoxybut-1-yn-1-yl)-1,3-benzodioxol-4-yl]-6-methoxy-7-(3-morpholin-4-ylpropoxy)quinazolin-4amine,
N-[5-bromo-7-(3-methoxyprop-1-yn-1-yl)-1,3-benzodioxol-4-yl]-6-methoxy-7-(3-morpholin-4-ylpropoxy)quinazolin-4-amine and
N-[5-chloro-7-(3-methoxyprop-1-yn-1-yl)-1,3-benzodioxol-4-yl]-7-[3-(dimethylamino)propoxy]-6-methoxyquinazolin-4-amine, or a pharmaceutically acceptable acid addition salt thereof.

10. A process for the preparation of a quinazoline derivative of the Formula I or a pharmaceutically-acceptable salt thereof, according to claim 1 which comprises:

(a) the reaction of a quinazoline of the Formula II

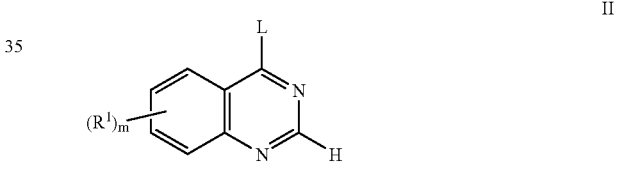

wherein L is a displaceable group and m and $R^1$ have any of the meanings defined in claim 1 except that any functional group optionally is protected, with a compound of the Formula III

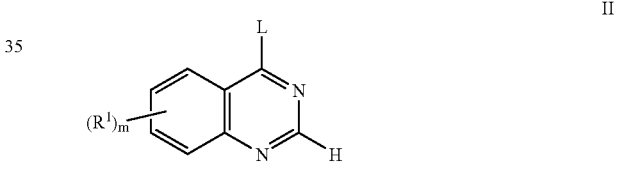

wherein Z is O, S, or $N(R^2)$ and n, $R^3$, $R^2$, $Z^2$ and $R^{14}$ have any of the meanings defined in claim 1 except that any functional group optionally is protected, whereafter any protecting group that is present is removed;

(b) for the production of those compounds of the Formula I wherein at least one $R^1$ group is a group of the formula $Q^1$-$X^1$— wherein $Q^1$ a heterocyclyl-(1-6C)alkyl group and $X^1$ is an oxygen atom, the coupling of a quinazoline of the Formula V

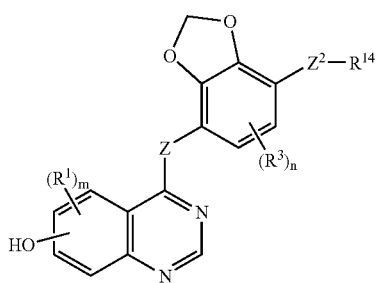

wherein m, $R^1$, Z, n, $R^3$, $Z^2$ and $R^{14}$ have any of the meanings defined in claim 1, except that any functional group optioanlly is protected, with an appropriate alcohol of the formula $Q^1$-OH wherein any functional group optionally is protected, whereafter any protecting group that is present is removed;

(c) for the production of those compounds of the Formula I wherein $R^1$ is an amino-substituted (1-6C)alkoxy group, the reaction of a compound of the Formula I wherein $R^1$ is a halogeno-substituted (1-6C)alkoxy group with a heterocyclyl compound or an appropriate amine;

(d) for the production of those compounds of the Formula I wherein an $R^1$ group contains a (1-6C)alkoxy or substituted (1-6C)alkoxy group or a (1-6C)alkylamino or substituted (1-6C)alkylamino group, the alkylation of a quinazoline derivative of the Formula I wherein the $R^1$ group contains a hydroxy group or a primary or secondary amino group;

(e) for the production of those compounds of the Formula I wherein Z is a SO or $SO_2$ group, wherein an $R^3$ substituent is a (1-6C)alkylsulphinyl or (1-6C)alkylsulphonyl group or wherein an $R^3$ substituent contains a SO or $SO_2$ group, the oxidation of a compound of the Formula I wherein Z is a S group or wherein an $R^3$ substituent is a (1-6C)alkylthio group or wherein an $R^3$ substituent contains a S group;

(f) the reaction of a compound of the Formula VI

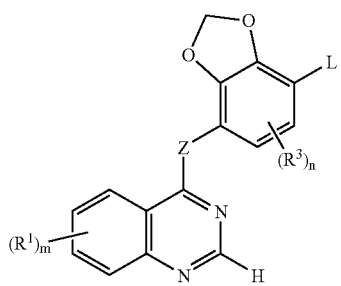

wherein L is a displaceable group as defined hereinbefore and m, $R^1$, Z, n and $R^3$ have any of the meanings defined in claim hereinbefore except that any functional group is optionally protected, with a compound of the Formula VII $$HZ^2\text{-}R^{14} \qquad \text{VII}$$

wherein $Z^2$ is a C≡C or $C(R^{13})$=$C(R^{13})$ group and $R^{13}$ and $R^{14}$ have any of the meanings defined in claim 1 except that any functional group optionally is protected, whereafter any protecting group that is present is removed;

(g) the reaction of a compound of the Formula I wherein $R^{14}$ is a carboxy group with an appropriate amine to form a further compound of the Formula I wherein $R^{14}$ is a carbamoyl, N-(1-6C)alkylcarbamoyl, N,N-di-L(1-6C)alkyl]carbamoyl or heterocyclylcarbonylamino group; or (h) a coupling reaction of a compound of the Formula VIII

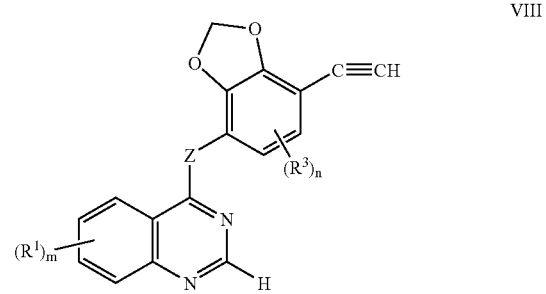

wherein m, $R^1$, Z, n and $R^3$ have any of the meanings defined in claim 1 except that any functional group optionally is protected, with a compound of the Formula IX $$L\text{-}R^{14} \qquad \text{IX}$$

wherein L is a displaceable group and $R^{14}$ has any of the meanings defined in claim 1 except that any functional group optionally is protected, whereafter any protecting group that is present is removed;

and optionally forming a pharmaceutically-acceptable salt of a quinazoline derivative of Formula I.

11. A pharmaceutical composition which comprises a quinazoline derivative of the Formula I, or a pharmaceutically-acceptable salt thereof as defined in claim 1 in association with a pharmaceutically-acceptable diluent or carrier.

12. A method for the treatment of solid tumour disease in a warm-blooded animal in need of such treatment which comprises administering to said animal an effective amount of quinazloine derivative of the Formula I, or a pharmaceutically-acceptable salt thereof, as claimed in claim 1.

* * * * *